(12) United States Patent
Drasler et al.

(10) Patent No.: US 6,287,335 B1
(45) Date of Patent: Sep. 11, 2001

(54) INTRAVASCULAR FOLDED TUBULAR ENDOPROSTHESIS

(76) Inventors: William J. Drasler, 4100 Dynasty Dr., Minnetonka, MN (US) 55345; Joseph M. Thielen, 3027 Cameron Ave. SE., Buffalo, MN (US) 55313

( * ) Notice: Subject to any disclaimer, the term of this patent is extended or adjusted under 35 U.S.C. 154(b) by 0 days.

(21) Appl. No.: 09/299,512

(22) Filed: Apr. 26, 1999

(51) Int. Cl.$^7$ .................................................. A61F 2/08
(52) U.S. Cl. ....................... 623/1.28; 623/1.14; 623/1.35; 623/1.36
(58) Field of Search ................................. 623/1.28, 1.13, 623/1.14, 1.29, 1.35, 1.36; 604/271

(56) References Cited

U.S. PATENT DOCUMENTS

| | | | |
|---|---|---|---|
| 4,545,082 | * 10/1985 | Hood | 623/1 |
| 4,732,152 | * 3/1988 | Wallsten et al. | 604/271 |
| 4,787,899 | * 11/1988 | Lazarus | 623/1 |
| 5,476,506 | * 12/1995 | Lunn | 623/1 |
| 5,507,769 | 4/1996 | Marin | 606/108 |
| 5,562,724 | 10/1996 | Vorwerk | 623/1 |
| 5,578,072 | 11/1996 | Barone | 623/1 |
| 5,591,228 | 1/1997 | Edoga | 623/1 |
| 5,591,229 | 1/1997 | Parodi | 623/1 |
| 5,632,763 | 5/1997 | Glastra | 606/191 |
| 5,676,697 | 10/1997 | McDonald | 623/1 |
| 5,683,449 | 11/1997 | Marcade | 623/1 |
| 5,683,453 | 11/1997 | Palmaz | 606/108 |
| 5,693,084 | 12/1997 | Chuter | 623/1 |
| 5,824,036 | * 10/1998 | Lauterjung | 623/1 |
| 5,824,037 | * 10/1998 | Fogarty | 623/1 |
| 5,824,039 | 10/1998 | Piplani | 623/1 |
| 6,053,938 | * 4/2000 | Goldmann et al. | 623/1 |
| 6,129,756 | * 10/2000 | Kugler et al. | 623/1.28 |

FOREIGN PATENT DOCUMENTS

WO98/58600  12/1998  (WO) .............................. A61F/2/06

* cited by examiner

Primary Examiner—Michael H. Thaler

(57) ABSTRACT

A bifurcated or straight intravascular folded tubular member is deliverable percutaneously or by small cutdown to the site of a vascular lesion. Its inserted state has a smaller nondeployed diameter and a shorter nondeployed length. The intravascular tubular member has a folded tubular section that is unfolded following insertion into the blood vessel. The length of the intravascular folded tubular member is sized in situ to the length of the vessel lesion without error associated with diagnostic estimation of lesion length. The folded tubular member is self-expandable or balloon-expandable to a larger deployed diameter following delivery to the lesion site. An attachment anchor can be positioned at the inlet or outlet ends of the intravascular folded tubular member to prevent leakage between the tubular member and the native vessel lumen and to prevent migration of the tubular member. The attachment anchor has a short axial length to provide a more focal line of attachment to the vessel wall. Such attachment is valuable in attaching to a short aortic neck in the treatment of abdominal aortic aneurysm. The attachment anchor can have barbs which are held in a protected conformation during insertion of the tubular member and are released upon deployment of the attachment anchor. The intravascular tubular member can be formed of woven multifilament polymeric strands with metallic strands interwoven along with them. Double weaving is incorporated to prevent leakage at crossover points.

44 Claims, 62 Drawing Sheets

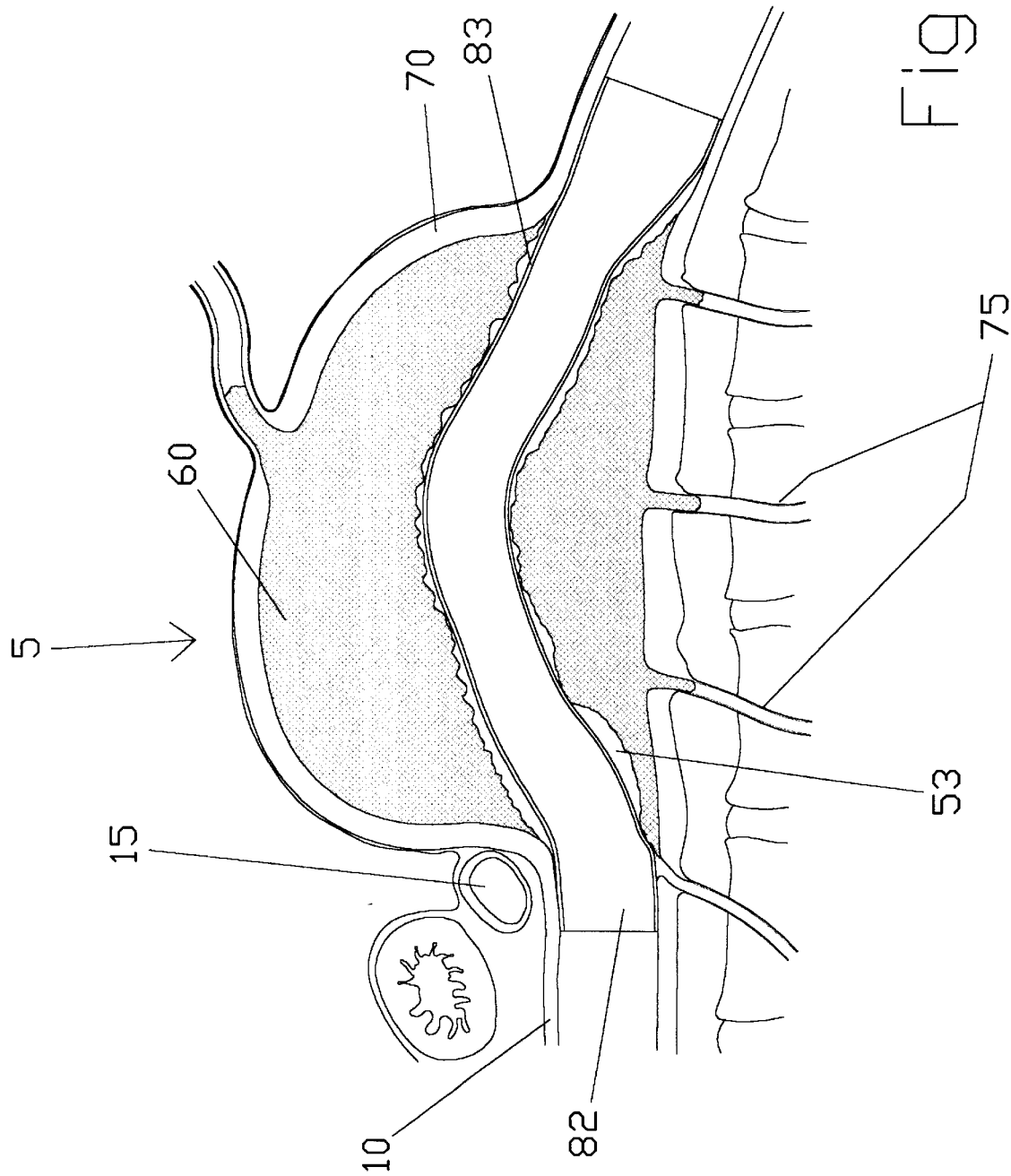

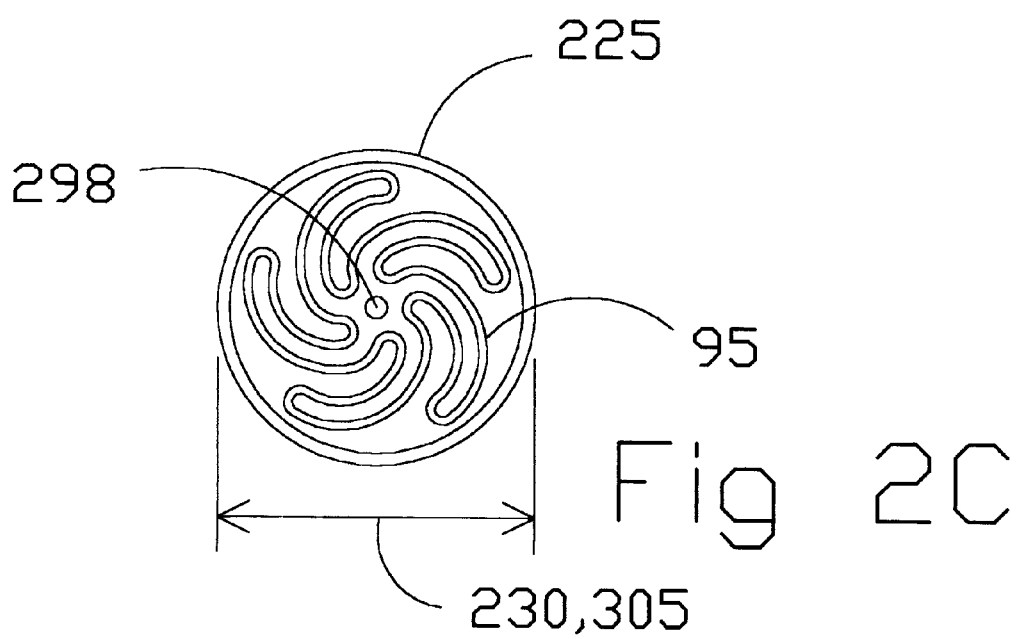

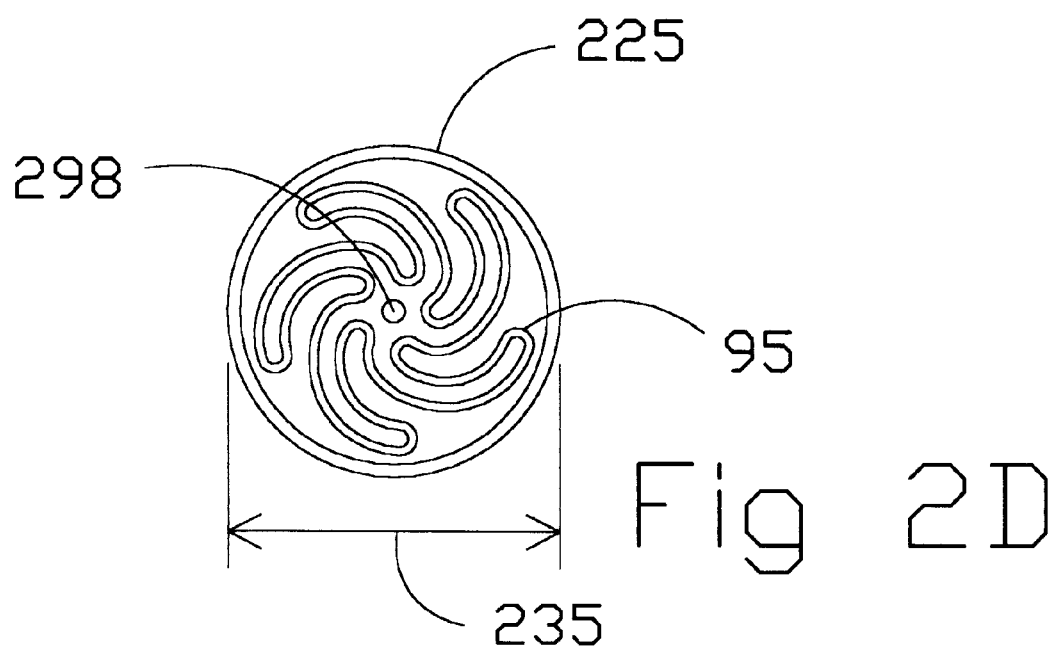

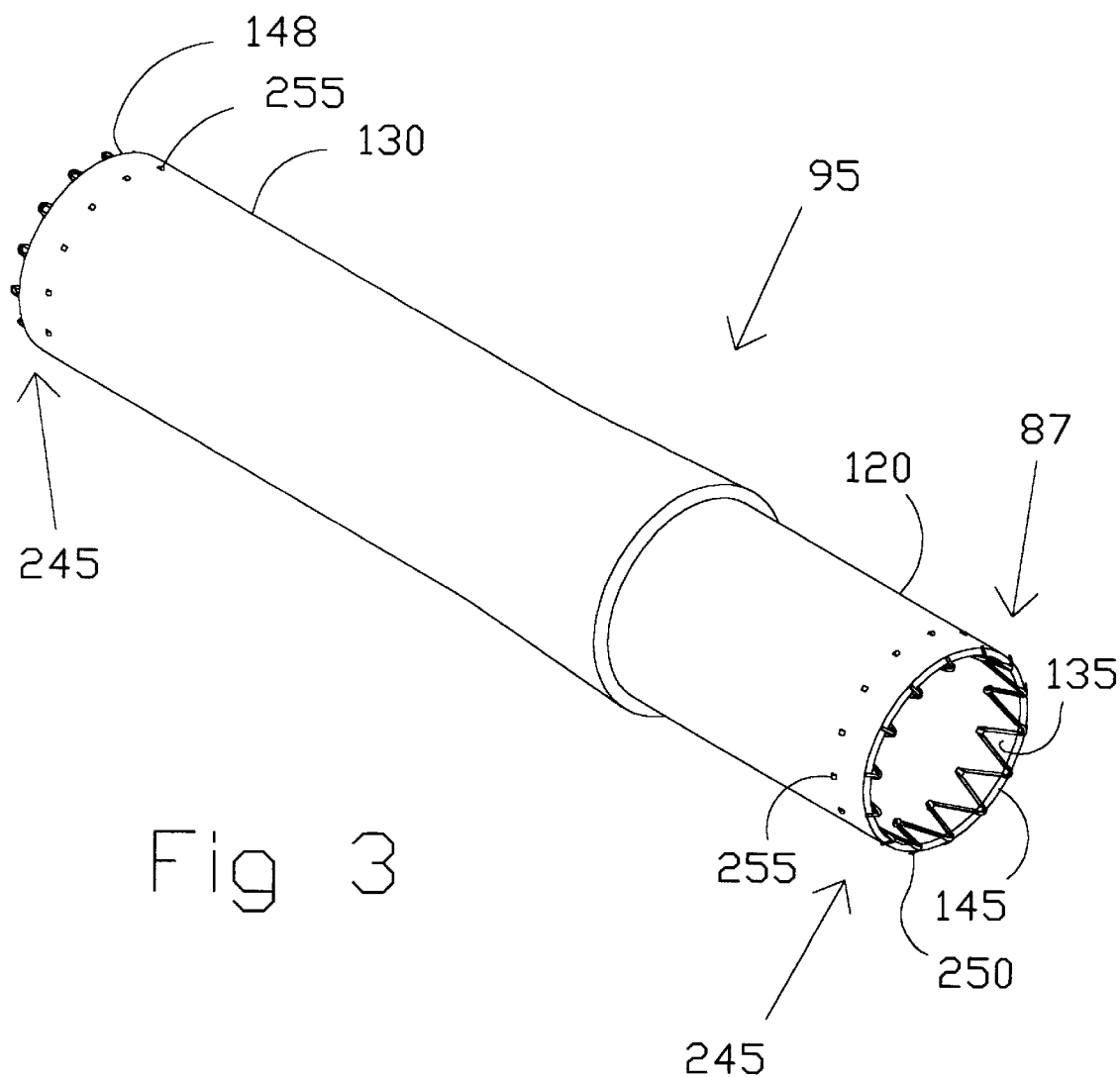

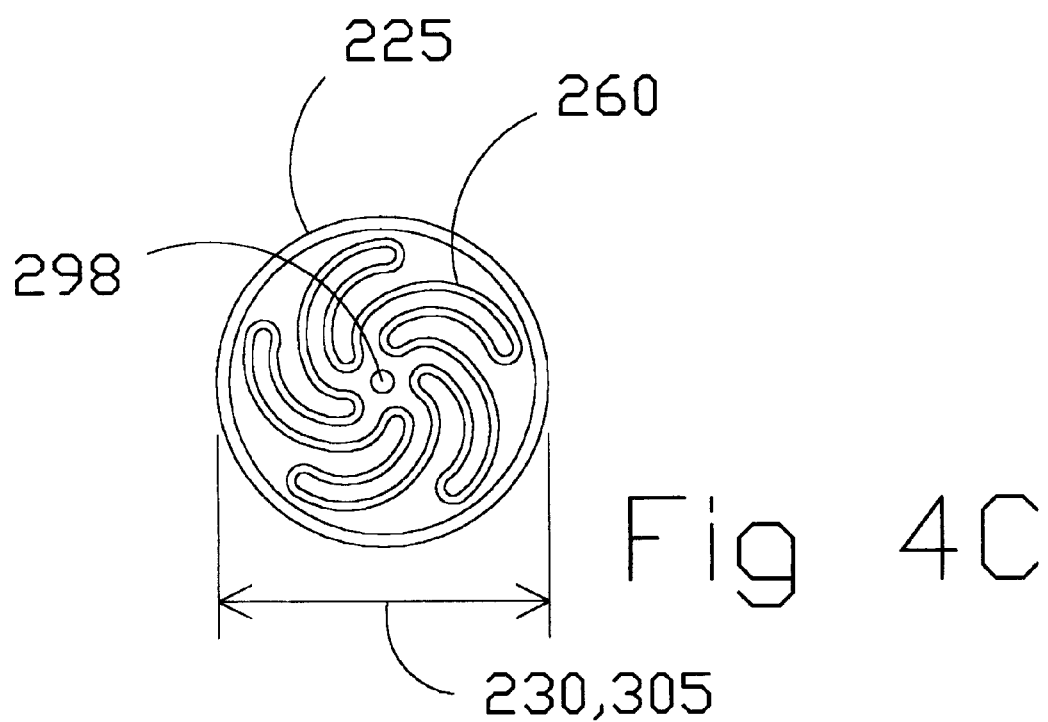

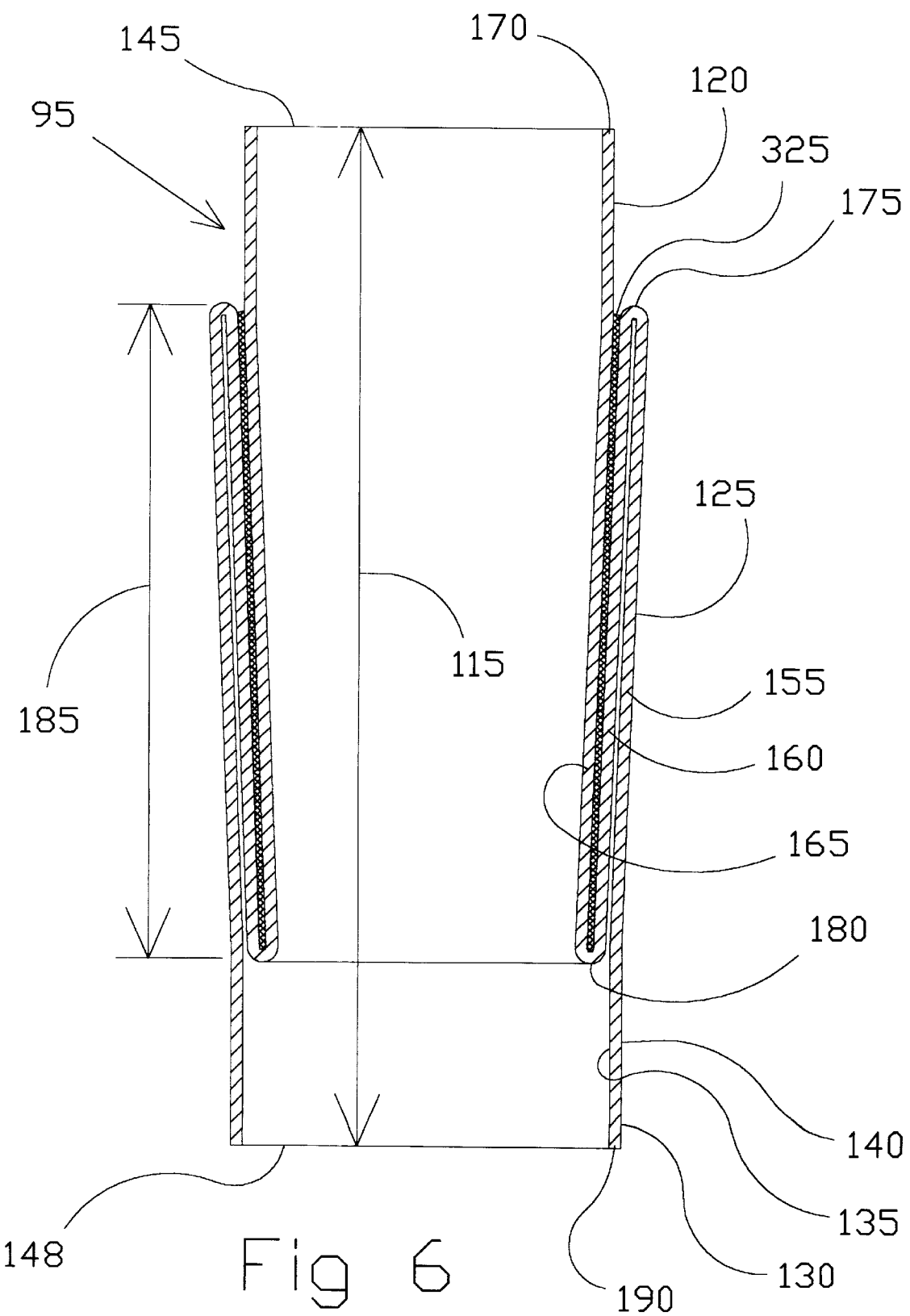

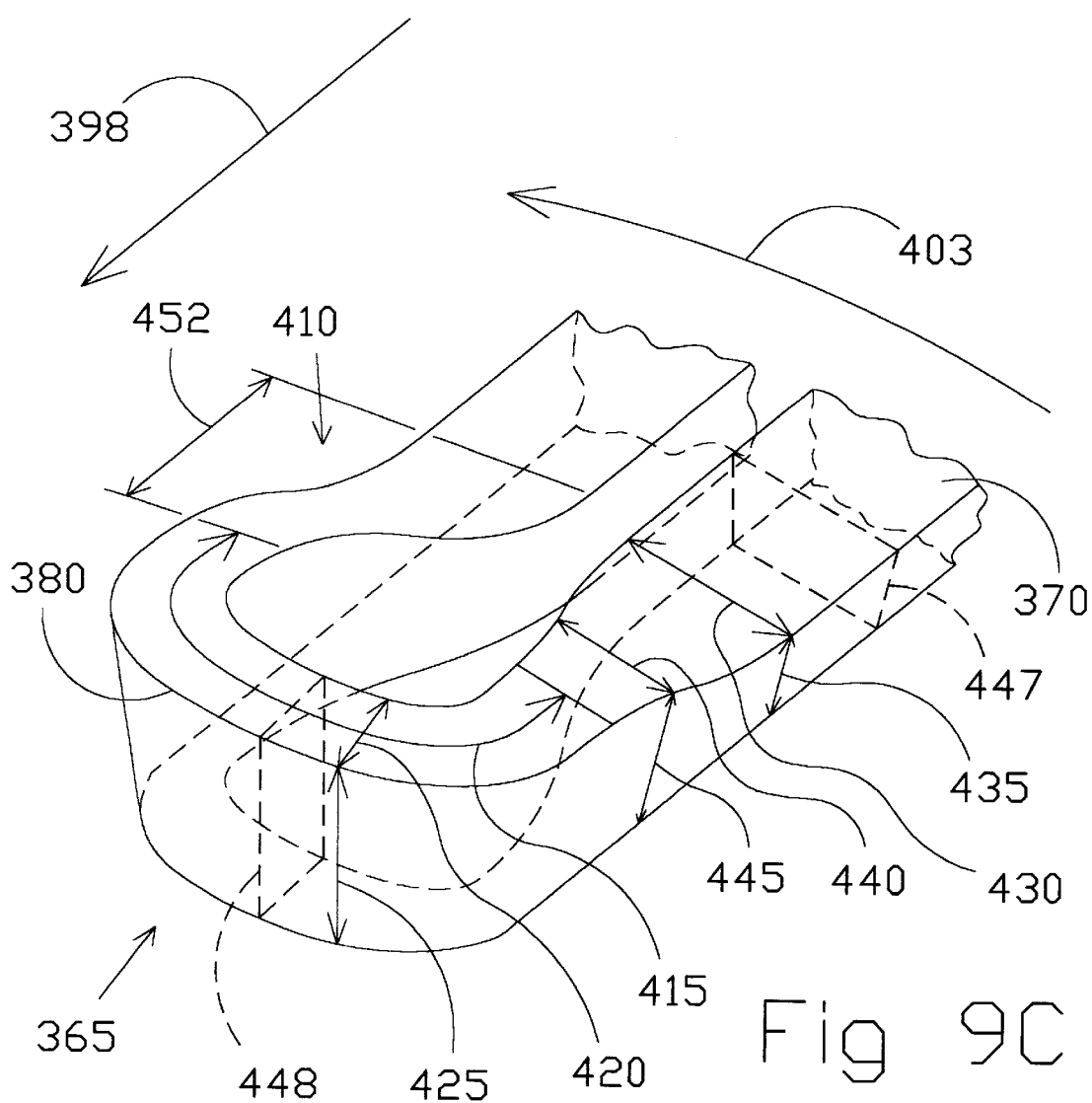

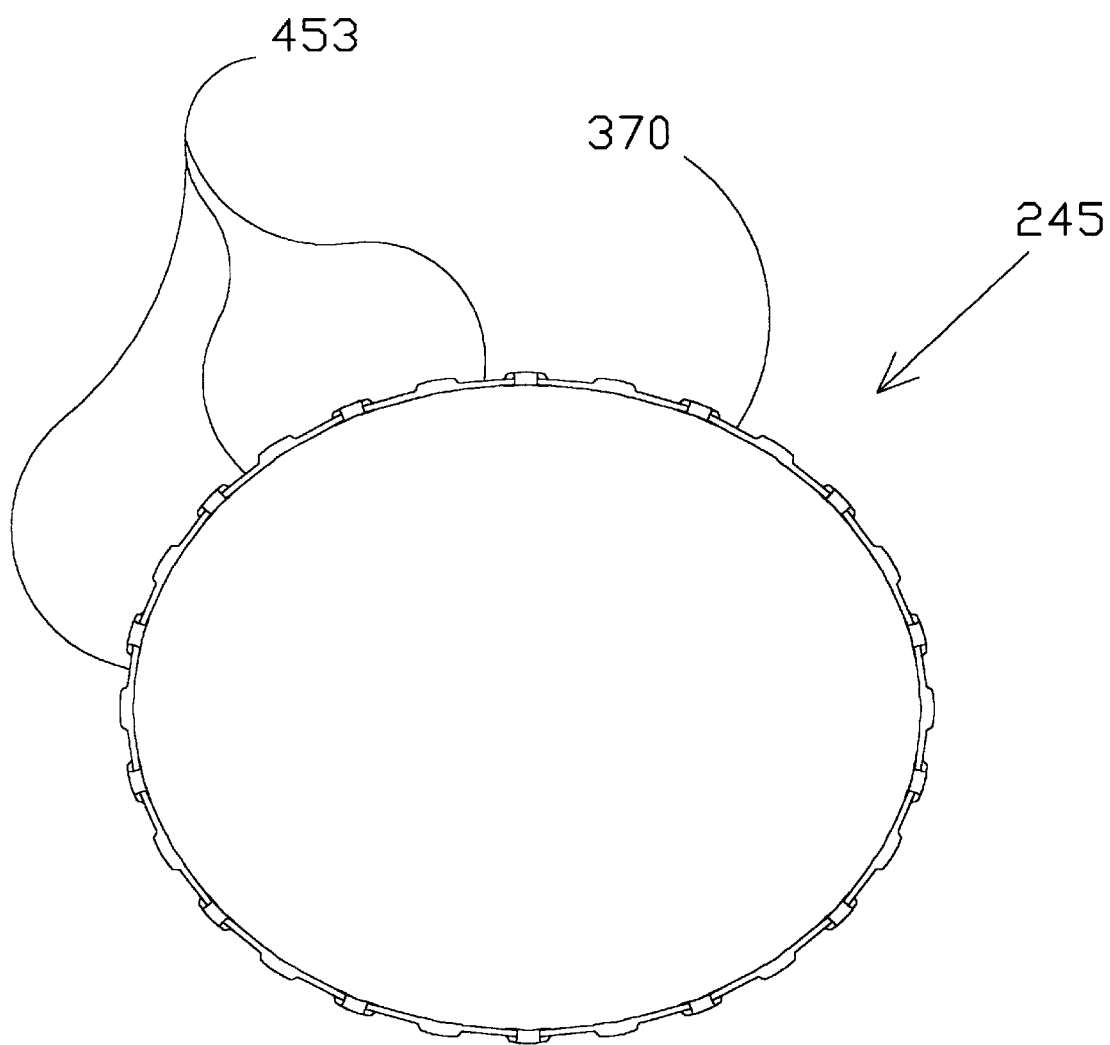

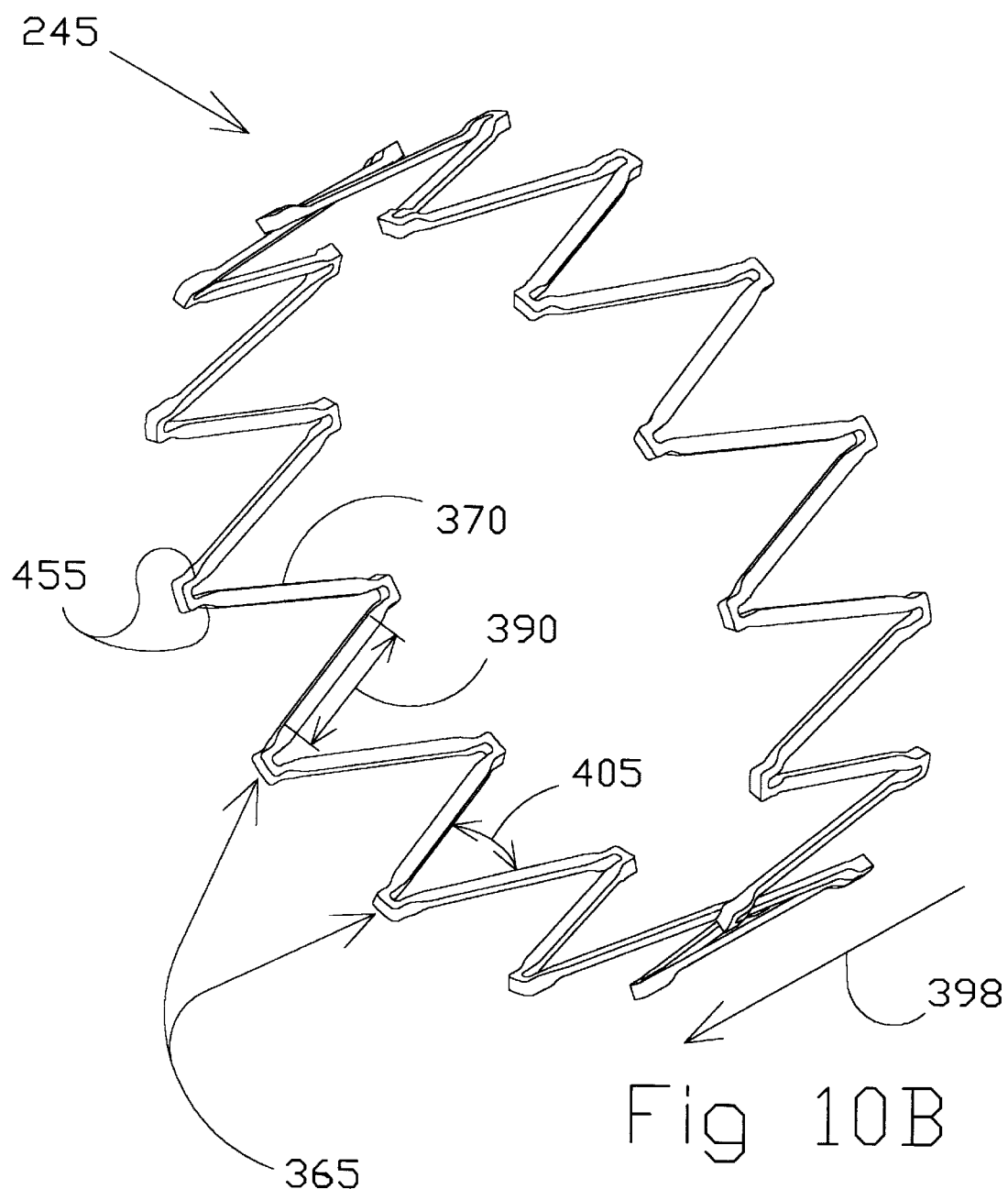

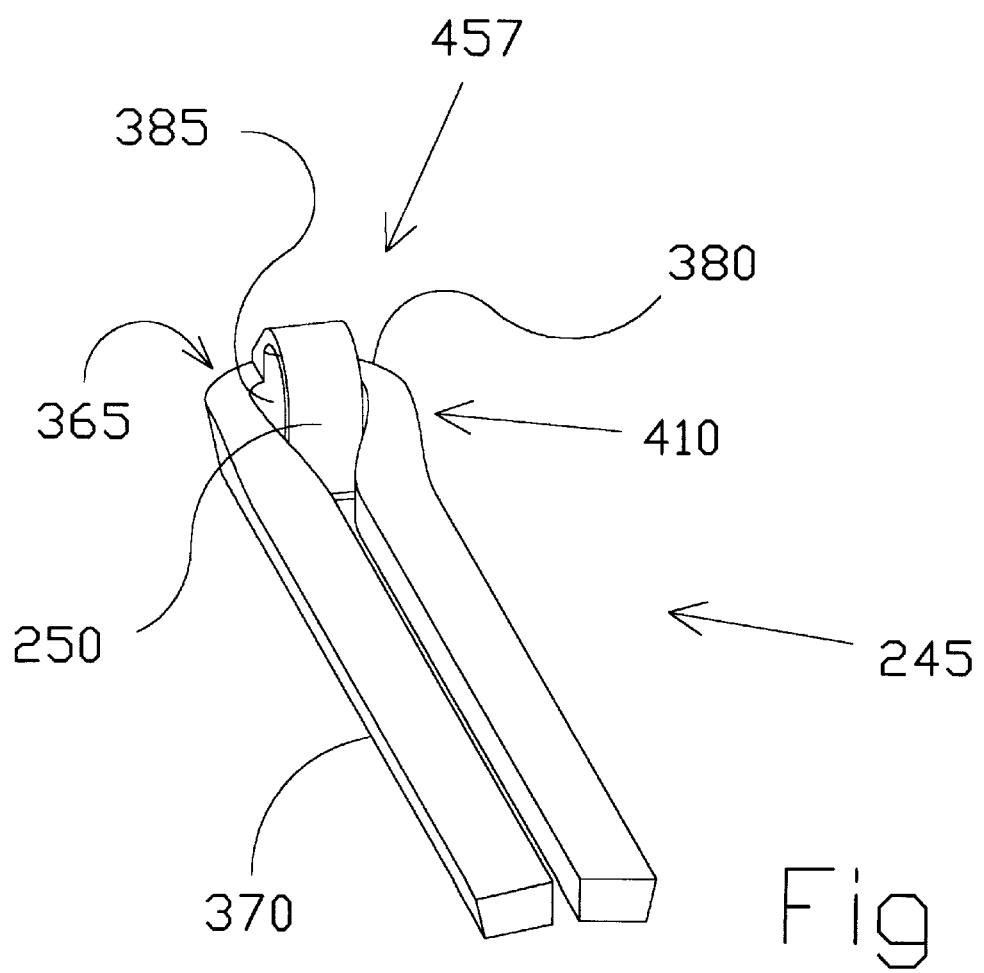

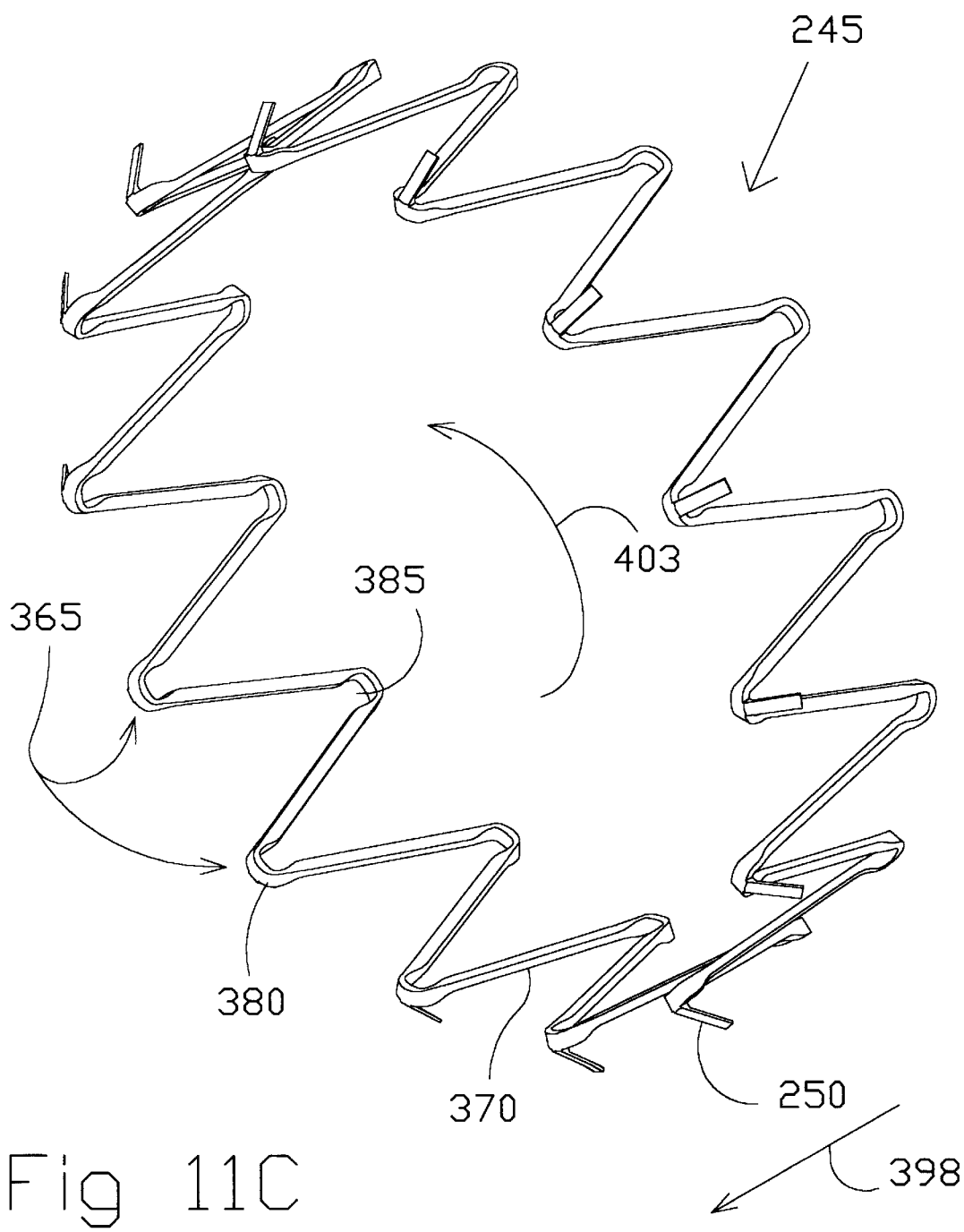

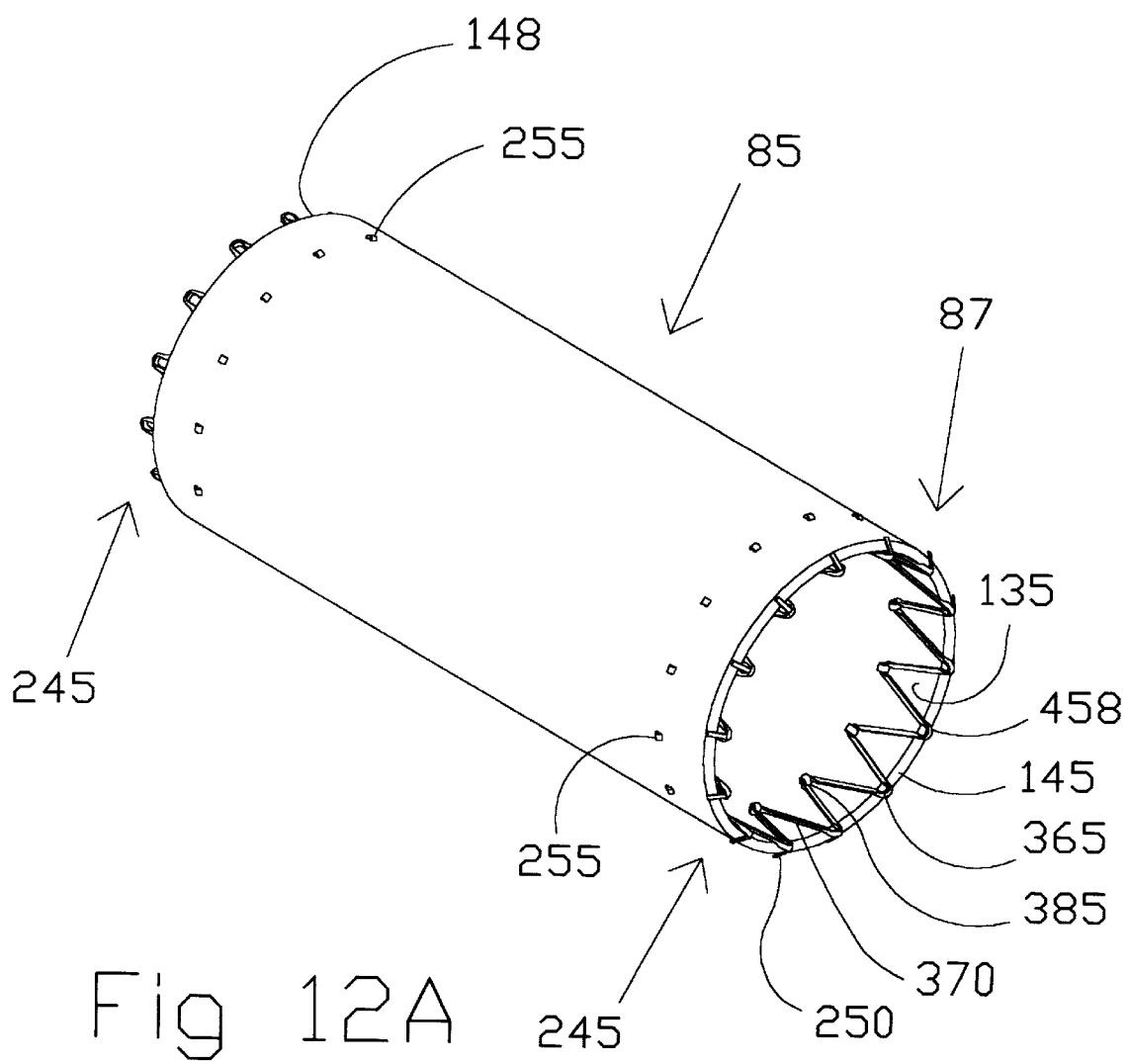

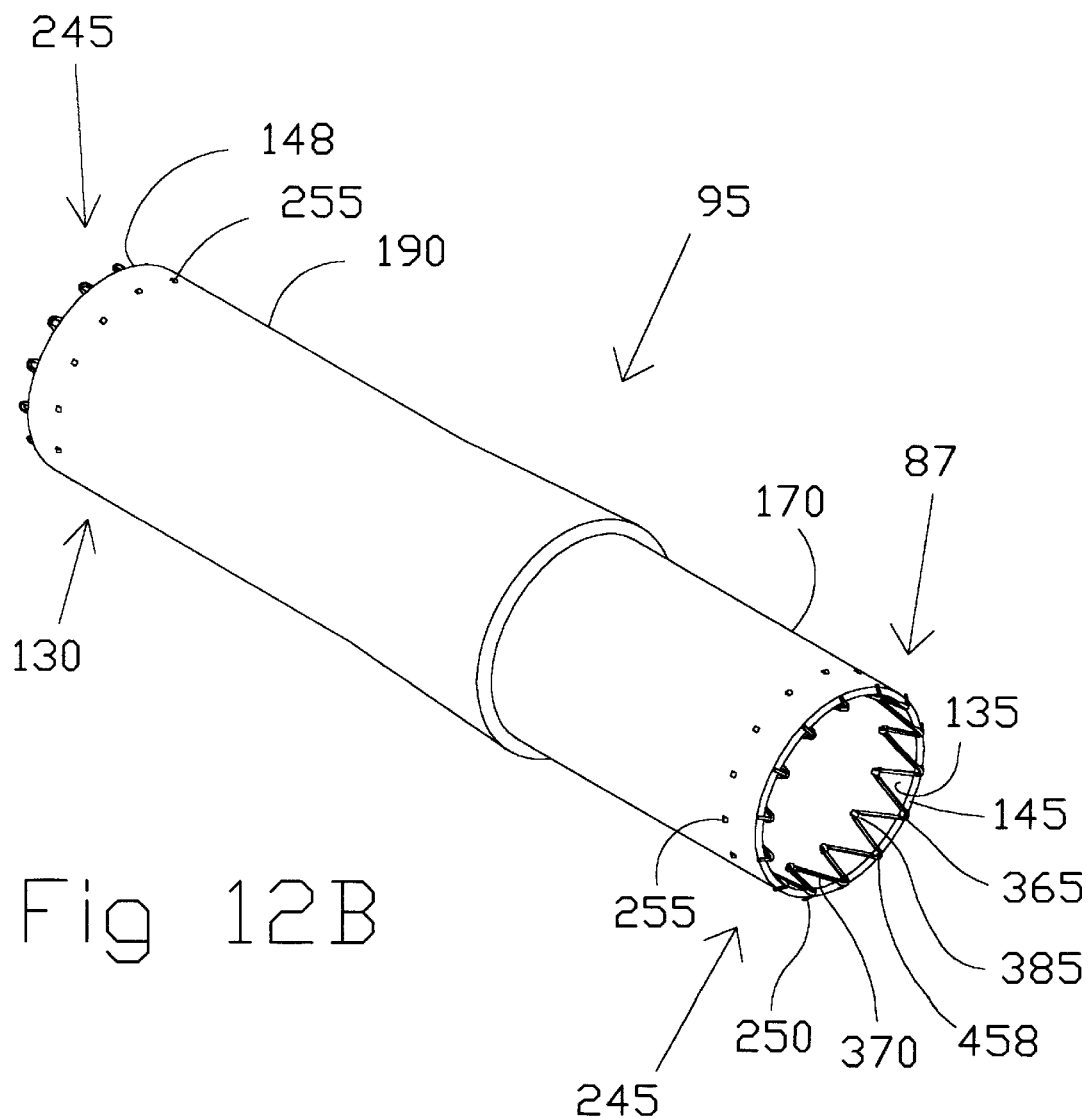

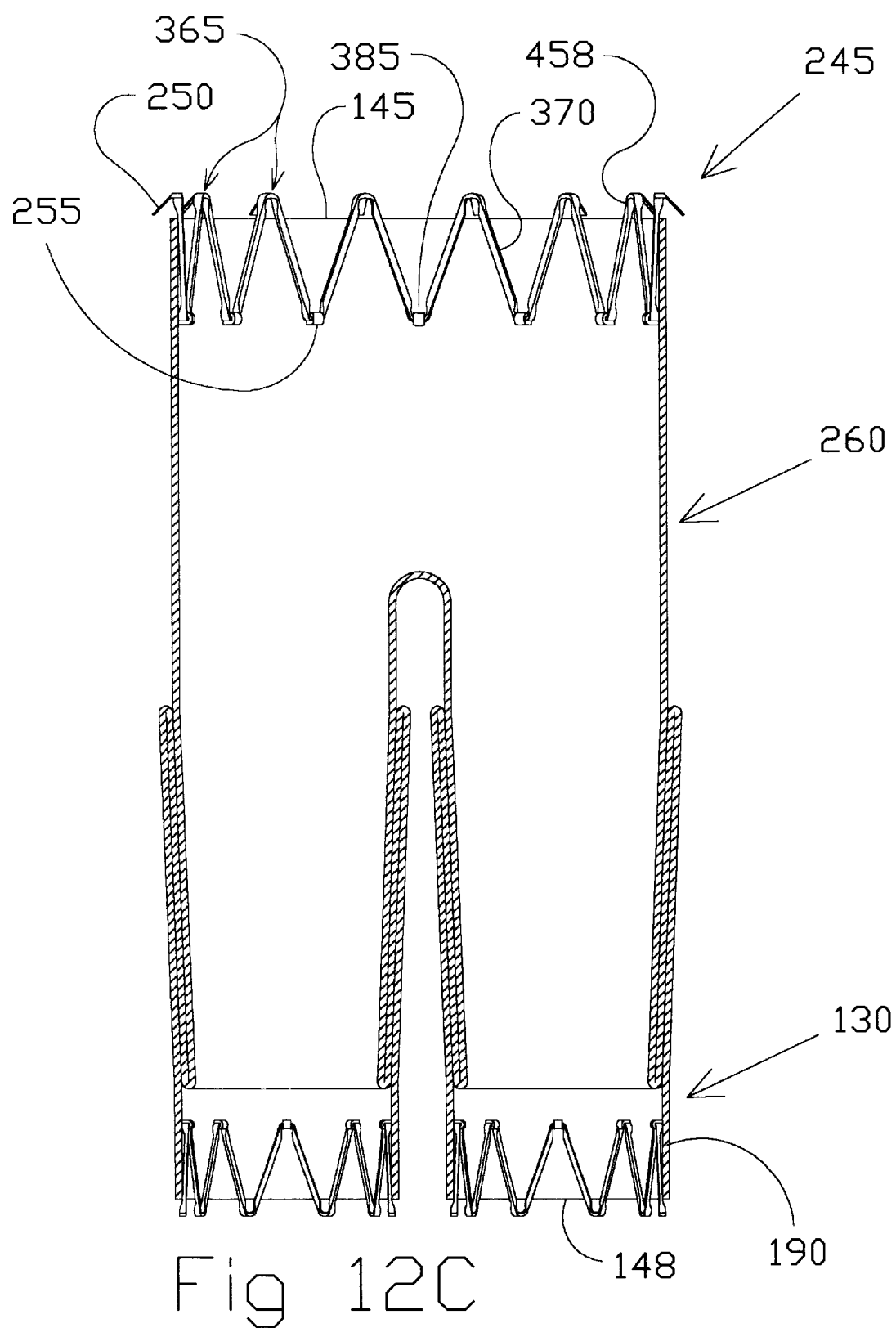

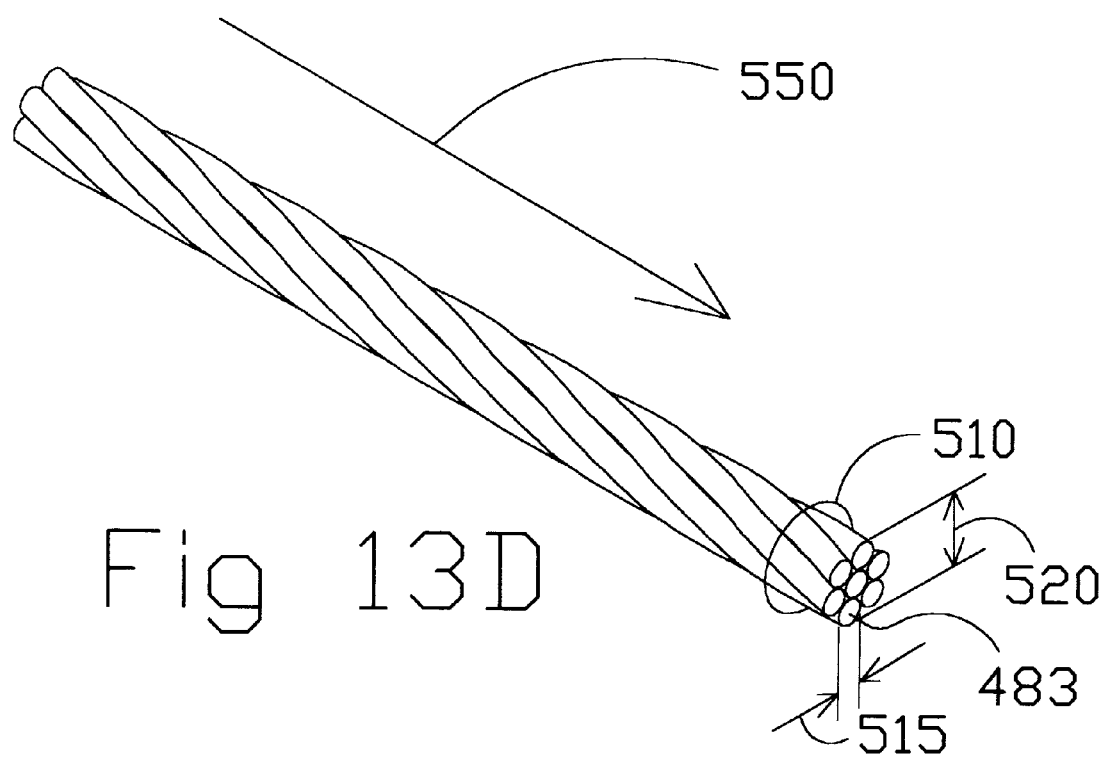

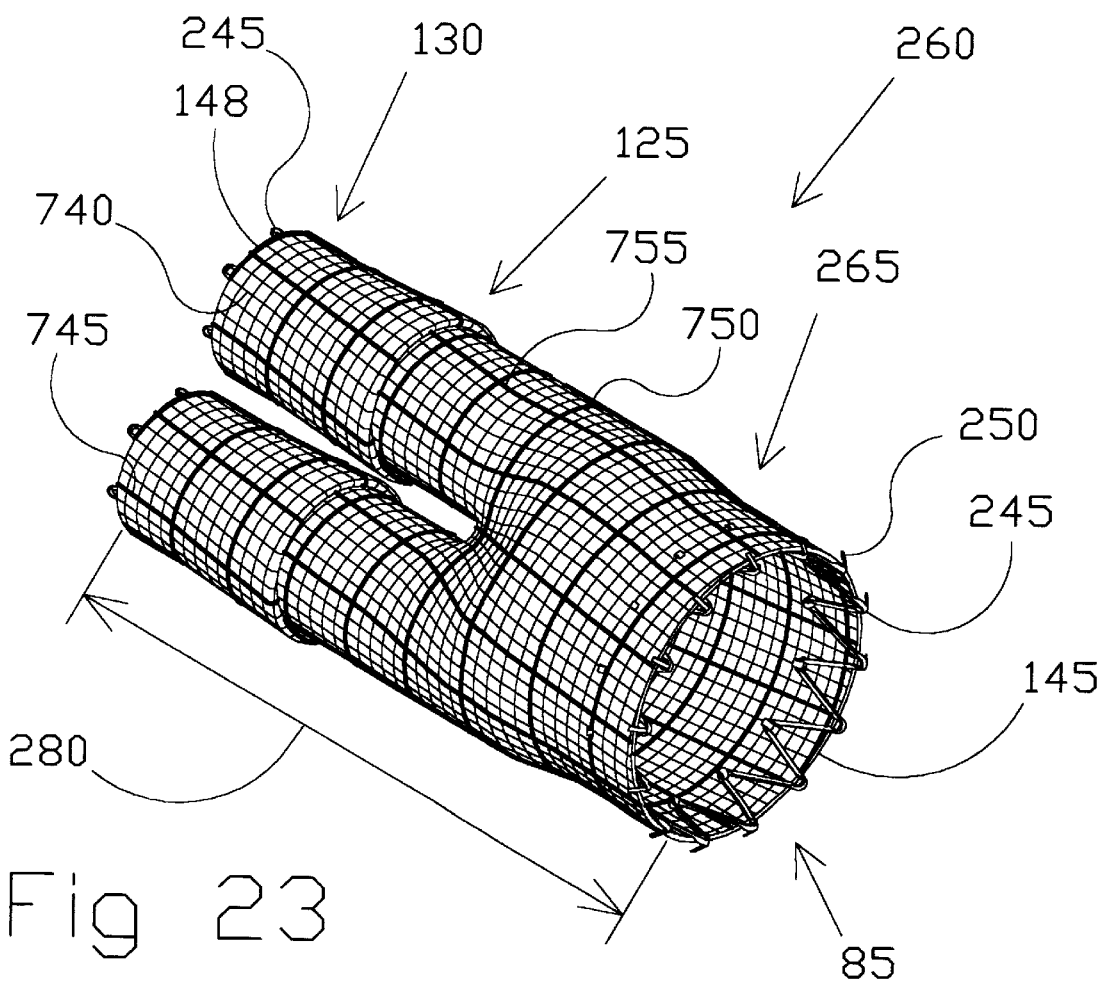

INTRAVASCULAR FOLDED TUBULAR ENDOPROSTHESIS

BACKGROUND OF THE INVENTION

1. Field of Invention

The present invention relates to a vascular implant that is implanted into an artery for repair or bypass of arterial injury. The vascular implant includes a stent-graft that is delivered intraluminally into an artery for repair of a vascular lesion and more specifically for repair of abdominal aortic aneurysm. The vascular implant further includes an attachment means that provides attachment of a stent-graft to a vessel wall.

2. Description of Prior Art

An abdominal aortic aneurysm is an outpouching of the wall of the aorta that can continue to expand over time possibly leading to rupture and mortality. The outpouched wall is generally filled with thrombus except for a generally tortuous pathway for blood flow through an opening in the thrombus. This thrombus can become organized over time as fibroblasts and other cell types infiltrate and form a more organized matrix material containing collagen and other tissue. Typically such aneurysms occur below or caudal to the renal arteries or veins and can extend distally into the right or left common iliac arteries or further distally into the right or left femoral arteries. The right renal vein which crosses over the ventral surface of the aorta can provide some support to the ventral surface of the aorta an help resist aortic distention. Aortic distention can occur very abruptly just distal to the renal vessels reaching a diameter of six centimeters or greater and causing the onset of accompanying symptoms and requiring repair. Generally the blood flow pathway through the thrombus does not follow these abrupt changes found in the vessel wall but rather continues on in a more direct albeit tortuous path through the thrombus found in the aneurysmal aorta. The abdominal aortic aneurysm can sometimes have a proximal neck or region where the aortic diameter appears to be of normal diameter. This proximal neck region is sometimes found just caudal to the renal vessels. The abdominal aortic aneurysm can sometimes also have a distal neck region located just proximal to the aorto-iliac bifurcation. In this minority of patients the abdominal aortic aneurysm does not extend to the iliac arteries or further distally. Aortic distention in the majority of patients can extend into one or both of the iliac or femoral arteries; repair of this abdominal aortic aneurysm can involve treatment of the iliac and femoral arteries as well. The common iliac artery divides to form the external and internal iliac arteries. The internal iliac artery (also called the hypogastric artery) is important in providing a supply or blood to the pelvic region, genital organs, and other areas and is most often not aneurysmal. The external iliac artery is commonly involved in the aneurysm and extends distally along an oftentimes very tortuous path to form the common femoral artery.

Surgical repair of an abdominal aortic aneurysm is an extensive procedure associated with a high incidence of morbidity and mortality and requiring many days of hospital stay. Older patients are often not capable of withstanding the trauma associated with this surgery. Repair of abdominal aortic aneurysm intraluminally through access from the common femoral artery can provide the patient with an alternate method of treatment for abdominal aortic aneurysm without the accompanying surgical trauma and long hospital stay. Placement of an intraluminal stent-graft can be performed by an interventionalist using a minimal surgical cutdown to an ipsilateral common femoral artery for access of the device to the arterial system of the body. Generally an additional access site is placed percutaneously in the contralateral common femoral artery. It is often preferred to place at least one more access site cranial to the abdominal aortic aneurysm generally through an axillary artery or other artery of the arm. Spiral computed tomography, duel-plane angiography, intravascular ultrasound, magnetic resonance imaging, and fluoroscopy provide some of the diagnostic techniques used to determine the position, diameter, and length of the aneurysm such that an appropriate intraluminal prosthesis can be selected for intraluminal implantation. Placement of the intraluminal stent-graft requires that a leak tight seal be made between the stent-graft and the aorta and between the stent-graft and each of the iliac or femoral arteries if they are involved in the aneurysm. Failure to provide such a leak tight seal will allow blood flow at arterial pressure to access the space between the stent-graft and the outpouched aorta. Continued exposure to arterial blood pressure can result in further expansion of the aneurysmal sac and could lead to sac rupture. Several intraluminal stent-grafts have been described for use in treatment of abdominal aortic aneurysms.

Barone describes in U.S. Pat. No. 5,578,072 an apparatus for repairing an abdominal aortic aneurysm. He describes a one-piece bifurcated aortic graft having a balloon expandable stent at one end to secure main trunk of the stent-graft to the aorta caudal to the renal arteries. The one-piece aortic graft has additional expandable stents positioned at the end of each leg of the bifurcated graft to secure the stent-graft to the iliac arteries. This design requires that the length of the main trunk and length of each limb be established prior to implantation using the diagnostic techniques described earlier. Due to the tortuous nature of the blood flow pathway, it is impossible to properly size the length of the graft using these diagnostic techniques prior to implatation. If the stent-graft is sized too short, then a portion of the aneurysm may be left unprotected. If the stent-graft is sized too long for example, then the blood flow to one or both of the internal iliac arteries may be compromised. The method of securing the main trunk of the stent-graft to the aorta caudal to the renal arteries described by Barone is also inadequate in many situations. A balloon expandable stent placed caudal to the renal vessels will very often be located within thrombus and will not have the strength or stability of the aortic vessel wall to support the stent or the stent-graft from migration caudally. Barone teaches that a securing means that is expanded outwardly over an axial length will hold the cranial end of the main trunk in position near the renal vessels. Barone also does not describe any means to prevent the stent-graft from being kinked or crushed as it travels through the thrombus laden blood flow pathway within the aortic aneurysm. Forces imposed upon the stent-graft due to the surrounding thrombus or thrombus organization could easily cause the stent-graft of Barone to become kinked or stenotic thereby impairing its performance. Barone discusses the need to place a stent proximal to the renal arteries for the case that the abdominal aortic aneurysm extends through the aortic region containing the renal arteries. He does not provide a suitable stent-graft for treating infrarenal aortic aneurysm with abrupt wall distension just distal to the renal vessels.

Parodi describes in U.S. Pat. No. 5,591,229 stent-graft devices that are similar to those described by Barone in the above patent. Additionally, Parodi describes a stent-graft for treatment of an abdominal aortic aneurysm that does not extend into the iliac region. This straight tubular stent-graft has a balloon expandable stent positioned at its cranial end for placement into the proximal neck of the aorta distal to the renal vessels. A balloon expandable malleable wire is placed at the distal end of the stent-graft to provide contact of the stent-graft with the aortic wall in the distal neck of the aorta. This stent-graft has a similar problem associated with estimating the graft length due to the tortuosity associated with the blood flow pathway through the thrombus laden aortic aneurysm. The other problem sited with the device described by Barone are similarly shared by the Parodi device.

Chuter describes in U.S. Pat. No. 5,693,084 a one-piece bifurcated stent-graft for treatment of abdominal aortic aneurysm having self expanding springs positioned at the proximal end of the main body and at the distal ends of each limb of the graft. The springs expand radially upon release to conform the ends of the stent-graft to the lumen of the aorta. This stent-graft suffers the same problem described for Barone in determining the length of the stent-graft prior to implant. Further, the stent-graft material is not supported throughout the entire stent-graft length thereby providing ample opportunity for stent-graft kinking and deformation within the aneurysm. Chuter has positioned six barbs that extend outward from the self expanding spring on the proximal end of the stent-graft. Due to the geometry of the springs, the positioning of the barbs into aortic wall rather than into the thrombus contained within the aneurysmal wall is not very precise. This can lead to stent-graft migration after a period of time post implant. Other problems associated with the Barone device similarly apply to the Chuter device.

McDonald describes in U.S. Pat. No. 5,676,697 a two-piece component bifurcated intraluminal stent-graft for treatment of abdominal aortic aneurysm. The first stent-graft component is a flexible tubular member with a side cut near the middle of the tubular member that opens up via a self expanding stent to form a waist region that is seated in the aorto-iliac bifurcation region. Two legs of the first stent-graft component are seated into each iliac artery using stents attached to the distal end of each leg. A second stent-graft component is introduced through one leg of the first component and allowed to self expand in the main trunk of the aorta and form a seal with the waist of the first component. The proximal end of the second component extends proximally within the aorta and makes a seal as it expands outwardly against the flow lumen. This device would have difficulty with positioning the proximal end of the second component within the proximal neck of the aorta. Extreme tortuosity found in the flow lumen of the aortic aneurysm would not allow this device to conform to its shape and would not allow a tight seal to be formed between the proximal end of the second component and the aorta. Difficulty in determining the appropriate length for each of the two components would limit the usefulness of this device.

Glastra describes in U.S. Pat. No. 5,632,763 a bifurcated component stent-graft assembly for treatment of abdominal aortic aneurysm. The assembly consists of a base stent-graft that is introduced into the main trunk of the aorta from an intraluminal approach. The base stent-graft has a generally cylindrical shape with a conical region located at the distal end. Two secondary cylindrical stents are introduced through two branching arteries, one in each leg and are seated in the conical region of the base stent-graft. This assembly has several potential problems associated with it. Determining the appropriate length of the base stent-graft and each of the secondary stent-grafts cannot be accurately performed considering that all of the arteries involved can be very tortuous and difficult to estimate in length. The seal that is required at the junction of the main to the secondary stent-grafts may have a tendency for leakage due to the geometry of that junction. Glastra describes two cylindrically shaped secondary stent-grafts that are placed adjacent to each other and are required to expand out and seal against a larger cylindrical base stent-graft; this seal would be difficult to form and maintain. Glastra does not address specific means for attachment of the proximal end of the base stent-graft to the aorta.

Marcade describes in U.S. Pat. No. 5,683,449 a modular system for forming a bifurcated stent-graft for use in treating abdominal aortic aneurysm. The system includes a number of components that are delivered intraluminally to the site of the aneurysm and brought into contact with each other within the aneurysmal space. The primary graft member has a proximal stent at one end and has an decreasing diameter as the stent-graft extends towards its distal end. The base member has a Y-shaped structure with a proximal end that contacts the distal end of the primary graft member. The base member also forms two branches on its distal end, each branch being brought into contact with a tubular graft member that extends into an iliac artery. This modular system still requires that each individual component be sized for length and diameter in order to fit the vast differences found between abdominal aortic aneurysm patients. Each junction between individual components is also a site for potential leakage of blood into the space between the stent-graft and the native arterial conduit. Marcade shows approximately five barbs positioned on the proximal stent. Due to the geometry of the stent it is not possible to obtain precise positioning of the barbs into the aortic wall tissue to ensure long term anchoring that would prevent stent-graft migration and maintain an adequate leak tight seal.

Vorwerk describes in U.S. Pat. No. 5,562,724 describes a component bifurcated device for treating abdominal aortic aneurysm consisting of a main body and two tubular stent-grafts. The main body has an open proximal end and a distal bag-shaped end with two outlet openings formed in it. Two tubular stent-graft legs can be introduced through the iliac arteries of the patient and attached to the two outlet openings of the main body. Sizing the appropriate length of the main body in addition to the two stent-graft legs is difficult due to the tortuosity found in the blood flow pathway of the aorta and iliac arteries. Leakage at the attachment site of the stent-graft legs to the main body also is a major concern.

Palmaz describes in U.S. Pat. No. 5,683,453 and Marin in U.S. Pat. No. 5,507,769 two tubular stent-grafts that travel in parallel from the infrarenal aortic neck to each iliac artery. Each stent-graft has a stent positioned at each end of the tube to form a seal with the native artery. This system would also have difficulty in determining the appropriate length of the stent-graft due to vessel tortuosity. In addition, this system requires that the two proximal stents deform against each other and with the proximal neck of the aorta to form a leak tight seal; it is not likely that an appropriate seal or attachment to the proximal aortic neck would be made. Extending a plurality of stent tubular members further within the length of stent-graft create a stent-graft that is too stiff to pass through a tortuous iliac artery to reach the site of the abdominal aortic aneurysm.

Egoda describes in U.S. Pat. No. 5,591,228 a method of introducing a bifurcated stent-graft for abdominal aortic aneurysm treatment using three access points into the arterial vasculature. As with other intraluminal stent-graft procedures, two access sites involve the common femoral arteries. Egoda describes a third access site made in the left subclavian artery through which the stent-graft can be introduced. This method may allow better control over both ends of the stent-graft during implantation. The length of the stent-graft must still be determined prior to implant and estimation of the length of the blood flow pathway is difficult to determine using standard diagnostic equipment due to the tortuosity of the vessels involved in the aneurysmal dilation.

A one-piece endovascular graft is described by Piplani in U.S. Pat. No. 5,824,039 for treating a bifurcated abdominal aortic aneurysm lesion. This device has springs located at inlet and outlet ends to hold the graft in place. The springs also have barbs attached. The springs have a large zig zag appearance similar to other prior art attachment means and the barbs are not well protected from inappropriate snagging prior to deployment of the endovascular graft.

Modular intraluminal prosthesis are described by Lauterjung in U.S. Pat. No. 5,824,036 and by Fogarty in U.S. Pat. No. 5,824,037. Lauterjung describes a composite system using a magnetic tipped guidewire to assist in the assembly of the prosthesis and employs a stent at the ends of the prosthesis and elsewhere. Fogarty describes a self-expanding or resilient frame with a plastically deformable liner over the frame limiting the resilient expansion. Each of these two composite or modular systems shares similar problems to the composite systems described earlier, including the potential for leakage at the junction sites as well as leakage at the junction of the prosthesis with the vessel lumen.

SUMMARY OF THE INVENTION

The present vascular implant overcomes the disadvantages of prior art stent-grafts, attachment means, and vascular tubular members used for endoprosthetic aortic or arterial aneruysmal repair, or for arterial bypass or other arterial or venous reconstruction. The vascular tubular member of the present invention includes a vascular tubular member that can be intravascularly delivered to the site of vessel injury such as an aortic aneurysm where it is deployed in a manner that will exclude the vessel injury or aneurysm. This intravascular tubular member conveys blood flow from a proximal arterial region that is located proximal to an arterial lesion or aneurysm to one or more distal arterial vessels. One embodiment of the present invention is an intravascular tubular member having a folded tubular section that allows the length of the graft to be adjusted during the time of deployment of the intravascular tubular member. This intravascular tubular member allows the physician to deploy the exact correct length of tubular member for each individual patient and allows the intravascular tubular member to fit different patients that require intravascular tubular members of different lengths. The intravascular tubular member further can have a proximal attachment anchor positioned at its proximal end that allows the proximal end to be positioned accurately in the aortic wall tissue adjacent and distal to the renal arteries. The attachment anchor of the present invention is an attachment anchor that does not undergo significant length change during deployment thereby allowing the position of the attachment anchor within the aortic aneurysm to be accurately determined. The intravascular tubular member can also be anchored to the aorta proximal to the renal vessels for the condition that the aortic aneurysm is abruptly distended adjacent and distal to the renal arteries. The attachment anchor can include barbs to more firmly anchor the intravascular tubular member to the vessel wall. The intravascular tubular member can also include a distal attachment anchor to anchor the distal end of the intravascular tubular member to one or more distal vessels.

The structure of the vascular tubular member includes a woven structure formed from either multifilament polymeric strands or a composite of multifilament polymeric strands woven along with metal strands. This structure of the vascular tubular member wall is such that it can be supported in both the axial and circumferential directions with metal strands. The circumferentially oriented metal strands provide anti-kink and anti-crush characteristics to the vascular tubular member. The axially oriented metal strands can provide the vascular tubular member with axial compression resistance and ensure that the folded tubular section is maintained in a straight tubular form. These characteristics will provide the tubular sections of the present invention with a more stable pathway for the intravascular tubular member through the thrombus found within a typical abdominal aortic aneurysm. The one-piece construction of the intravascular tubular member of this invention does not allow for leakage at modular junctions such as that which can occur with prior art component or modular intravascular tubular member systems described earlier. One primary application for the intravascular tubular member of the present invention is in the treatment of abdominal aortic aneurysms. Although the description of the invention in this disclosure is directed toward treatment of abdominal aortic aneurysm, it is understood that the present invention is intended for treatment of other vascular lesions both arterial and venous including vessel bypass, traumatic injury, aneurysmal repair, and other lesions.

The intravascular tubular member of the present invention can be formed from a single straight tube having a proximal end and a distal end. As the intravascular tubular member is being inserted into the patient, it has a smaller nondeployed diameter and a shorter nondeployed length. After the intravascular tubular member is fully deployed, it has a larger deployed diameter and a longer deployed axial length. The straight intravascular folded tubular member is comprised of three sections, a proximal tubular section that includes a proximal tube with an open inlet end, a folded tubular section which includes a folded tube that is able to extend in axial length, and a distal tubular section that includes a distal tube with an open distal end. The proximal, folded, and distal sections are of a length that allows ease of insertion and implantation of the intravascular folded tubular member to vascular application. Alternately, the distal section can be very short and may only include the outlet end of the folded section. In the folded tubular section the folded tube is folded back and forth upon itself generating two circumferential fold lines and forming the folded tubular section of the intravascular folded tubular member. In the folded tubular section a portion of the outer surface of the intravascular folded tubular member is in direct contact with another portion of the outer surface, and a portion of the inner surface is in direct contact with another portion of the inner surface of the intravascular folded tubular member. The nondeployed axial length of the intravascular folded tubular member is shorter than the deployed axial length; the folded tubular section length will shorten as the deployed axial length of the intravascular folded tubular member gets longer. The folded tubular section is positioned distal to the proximal tubular section which can have a proximal attachment anchor attached at the proximal end. Distal to the folded tubular section is a distal tubular section that can have a distal attachment anchor attached at or near the distal end.

The intravascular folded tubular member can be delivered intraluminally by compressing the intravascular folded tubular member radially to form a compressed conformation that can be delivered to the abdominal aorta or other vessel through a sheath or other delivery means placed in a common femoral artery. Upon delivery of the intravascular folded tubular member into the aorta, the intravascular folded tubular member expands to its deployed diameter. For a self-expanding intravascular folded tubular member the deployed diameter is between the nondeployed diameter and an equilibrium diameter that the intravascular folded tubular member would attain if fully deployed without a restricting force applied from the vessel with which it is in contact. The deployed diameter is generally approximately equal to the diameter of the native vessel that is being repaired. The intravascular folded tubular member can also be expanded by a catheter containing a mechanical expansion means such as a balloon. A proximal attachment anchor can be deployed to form an attachment that seals the proximal end of the intravascular folded tubular member to the aortic wall adjacent and distal to the renal vessels. The proximal attachment anchor does not undergo a significant axial length change during its deployment and as a result can be placed accurately in a position adjacent to the renal vessels for a more reliable attachment to the aortic wall. This reduces any chance for distal migration of the intravascular folded tubular member over time. Attachment of the intravascular folded tubular member to the attachment anchor of the present invention occurs at significantly more sites than is found with other prior art abdominal aortic aneurysm intravascular folded tubular members with zig-zag wire attachment means. The increased number of attachment sites provides a better seal of the attachment anchor and the intravascular folded tubular member to the aortic wall. Barbs can be located on the attachment anchor of the present invention such that they are folded inward during insertion of the device and extend outwards upon deployment of the intravascular folded tubular member.

The distal end of the intravascular folded tubular member is then positioned at an appropriate location within the abdominal aorta, typically at the site of the distal aortic neck if such a neck exists. It is common to position the distal end of the intravascular folded tubular member into an iliac or femoral artery. As the distal end of the intravascular folded tubular member is being positioned, a portion of the folded tubular section will be unfolded allowing intravascular folded tubular member material contained within the folded tubular section to unfold thereby allowing the intravascular folded tubular member to lengthen to an appropriate deployed axial length that is required to isolate an aneurysm, bypass an artery, or repair in some other way an artery for that individual patient. The length of the tortuous blood flow pathway through the thrombus in the aortic aneurysm can be accurately and appropriately sized in situ when using the intravascular folded tubular member of this invention.

The material of construction for the wall of the vascular tubular member with a folded tubular section as described previously can be any material that is used in vascular grafts or a combination of materials used in vascular grafts and endovascular stents. Typical vascular graft materials include expanded polytetrafluoroethylene, polyester, silicone, carbon, polyurethanes, biological tissues, silk, composite materials, and others. Some of these materials can be formed into a tube through processing methods that include paste extrusion, electrostatic spinning, spinning without electrostatics, salt leaching, and others. Additionally, the vascular tubular member of this invention which includes the intravascular folded tubular member can be formed from fibers of the materials listed above that have been woven, braided, knitted, or formed into a tubular member. The fibers can preferably be formed of many filaments of a very small diameter and which are wound to form a multifilament fiber or strand Such a multifilament fiber can offer an enhanced sealing capability at the crossover points of a woven or braided fabric vascular tubular member material. It is therefore preferred that a woven or braided tubular member be formed with multifilament yarn or multifilament fibers to reduce blood leakage at crossover points of polymer strand with polymer strand or polymer strand with metallic strand. Typical materials used in the construction of endovascular grafts and stents include Nitinol, stainless steel, tantalum, titanium, platinum, and other metals, metal alloys, and other suitable materials of large elastic modulus. Strands of these and other materials can be interwoven or interbraided with the polymeric materials used in vascular grafts to form a composite wall structure of the present invention.

A tubular double weaving method can be applied to the construction of the wall of the present vascular tubular member. A construction that involves weaving both polymeric fiber and metallic strands in both longitudinal and circumferential directions can encounter crossover points of one metal strand with another. At such crossover points, leakage or seepage of blood can occur from inside the vascular tubular member to the space outside the vascular tubular member. To reduce or eliminate small pores at the crossover points a tubular double weave is preferred when a metal strand is woven on both the axial and circumferential directions. With this technique a metal strand in one direction is brought out of the surface or the plane of the weave at the crossover point. The woven polymeric material without the metal strand forms a continuous plane of weave beneath the crossover point with good sealing due to the multifilament strands. Thus, leakage cannot occur at metallic strand to metallic strand crossover points due to the elimination of the pores or leakage sites due to the double weaving.

The attachment anchor that can be positioned at the proximal and distal ends of the intravascular tubular member can be of the self-expanding design or it can require an internal force application to force it outward, such as that provided by a balloon expandable means. The attachment anchor can be used with an intravascular tubular member that has a folded tubular section or it can be used with any other tubular member found in the prior art or that is being used for intravascular treatment of vessel injury. The metal strands that can be interwoven or interbraided into the wall structure of the intravascular tubular member can preferably be of a spring nature such that they self expand from the compressed state to form the deployed diameter; the metal wires can also undergo a plastic deformation as the intravascular tubular member undergoes expansion from its compressed conformation to its deployed diameter upon exposure to forces imposed by a balloon catheter placed within its lumen.

One preferred embodiment the intravascular folded tubular member of the present invention is a one-piece bifurcated tubular structure or means that is used in the treatment of abdominal aortic aneurysm. The intravascular folded tubular member has a proximal tubular section with a single open inlet end and a bifurcated main trunk that provides passage into two proximal leg tubes. Each proximal leg tube is joined to a folded tubular section, and each folded tubular section is joined to a distal section. The proximal tubular section has a deployed diameter approximately equal to the diameter of the aorta at the aortic proximal neck immediately adjacent and distal to the renal vessels. The two proximal leg tubes can have a diameter approximately equal to the diameter of the iliac artery or femoral artery into which they are to extend. The proximal end of the main trunk can have an attachment anchor attached to provide accurate attachment of the open proximal end within the proximal neck of the aorta. The attachment anchor can include barbs or hooks that provide a more definite attachment of the intravascular folded tubular member to the wall of the aorta to prevent migration, provide a leak-tight seal, and help support the aorta from further distension at that location. The folded tubular sections each have two circumferential fold lines and are folded back and forth in a manner similar to that described earlier for the straight intravascular folded tubular member. Each folded tubular section has a portion of the outer surface of the intravascular folded tubular member in direct contact with a another portion of the outer surface, and it has a portion of the inner surface of the intravascular folded tubular member in direct contact with another portion of the inner surface. The folded tubular sections allow the bifurcated folded tubular member to assume a shorter non-deployed axial length during the delivery of the intravascular folded tubular member than its deployed axial length. Each folded tubular section is attached to a distal tubular section with an open distal end. The open distal end of each distal tubular section can have an attachment anchor attached to form a precise and leak-free attachment to the iliac or femoral arteries.

A preferred bifurcated intravascular tubular structure or member of the present invention consists of a proximal tubular section or means with a proximal attachment anchor attached to its inlet end, two folded tubular sections attached to the proximal tubular section, two distal tubular sections attached to the two folded tubular sections, and two distal attachment anchor attached to each open distal end. The bifurcated intravascular tubular means is generally introduced into the aneurysmal abdominal aorta intraluminally through a surgical cut down or percutaneous access made into one common femoral artery. A sheath or other introducing means provides suitable access for the intravascular folded tubular member into the blood flow pathway of the aorta. Attachment of the proximal attachment anchor to the aorta is generally made adjacent and distal to the renal vessels. This attachment anchor can be a self-expanding attachment anchor or a balloon expandable attachment anchor. The attachment anchor is preferably short in axial length, has minimal length change upon deployment to allow more accurate placement, and can have barbs extending outward upon deployment to provide better attachment of the intravascular folded tubular member to the vessel wall. The two distal sections of the bifurcated tubular means are generally positioned in the right and left iliac arteries, respectively. The distal ends of the two distal section along with the two distal attachment anchor are positioned at an appropriate location within the iliac or femoral arteries so as to properly exclude the abdominal aortic aneurysm and any additional iliac or femoral aneurysm. As these distal ends are being positioned, the two folded tubular sections will unfold an appropriate amount to allow the deployed axial length of the bifurcated tubular means to be precisely sized to the individual patient. Variations between patients can be accommodated with the folded tubular sections as well as inaccuracies between angiographic length estimations of the aortic aneurysm and the actual length of the aneurysm.

Distal attachment anchor which are attached to the distal ends of the distal tubular sections can be deployed to form a secure and leak-tight attachment to each iliac artery or femoral artery. The wall structure of the bifurcated folded tubular member is similar to that described for the single straight tube. A woven or braided composite of a polymeric multifilament fiber interwoven or interbraided with a metal fiber can be formed into a one-piece Y-shaped tubular means of the present invention for treatment of abdominal aortic aneurysm with a bifurcated intravascular folded tubular member. Tubular double weaving can be used to reduce leakage sites at crossover points of the metal fibers or strands.

Another embodiment for the abdominal aortic aneurysm intravascular folded tubular member of the present invention has a proximal section with a bifurcated main trunk having an open inlet end and joined to two proximal leg tubes. In this embodiment only one proximal leg tube is joined to a folded section. The other proximal leg tube has an open distal end that is adapted to accommodate a cylindrically shaped intravascular folded tubular member that can be inserted into the open distal end and sealingly engaged with the proximal leg tube using an engagement means positioned on the cylindrically shaped intravascular folded tubular member. This sealing engagement on one side of the proximal section is similar to the modular systems shown for treatment of abdominal aortic aneurysm in the prior art. This embodiment allows one part of the bifurcated intravascular folded tubular member to be unfolded and extended in length in a manner similar to previous embodiments described in this invention, and the other part of the bifurcated intravascular folded tubular member to be extended by adding additional intravascular folded tubular member segments in a modular fashion as described in the prior art.

The folded tubular section for the straight or bifurcated intravascular folded tubular member of the present invention has three layers of intravascular folded tubular member wall that lie in direct contact with or in apposition with each other, an outer wall, a center wall, and an inner wall. These three layers extend from a proximal end to a distal end of the folded tubular section. The length of the folded tubular section becomes shorter as the intravascular folded tubular member becomes extended axially during the deployment of the intravascular folded tubular member. In the folded tubular section a portion of the outer surface of the tubular means is in direct contact with the outer surface of another portion of the tubular means, and a portion of the inner surface is in direct contact with another portion of the inner surface. As the folded tubular section becomes unfolded during the deployment it is desirable for the center wall to not wrinkle during the unfolding process. Such wrinkling can occur if the inner and outer wall slide with respect to the center wall rather than unfolding smoothly from the proximal or distal ends of the folded section. One way of significantly reducing or preventing this wrinkling from occurring is to apply a bonding agent or adhesive to the outside surfaces of the folded tubular section. This adhesive is preferably one that resists the shearing motion that is associated with the relative sliding motion that can cause wrinkles to form. The adhesive should also be capable of undergoing fracture due to exposure to extensional or tension stresses that are generated during the desirable unfolding from the proximal or distal ends of the folded section.

Following deployment of the intravascular folded tubular member of the present invention, it may be desirable to ensure that further unfolding of the folded region does not occur. one or more securing pins or other securing means can be placed through all three walls of the folded tubular section to prevent any further unfolding that may occur after implantation.

The vascular implant of the present invention includes an attachment anchor that can be attached to the inlet or outlet ends of the intravascular tubular member of this invention, the intravascular folded tubular member of this invention, or of any other prior art tubular means used for intravascular implant. The attachment anchor is formed from a metal tube using machining methods that include mechanical, laser, chemical, electrochemical, or other machining methods to form a pattern of nodes and struts. The nodes and struts are intended to provide independent adjustment of expansion force provided by the attachment anchor uniformly outward against the vessel wall due to its expansion deformation and crush elastic force provided by the attachment anchor against external forces that tend to cause the attachment anchor to form an oval shape associated with crush deformation. The independent adjustment of expansion forces due to deformation in the cylindrical surface of the attachment anchor from the crush force which produces a deformation to a smaller radius of curvature in the radial direction of the attachment anchor such as forming an oval shape, allows the attachment anchor of the present invention to have a shorter axial length for a better focal line attachment to the vessel wall.

The nodes are formed of at least one hinge and two transition regions. The transition regions are each attached to a strut. A series of struts and nodes are positioned such that the struts are aligned adjacent to each other forming a single folded ring of struts and nodes with a generally cylindrical shape in a nondeployed state with a smaller nondeployed diameter. The attachment anchor of the present invention can be a balloon-expandable or a self-expanding attachment anchor. During expansion of the balloon-expandable attachment anchor, an expanding means such as a balloon dilatation catheter can be inserted along a central axis of the attachment anchor and expanded. The hinges undergo a plastic expansion deformation as the attachment anchor is expanded to a deployed state with a larger deployed diameter. In a deployed state the hinge exerts an outward expansion force through the struts which in turn push against the blood vessel to hold the vessel outwards and hold the intravascular tubular member against the vessel wall without leakage. A self-expandable attachment anchor is held, for example, within a deployment sheath at a smaller nondeployed diameter for delivery into the vasculature. The hinge is deformed elastically in its nondeployed state and exerts an outward force against the sheath. Upon release from the sheath the self-expandable attachment anchor expands outward until it comes into contact with the vessel wall or the intravascular tubular member. The hinge exerts an outward elastic expansion force through the struts which in turn push against the blood vessel to hold the vessel outwards and hold the intravascular tubular member against the vessel wall without leakage.

Hinges of the present invention have a larger radial dimension than the struts and a thinner width than the struts; the hinge length further having a major role in establishing the outward expansion forces generated by the hinges. The hinge length can be short to focus the expansion deformation of the hinge into a smaller area. For a balloon-expandable attachment anchor the smaller hinge length increases the percentage of metal in the hinge that undergoes a plastic deformation. The result is less rebound of the attachment anchor back towards its nondeployed state following balloon expansion. For a self-expandable attachment anchor the smaller hinge length will generate a greater expansion force for a smaller localized expansion deformation of the hinge. A longer hinge for a self-expandable attachment anchor provides a smaller drop-off of outward expansion force than a smaller hinge length for a specific deployment angle of the attachment anchor. The larger hinge length allows a similar outward force to be applied to the blood vessel wall for a wider range of vessel diameters for the same attachment anchor. For a balloon-expandable attachment anchor an increase in hinge width causes a greater amount of plastic deformation and provides a larger expansion force generated by the hinge than a smaller hinge width. For a self-expandable attachment anchor an increase in hinge width causes a larger outward expansion elastic force to be exerted against the vessel wall. A hinge radial dimension larger than the strut radial dimension produces a larger outward expansion force for both the balloon-expandable or self-expandable attachment anchor. The large hinge radial dimension does not allow the hinge to bend in a radial direction to form an oval such as would like to occur during exposure to a crush deformation.

The struts of the attachment anchor have a larger width than the hinge width such that the hinges can transfer their outward force through the struts to the vessel wall without allowing any bending of the struts in the cylindrical surface of the attachment anchor. The struts have a small radial dimension in comparison to the hinge radial dimension to allow the struts to deform elastically to a smaller radius of curvature in the radial direction of the attachment anchor upon exposure to a crush deformation. The strut width allows the struts to deform elastically at any prescribed crush force during exposure to a crush deformation. A longer strut length allows a greater percentage of the perimeter of the attachment anchor to be associated with the struts in comparison to the hinges or nodes. The longer struts provide the attachment anchor with an increased flexibility in the radial direction when exposed to a crush deformation. Conversely, a shorter strut provides the attachment anchor with a greater stiffness in the crush deformation mode with other attachment anchor dimensions remaining the same. The greater stiffness associated with an attachment anchor with such a shorter length strut allows the strut to be formed with a thinner radial dimension or smaller width and still have the same flexibility in crush deformation as a longer strut.

The attachment anchor of the present invention can be formed out of a higher modulus metal that other attachment devices. Other prior art attachment devices cannot be formed of the highest modulus metal because their expansion force cannot be changed without also affecting their crush force. With the present attachment anchor the outward expansion force can be designed independently from the crush force provided by the attachment anchor. The present attachment anchor can be formed such that it is short in axial length in order to provide a more focused line of attachment to the vessel wall. Short stents formed with prior art designs can be designed to provide an appropriate outward expansion force, however this prior art stent would be too stiff or too flexible in a crush deformation and would be without the ability to adjust the crush deformation force with respect to the outward expansion force. The present attachment anchor can be designed to provide both an appropriate expansion force and an appropriate crush force. The hinge of the present attachment anchor can also provide more expansion force than other prior art attachment devices due to the use of higher modulus metal and due to the dimensions chosen for the hinge width, length, and radial dimension. The close efficient packing of the struts parallel to each other provides the present attachment anchor with a large expansion ratio. The short strut length allows the strut width to be minimized while still maintaining an appropriate flexibility in crush deformation further maximizing the expansion ratio provided by the present attachment anchor. The strong expansion force provided by the hinge allows an appropriate expansion force to be generated such that the attachment anchor of this invention with short axial length can provide adequate expansion forces to hold a large vessel such as the aorta outward and prevent leakage between the intravascular tubular member and the vessel wall.

The vascular tubular member tubular wall structure can be formed from a composite of polymeric and metallic strands that are either woven or braided to provide different characteristics in its axial and circumferential directions. In a weaving process for tubular structures one or more strands have substantially a circumferential direction and another group of strands have generally an axial direction. In a weaving process the substantially circumferential strands generally have a gradual helical wind that is approximately perpendicular to the longitudinal axis of the vascular tubular member but the strands are continuous and actually form a helix. A polymeric strand can be made up of substantially straight filaments to form a straight polymeric strand. This straight polymeric strand can be woven in a circumferential direction forming a straight circumferential polymeric strand, or woven in an axial direction forming a straight axial polymeric strand. The polymeric strand can also undergo a thermal, mechanical, or chemical forming process that can heat set, mechanically set, or chemically deform the polymer filaments or the strand to have local bends, helical spirals, or curves in it. The local bends can be spaced very close together with spacing approximately equal to the diameter of the filament. Alternately, the local bends can be spaced apart further than the diameter of a fiber that is made up of many filaments. This curved polymeric strand will have the characteristic that it can stretch or elongate in its axial direction. This curved polymeric strand can be woven in a circumferential direction forming a curved circumferential polymeric strand, or it can be woven in an axial direction forming a curved axial polymeric strand. The straight or curved polymeric strand could be made from filaments of expanded polytretrafluoroethylene, from filaments of Dacron polyester, polyurethane, or from other suitable polymeric filaments.

The metallic strands that could be interwoven between the polymeric strands could be formed from a straight metallic strands, fibers, or wire formed from a metal such as Nitinol, stainless steel, titanium, tantalum, or other suitable metal or alloy. The wire can be round in cross section or it can be flat wire with a more rectangular cross section. It is preferable for one embodiment that the wire or metallic strand be of an elastic nature that does not exceed its elastic limit during the deployment of the vascular tubular member of the present invention. The wire in another embodiment could undergo plastic deformation during the deployment of the vascular tubular member. This straight metallic strand can be woven in the circumferential direction forming a straight circumferential metallic strand, or it can be woven in the axial direction forming a straight axial metallic strand. The metallic strand can also undergo a thermal, mechanical, or chemical forming process that can heat set, mechanically set, or chemically set the metallic strand to have local bends, helices, or curves in it. This curved metallic strand will have the characteristic that it can either stretch or compress in its overall axial direction. This curved metallic strand can be woven in a circumferential direction forming a curved circumferential metallic strand, or it can be woven in an axial direction forming a curved axial metallic strand. When woven in an axial direction, the curved wire is held under tension and is therefore held in a straight conformation. Upon release of the metallic strand, it forms the curved shape that was formed into the metallic strand prior to weaving. Circumferentially weaving a curved metallic strand requires additional effort due to the tortuous pathway followed by the strand during the weave.

The vascular tubular member wall structure of the present invention can include a woven tubular structure consisting of curved and straight, polymeric and metallic strands in the circumferential and axial directions. In one structure straight circumferential polymeric strands and one or more straight circumferential metallic strands are interwoven circumferentially and straight axial polymeric strands are woven axially. This structure is easy to form and has good hoop strength that will resist kinking due to the metallic component. The folded tubular section has good approximation between the inner, center, and outer walls since only the polymeric strands are extending axially allowing the circumferential fold lines to have a very small radius of curvature.

In another vascular tubular member wall structure additional straight axial metallic strands are interwoven with the straight axial polymeric strands of the structure just presented above. The additional straight axial metallic strands provide the folded tubular section with the characteristic that resists wrinkling in the folded tubular section. A tubular double weave can be used whenever two metal strands form a crossover point. One of the metal strands can be brought out of the plane of the weave prior to the crossover point and reenter the plane of the weave after the crossover point. The weaving plane is thus continuous without one of the metal strands and leakage at that crossover point will not occur. The additional straight axial metallic strands offer axial strength against compressive deformation but can cause the vascular tubular member to become stiff and more difficult to negotiate the tortuous turns of the iliac and femoral arteries.

In still another vascular tubular member wall structure a curved axial metallic strand is interwoven with straight axial polymeric strands in the vascular tubular member wall structure just presented above instead of straight axial metallic strands. The curved axial metallic strands provide a benefit to the folded tubular section to resist wrinkling during the unfolding process. The curved axial metallic strands also provide the vascular tubular member with good axial support against compressive forces generated by the thrombus and other physiological forces that can be placed upon the vascular tubular member. The curved axial metallic strands can compress elastically and thereby will not provide this vascular tubular member wall structure with good flexibility and will resist vascular tubular member kinking.

In yet another vascular tubular member wall structure straight circumferential polymeric strands are interwoven with one or more curved circumferential metallic strands in the circumferential direction and straight axial polymeric strands are interwoven with curved axial metallic strands in the axial direction. The curved circumferential metallic strands found in this structure allows the folded tubular section to unfold with greater ease due to their ability to elongate diametrically as, for example, one curved circumferential metallic strand located in an inner or outer wall passes adjacent to another curved circumferential metallic strand located in the center wall. The curves or bends in the curved circumferential metallic strands also allows the vascular tubular member to expand out uniformly to its deployed diameter which can be smaller than the equilibrium diameter of the vascular tubular member and provide uniform contact with the aortic wall.

In one more vascular tubular member wall structure curved circumferential polymeric strands are interwoven with one or more straight circumferential metallic strands in the circumferential direction and straight axial polymeric strands are interwoven with curved axial metallic strands in the axial direction. The curved circumferential polymeric strands provide an amount of circumferential stretch in the diametric direction. The other components of the weave restrict excessive circumferential stretch. This vascular tubular member structure can also be modified slightly to provide an additional characteristic. Near the proximal end of the tubular means the straight circumferential metallic strands can be eliminated thereby allowing the vascular tubular member to expand to a larger circumference. This circumferential expansion allows the vascular tubular member of the present invention to accommodate a reasonable tolerance in the estimated aortic neck diameter of a few millimeters. Similar circumferential accomodation also applies to the iliac artery.

Accomodation of the estimated aortic diameter with a vascular tubular member of a fixed non-flexible wall material with a maximum diameter can also be accomplished by ensuring that the vascular tubular member chosen can expand to a slightly larger diameter than the aortic diameter. Any embodiment of vascular tubular member wall structure of this disclosure can provide this characteristic. Any excess graft wall material will result in a wrinkle or fold if the perimeter of the tubular member is slightly larger than the perimeter of the aorta, for example. Provided that this wrinkle or fold is held tightly against the aortic wall by the proximal attachment anchor, leakage at the proximal site will not occur.

In yet one more vascular tubular member wall structure curved circumferential polymeric strands are interwoven with one or more curved circumferential metallic strands in one direction and the axial direction is the same as the vascular tubular member wall structure just described above. This structure offers the ability to stretch in the circumferential direction to a limited extent controlled by the amount of curvature provided to the circumferential strands. This vascular tubular member wall structure provides good anti-kink characteristics, good axial support against compression, good flexibility, and will accommodate a reasonable tolerance in the aortic neck diameter, and a tolerance on the iliac artery diameter.

In still one more vascular tubular member wall structure curved circumferential polymeric strands are interwoven with one or more curved circumferential metallic strands in one direction and the axial direction contains curved axial polymeric strands interwoven with curved axial metallic strands. This structure offers the ability to stretch in the circumferential and axial direction to a limited extent controlled by the amount of curvature provided to the circumferential and axial strands, respectively. This structure can extend in each direction throughout the entire tubular means. This vascular tubular member wall structure provides good anti-kink characteristics, good axial support against compression, good flexibility, and will accommodate a reasonable tolerance in the aortic neck diameter, and a tolerance on the iliac artery diameter.

All of the vascular tubular member wall structures presented in this disclosure can be formed with the axial metallic strands being directed with an augmented amount of helical turn. This is accomplished by taking metallic strand out of the weaving plane, stepping over to a new site that is displaced circumferentially, and inserting the metallic strand back into the plane of the weave. This stepping over process allows the axial metallic strand to assume a helical pathway along the axial direction of the vascular tubular member. This augmented amount of helical turn is in addition to the gradual helical turn naturally found in the axially oriented metallic strands due to their natural desire to orient perpendicular to the generally circumferential strands which also have a slight helical turn since they are wound in a continuous helix. The augmented helical turn of the metallic strands in the generally axial direction provides the vascular tubular member with an ability to bend without kinking even when straight metallic strands are used in the axial direction. Enhanced helical turn in the circumferential direction can also be accomplished by weaving two or more metallic strands into the circumferential weave. This can provide a steeper angel for the helical wind and provide additional axial flexibility without kinking.

In a preferred embodiment curved polymeric strands are wound in both the circumferential and axial direction to provide the vascular tubular member with a supple feel and good bending characteristics without kinking. For simplicity of manufacturing, one or more straight metallic strands are wound in the circumferential direction. Either curved metallic strands or straight metallic strands with the step over characteristic described above is used in the axial direction to provide the necessary compressive strength as well as provide good flexibility to the vascular tubular member. An entire straight or bifurcated vascular tubular member can be formed from a single contiguous woven material comprised of the polymeric and metallic strands described above. The vascular tubular member is woven without seam in its proximal, folded or distal section. For the bifurcated tubular member this is accomplished by splitting the number of strands that extend axially such that approximately half of those present in the main trunk extend down one proximal leg and half extend down the other proximal leg.

The vascular tubular member wall structure of the present invention can also be formed from a braiding process wherein straight polymeric and straight metallic strands are braided in a right hand spiral forming straight right spiral polymeric strands and straight right spiral metallic strands. These strands can be made with localized bends or curves in them as described earlier, and these strands can be braided into a right hand spiral to form curved right spiral polymeric strands and curved right spiral metallic strands. Similarly the straight and curved, polymeric and metallic strands can be braided into a left hand spiral.

In one vascular tubular member wall braided structure a straight right spiral polymeric strand and a straight right spiral metallic strand are interbraided together in one direction and a straight left spiral polymeric strand and a straight left spiral metallic strand are interbraided in the opposite direction. The braiding process provides some ability for this wall structure to accommodate reasonable tolerances in the estimation of the proximal aortic neck diameter in order to provide a good diametric fit between the vascular tubular member and the proximal aortic neck. The presence of the straight and curved metallic strands provides good axial and circumferential strength and stability against compression in the radial or axial direction in comparison to other prior art materials of construction.

In other vascular tubular member embodiments the braided structure can involve either curved metallic strands or curved polymeric strands. These curved metallic or polymeric strands will provide the vascular tubular member with a greater flexibility due to the ability of these metallic strands to compress as the vascular tubular member is exposed to a tortuous pathway.

It is understood that the woven and braided vascular tubular member wall structures presented are not intended to be complete and that other combinations of straight and curved, polymeric and metallic strands can be used with weaving or braiding with the associated characteristics and advantages that have been described or taught in this disclosure.

The bifurcated tubular member used in the treatment of abdominal aortic aneurysm described in this invention can have a proximal attachment anchor attached at the proximal end of the bifurcated main trunk. This attachment anchor provides a circumferential expansion and attachment to the aorta without significant change in axial length. This small axial length change allows this attachment anchor to be placed very near to the renal arteries with precision and reduce the likelihood for distal migration of the vascular tubular member. A greater number of barbs can be placed on the attachment anchor due to the geometry of the attachment anchor which has a short axial length and involves a hinge to supply the outward forces of the attachment anchor. The increased number of barbs will better hold the vascular tubular member to the aorta around the entire circumference.

The bifurcated folded tubular member of the present invention can also have a proximal attachment anchor that is displaced proximally from the proximal end of the main trunk. The displaced attachment anchor can be joined to the bifurcated main trunk by the metal strands that are woven axially or helically into the vascular tubular member or by the metal strands that are braided into the vascular tubular member. The displaced proximal attachment anchor is intended in one embodiment to provide attachment proximal to the renal arteries in a region of the aorta that is significantly proximal to the aneurysmal region of the aorta. Since many abdominal aortic aneurysms occur adjacent to the renal vessels and generally distal to the renal vessels, it is sometimes necessary to find a proximal attachment site that is proximal to the renal arteries. The displaced proximal attachment anchor will provide this attachment capability and prevent any distal migration of the intravascular tubular member. The small metallic strands that connect the displaced attachment anchor to the main trunk of the intravascular tubular member can cross over a renal artery without causing a significant thrombotic or occlusive effect. The metallic strands are positioned around the circumference to provide the main trunk with support from the attachment anchor along its entire circumference. Only a minimal number of metallic strands extend to the displaced attachment anchor in order to reduce the chances for thrombus formation at the entrances to the renal arteries. The number of strands can range from two to approximately sixteen. An additional proximal attachment anchor may be attached to the open proximal end of the main trunk in addition to the displaced attachment anchor to provide a tight leak-free seal with the aorta. The displaced attachment anchor can have barbs to enhance attachment to the aorta or it can be an attachment anchor without barbs as described earlier. The metallic strands can be attached to selected securing sites of the attachment anchor.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1A is a sectional view of a vascular tubular member implanted within an abdominal aortic aneurysm;

FIG. 2C is a cross sectional view of a straight intravascular folded tubular member near the inlet end in a nondeployed state;

FIG. 2D is a cross sectional view of a straight intravascular folded tubular member near the outlet end in a non-deployed state;

FIG. 3 is an isometric view of a straight intravascular folded tubular member in a nondeployed state with an attachment means at inlet and outlet ends;

FIG. 4C is a sectional view of a bifurcated intravascular folded tubular member in a nondeployed state within a delivery sheath near the inlet end;

FIG. 6 shows a sectional view of a folded tubular section in a nondeployed state with a bonding agent applied;

FIG. 9C is an enlarged detailed isometric view of a node of an attachment anchor with one hinge;

FIG. 9D is a perspective view of an attachment anchor with an oval attachment anchor surface;

FIG. 10B is an isometric view of an attachment anchor with two hinges per node in a deployed state;

FIG. 11B is an enlarged view of a portion of an attachment anchor with barbs in a nondeployed state;

FIG. 11C is an isometric view of an attachment anchor with barbs in a deployed state;

FIG. 12A is an isometric view of attachment anchors positioned at an inlet end and an outlet end of an intravascular tubular member;

FIG. 12B is an isometric view of attachment anchors positioned at an inlet end and an outlet end of a straight intravascular folded tubular member;

FIG. 12C is a partially sectioned view of attachment anchors positioned an inlet and outlet ends of a bifurcated intravascular folded tubular member;

FIG. 13D is a perspective view of a multifilament strand formed of filaments;

FIG. 23 is a bifurcated intravascular folded tubular member formed of a woven wall structure of multifilament polymeric strands interwoven along with monofilament metallic strands and having attachment anchors at the inlet and outlet ends.

DETAILED DESCRIPTION OF THE PREFERRED EMBODIMENTS

The present invention is a vascular implant intended for use to repair injured arteries or veins of the body. Such injuries can include aneurysms, stenoses, diffuse atherosclerosis, traumatic injury, or other injury that requires vascular repair or bypassing of the vessel. The vascular implant includes a vascular tubular member that conveys blood flow from a region of the repaired blood vessel proximal to the vessel injury to a region distal to the vessel injury. The vascular tubular member is primarily intended to be an intravascular tubular member for intravascular use using percutaneous access to the interior of the vessel or a minimal surgical cutdown to access a blood vessel either proximal or distal to the injured vessel that is to be repaired. The intravascular tubular member is entered into the proximal or distal blood vessel in a smaller diameter nondeployed conformation and is delivered to the site of the vessel injury where it enlarges to a larger diameter providing a passage for blood flow. An embodiment of the present invention is an intravascular folded tubular member that also enlarges in length following delivery to the site of vessel injury. One intravascular repair application that is in particular need of improvement is the repair of aortic aneurysms and most common the repair is one involving the abdominal aorta. The present invention is well suited to provide improvements in treating abdominal aortic aneurysms although it can also be used effectively in the repair of vessels throughout the body. The intravascular tubular member can include an attachment means attached to the proximal end or distal end of the intravascular tubular member to hold the intravascular tubular member firmly into contact with the wall of the injured blood vessel, prevent blood leakage at the proximal end or distal end, and prevent distal migration of the intravascular tubular member. The vascular implant of the present invention includes an attachment means that can be used with other prior art intravascular devices in addition to the intravascular tubular member of the present invention. The vascular tubular member includes not only the intravascular tubular member but also includes a surgical vascular graft that can be implanted surgically for repair of vascular injury. A vascular tubular member can include other tubular members that can have a generally tubular shape and have application in the repair of blood vessels. A woven and braided wall structure is presented that has application to both surgical vascular grafts as well as intravascular tubular members. It is understood that the present invention is not limited to the embodiments presented in this disclosure. The present invention can also be applied to other tubular organs of the body besides blood vessels. Such tubular organs include but are not limited to the intestines, esophagus, trachea, bile ducts, or other ducts of the body.

Figure 1B:
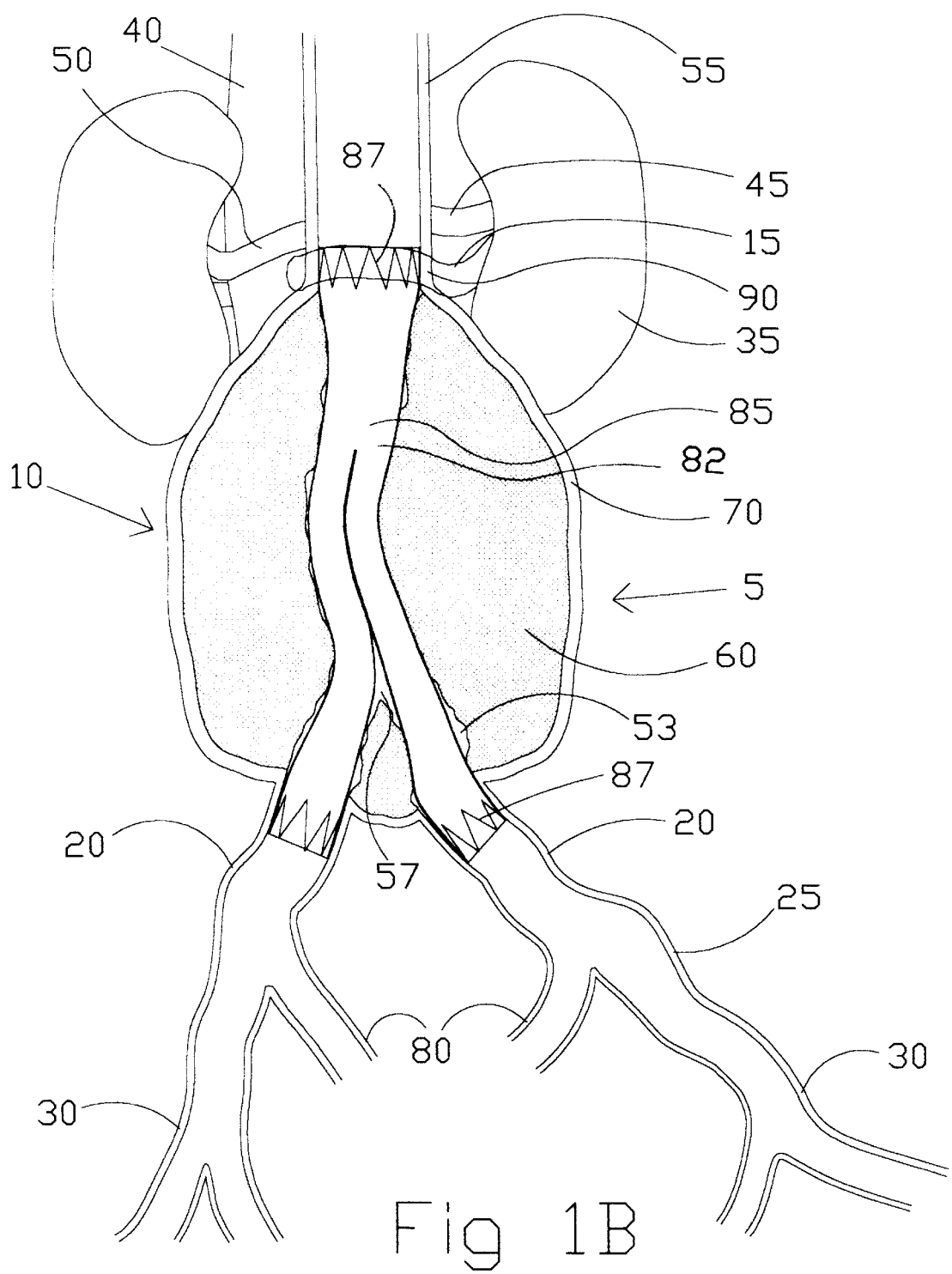
FIG. 1B is a sectional view of an intravascular tubular member implanted in a bifurcated abdominal aortic aneurysm.

FIGS. 1A and 1B show a side and frontal view of abdominal aortic aneurysms 5. The abdominal aortic aneurysm 5 can be used as an example of an arterial injury that can be treated with one or more embodiments of the present invention. Distension of the abdominal aorta 10 often extends from distal to the left renal vein 15 to the common iliac artery 20, external iliac artery 25, common femoral artery 30 or to more than one artery. The left renal vein 15 follows a path anterior to the aorta from the left kidney 35 to the inferior vena cava 40. The left renal vein 15 can provide some support to assist the abdominal aorta 10 from further distension proximal to the left renal artery 45 and right renal artery 50. A blood flow native lumen 53 extends from the suprarenal aorta 55 through the distended abdominal aorta 10, through the aorto-iliac bifurcation 57, and into each common iliac artery 20, each external iliac artery 25, and each common femoral artery 30. Thrombus 60 fills the cavity that exists between the blood flow native lumen 53 and the abdominal aortic wall 70. Lumbar arteries 75 located on the posterior side of the aorta and other arteries of the region can be occluded due to the presence of thrombus 60 or may remain patent depending upon the severity of the aneurysm. Each internal iliac artery 80 is often patent and should be allowed to remain patent when repairing an abdominal aortic aneurysm 5 if possible. An embodiment of the vascular implant 82 of the present invention is shown in FIG. 1A. The vascular implant 82 can include a vascular tubular member 83 that can be placed surgically within the native lumen or the vascular implant 82 can be an intravascular tubular member 85 that could have a bifurcation and could be placed percutaneously or with minimal surgical cutdown through a distal or other connecting vessel to reach the site of vessel injury as shown in FIG. 1B. In FIG. 1B the intravascular tubular member could have been inserted by a sheath placed in one of the common femoral arteries 30 and delivered to the abdominal aorta 10. The intravascular tubular member 85 can have an attachment means 87 attached to it to help provide a seal between the intravascular tubular member 85 and the native lumen 53 and help reduce migration of the intravascular tubular member 85. The vascular implant 82 can include the attachment means 87 which can be used with the intravascular tubular member 85 of the present invention or it can be used with other stent-graft devices. The intravascular tubular member 85 can be bifurcated with a bifurcation that extends from a proximal aortic neck 90 to each common iliac artery 20, common femoral artery 30, or other distal artery. The intravascular tubular member 85 can also have other configurations and embodiments which will be explained further in this disclosure.

Folded Tubular Members

A first embodiment of the present invention (see FIGS. 2A–2D) is a straight intravascular folded tubular member 95 for repairing an arterial lesion, an aneurysm, or other vascular injury found in a blood vessel. The straight intravascular folded tubular member 95 is intended to provide a blood flow passage 100 from a region of the blood vessel proximal to the vascular injury to a region of blood vessel distal to the vascular injury. The preferred method of deploying the straight intravascular folded tubular member 95 is to insert it through a percutaneous access through a sheath as is well known in the industry or with a small surgical cutdown to provide direct access to a blood vessel located either proximal or distal to the vascular injury.

Figure 2A:
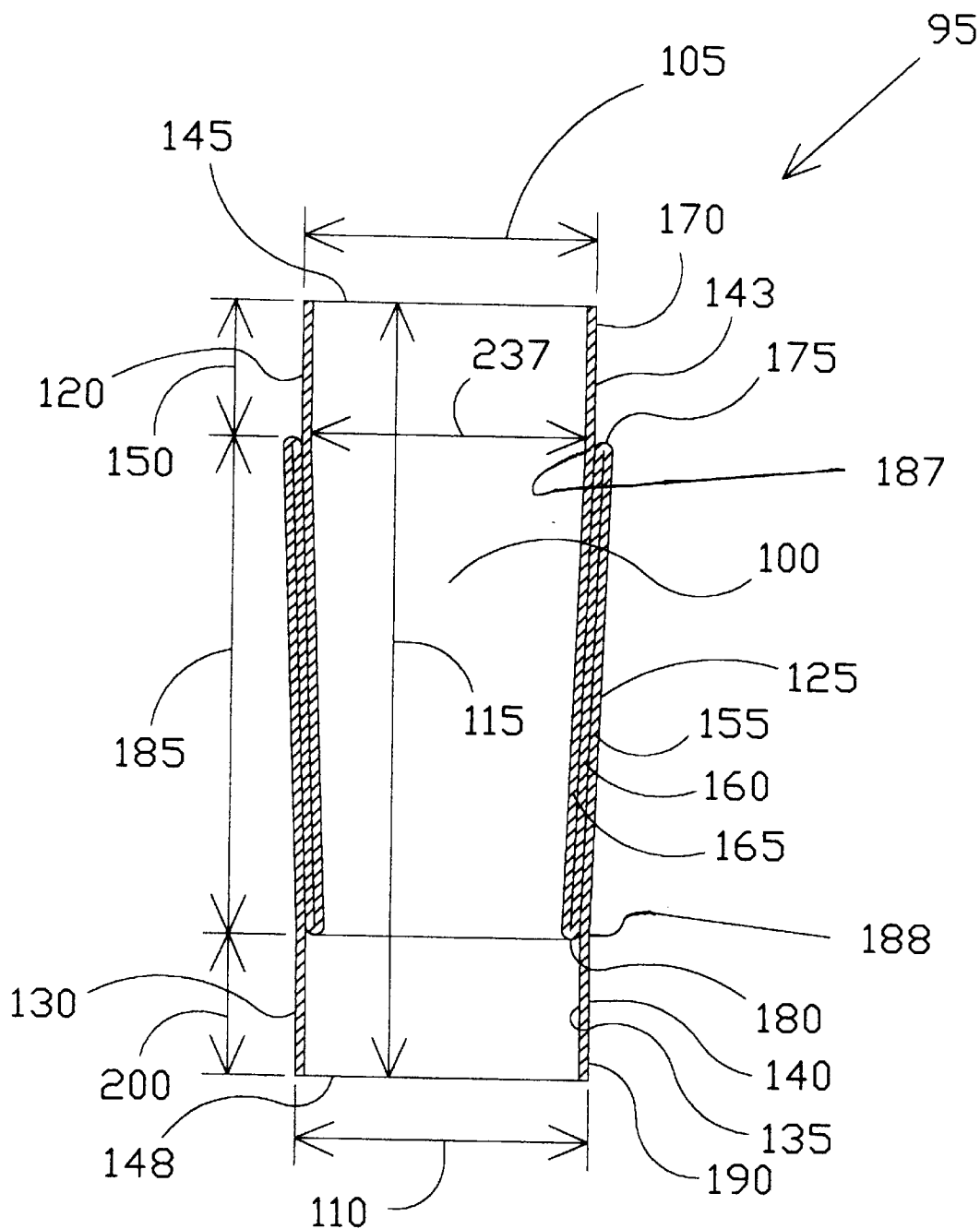
FIG. 2A is a sectional view of a straight intravascular folded tubular member in a partially deployed state.

FIG. 2A shows the straight intravascular folded tubular member 95 in a radially deployed state with a radially deployed inlet end diameter 105, a radially deployed outlet end diameter 110, and a straight nondeployed tubular member length 115. The straight intravascular folded tubular member 95 has a straight proximal tubular section 120, a folded tubular section 125, a distal tubular section 130, an inner surface 135 and an outer surface 140. The inner surface 135 and outer surface 140, and intravascular tubular member wall 143 each extend continuously from an inlet end 145 through the straight proximal tubular section 120, through the folded tubular section 125, and through the distal tubular section 130 to an outlet end 148 of the folded tubular section 125. The continuous intravascular tubular member wall 143 can have attachments between the straight proximal tubular section 120 and the folded tubular section 125 and between the folded tubular section 125 and the distal tubular section 130 although it is preferred to form the intravascular tubular member wall 143 with each of these sections joined contiguously from the same material without attachments between sections. The inner surface 135 of the straight proximal tubular section 120 and the distal tubular section 130 is a blood flow surface in contact with blood flow. A portion of the inner surface of the folded tubular section 125 is a blood flow surface in contact with blood flow. The straight proximal tubular section 120 has inlet end 145 that provides passage for blood flow into the straight proximal tubular section 120 and into the straight intravascular folded tubular member 95. The straight proximal tubular section 120 has a straight nondeployed proximal tubular section length 150. The straight proximal tubular section 120 is joined either contiguously or with an attachment to the folded tubular section 125. The folded tubular section 125 is formed from a continuous tube that is folded back and forth upon itself to form three separate walls, a folded tubular section outer wall 155, a folded tubular section center wall 160, and a folded tubular section inner wall 165. The folded tubular section inner wall 165 is joined either contiguously or with attachment to a straight proximal tubular section wall 170 to form a continuous wall. The folded tubular section 125 has a proximal circumferential fold line 175 and a distal circumferential fold line 180 and has a nondeployed folded tubular section length 185 extending from the proximal circumferential fold line 175 to the distal circumferential fold line 180. The portion of the intravascular tubular member wall 143 that forms the folded tubular section 125 has an upstream end 187 and a folded tubular section downstream end 188. The straight proximal tubular section wall 170 is joined to the folded tubular section upstream end 187 and the distal tubular section wall 190 is joined to the folded tubular section downstream end 188. In the folded tubular section 125, a portion of the inner surface 135 of the straight intravascular folded tubular member 95 is in apposition with another adjoining portion of the inner surface 135. Similarly, in the folded tubular section 125 a portion of the outer surface 140 is in apposition with another adjoining portion of the outer surface 140. The folded tubular section outer wall 155 is joined either contiguously or with an attachment to a distal tubular section wall 190 of the distal tubular section 130 to form a continuous wall. The distal tubular section 130 has an outlet end 148 to provide passage of blood flow out of the distal tubular section 130 and out of the straight intravascular folded tubular member 95. The distal tubular section 130 has a nondeployed distal tubular section length 200 extending from the folded tubular section 125 to the outlet end 148. The straight intravascular folded tubular member 95 has a straight nondeployed tubular member length 115 that extends from the inlet end 145 to the outlet end 148. The straight intravascular folded tubular member 95 has a blood flow passage 100 which provides passage of blood flow from the inlet end 145 to the outlet end 148. The distal circumferential fold line 180 is in contact with the blood flow passage 100 such that shear forces acting by the blood onto the inner surface 135 will not act to generate separation between the three walls of the folded tubular section 125. The distal tubular section 130 has a nondeployed distal tubular section length 200 that can provide significant length in accordance with the length requirements for a specific vascular application. Alternately, it is understood that the nondeployed distal tubular section length 200 can be very short such that it includes essentially only the outlet end 148 without any significant length.

Figure 2B:
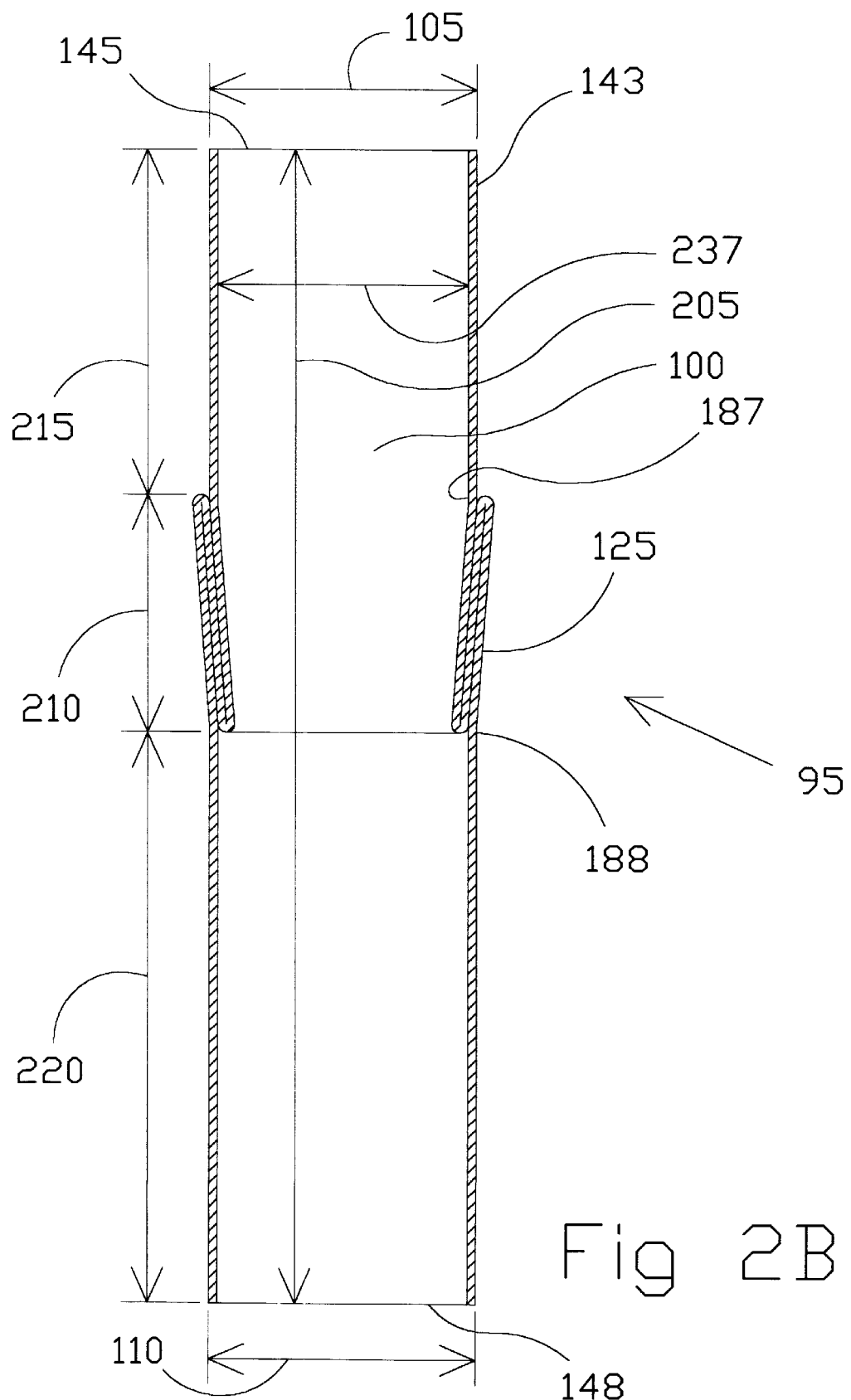
FIG. 2B is a sectional view of a straight intravascular folded tubular member in a fully deployed state.

FIG. 2B shows the straight intravascular folded tubular member 95 in a fully deployed state or in an implanted state with a radially deployed inlet end diameter 105, a radially deployed outlet end diameter 110, and a straight deployed tubular member length 205. The inlet end 145 and outlet end 148 have been extended in axial position with respect to each other. To accomplish the longer straight deployed tubular member length 205 the folded tubular section 125 has unfolded such that its deployed folded tubular section length 210 is shorter in the fully deployed state or implanted state (see FIG. 2B) than the nondeployed folded tubular section length 185 in the non-axially deployed state shown in FIG. 2A. The straight deployed proximal tubular section length 215 and the deployed distal tubular section length 220 are longer in the deployed state as shown in FIG. 2B than the straight nondeployed proximal tubular section length 150 and the nondeployed distal tubular section length 200, respectively in the non-axially deployed state. It is possible for the deployed distal tubular section length 220 to have increased more in length than the straight deployed proximal tubular section length 215 as the straight intravascular folded tubular member 95 goes from a partially deployed state to a fully deployed state. Alternately, both the straight deployed proximal tubular section length 215 and deployed distal tubular section length 220 could have increased the same amount as the straight deployed tubular member length has extended from a partially deployed state to a fully deployed state as will be explained further later. All reference numerals correspond to those elements previously or otherwise described.

FIGS. 2C and 2D show cross sectional views of the straight intravascular folded tubular member 95 in a nondeployed state, a non-radially deployed state, or insertion state. The length of the straight intravascular folded tubular member in FIGS. 2C and 2D is the same as in FIG. 2A. In one embodiment for delivering or inserting a self-expanding straight intravascular folded tubular member 95, for example, an outer delivery sheath 225 holds the straight intravascular folded tubular member 95 with a smaller insertion diameter or nondeployed inlet end diameter 230 and with a smaller insertion diameter or nondeployed outlet end diameter 235. To deliver the straight intravascular folded tubular member 95 to the site of the vascular injury, the delivery sheath 225 containing the straight intravascular folded tubular member 95 is entered into a vessel either proximal or distal to the vascular lesion. Upon removal from the delivery sheath 225, the straight intravascular folded tubular member 95 expands from the nondeployed state to form the partially deployed state with a larger radially deployed inlet end diameter 105 and radially deployed outlet end diameter 110 as shown in FIG. 2A. Following delivery of the straight intravascular folded tubular member 95 to the site of the lesion, the straight intravascular folded tubular member 95 is extended from a straight nondeployed tubular member length 115 to an appropriate straight deployed tubular member length 205 representative of an implanted state. Mechanical dilitation of the tubular member can be further employed if needed such as with a balloon dilitation catheter to expand the straight intravascular folded tubular member 95 to its radially deployed inlet end diameter 105 and radially deployed outlet end diameter 110 to ensure that the straight intravascular folded tubular member has attained a larger deployed diameter 237 (see FIGS. 2A and 2B). The delivery sheath 225, in addition to a balloon dilitation catheter, or other delivery system means can be used to deliver the straight intravascular folded tubular member 95 to the site of vascular injury and deploy it from a nondeployed state or insertion state with a smaller insertion diameter or nondeployed diameter to a deployed state or implanted state with a larger deployed diameter 237 or implanted diameter. The straight intravascular folded tubular member can also be a balloon-expandable device. In this case the straight intravascular folded tubular member, either with or without an attachment means can be mounted in a nondeployed state onto the balloon of a balloon dilitation catheter. Upon delivery to the site of the lesion, the balloon can be expanded to cause the straight intravascular folded tubular member to assume its radially deployed state.

Figure 2E:
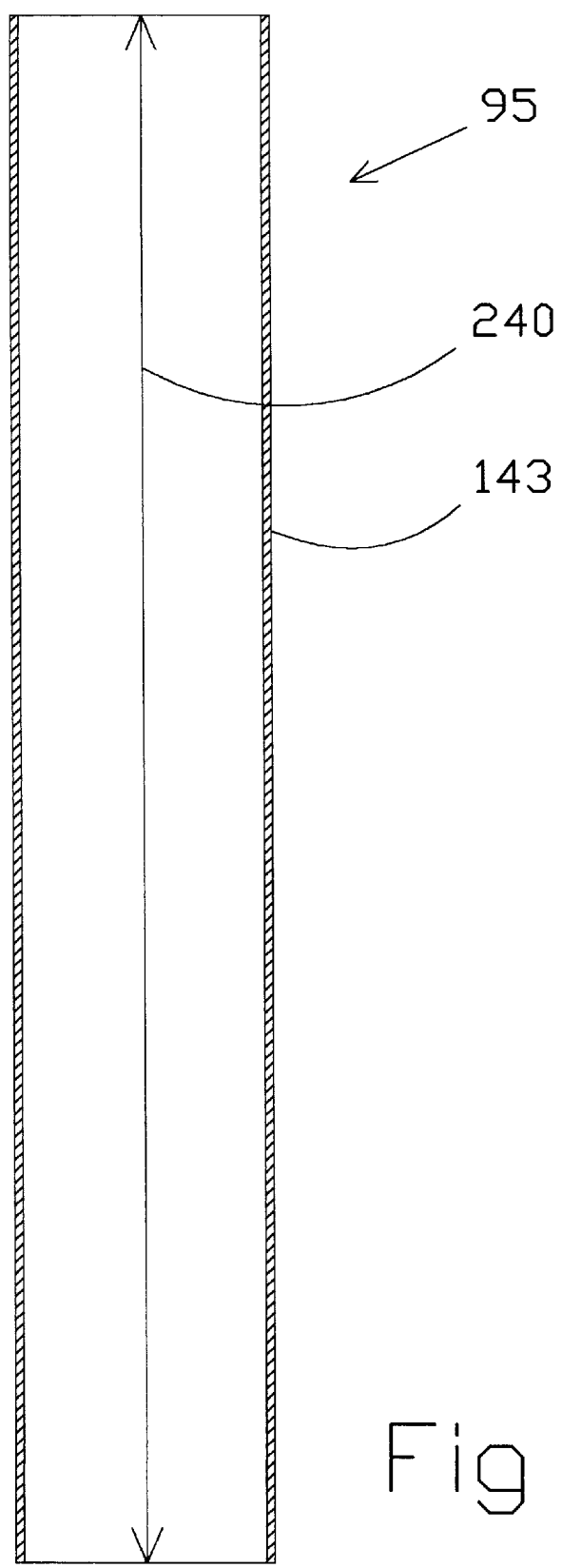
FIG. 2E is a sectional view of a straight intravascular folded tubular member in an unfolded state.

FIG. 2E shows a straight intravascular folded tubular member 95 in an unfolded state with a straight unfolded tubular member length 240 prior to forming the folded tubular section 125 shown in FIG. 2A and 2B. The straight intravascular folded tubular member 95 can be formed out of any material used in vascular grafts, in stent-grafts, or implanted vascular conduits such as tubular expanded polytetrafluoroethylene (ePTFE), woven expanded polytetrafluoroethylene fibers, woven or knitted polyester, polyurethane, silicone, or other materials such as composite woven or braided materials presented later in this disclosure.

The straight intravascular folded tubular member 95 can have but is not required to have an attachment means 87 at the inlet and outlet end 148 as shown in FIG. 3. This attachment means can be a prior art stent used for vascular implant. Such an attachment means 87 if present generally serves to hold the straight intravascular folded tubular member 95 in place and ensure a leak free fit with the native vessel proximal or distal to the vessel injury. The straight intravascular folded tubular member 95 can be placed within a blood vessel and with the inlet end 145 and outlet end 148 being attached to the native vessel using a separate prior art stent or attachment means of any type that is placed near the inlet end 145 and outlet end 148 to form an attachment with the native vessel. If appropriate, a surgical cutdown could be conducted and sutures used to hold the inlet end 145 and outlet end 148 of the straight intravascular folded tubular member 95 in place with a leak free seal. The straight intravascular folded tubular member 95 could also be formed from a material that maintained a tubular or cylindrical shape with an outward extending force and did not require an attachment means. Existing vascular graft materials including polyurethane, silicone, and others are capable of providing this characteristic and may not require an additional attachment means in some implant situations. Such implant situations include repair of blood vessels with luminal injury that would benefit by a vascular graft but with adequate vessel integrity and anatomy such that graft migration and sealing are not of acute concern.

It is often times preferable to include an attachment means 87 to ensure a tight seal between the straight intravascular folded tubular member 95 and the vessel wall and to prevent migration of the straight intravascular folded tubular member 95. An attachment anchor 245 which is included in the present invention and is discussed in more detail later in this disclosure is shown attached to the inlet end 145 and outlet end 148 of the straight folded tubular member 95. FIG. 3 shows the straight intravascular folded tubular member 95 in a deployed state with the attachment anchor 245 containing barbs 250 attached to the straight proximal tubular section 120 near the inlet end 145 with securing fibers 255 or other securing means. Almost any attachment means such as a stent found in the prior art can be used as the attachment means for the inlet end 145 and outlet end 148 of the straight intravascular folded tubular member 95. The attachment anchor 245 of the present invention shown in FIG. 3 can provide more enhanced anchoring properties than found with other prior art attachment means and will be discussed later in this disclosure. The attachment anchor 245 with barbs 250 is positioned on the inner surface 135 of the straight intravascular folded tubular member 95 such that it forcibly holds the straight intravascular folded tubular member 95 outward against the vessel wall after the attachment anchor 245 has been deployed to a larger diameter. The attachment anchor 245 has barbs 250 that extend outward to provide enhanced anchoring of the straight intravascular folded tubular member 95 to the vessel wall. This anchoring helps to prevent migration of the straight intravascular folded tubular member 95 and in the case of abdominal aortic aneurysm repair can help to support the aortic wall from further aneurysmal dilitation. The attachment anchor 245 without barbs 250 is shown attached to the distal tubular section 130 at or near the outlet end 148 with securing fibers 255. The attachment anchor 245 is positioned on the inside of the straight intravascular folded tubular member 95 such that it forcibly holds the straight intravascular folded tubular member 95 outward against the vessel wall. For ease of description, the straight intravascular folded tubular member 95 is shown with an attachment anchor 245 with barbs 250 attached to the straight proximal tubular section 120 and an attachment anchor 245 without barbs 250 attached to the distal tubular section 130. Either the straight proximal tubular section 120 or the distal tubular section 130 could have the attachment anchor 245 with or without barbs 250 attached and still be within the teachings of the present disclosure.

Another embodiment of the present invention is a bifurcated intravascular folded tubular member 260 shown in FIGS. 4A–4D and described collectively below. This embodiment is intended for vascular repair of a blood vessel trunk that has a bifurcation wherein one or both native vessel legs bifurcating off of the vessel trunk are also in need of repair. Blood flow from the common blood vessel trunk of the vessel proximal to the site of vessel injury into the bifurcated intravascular folded tubular member 260. The bifurcated intravascular folded tubular member 260 has an inlet end 145 that provides passage for blood flow into the bifurcated intravascular folded tubular member 260 (see FIG. 4B). The bifurcated intravascular folded tubular member 260 has two outlet ends 148 that provide passage for blood flow out of the bifurcated intravascular folded tubular member 260 into two distal vessels located distal to the vessel lesion. One common application for this embodiment is in the repair of abdominal aortic aneurysms where one or both common iliac, external iliac, or femoral arteries are involved in the aneurysmal dilation of the vessel wall. The bifurcated intravascular folded tubular member 260 has a bifurcated proximal tubular section 265 with an inlet end 145, a bifurcated main trunk 270 joined either contiguously or with an attachment to two proximal leg tubes 275. The bifurcated intravascular folded tubular member 260 has an inner surface 135 and an outer surface 140. Each of the proximal leg tubes 275 are joined either contiguously or with an attachment to a folded tubular section 125. Each folded tubular section 125 is joined either contiguously or with an attachment to a distal tubular section 130. Each distal tubular section 130 has an outlet end 148 that provides passage for blood flow out of each distal tubular section 130 and out of the bifurcated intravascular folded tubular member 260.

Figure 4A:
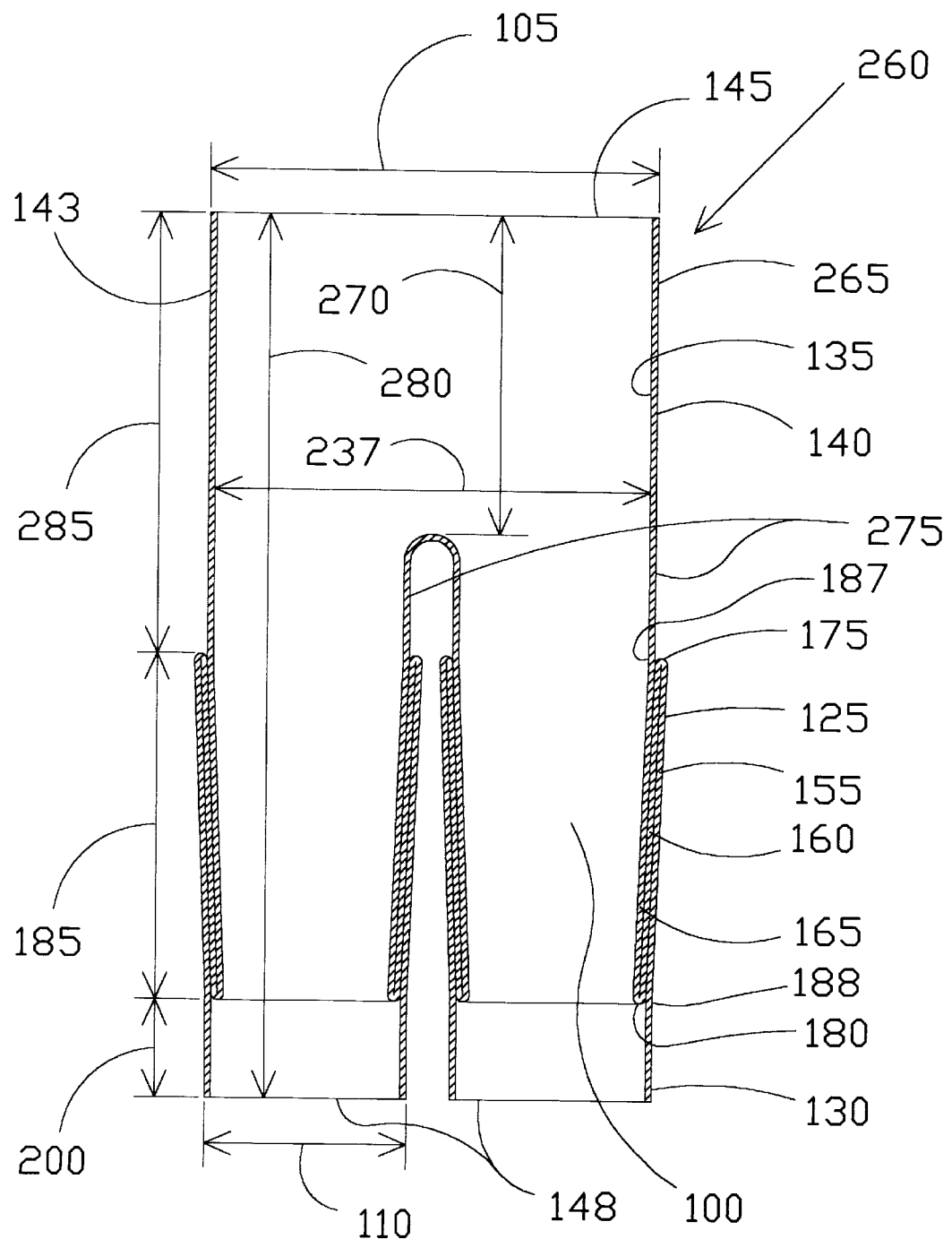
FIG. 4A is a sectional view of a bifurcated intravascular folded tubular member in a partially deployed state.

The bifurcated intravascular folded tubular member 260 is shown in a partially deployed state in FIG. 4A. The inlet end 145 has a larger radially deployed inlet end diameter 105 and each outlet end 148 has a larger radially deployed outlet end diameter 110. A continuous intravascular tubular member wall 143 extends from the inlet end 145 to each outlet end 148. The continuous intravascular tubular member wall 143 can have attachments between the bifurcated proximal tubular section 265, the folded tubular section 125, and the distal tubular section 130 of the intravascular tubular member wall 143 or the intravascular tubular member wall 143 can be contiguous without attachments. The radially deployed bifurcated intravascular folded tubular member 260 has a shorter bifurcated nondeployed tubular member length 280 than the bifurcated deployed tubular member length 290. The bifurcated intravascular folded tubular member 260 shown in this embodiment is similar to the straight intravascular folded tubular member 95 shown in FIGS. 2A–2D except that the present embodiment has a bifurcated proximal tubular section 265 that is bifurcated and it has two folded tubular sections 125 joined to the bifurcated proximal tubular section 265 instead of one, each folded tubular section 125 being joined to a distal tubular section 130. The structure of each folded tubular section 125 of the bifurcated intravascular folded tubular member 260 is the same as the structure of the folded tubular section 125 of the straight intravascular folded tubular member 95 shown in FIGS. 2A–2E. Each folded tubular section 125 has a continuous tubular wall that is folded back and forth upon itself to form a folded tubular section inner wall 165, a folded tubular section center wall 160, and a folded tubular section outer wall 155. In the folded tubular section 125 a portion of the inner surface 135 is in apposition with another portion of the inner surface 135. In the folded tubular section 125 a portion of the outer surface 140 is in apposition with another portion of the outer surface 140. Each folded tubular section 125 has a proximal circumferential fold line 175 to a distal circumferential fold line 180 and has a nondeployed folded tubular section length 185 extending between the proximal 175 and distal 180 fold lines. Each folded tubular section 125 has a wall with an upstream end 187 and a downstream end 188. The wall of the bifurcated proximal tubular section 265 is joined to folded tubular section upstream end 187, and the distal tubular section wall 190 is joined to the folded tubular section downstream end 188. The bifurcated proximal tubular section 265 has a bifurcated nondeployed proximal tubular section length 285 and the distal tubular section 130 has a nondeployed distal tubular section length 200. The nondeployed distal tubular section length 200 can have significant length to accommodate a variety of vascular applications with varying lengths of vascular injury. Alternately, the nondeployed distal tubular section 130 can have negligible length and the distal tubular section 130 can consist of the outlet end 148. All reference numerals correspond to those elements previously or otherwise described.

Figure 4B:
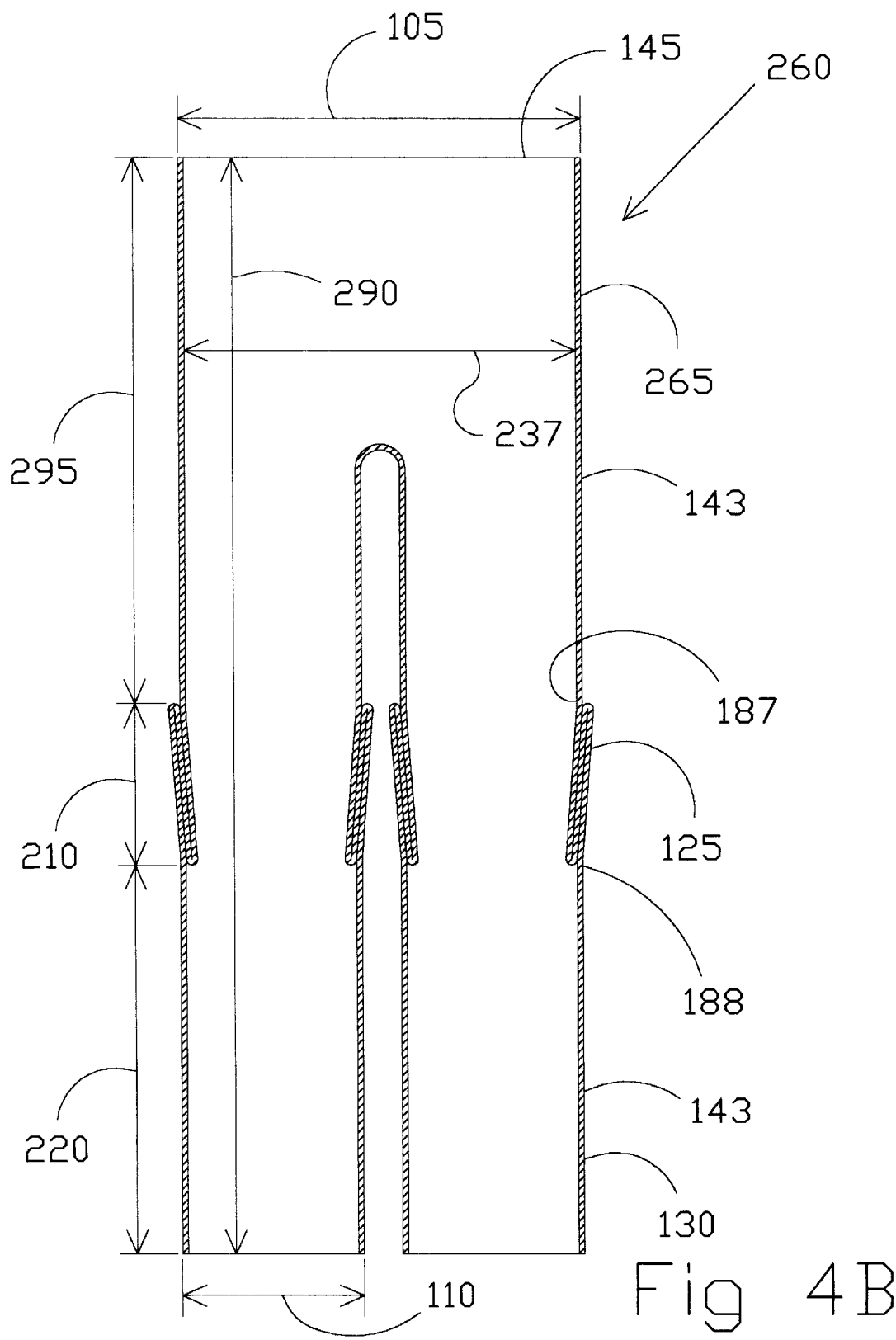
FIG. 4B is a sectional view of a bifurcated intravascular folded tubular member in a fully deployed state.

FIG. 4B shows the bifurcated intravascular folded tubular member 260 in a fully deployed state or implanted state, being deployed to both a larger radially deployed inlet end diameter 105, a larger radially deployed outlet end diameter 110, and a longer bifurcated deployed tubular member length 290. During full deployment to a bifurcated deployed tubular member length 290, the bifurcated proximal tubular section 265 extends in length to a bifurcated deployed proximal tubular section length 295, the distal tubular section 130 extends in length to a deployed distal tubular section length 220, and the folded tubular section 125 reduces in length to a deployed folded tubular section length 210. This extension in length from a shorter bifurcated nondeployed tubular member length 280 to a longer bifurcated deployed tubular member length 290 is accomplished as the folded tubular section 125 unfolds an appropriate amount to achieve an appropriate bifurcated deployed tubular member length 290 for the bifurcated intravascular folded tubular member 260. During the unfolding process it is possible for either the bifurcated nondeployed proximal tubular section length 285 or the nondeployed distal tubular section length 200 to extend more than the other tubular section length extends in forming the bifurcated deployed tubular member length 290.

Figure 4D:
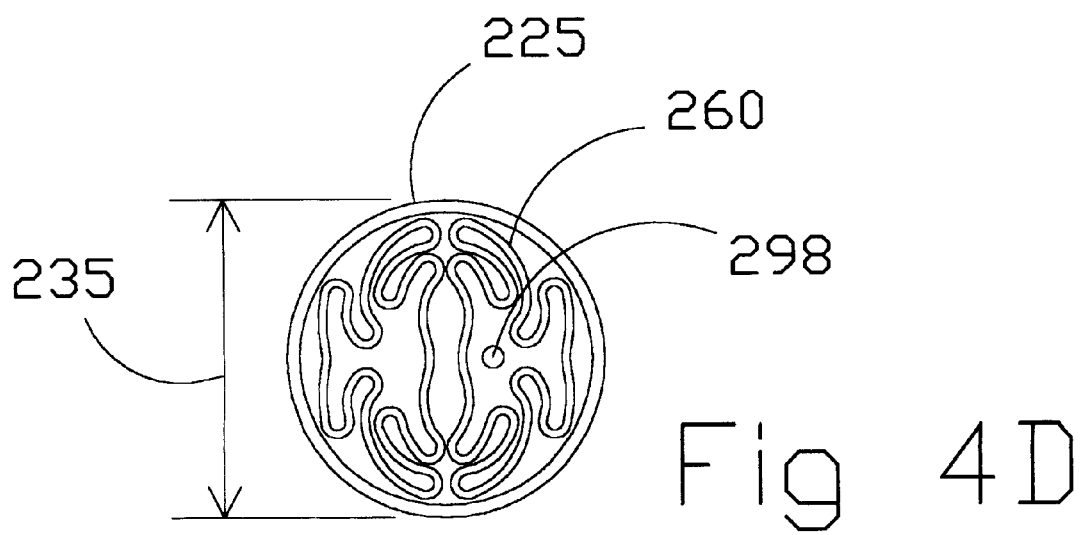
FIG. 4D is a sectional view of a bifurcated intravascular folded tubular member in a nondeployed state within a delivery sheath near the outlet ends.
Figure 4E:
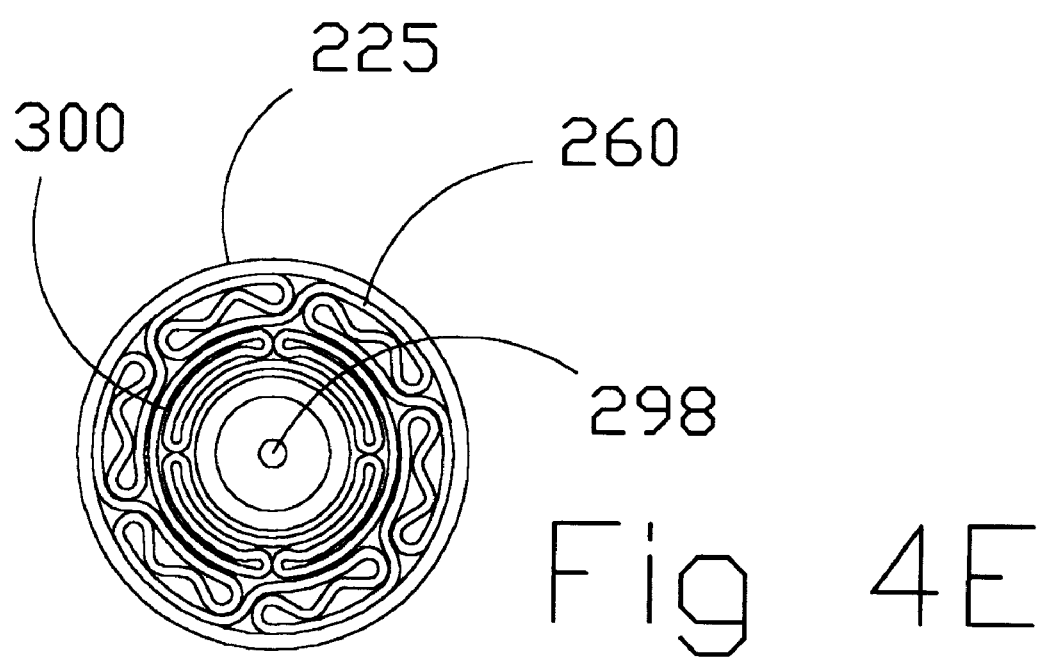
FIG. 4E is a sectional view of a bifurcated intravascular folded tubular member in a nondeployed state on a balloon dilitation catheter near the inlet end.
Figure 4F:
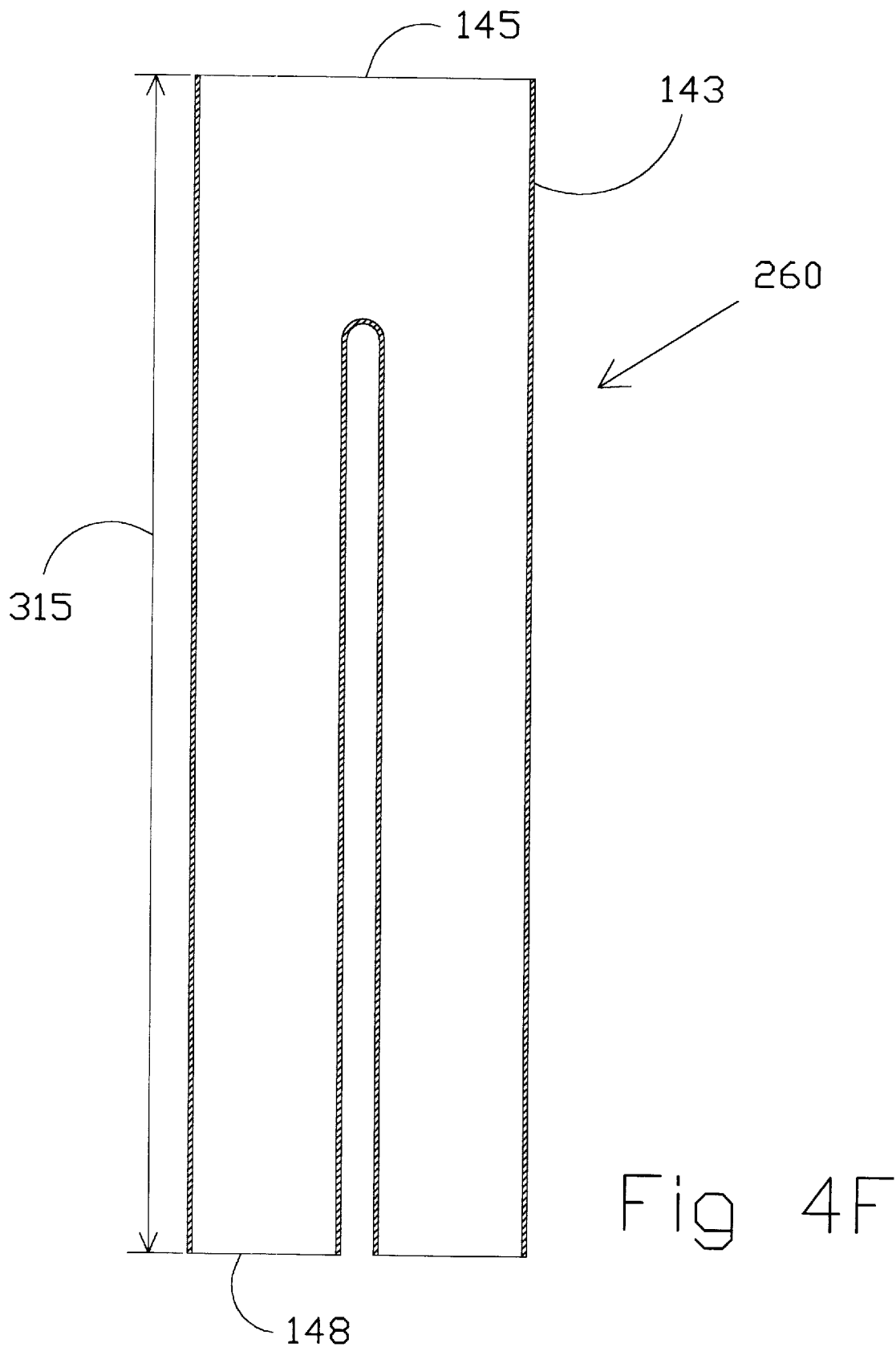
FIG. 4F is a sectional view of a bifurcated folded tubular member in an unfolded state.

The bifurcated intravascular folded tubular member 260 is generally intended to be delivered to the site of a lesion such as an aortic aneurysm in a nondeployed or insertion state as shown in cross section in FIGS. 4C and 4D. FIG. 4C shows a cross sectional view of the bifurcated intravascular folded tubular member 260 near the inlet end 145 in a nondeployed state; FIG. 4D shows a cross sectional view of the bifurcated intravascular folded tubular member 260 near the outlet end 148 in a nondeployed state. A guidewire 298 is shown extending through one distal tubular section 130 of FIG. 4D and through the center of the bifurcated proximal tubular section 265 in FIG. 4C. The bifurcated intravascular folded tubular member 260 can also be mounted on a balloon dilitation catheter 300 (see FIG. 4E) and delivery system capable of expanding the bifurcated intravascular folded tubular member 260 from a nondeployed state or insertion state to a larger deployed diameter 237 representative of the radially deployed state of FIG. 4A or fully deployed state of FIG. 4B. As an intravascular tubular member 85 of the present invention the straight intravascular folded tubular member 95 and the bifurcated intravascular folded tubular member 260 are intended to be delivered to the site of vascular injury with a smaller nondeployed diameter 305 that can easily fit within a small surgical access or percutaneous access in a blood vessel either proximal or distal to the vascular injury. Once the intravascular tubular member is delivered to the site of vessel injury it will expand out to larger deployed diameter 237 that is approximately equal to the diameter of the native vessel that is to be repaired. In one embodiment the bifurcated intravascular folded tubular member 260 can be held with a smaller nondeployed inlet end diameter 230 and nondeployed outlet end diameter 235 by a delivery sheath 225. For treatment of abdominal aortic aneurysm 5 the delivery sheath 225 containing the bifurcated intravascular folded tubular member 260 is generally introduced into one common femoral artery 30 and advanced proximally through the native lumen 53 of the common iliac artery 20 and abdominal aorta 10 to the proximal aortic neck 90 generally located just distal to the renal arteries 45 & 50 (see FIGS. 1A and 1B). The bifurcated intravascular folded tubular member 260 is released from the delivery sheath 225 such that the inlet end 145 is positioned distal to the renal arteries 45 & 50 and the bifurcated intravascular folded tubular member 260 expands to the radially deployed inlet end diameter 105. This can be accomplished, for example, for a bifurcated intravascular folded tubular member that is self-expandable or has an attachment means attached to the inlet or outlet ends that is self-expandable. The delivery sheath 225 is removed delivering the bifurcated intravascular folded tubular member 260 to the abdominal aorta 10 in a partially deployed state as shown in FIG. 4A. Alternately, the present invention can be made to expand from a nondeployed state of smaller nondeployed inlet end diameter 230 or nondeployed outlet end diameter 235 to a deployed state of larger radially deployed inlet end diameter 105 or radially deployed outlet end diameter 110 using a mechanical expansion device such as a balloon dilitation catheter 300. In this case the bifurcated intravascular folded tubular member or the attachment means which can be attached thereto can be balloon-member expandable. Each outlet end 148 of the two distal tubular sections is positioned at the appropriate location within the common iliac artery 20, external iliac artery 25, or common femoral artery 30. This positioning causes each of the folded tubular sections to unfold to provide the appropriate lengths for each of the two deployed folded tubular section lengths 210. The bifurcated intravascular folded tubular member 260 is then fully deployed and extends from a region of the abdominal aorta proximal to the vessel injury or aneurysm to two distal iliac or femoral arteries. The inlet end 145 of the bifurcated intravascular folded tubular member 260 provides passage for blood flow from the abdominal aorta proximal to the vessel injury into the blood flow passage 100 and each outlet end 148 providing passage for blood flow to each of two distal arteries located distal to the vessel injury. FIG. 4F shows the bifurcated intravascular folded tubular member 260 in an unfolded state with a bifurcated unfolded tubular member length 315 as it might appear prior to forming each folded tubular section 125 found in FIGS. 4A and 4B. All reference numerals correspond to those elements previously or otherwise discussed.

Figure 5:
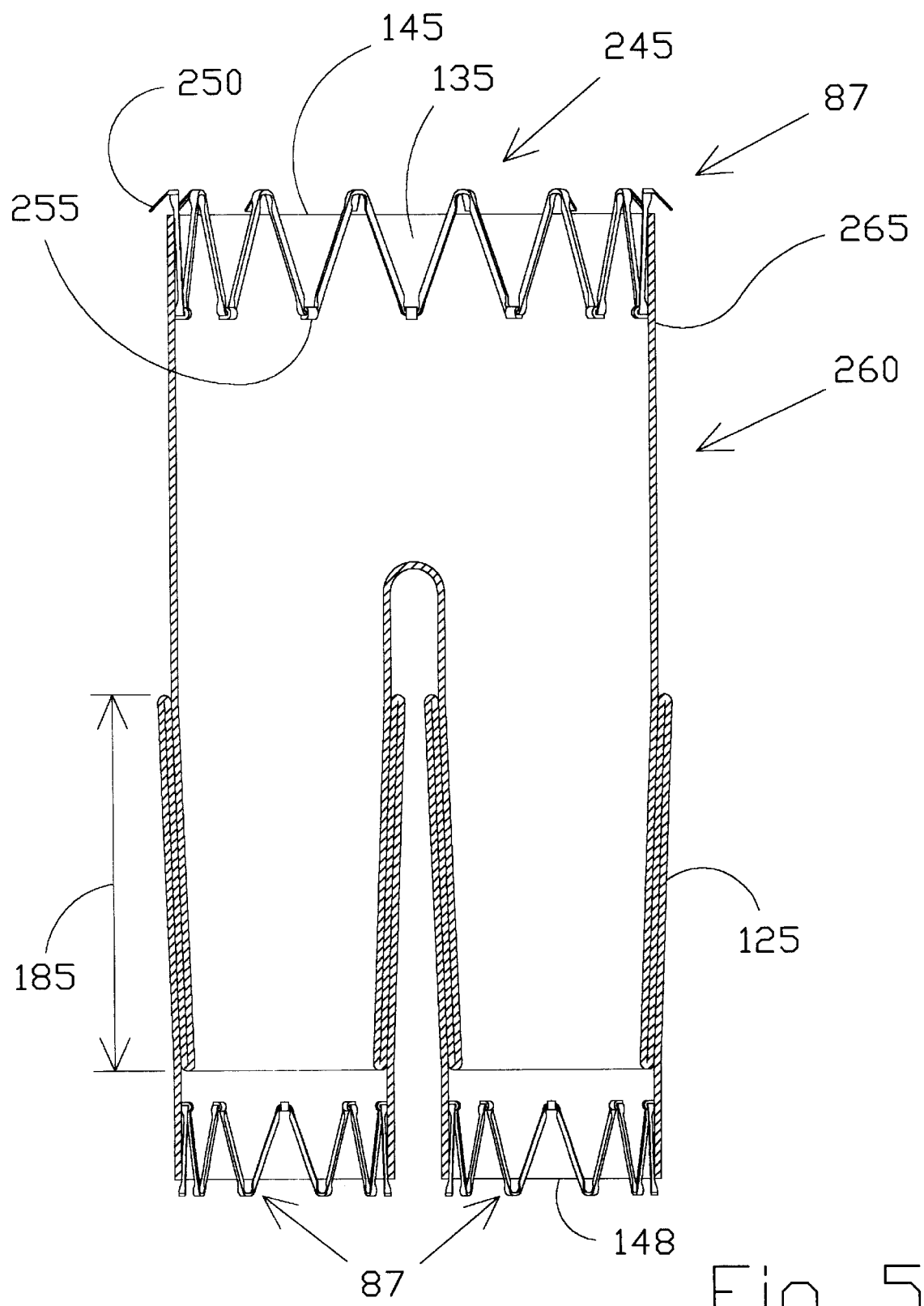
FIG. 5 is a partially sectioned view of a bifurcated folded tubular member in a nondeployed state with attachment means at the inlet and outlet ends.

An additional preferred embodiment of a bifurcated intravascular folded tubular member 260 is shown in FIG. 5 with an attachment anchor 245 or other attachment means 87 at the inlet end 145 and at each outlet end 148. The attachment means 87 can be any barbed or non-barbed attachment means found in the prior art or device that can be used to anchor the ends of an intravascular tubular member. The attachment means 87 serves to hold the bifurcated intravascular folded tubular member 260 firmly against the vessel wall at its inlet end 145 and outlet end 148 to prevent migration, and reduce leakage between the bifurcated intravascular folded tubular member 260 and the native lumen 53 (see FIGS. 1A and 1B). The bifurcated intravascular folded tubular member 260 is not required to have an attachment means. A separate stent such as found in the prior art placed on the inner surface 135 at the inlet end 145 and outlet end 148 of the bifurcated intravascular folded tubular member 260 can be used to prevent migration and leakage. At the inlet end 145 an attachment anchor 245 of the present invention with barbs 250 similar to that shown in FIG. 3 can be attached. This attachment anchor 245 will be described in detail later in this disclosure. Securing fibers 255 or other securing means attach the attachment anchor 245 to the inner surface 135 of the bifurcated proximal tubular section 265 near the inlet end 145. The attachment anchor 245 with barbs 250 can be short to allow it to be placed more accurately near the renal arteries without extending distally beyond the aortic neck into the aneurysmal space. The attachment anchor 245 shown allows an increased number of barbs 250 to be positioned along the circumference of the attachment anchor 245. This increased number of barbs 250 allows the bifurcated intravascular folded tubular member 260 to be anchored well to the aortic wall to prevent leakage of blood, prevent migration, and may also provide some additional support to prevent further dilation of the abdominal aorta. An attachment anchor 245 without barbs 250 is attached to the inner surface 135 of each distal tubular section 130 at each outlet end 148 using securing fibers 255. Each attachment anchor 245 either with or without barbs 250 can be constructed out of an elastic metal such as Nitinol, stainless steel, or other metal or metal alloy that provides the attachment anchor 245 with a self expanding characteristic. Alternately, the attachment anchor 245 can be formed out of a metal such as stainless steel, titanium, tantalum, platinum, or other metal or metal alloy that undergoes plastic deformation to attain a deployed attachment anchor diameter 320.

Unfolding of Folded Tubular Section

It can be desirable for the folded tubular section 125 to unfold evenly or in a controlled manner without wrinkling as it moves from a nondeployed folded tubular section length 185 to a deployed folded tubular section length 210. Furthermore it is desirable for the folded tubular section 125 (see FIG. 4B) to remain at a constant deployed folded tubular section length 210 with the straight or bifurcated intravascular folded tubular member 95 & 260 in a fully deployed state. FIG. 6 shows the nondeployed state of the folded tubular section 125 including its junction to the straight proximal tubular section 120 and its junction to the distal tubular section 130. This discussion applies equally well for the folded tubular section 125 joined to the bifurcated proximal tubular section 265 (see FIGS. 4A and 4B). As shown in FIG. 6 a bonding agent 325 can be applied to the portion of the outer surface 140 of the folded tubular section 125 that is in apposition with another portion of the outer surface 140 of the folded tubular section 125. The bonding agent 325 can be an adhesive such as cyanoacrylate, epoxy, polyurethane, or other adhesive that would allow the bonded region to peel at the proximal circumferential fold line 175 preferential to the distal circumferential fold line 180 and allow expansion of the straight intravascular folded tubular member 95 from a straight nondeployed tubular member length 115 to a straight deployed tubular member length 205 as described earlier in FIGS. 2A and 2B. The adhesive would resist wrinkling of the folded tubular section center wall 160 due to relative movement or slippage of the folded tubular section center wall 160 with respect to the folded tubular section inner wall 165 or folded tubular section outer wall 155. Placement of the bonding agent 325 on the portions of the outer surface 140 of the folded tubular section 125 which are in apposition would not significantly affect thrombosis of the straight intravascular folded tubular member 95 or bifurcated intravascular folded tubular member 260 (see FIGS. 4A and 4B) since the outer surface 140 is not in contact with blood flow. Placement of the bonding agent 325 on the outer surface 140 of the folded tubular section 125 that is in apposition can allow the distal tubular section 130 to elongate preferentially to, or with a greater length change than, the straight proximal tubular section 120 or bifurcated proximal tubular section 265 (see FIGS. 4A and 4B) for the case of the bifurcated intravascular folded tubular member 260. A bonding agent 325 that would not create thrombosis could also be applied to the portions of the inner surface 135 of the folded tubular section 125 that were in apposition. This would further reduce wrinkling of the folded tubular section center wall 160 and allow the folded tubular section 125 to unfold in a controlled manner, with unfolding providing for more even extension of the straight proximal tubular section 120 with respect to the distal tubular section 130.

Figures 7A, 7B, 7C, 7D, 7E:
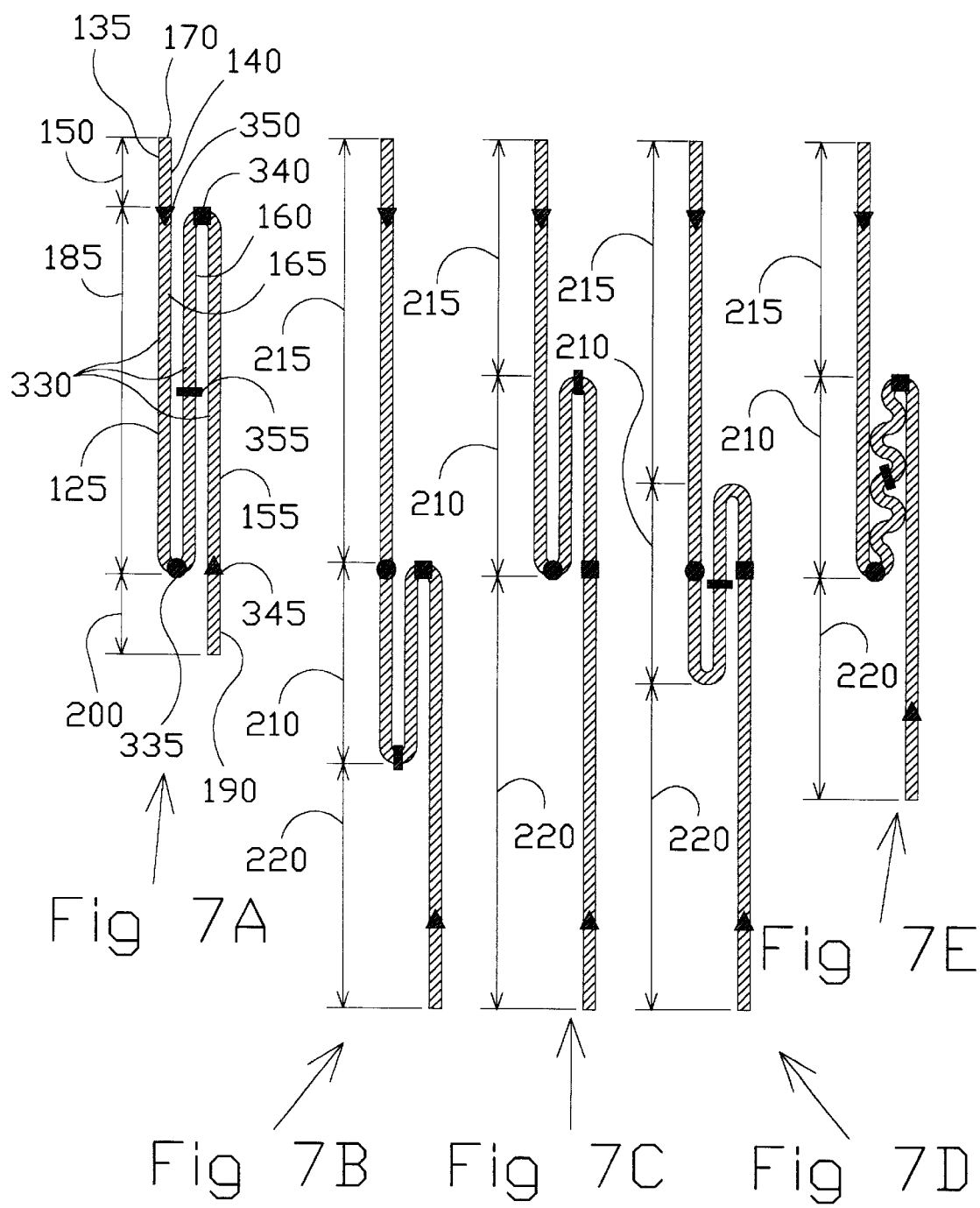
FIG. 7A is a schematic sectional view of the folded tubular section in a nondeployed state.
FIG. 7B is a schematic sectional view of the folded tubular section unfolded from the circle to the point-down triangle.
FIG. 7C is a schematic sectional view of the folded tubular section unfolded from the square to the point-up triangle.
FIG. 7D is a schematic sectional view of the folded tubular section unfolded evenly.
FIG. 7E is a schematic sectional view of the folded tubular section with wrinkling.

The unfolding of the folded tubular section inner wall 165, folded tubular section center wall 160, and folded tubular section outer wall 155 (see FIGS. 2A and 4A) can be seen more clearly in the schematic sectional drawings of FIGS. 7A–7E which show folded tubular section walls 330 along with their junction to the straight proximal tubular section wall 170 and the distal tubular section wall 190. It is understood that this teaching of unfolding applies equally well to each folded tubular section 125 found in the bifurcated intravascular folded tubular member 260 of FIGS. 4A and 4B. FIG. 7A shows the folded tubular section 125 having the folded tubular section walls 330 with the outer surface 140 of the folded tubular section inner wall 165 in apposition with the outer surface 140 of the folded tubular section center wall 160. The inner surface 135 of the folded tubular section center wall 160 is in apposition with the inner surface 135 of the folded tubular section outer wall 155. Markers in the form of a circle 335, square 340, point-up triangle 345 and point-down triangle 350, and rectangle 355 mark positions on the folded tubular section 125 of FIG. 7A with a nondeployed folded tubular section length 185 for reference purposes. In FIG. 7B the deployed folded tubular section length 210 has been reduced as the folded tubular section center wall 160 from the circle 335 to the rectangle 355 has unfolded to become the folded tubular section inner wall 165. The straight deployed proximal tubular section length 215 has lengthened from the straight nondeployed proximal tubular section length 150 more than the deployed distal tubular section length 220 has increased from the nondeployed distal tubular section length 200. This form of unfolding can generally occur when bonding agent 325 is placed only on portions of the inside surface of the folded tubular section 125 in apposition with another portion of inside surface. In FIG. 7C the deployed folded tubular section length 210 has been reduced from FIG. 7A as the folded tubular section center wall 160 from the rectangle 355 to the square 340 has unfolded to become the folded tubular section outer wall 155. The deployed distal tubular section length 220 has lengthened more than the straight deployed proximal tubular section length 215 has lengthened. This form of unfolding can be generated by placement of a bonding agent 325 on portions or the outer surface 140 of the folded tubular section 125 in apposition with another portion of outside surface as described in FIG. 6. In FIG. 7D the deployed folded tubular section length 210 has been reduced from the nondeployed folded tubular section length 185 shown in FIG. 7A as a portion of the folded tubular section center wall 160 has unfolded to become a portion of both the folded tubular section inner wall 165 and the folded tubular section outer wall 155. The straight deployed proximal tubular section length 215 and the deployed distal tubular section length 220 have both increased. This form of unfolding can occur if the folded tubular section inner wall 165 and folded tubular section outer wall 155 unfold evenly. Placing an effectively similar bonding agent 325 on both the inner surface 135 and outer surface 140 can result in this even unfolding pattern. Similar results can occur with no bonding agent placed on the folded tubular section 125. In FIG. 7E the deployed folded wall section length has been reduced from FIG. 7A. The folded tubular section center wall 160 has not unfolded but has rather wrinkled to allow the straight deployed proximal tubular section length 215 and the deployed distal tubular section length 220 to increase. The use of a bonding agent 325 as explained in FIG. 6 can enhance the ability of the straight intravascular folded tubular member 95 and bifurcated intravascular folded tubular member 260 of the present invention to unfold in a manner similar to the methods described in FIGS. 7A–7D and not wrinkle in an uncontrolled manner as shown in FIG. 7E.

Figure 8:
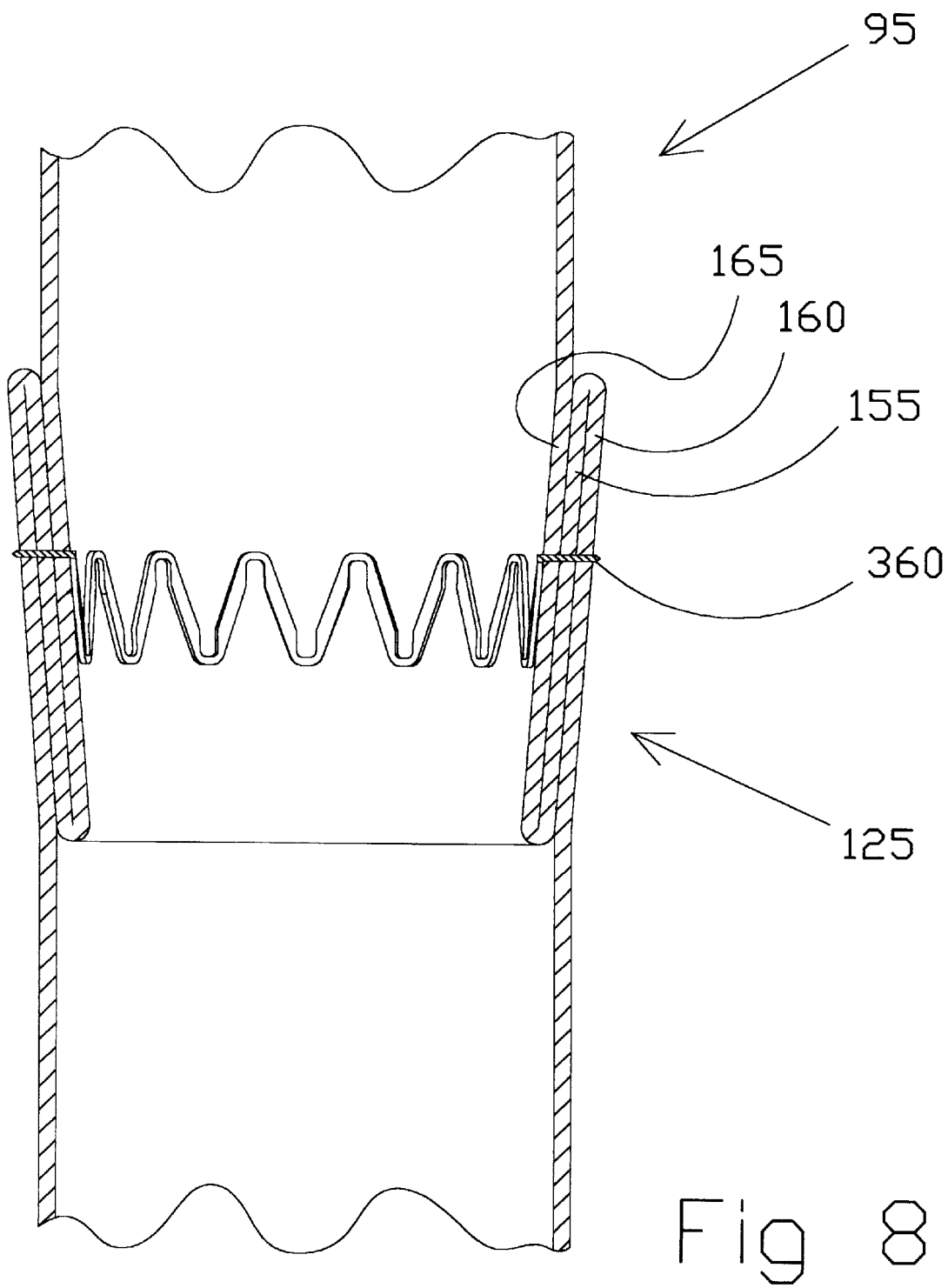
FIG. 8 is a sectional view of a folded tubular section with holding pins.

FIG. 8 shows a folded tubular section 125 with holding pins 360 extending through the folded tubular section inner wall 165, folded tubular section center wall 160, and folded tubular section outer wall 155. Following full deployment of the straight intravascular folded tubular member 95 or bifurcated intravascular folded tubular member 260 such holding pins 360 or other form of holding means can be placed to ensure that further elongation of the intravascular tubular member cannot occur. The holding pins 360 can be the same as the barbs 250 located on the attachment anchor 245 of the present invention.

Attachment Anchor

Figure 9A:
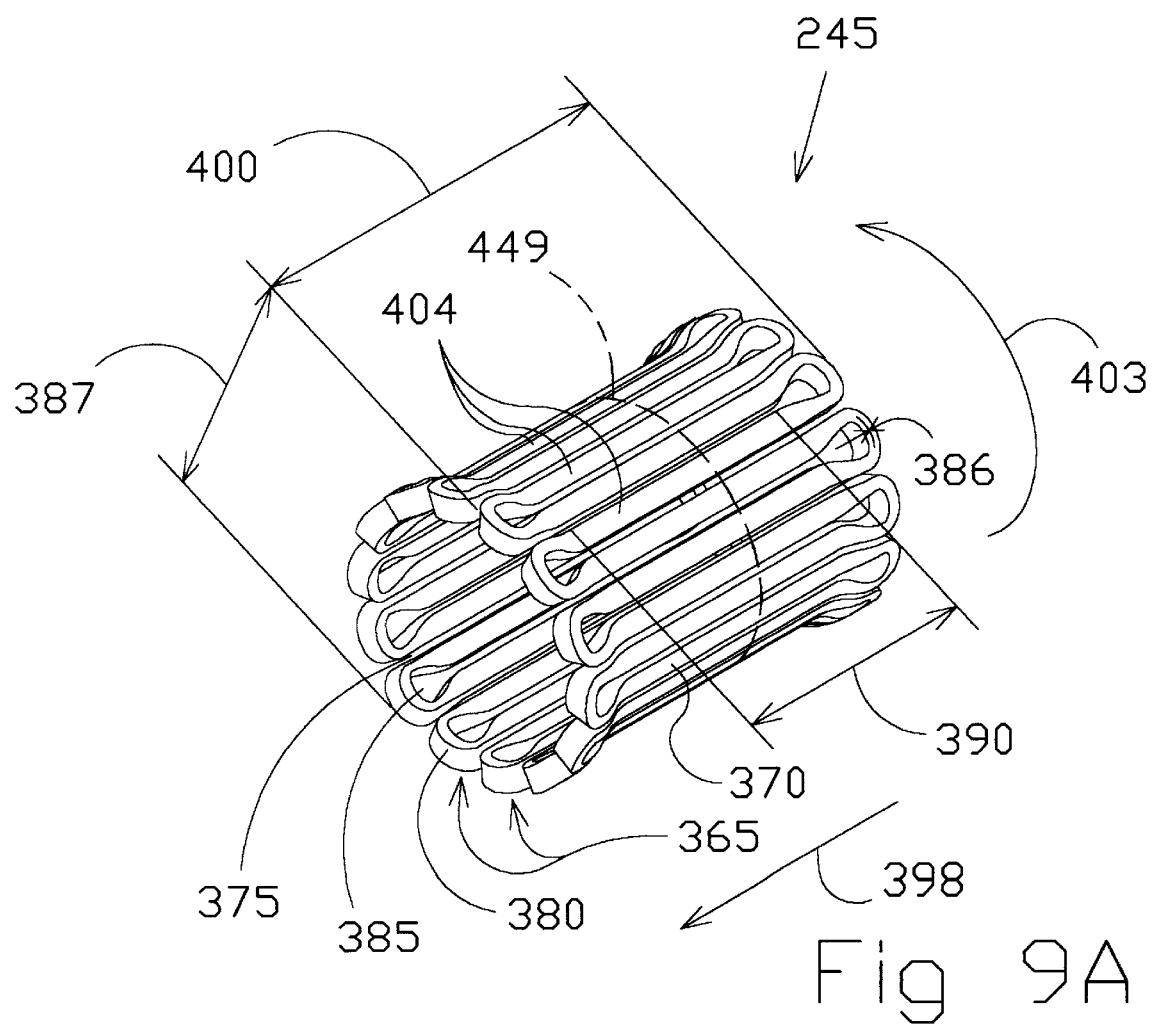
FIG. 9A is an isometric view of an attachment anchor with one hinge per node in a nondeployed state.
Figure 9B:
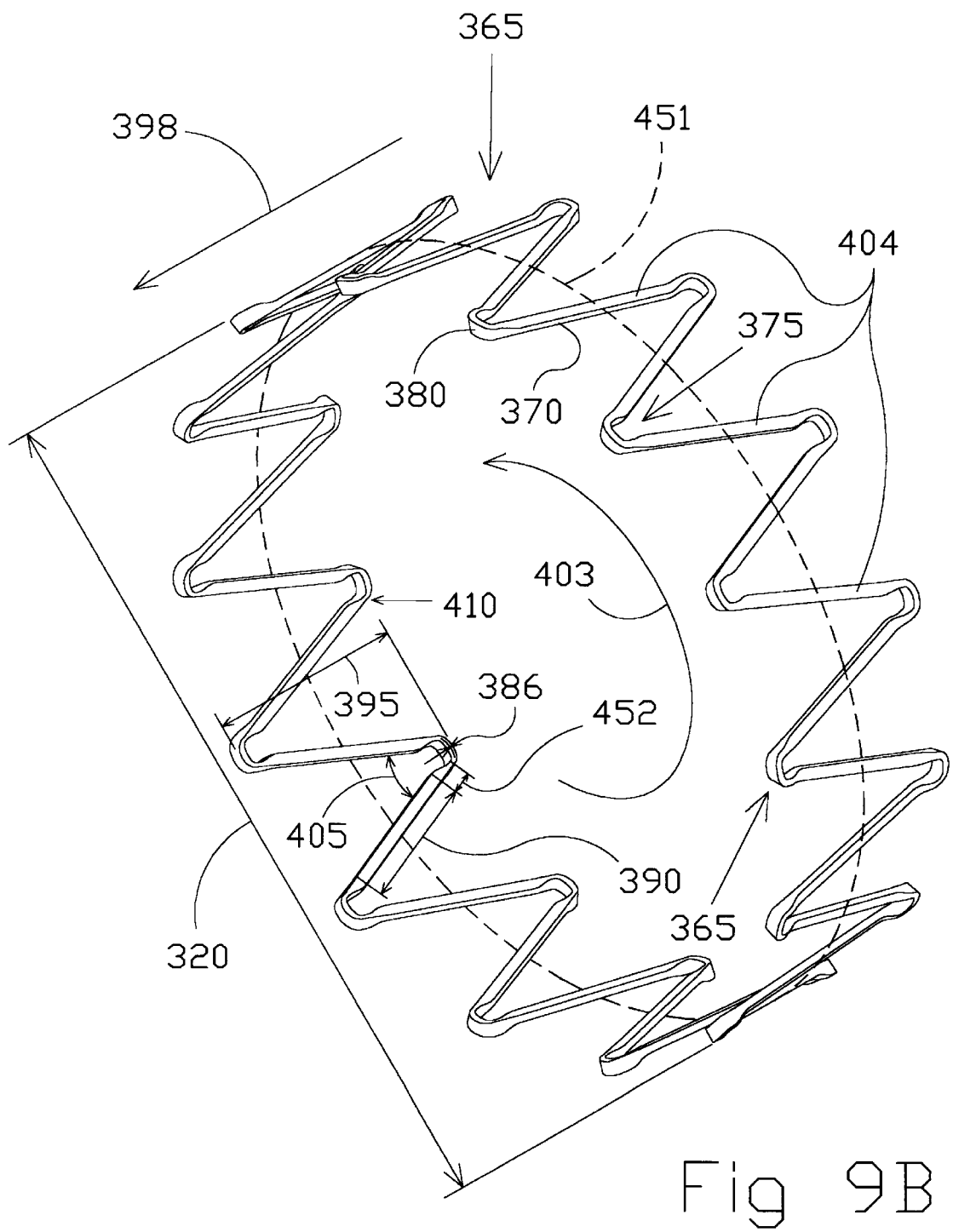
FIG. 9B is an isometric view of an attachment anchor with one hinge per node in a deployed state.

FIG. 9A is an isometric view of an embodiment of the attachment anchor 245 of the present invention without barbs in a nondeployed state. FIGS. 9A–9C will be discussed collectively. This attachment anchor 245 is similar to the attachment anchor shown in FIG. 5 except that the barbs 250 are not present. The attachment anchor 245 of the present invention is comprised entirely out of nodes 365 and struts 370 arranged in a ring structure. The attachment anchor 245 of the present embodiment is comprised of a series of nodes 365 and struts 370 arranged in a generally cylindrical shape. The axially oriented struts 370 are separated by interstrut openings 375. Each of the nodes 365 include at least one hinge 380 and have an intranodal opening 385 that connects with one of the interstrut openings 375. This attachment anchor 245 can be machined from a metal cylinder using machining techniques including mechanical machining, laser machining, chemical machining, electrochemical etching, electric discharge machining, and other machining methods. The metal used in the formation of the attachment anchor 245 can include stainless steel, Nitinol, tantalum, titanium, platinum, gold, or other metals or metal alloys. Nitinol, some stainless steel compositions, or other metals with elastic properties are suited to an attachment anchor 245 that is self-expandable; other stainless steel compositions, titanium, and other metals or metal alloys with plastic deformation properties can be suited to an attachment anchor 245 that is balloon-expandable. The metal can be chosen to provide a high yield strength or have a high elastic modulus or Young's modulus that can provide the attachment anchor 245 with a high expansion force while maintaining a lower profile and a more supple feel in a crushing deformation. A crushing deformation tends to deform the generally cylindrically shaped attachment anchor 245 into an oval shape. The design of the nodes 365 and the struts 370 can be chosen to provide appropriate outward expansion forces by the attachment anchor 245 for a particular application. Typically a larger diameter and thicker walled blood vessel would require an attachment anchor 245 with greater expansion forces outward against the blood vessel wall than a smaller diameter, thinner walled blood vessel. The attachment anchor 245 must provide adequate outward expansion force to hold the intravascular tubular member of the present invention outward against the blood vessel wall without leakage, it must resist any compression forces offered by the blood vessel, and it must prevent migration of the intravascular tubular member. The attachment anchor 245 is a radially expandable vascular implant that can be a self-expandable attachment anchor 245 or a balloon-expandable attachment anchor 245. The design of the node 365 can be altered to provide for a completely elastic deformation of the metal in the hinge 380 or to provide for plastic deformation of the metal in the hinge 380. The intranodal openings 385 provide sites for attachment of securing fibers 255 (see FIGS. 3 and 5) to the attachment anchor 245 in order to hold the attachment anchor 245 to a straight intravascular folded tubular member 95, or to a bifurcated intravascular folded tubular member 260 as described in FIGS. 3 and 5, or to any other tubular member or tubular means that is used as an intravascular graft or intravascular tubular member. The attachment anchor 245 of the present invention can be used with other prior art stent-graft devices to anchor such devices to a blood vessel. In a nondeployed state, the struts 370 are adjacent and parallel to each other and in direct apposition to each other to provide the closest position of struts 370 with respect to each other. This provides the attachment anchor 245 with an ability to attain the largest expansion ratio of attachment anchor diameters from a deployed state to a nondeployed state. The attachment anchor has a hinge width radius of curvature 386 (FIG. 9B) which describes the radius of curvature with the direction of the radius of curvature aligned with the direction of the hinge width 420 (FIG. 9C). The attachment anchor 245 has a nondeployed attachment anchor diameter 387.

FIG. 9A shows an isometric view of the attachment anchor 245 in a nondeployed state with a smaller nondeployed diameter 387 or insertion diameter and FIG. 9B shows the attachment anchor 245 in a deployed state with a larger deployed attachment anchor diameter 380. The strut length 390 remains constant from the nondeployed or insertion state to the deployed or implanted state. A deployed attachment anchor length 395 in an axial direction 398 is shorter than the nondeployed attachment anchor length 400 but the amount of length change is minimal due in part to the increased number of deformation sites or nodes 365 found in the present attachment anchor 245 in comparison to other prior art attachment devices. Additionally, the greater number of deformation sites or nodes allows each deformation site to undergo a smaller deformation with less attachment anchor length change. The interstrut openings 375 between the struts 370 in a circumferential direction 403 in a nondeployed state can be negligible and the struts 370 can be in direct contact with each other. The generally cylindrical shape of the attachment anchor has a generally cylindrical uniformly curved attachment anchor surface 404 formed by the struts 370 and nodes 365. In addition, the attachment anchor can be deployed to a small deployment angle 405 of less than 60 degrees which further reduces the amount of attachment anchor length change in going from a nondeployed state to a deployed state. The deployment of the attachment anchor 245 to a smaller deployed angle 405 in comparison to other prior art attachment devices can be accomplished due to the greater number of nodes 365 found on the present attachment anchor 245. Alternately, the attachment anchor 245 of the present invention can be deployed to a larger deployment angle 405 than other prior art attachment means formed with round wires due to the greater force that can be generated by the hinge 380 of the present invention in comparison to a round wire. This greater force can be generated due to the hinge design and due to the higher modulus material that can be used for the hinge. The larger deployment angle 405 can provide the present attachment anchor 245 with a greater expansion ratio of deployed attachment anchor diameter 320 to nondeployed attachment anchor diameter 387. The attachment anchor 245 is deployed from a smaller insertion diameter or nondeployed attachment anchor diameter 387 in its nondeployed or insertion state to a larger deployed attachment anchor diameter 320 or insertion diameter in its deployed or implanted diameter. The ratio of deployed attachment anchor diameter 320 to nondeployed attachment anchor diameter 387 is maximized by positioning the struts 370 parallel and in apposition to each other in the nondeployed state.

FIG. 9C is an enlarged isometric view of a portion of the attachment anchor 245 shown in FIG. 9A. Each of the nodes 365 comprises the hinge 380 and two transition regions 410. The hinge 380 has a hinge length 415, a hinge width 420, and a hinge radial dimension 425. The strut 370 has a strut width 430, a strut radial dimension 435, and a strut length 390 as shown in FIG. 9A. The hinge 380 has a greater hinge radial dimension 425 than the strut radial dimension 435 and the hinge 380 has a smaller hinge width 420 than the strut width 430. Each of the transition regions 410 extends from the hinge 380 to the strut 370. It has a transition width 440 that varies from the smaller hinge width 420 to the larger strut width 430 and a transition radial dimension 445 that varies from the larger hinge radial dimension 425 to the smaller strut radial dimension 435. The transition regions 410 provides a smooth uniform transition of metal strength and conformation from each hinge 380 to each of the struts 370. The struts 370 have a strut cross sectional area 447 that can be different from and varied independently from a hinge cross sectional area 448. As shown in FIGS. 9A and 9B the attachment anchor 245 has a nondeployed attachment anchor perimeter 449 and a deployed attachment anchor perimeter 451. The transition regions 410 have an abrupt transition region length 452 that is as short as possible without causing a discontinuity in cross sectional area in order to maximize the hinge length 415 and strut length 390. The cross sectional areas of the transition regions are maintained to be larger than either the strut cross sectional area 447 or the hinge cross sectional area 448.

An embodiment of the attachment anchor 245 is a self-expandable vascular implant that can be used with the straight intravascular folded tubular member 95, bifurcated intravascular folded tubular member 260 of the present invention, or with any other intravascular tubular means that is used for intravascular repair of blood vessels. The hinge length 415 can be long, extending approximately from one of the transition regions 410 to another as shown in FIG. 9C and having a hinge length 415 equal to or greater than approximately twice the strut width 430. For a self-expandable attachment anchor 245 with a long hinge length 415 several advantages are obtained over prior art attachment devices such as those formed from zig zag shaped wire. The long hinge length 415 provides a smaller drop-off of the expansion elastic force exerted outward against the vessel wall by the attachment anchor 245 as the attachment anchor 245 extends from a nondeployed state to a deployed state with an elastic deformation. This smaller drop-off of outward expansion force provides a similar outward force over a variety of diameters for which the same attachment anchor can be used. The attachment anchor 245 of the present invention can therefore exert a greater outward force in a fully deployed state as shown in FIG. 9C than one with a shorter hinge length 415 and similar hinge width 420 and hinge radial dimension 425 and the same outward expansion force in a nondeployed state. In addition, the hinge 380 of the present attachment anchor 245 is responsible for generating the outward force, and the hinge 380 is positioned with significant circumferential direction 403. The strut 370 does not significantly contribute to generating the outward expansion force generated by the attachment anchor 245. The deployed or nondeployed attachment anchor length 395 & 400, in substantially an axial direction 398, can be smaller than other prior art or zig zag wire type attachment devices that provide similar outward expansion forces. This allows the attachment anchor 245 to form a more focused line attachment to the vessel wall consisting of a ring of small axial length in the axial direction 398 for contact between the attachment anchor 245 and the vessel wall or a focused attachment between the attachment anchor 245 and the vascular tubular member 85 that resides between the attachment anchor 245 and the blood vessel wall. Prior art zig zag wire attachment devices have a portion of the wire bent in a hair-pin turn and another portion that is not bent as significantly forming a wire strut. Prior art zig zag wire attachment devices generate a majority of their elastic outward force from the portion that is significantly bent. These prior art devices rely in part on the bending of the wire that is not significantly bent to generate the elastic force that is exerted outward against the vessel wall. These bending wires from zig zag wire attachment devices extend in significantly an axial direction 398 with a greater axial length than the struts of an embodiment of the present invention. The attachment anchor 245 of the present invention can be constructed with a smaller deployed attachment anchor length 395 than prior art devices and can be positioned closer to the renal vessels of the aorta with less chance of distal migration.

Alternately, the attachment anchor 245 of the present invention can be used with a mechanical expanding means such as the dilitation balloon of a balloon expansion catheter. The attachment anchor 245 can be forced to expand due to the dilitation balloon causing the metal located in the hinge 380 to deform plastically and hold the intravascular tubular member of the present invention or other intravascular stent-graft out against the aortic wall. The struts 370 for the balloon-expandable attachment anchor 245 do not contribute significantly to the outward expansion force generated by the hinge 380 of the attachment anchor 245. The struts 370 transfer the outward expansion force generated by the hinge 380 from one node to another to the vessel wall to hold the vessel wall outward, provide a seal, and help prevent migration of the intravascular tubular member. The hinge 380 of the attachment anchor 245 can be adjusted in hinge length 415, hinge width 420, or in hinge radial dimension 425 to provide the necessary outward forces to hold the intravascular tubular member 85 of the present invention or other prior art intravascular stent-graft outwards against the aorta.

The attachment anchor 245 of this embodiment, whether a balloon-expandable attachment anchor or a self-expandable attachment anchor, has a single ring structure formed of nodes 356 and struts 370 with the struts 370 folded back and forth adjacent to each other in the nondeployed state. The hinge length 415, width 420, and radial dimension 425 provide an expansion deformation in the uniformly curved attachment anchor surface 404 that produces an outward expansion force exerted against the vessel wall or the intravascular tubular member wall 143 in its expanded state. The struts 370 transfer the forces generated by the hinges 380 to the vessel or intravascular tubular member wall 143. The struts 370 do not deform within the uniformly curved attachment anchor surface 404 due to the larger strut width 430 in comparison to the hinge width 420. If the attachment anchor 245 is subjected to a crush deformation such that it forms an oval attachment anchor surface 453, the struts 370 will bend in a radial direction due to the relatively small strut radial dimension 435 with an elastic deformation. The strut length, width, and radial dimension all provide the strut with an ability to flex elastically during the crush deformation. The hinge will not deform in the radial direction upon exposure to a crush deformation due to the large hinge radial dimension 425 in comparison to the strut radial dimension 435. A longer strut length 390 along with a fewer number of nodes will allow the attachment anchor 245 to have a greater percentage of the attachment anchor associated with the struts 370 in comparison to the hinges 380 and hence provide the attachment anchor with a greater flexibility in bending due to a crush deformation.

Other prior art attachment means including those with zig zag designs have a long axial length to reduce the number of zig zags that are used around their circumference and hence reduce the amount of volume occupied by the attachment means per axial length times the deployed diameter. Most zig zag designs in a nondeployed state consist of a series of hair pin turns connected by straight wire segments that are generally not parallel to each other. The hair pin turns have a radius of curvature that limits the number of hair pin turns that can be used or that will fit along a circumference of an attachment means. The attachment anchor 245 of the present invention has struts 370 that are generally parallel to each other and can be in direct apposition or contact with each other in a nondeployed state (see FIG. 9A) and each hinge 380 is machined such that it is smaller in hinge length 415 than a curvature diameter for the hair pin turn for the attachment means of the prior art. The hinge length 415 can have a length of approximately twice the strut width 430.

The hinge conformation allows it to generate a larger outward force than that generated by prior art wire hair-pin turns formed with a similar curvature diameter. Therefore, many more nodes 365 of the present invention each with a hinge 380 can be placed around the circumference of the nondeployed attachment anchor 245. This greater number of nodes 365 and accompanying struts 370 allows each of the struts 370 to be shorter in length than other prior art attachment means in order to achieve a specific expansion ratio of deployed diameter 237 to nondeployed diameter 238 and a specific outward force. The presence of the hinge 380 allows the outward expansion force provided by the attachment anchor 245 within the uniformly curved attachment anchor surface 404 to be controlled by setting the hinge radial dimension 425, hinge length 415, and hinge width 420. The expansion deformation occurs with the hinges deforming within the uniformly curved attachment anchor surface 404. A higher strength metal can be used with the present hinge 380 allowing a greater outward expansion force to be exerted with a thinner hinge width 420 or with less metal volume per nondeployed hinge length 415 being used in the attachment anchor 245. This provides a smaller attachment anchor diameter in the nondeployed state which can fit into a smaller diameter sheath. This outward expansion force is controlled independently from the crush force which is controlled by the strut dimensions.

A thin strut radial dimension 435 can provide the attachment anchor 245 with a flexibility to form an oval attachment anchor surface 453 when exposed to a crush deformation by allowing the thin struts 370 to bend in the radial direction in forming an oval shape as shown in FIG. 9D. The oval attachment anchor surface 453 of FIG. 9D that is found when the attachment anchor 245 is exposed to crush deformation is not found in the uniformly curved attachment anchor surface 404 which is maintained in a cylindrical shape during normal expansion deformation of the attachment anchor 245. The result is that the attachment anchor 245 can fit into a small diameter delivery sheath 225 in its nondeployed or nonexpanded state yet has high expansion force and is flexible in crush deformation. This combination of properties is not possible with the round wire zig zag or other attachment means described in the prior art in which the expansion force and crush force of the attachment device are tied together. Alternately, it is further understood that the strut radial dimension 435 can be formed large enough such that the struts 370 will not flex easily if exposed to a crush deformation. In this case the attachment anchor will retain a substantially cylindrical shape with a uniformly curved attachment anchor surface 404 and will be resistant to forming an oval shape characteristic of crush deformation. The strut deformation due to crush is always an elastic deformation and is more easily deformed than the hinge in a radial direction.

The short attachment anchor length with a greater number of nodes 365, and struts 370 allows the attachment anchor 245 to be placed such that it is more firmly anchored into healthy blood vessel with a more focal line of attachment to the vessel. For the example of the abdominal aortic aneurysm 5, the attachment anchor 245 can be placed closer to the aortic neck and nearest to the renal arteries 45 & 50 in order to get a more firm anchoring into the aortic wall 70 and not into the thrombus 60 that lines the native lumen 53 for most of the lumen of the abdominal aorta 10 (see FIGS. 1A and 1B). The shorter length also provides an advantage for forming a better seal of the intravascular tubular member with the vessel wall. The shorter length and increased number of nodes 365 further allows more barbs 250 to be placed along the circumference of the attachment anchor 245. This increase in number of barbs 250 (see FIGS. 3 and 5) provides better attachment at an increased number of sites. The result is an increased ability to form a leak free seal between the native blood vessel and the inlet end 145 or outlet end 148 of any intravascular tubular member or other stent-graft device. Furthermore, the attachment anchor 245 with short length and with the increase number of barbs 250 is more likely to provide an intravascular tubular member or other stent-graft device of any type a greater resistance to distal migration.

For a self-expandable attachment anchor 245 an increase in hinge width 420 or hinge radial dimension 425 will increase the amount of outward force provided by the attachment anchor 245 for the same deployment angle 405 or amount of expansion deformation. Increasing the hinge length 415 will result in a smaller drop-off in outward force provided by the attachment anchor 245 as it expands from a nondeployed state to a deployed state. Therefore, by changing the dimensions of the hinge 380, the outward force delivery characteristics of the attachment anchor 245 can be adjusted to provide the desired outward elastic expansion force. The strut width 430 and strut radial dimension 435 can be adjusted to provide struts 370 that will remain elastic during the expansion of the attachment anchor 245 or during crush deformation with greater flexibility due to bending to an arc with the radius of curvature in the direction of the smaller strut radial dimension 435 and more rigidity in the direction of bending of the larger strut width 430. The small strut radial dimension 435 allows the attachment anchor 245 to be soft and pliable in a crushing type of deformation while maintaining a large expansion force in the circumferential direction 403 needed to hold the blood vessel outward with appropriate force and without leakage between the intravascular tubular member 85 and the vessel wall.

For a balloon-expandable attachment anchor 245 the dimensions of the hinge 380 can affect its ability to yield under the expansion force of the dilitation balloon and its ability not to yield under the forces applied to it by the aorta. Increasing the hinge width 420 and hinge radial dimension 425 will increase the amount of yield force that is required to expand the attachment anchor 245 from a nondeployed state to a deployed state; it will also increase the amount of yield force that must be exceeded for the aorta to collapse the attachment anchor 245. Increasing the hinge width will reduce the amount of deployment angle 405 that is required before plastic deformation will occur and the hinge 380 will no longer return to its original position or equilibrium position with all external forces removed. Reducing the hinge length 415 will cause the metal in the hinge 380 to deform a greater extent during the expansion from the nondeployed state to the deployed state. The hinge 380 with a smaller hinge length 415 will have a greater tendency to undergo a plastic deformation for a smaller expansion deformation. The struts 370 for the balloon-expandable attachment anchor 245 also remain elastic during the expansion deformation as well as during crush deformation.

An increase in strut length 390 also increases the flexibility of the attachment anchor 245 in undergoing a crush deformation to an oval shape. Since the struts 370 are smaller in the radial dimension 435 than the hinge 425 or the transition region 445, the struts bend more easily in the radial direction. Increasing the length 390 of the struts 370 provides a greater percentage of the attachment anchor 245 that is associated with the struts 370 in comparison with hinges 380 or transition regions 410 and therefore provides a greater flexibility in the radial direction during crush deformation.

Figure 10A:
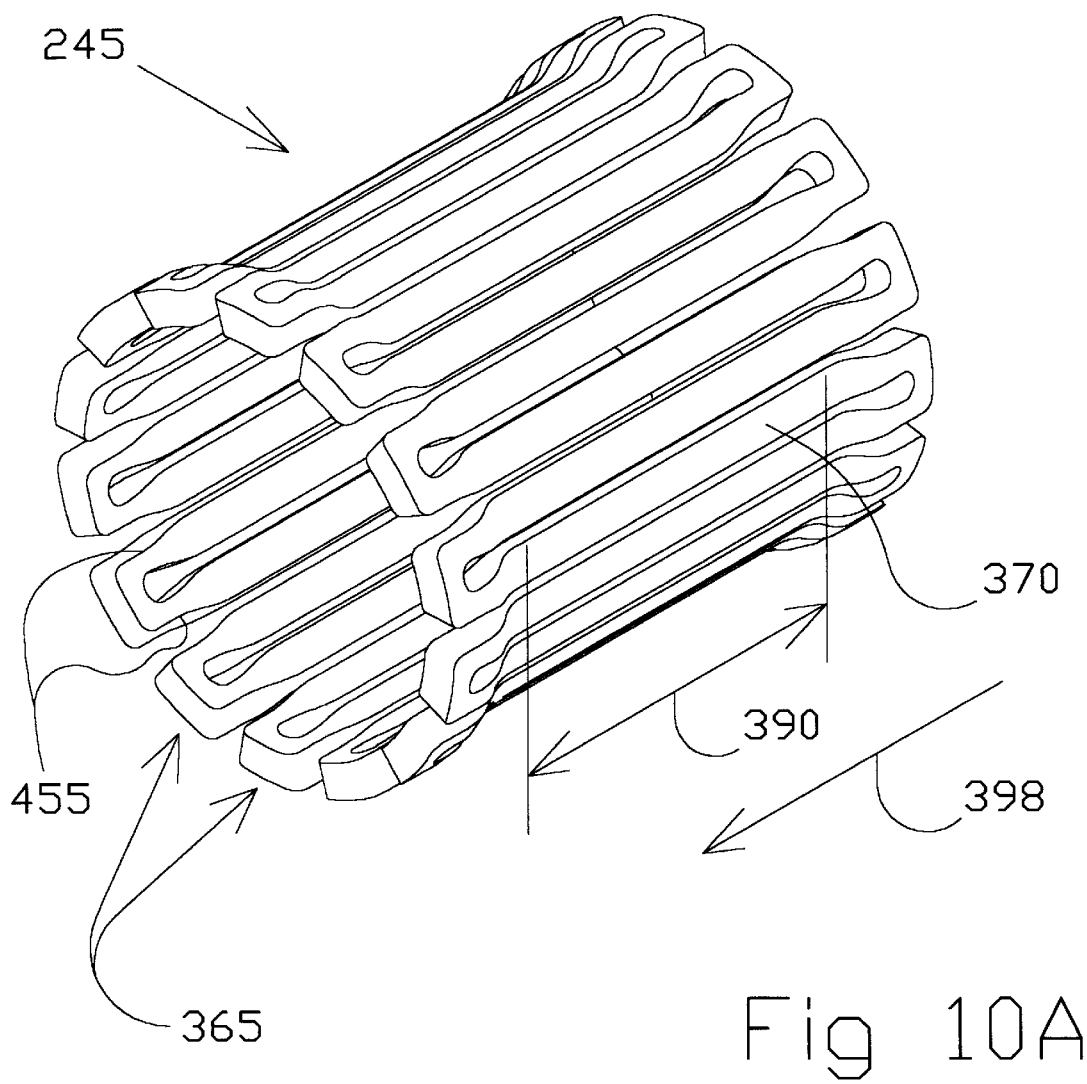
FIG. 10A is an isometric view of an attachment anchor with two hinges per node in a nondeployed state.
Figure 10C:
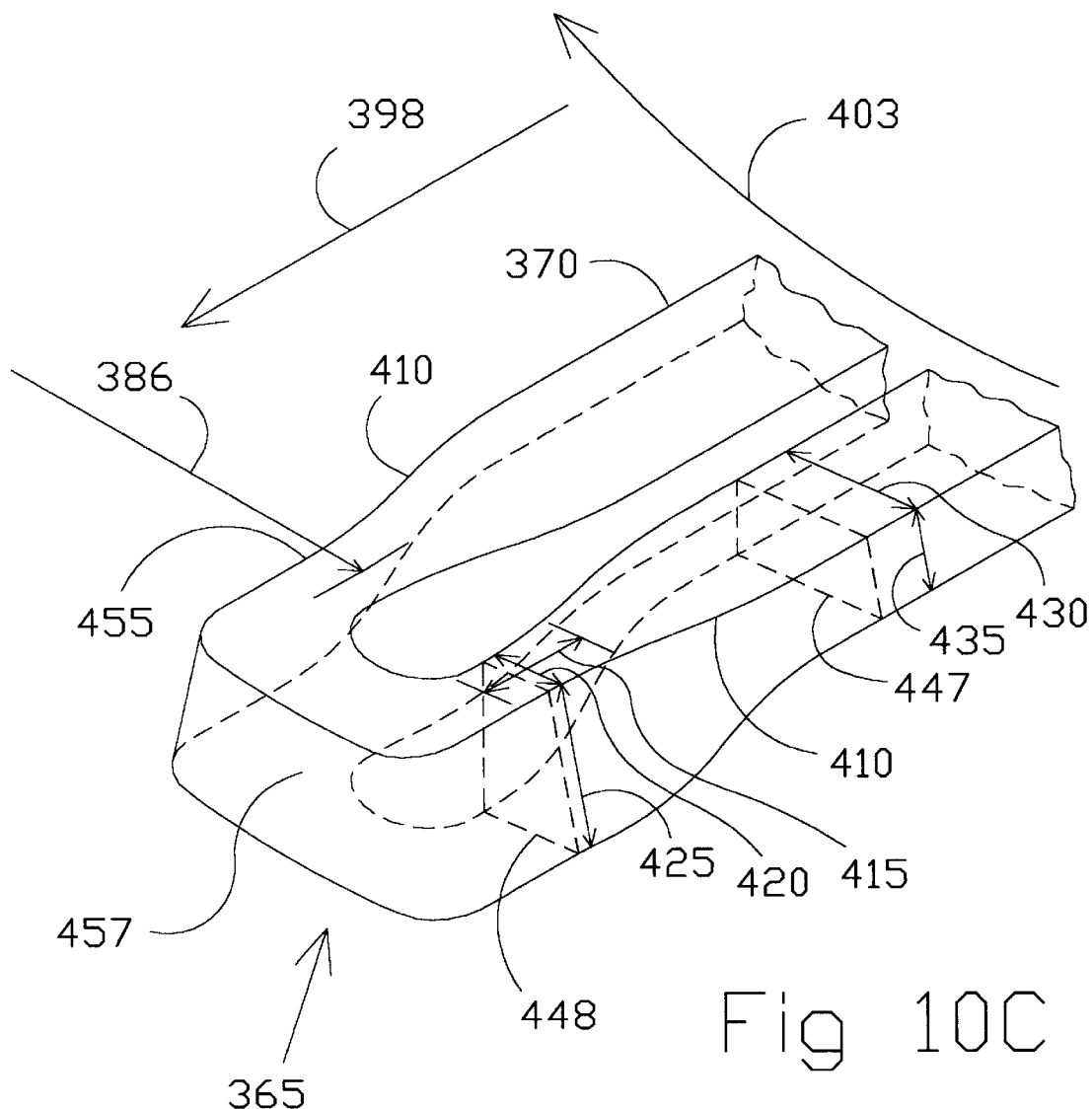
FIG. 10C is an enlarged detailed isometric view of a node of an attachment anchor with two hinges.

An alternate embodiment for the attachment anchor 245 is shown in FIGS. 10A and 10B. FIG. 10A shows the attachment anchor 245 in a nondeployed state with the attachment anchor 245 not expanded. FIG. 10B shows the attachment anchor 245 after it has been expanded to a deployed state. The main difference between this embodiment and the one presented in FIG. 9A–9C is the shape of the nodes 365 and the presence of two hinges 455 on each of the nodes 365. The nodes 365 and struts 370 are aligned in series in the same way as the embodiment shown in FIGS. 9A–9C. Each node 365 of this embodiment is joined to two struts 370 and each strut 370 is joined to two nodes 365 in a manner similar to that shown for the embodiment of FIGS. 9A–9C. All reference numerals correspond to those elements previously or otherwise described. A detailed isometric view of one of the nodes 365 plus a portion of two struts 370 is shown in FIG. 10C. Each of the nodes 365 is comprised of a hub 457, two hinges 455, and two transition regions 410. The hub 457 provides a less flexible portion of each node 365 to which the two more flexible hinges 455 can be joined. Deformation is substantially less or absent from the hub 457. The transition regions 410 are similar in design and function to the transition regions 410 described in FIG. 9C. The two hinges 455 perform a similar function as the single hinge 380 described in FIG. 9C. Each of the hinges 455 has a smaller hinge width 420 and a longer hinge radial dimension 425 in comparison to the larger strut width 430 and shorter strut radial dimension 435, respectively. The length of the transition region 410 is abrupt or short to conserve length that can be used as length for the struts 370 or the hinge 380.

For a self-expandable attachment anchor 245 each of the hinges 455 is designed to deform elastically during the expansion of the attachment anchor 245 from a nondeployed state to a deployed state. A metal of very high yield strength and high elastic modulus can be used for the attachment anchor 245 of the present invention. A higher strength metal provides the attachment anchor 245 of the present invention with an ability to have all components or elements have a smaller radial dimension than other prior art attachment devices. Increasing the hinge radial dimension 425 and the hinge width 420 will provide an increase in the outward elastic expansion force provided by the attachment anchor 245 in holding the intravascular tubular member 85 of the present invention or other intravascular stent-graft against the aorta. Reducing the hinge length 415 will provide a larger outward force of the attachment anchor 245 against the vessel wall in the deployed state with a specific deployment angle 405 and provided that the hinge radial dimension 425 and hinge width 420 remain constant for comparison purposes. The hinge length 415 defines the region of the nodes 365 wherein the majority of the expansion deformation occurs. The hinge length 415 includes the region of each node 365 having a smaller hinge width 420 than the strut width 430 and that remains approximately constant in strut width 430 for a distance. The hinge length 415 can include a region of a minimum hinge width 420. The hinge length 415 can be long such as the case shown in FIG. 9C or it can be very short as the case shown in FIG. 10C. With two hinges 455 associated with each of the nodes 365 it is possible to provide each of the hinges 455 of each of the nodes 365 with different dimensions and different expansion characteristics. The hub 457 can provide a site for forming a contiguous junction to a barb 250. The two hinges 455 shown in FIG. 10C can be easier to machine than a single hinge 380 as shown in FIG. 9C.

For a balloon-expandable attachment anchor 245 an increase in the hinge radial dimension 425 will cause an increase in the yield force needed by a dilitation balloon to cause the attachment anchor 245 to expand and will increase the yield force necessary to cause collapse of the attachment anchor 245 due to compressive forces applied by the abdominal aorta or other treated artery on the deployed attachment anchor 245. An increase in the hinge width 420 will cause the expansion deformation from a nondeployed state to a deployed state to cause more plastic deformation of the metal hinges 455 for a specific deployment angle 405 and will require a larger expansion deformation force. Increasing the hinge length 415 will reduce the amount of plastic deformation and reduce the rate of change in force for a particular expansion deformation or deployment angle 405. Adjusting the hinge length 415, hinge width 420, and hinge radial dimension 425 allows the balloon-expandable attachment anchor 245 to be specifically designed to provide appropriate yield forces for a specific vascular application. This is not able to be accomplished with the wire zig zag or other attachment devices described by the prior art.

Stress versus Strain

The stress versus strain relationship for a metal bar or beam such as a strut 370 or a hinge 380 & 455 can in general be estimated by Hooke's law which states that stress applied to the metal bar is equal to an elastic modulus times the strain or deformation to which the bar will deform. This elastic modulus or Young's modulus is a material property characteristic of the particular metal being used for the bar. The deformation can be a bending deformation that is characteristic of the expansion deformation encountered by the strut 370 or the hinge 380 & 455. A bar in an unstressed state that is exposed to an applied stress below its elastic limit or yield stress will undergo an elastic flexure or elastic deformation which is reversible and the bar will return to its unstressed state upon removal of the applied stress. If the bar is exposed to an applied stress that is larger than its yield stress or if it is deformed to an inelastic flexure that is greater than its elastic limit or proportional limit, or if it is deformed beyond its yield point, plastic deformation will occur and the bar will not return to its original unstressed state with the original conformation or shape of the bar. The bar will generally return part way back to its initial unstressed state due to the elastic portion of the deformation.

Exposing a bar to a torque or moment can result in bending the bar from a straight shape to a bent conformation with a radius of curvature. The relationship between the applied moment and the radius of curvature can be estimated by the equation that states that moment is equal to Young's modulus times moment of inertia divided by radius of curvature. The moment of inertia is different for different cross sectional shapes of the bar that is being bent. For a bar having a circular cross section and having a diameter, the moment of inertia is given by Pi times the diameter to the fourth power divided by 64. For a rectangular bar cross section with one side of magnitude B and another side of magnitude H, where B is the magnitude of the side in the radial direction of the radius of curvature and H is the magnitude of the side perpendicular to B, the moment of inertia is given by B to the third power times H divided by 12. Similarly, the bar can be bent from one radius of curvature to a second radius of curvature with a similar type of analysis as described above by examining a change in radius of curvature that is comparable to that starting from a flat surface as just described.

The hinge cross sectional area 448 is equal to the multiplication product of the hinge width 420 and the hinge radial dimension 425. Each hinge 380 & 455 has a large hinge radial dimension 425 that does not allow for significant bending deformation along a radius of curvature with a radius aligned along the hinge radial dimension. Bending deformation for each hinge 380 & 455 occurs to form a radius of curvature with the radius aligned with the hinge width 420, and this radius of curvature is referred to as the hinge width radius of curvature 386. The hinge can undergo an expansion deformation with bending occurring in the uniformly curved attachment anchor surface 404. The moment of inertia for the hinge 380 & 455 can be estimated by using the hinge width 420 to correspond with the magnitude B and the hinge radial dimension 425 to correspond with the magnitude H. The strut cross sectional area 447 is equal to the multiplication product of the strut width 430 and the strut radial dimension 435. The moment of inertia for each of the struts 370 can be estimated using the strut radial dimension 435 to correspond with the magnitude B and the strut width 430 to correspond with the magnitude H. In the attachment anchor 245 of the present invention the hinge cross sectional area 448 can be varied independently of the strut cross sectional area 447 to provide the attachment anchor 245 with a variety of expansion force characteristics and other properties. For example, the hinge width 420 and hinge radial dimension 425 can be equal to the diameter of a round wire and produce a moment that is 1.67 times larger than the round wire based on the equation for moment stated earlier. Thus for a similar magnitude of hinge width in comparison to the diameter of a round wire, the attachment anchor 245 in a nondeployed state can provide a greater outward extension force by the hinge 380 & 455 to the struts 370 than a circular cross sectional or round wire. The hinge radial dimension 425 can also be increased in magnitude to provide an even greater moment of inertia to the hinge 380 & 455 such that even larger moment is generated to produce larger extensional forces by the attachment anchor 245. Increasing the hinge radial dimension 425 such that it is significantly larger than the hinge width 420 will also have a profound effect on increasing the moment of inertia for bending to a radius of curvature with the radius in the radial direction. Hence the hinges 380 will not allow bending to occur in the radial direction such as found in the struts 370 in forming an oval shape during crush deformation.

As another embodiment for the design of the attachment anchor 245, the hinge radial dimension 425 can be formed such that it is approximately equal to the diameter of a prior art zig zag wire that is used as an attachment means and the hinge width 420 can be smaller that the diameter of the zig zag wire. In this embodiment the hinge 380 & 455 would undergo a smaller amount of localized deformation associated with a bend to a specific radius of curvature than the zig zag wire. The attachment anchor 245 could be formed out of a metal with a higher elastic modulus than the prior art zig zag wire attachment means without undergoing plastic deformation. The hinge 380 & 455 of the present attachment anchor 245 can thus produce an equal or greater moment than a round wire with a diameter larger than the hinge width 420 and remain elastic. This embodiment is particularly useful for a self expanding attachment anchor 245.

For a balloon-expandable attachment anchor 245 the hinge length 415 can be shortened such that the bending deformation of the hinge 380 & 455 associated with expansion from the nondeployed state to the deployed state exceeds the yield point of the metal used to form the attachment anchor 245. For a bending deformation of the hinge 380 & 455 from one hinge width radius of curvature 386 to another hinge width radius of curvature 386, an increase in the hinge width 420 will also serve to increase the amount of hinge 380 & 455 material exposed to deformation beyond the yield point of the metal. Hence both hinge length 415 and hinge width 420 can be adjusted to provide inelastic flexure of the metal and plastic deformation. The hinge radial dimension 425 can be further adjusted to control the amount of force that is required to expand the attachment anchor 245 to a particular amount of deformation during deployment of the attachment anchor 245 and to control the amount of force exerted by the attachment anchor 245 against the vessel wall in its deployed attachment anchor diameter 320.

The strut cross sectional area 447 can be different than the hinge cross sectional area 448 and can be varied independently from it. The strut width 430 is designed to be large enough such that during expansion of the attachment anchor 245 the struts 370 do not bend or flex significantly within the uniformly curved attachment anchor surface 404 of the attachment anchor 245 with a radius of curvature in a radial direction aligned with the strut width 430. The hinge 380 & 455 can therefore transfer its moment to the strut 370 which then exerts an outward force upon the vessel wall to hold it outwards. Since the strut width 430 and strut radial dimension 435 provide a rectangular cross sectional shape for the strut 370 the strut width 430 can be smaller than the diameter of a round wire and provide a greater moment in resisting bending deformation to a radius of curvature with a radius in the direction of the strut width 430. The struts 370 will not bend in within the uniformly curved attachment anchor surface 404 such as in the direction of their strut width 430.

The strut radial dimension 435 is formed to be thinner than the hinge radial dimension 425 such that it can flex to form a radius of curvature with a radius aligned with the strut radial dimension 435; this bending deformation is similar to a crush deformation that would cause the attachment anchor 245 to form an oval attachment anchor surface 453 rather than the cylindrical uniformly curved attachment anchor surface 404 that it normally has. The struts 370 would remain elastic due to its thin wall, due to a choice of metal such that the struts 370 do not exceed the elastic limit of the metal, and due to a longer strut length that distributes the bending along a longer length. The metal chosen for forming the attachment anchor 245 could be chosen from a high modulus material and still remain flexible to allow this bending deformation to form an oval shape due to the thin radial dimension. The prior art attachment means formed of a round wire or other prior art structures of high modulus could not provide a combination of a large outward extension force and a low or soft crushing force since the properties of the round wire or other prior art structures affect both the extension force and the crush force. With this embodiment of the present invention, an attachment anchor 245 could be formed entirely out of a high modulus metal with the hinge 380 & 455 providing a large moment for expansion deformation in the uniformly curved attachment anchor surface 404 and the strut 370 allowing the attachment anchor 245 to be bent to an oval shape to accommodate variations in the shape of the aorta or other blood vessel. The hinge 380 & 455 does not allow bending in the radial direction due to crush deformation forces and the strut 370 does not bend in the uniformly curved attachment anchor surface 404.

The struts 370 can be increased in their radial dimension 435 to provide additional resistance to bending in crush deformation. The strut radial dimension is still maintained smaller than the hinge radial dimension 425 and smaller than the strut width 430. The strut radial dimension 435 is not as large as the hinge radial dimension 425 such that the strut always flexes preferentially to the hinge in a crush deformation and the strut 370 is designed to flex elastically. The strut cross sectional area 447 has been altered independently of the hinge cross sectional area 448. An increase in strut radial dimension 435 will provide the strut 370 with a resistance to additional bending to a radius of curvature with a radius aligned with the direction of the strut radial dimension 435. This embodiment of the attachment anchor 245 will be resistant to crush deformation that would cause the attachment anchor 245 to form an oval shape. The strut radial dimension 435 is still less than the hinge radial dimension 425 and the strut remains elastic when exposed to crush deformation.

The strut length 390 for the attachment anchor 245 of the present invention can be small and thereby require a greater number of struts 370 with smaller strut length 390 in order to extend and provide contact with the vessel wall with an adequate outward expansion force. The increased number of struts 370 and shorter strut length 390 provides a more focused line of attachment of the attachment anchor 245 to the blood vessel wall. In the case of abdominal aortic aneurysm repair, the attachment anchor 245 can be placed closer to the renal arteries with a better attachment to the vessel wall proximal to the thrombus lining. In an expanded state of the attachment anchor 245, the moment exerted by each hinge 380 & 455 is transmitted to a torque exerted by the strut 370 outward against the vessel wall. This outward torque can be resolved into a product of the outward force against the vessel wall and the strut length 390. The hinge 380 & 455 can therefore transfer its moment to the strut 370 which then exerts an outward force upon the vessel wall to hold it outwards.

The present attachment anchor 245 can be optimally suited to provide a smaller strut length 390 and a greater number of struts 370 and nodes 365 in order to apply a specific outward force against the vessel or tubular member wall for a nondeployed attachment anchor perimeter 449 and a deployed attachment anchor perimeter 451. Strut length has an effect upon the flexibility characteristics of the attachment anchor in a crush deformation mode. A longer strut length provides the attachment anchor with a greater percentage of the perimeter of the attachment anchor in a deployed state that is associated with the struts in comparison to the nodes. Since the struts are more flexible in a crush deformation than the nodes, longer strut length provides a greater flexibility in forming an oval shape. To provide an attachment anchor having longer strut length with the same crush flexibility as a shorter strut, the strut radial dimension would be increased to provide the appropriate bending moment in the radial direction. The strut width can be reduced to provide the appropriate resistance to bending in the attachment anchor surface during expansion deformation. The attachment anchor 245 has nodes with hinges 380 & 455 that are machined into the metal rather than having a wire formed into a loop such as found in prior art attachment means. Each hinge 380 & 455 can be machined with a smaller hinge width radius of curvature 386 than can be formed from a round wire of diameter similar in magnitude to the hinge width 420. Furthermore the hinge 380 & 455 of the present invention can generate a greater moment than can be generated by a round wire as found in prior art attachment means. The struts 370 are similarly formed by machining to form struts 370 of approximately similar or smaller strut width 430 than the diameter of a round wire of similar strength or moment of inertia allowing the struts 370 to be aligned adjacent to each other or touching each other and parallel to each other in a close packed conformation in a nondeployed state. In a deployed state the present attachment anchor 245 can provide a greater outward force against the vessel wall due to the greater moment generated by each hinge 380 & 455. The present attachment anchor 245 can be formed with a nondeployed attachment anchor length 400 that is less than appoximately 0.20 to 0.30 inches for abdominal aortic aneurysm repair of an aorta with a deployed diameter 237 of approximately 25 millimeters and less than approximately 0.10 to 0.20 inches for an attachment anchor length 400 in vessels that are less than approximately 6 millimeters in diameter. The number of struts 370 along the deployed attachment anchor perimeter 451 of the attachment anchor 245 can be at least approximately 26 to 32 for abdominal aortic aneurysm repair of an aorta with a 25 millimeter diameter and at least approximately 14 to 20 for use in a vessel of approximately 6 millimeter diameter.

Alternately, the attachment anchor 245 of the present invention can be formed of large strut length 390 greater than approximately 0.3 inches, a thinner strut width 430, and a larger strut radial dimension 435 and having a lesser number of struts 370 than the approximately 14 struts stated for the previous embodiment. The attachment anchor 245 of the present invention can be formed with any number of struts 370 and with any strut length 390 that is suited to a particular application. The hinge 380 & 455 of the present invention can provide a greater moment than the moment provided by prior art round wire zig zag attachment means and other prior art attachment means. Therefore the hinge 380 & 455 of the present invention can transfer a large torque to a strut 370 of larger strut length 390 than the length of other prior art round wire struts and provide a greater outward force against the blood vessel to hold it outward than a round wire attachment means. The attachment anchor 245 of the present invention can therefore be used to provide a short or a long strut length 390 with varying strut radial dimensions and strut widths. The number of struts 370 can similarly be varied such that an attachment anchor 245 with longer struts 370 can be formed with less struts 370 than other prior art attachment means.

The deployment angle 405 of the present attachment anchor 245 is generally intended to be small enough such that the change in nondeployed attachment anchor length 400 in a nondeployed state to a deployed attachment anchor length 395 in a deployed state does not affect the positioning of the attachment anchor 245 within the blood vessel prior to deploying it to a deployed state. A total deployment angle 405 of less than 60 degrees results in a change in the attachment anchor length from the nondeployed state to the deployed state of approximately 15 percent. The present attachment anchor 245 can be designed such that the hinge 380 & 455 will provide any deployment angle 405 from 1 to 80 degrees. To maintain a small change in attachment anchor length from a nondeployed state to a deployed state a deployed angle of less than 45 degrees can be attained by the present attachment anchor 245. Alternately, in order to provide the attachment anchor 245 with the least number of nodes 365 and struts 370 while still providing for the greatest expanded deployed attachment anchor diameter 320, it is desirable to provide a deployment angle 405 that is greater than 45 degrees. The hinge 380 & 455 of the present invention can be formed from a metal of large Young's modulus as stated earlier. The hinge 380 & 455 can be formed of a thin hinge width 420 and a long hinge length 415 such that the moment maintained by the hinge 380 & 455 will still be adequate even at a large bending deformation angle or deployment angle 405. Thus the hinge 380 & 455 of the present invention can supply adequate outward force at a deployment angle 405 greater than 45 degrees and up to 180 degrees.

The attachment anchor 245 of the present invention can have one or two hinges 455 positioned on each node 365. For the embodiment with two hinges 455, the hinges 455 can be equivalent to each other in dimension and perform similarly to having one larger hinge such as a single hinge 380 of another embodiment. Alternately, each hinge 455 on a particular node can be formed with a different hinge length 415 or hinge width 420 than the other. The moment that is generated by each hinge 455 after exposure to a similar bending deformation would therefore be different. The struts 370 joined via transition regions to each of the hinges 455 can be adjusted such that the strut lengths 390 are different. This embodiment of an attachment anchor 245 with struts 370 of different strut length 390 connected to the same node can apply a uniform force outward against the blood vessel wall although the longer strut could undergo a greater amount of bending deformation in a crush mode.

Figure 10D:
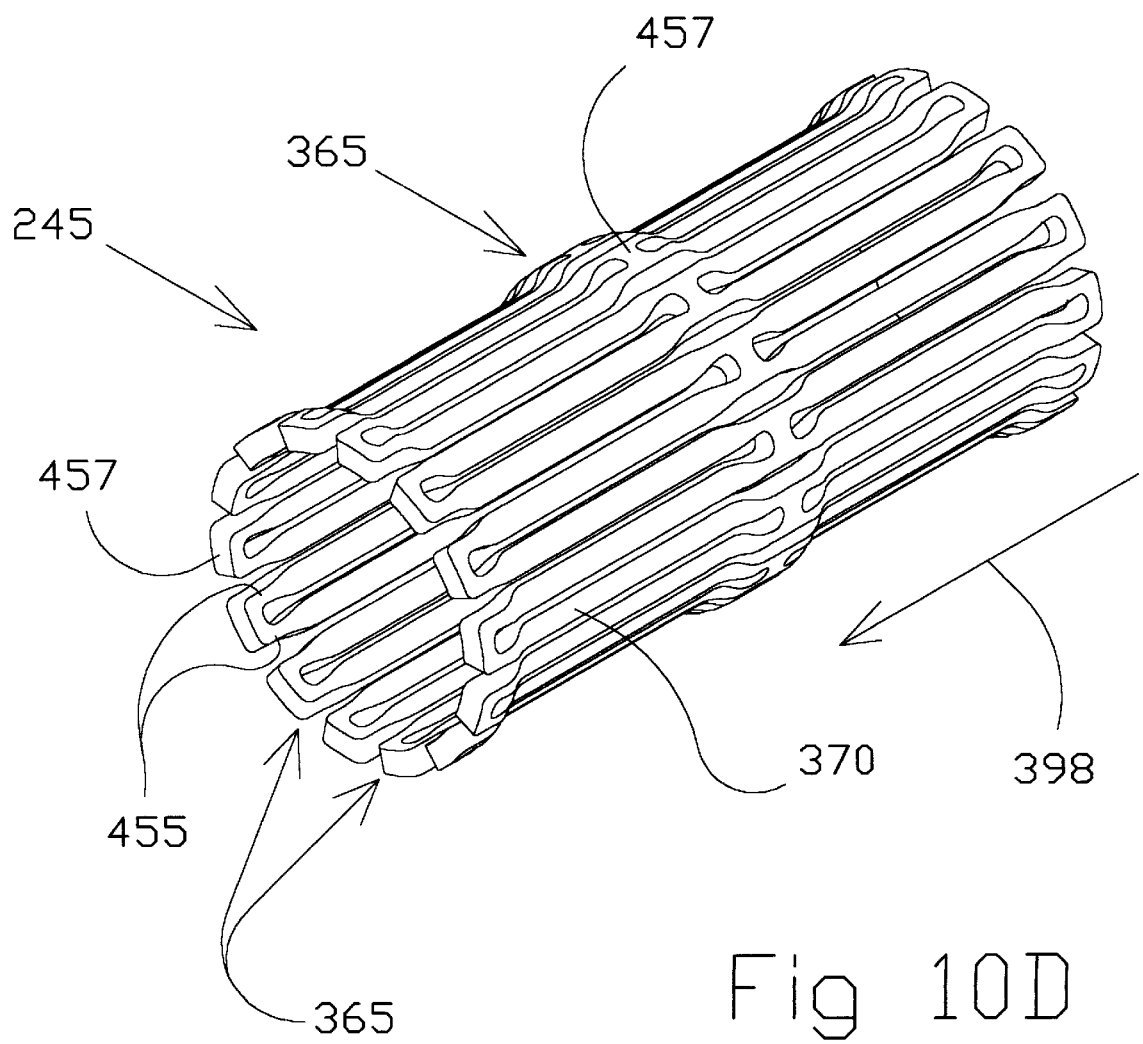
FIG. 10D is a perspective view of an attachment anchor with nodes and struts in a closed configuration in a nondeployed state.
Figure 10E:
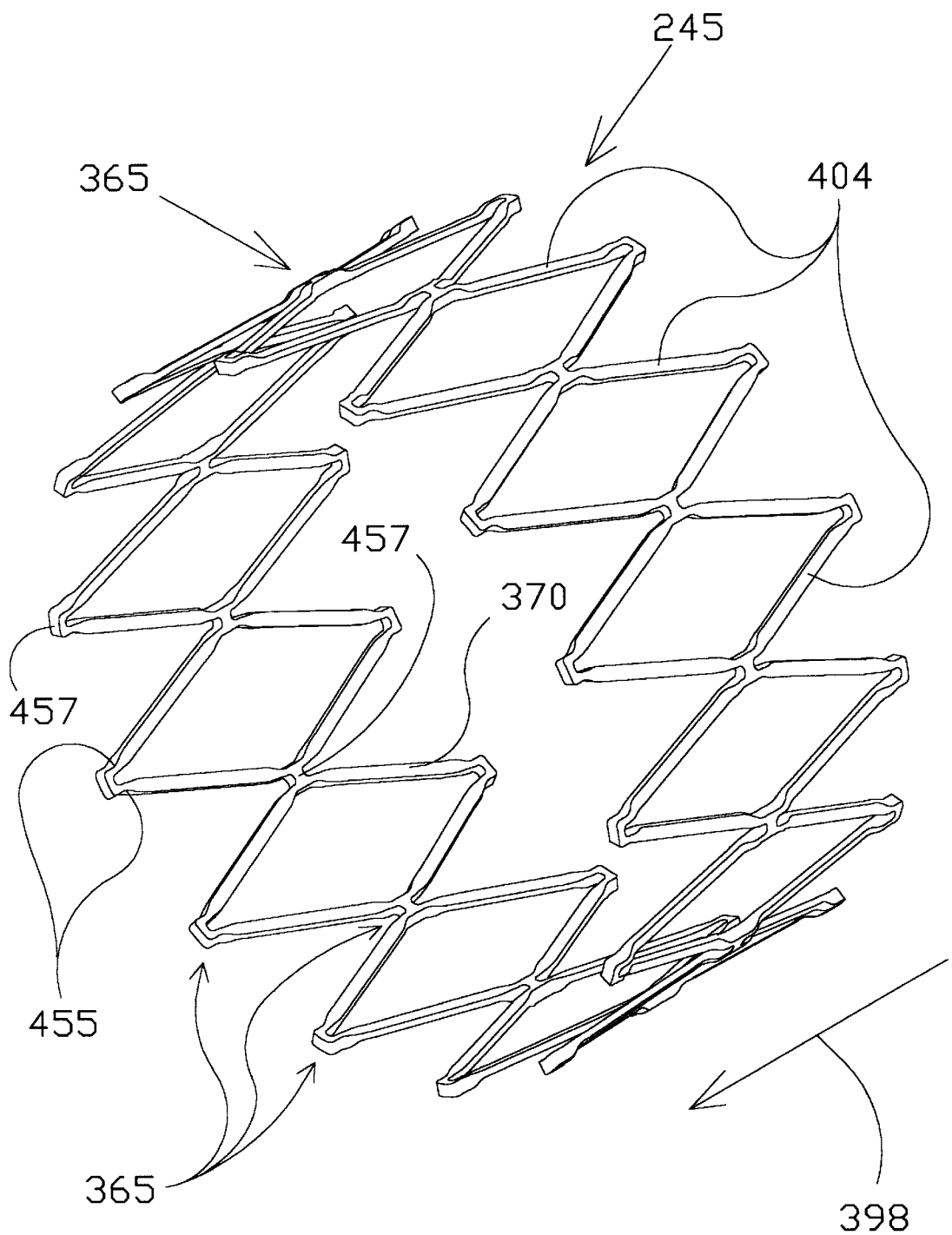
FIG. 10E is a perspective view of an attachment anchor with nodes and struts in a closed configuration in a deployed state.

An alternate embodiment for the attachment anchor 245 of the present invention is shown in a nondeployed state in FIG. 10D and in a deployed state in FIG. 10E. The attachment anchor 245 is formed entirely out of nodes 365 and struts 370 arranged to form a ring with a cylindrical shape. The attachment anchor 245 of this embodiment has a uniformly curved attachment anchor surface 404 in its deployed state shown in FIG. 10D. The attachment anchor 245 of this embodiment has the same description and function for the hinges 455, hubs 457, and struts 370 as were described and shown in FIGS. 10A–10C. The hinges 455 have hinge dimensions that allow the hinges to undergo expansion deformation within the uniformly curved attachment anchor surface 404 but will not deform in a radial direction due to a crush deformation. The struts 370 have strut dimensions that allow them to bend elastically as the attachment anchor 245 bends to an oval shape during crush deformation but the struts 370 will not bend in the uniformly curved attachment anchor surface 404. Barbs 250 can be a component of any of the nodes 365 in a manner described for the embodiment shown in FIGS. 10A–10C. This embodiment can be a balloon-expandable or a self-expandable attachment anchor 245. The metal used to form the attachment anchor 245 along with the dimensions used for the hinge 455 determine whether a plastic deformation or an elastic deformation of the hinge 455 will occur during the expansion deformation from a nondeployed state to a deployed state as described earlier for the embodiment shown in FIGS. 10A–10C. This embodiment (see FIGS. 10D and 10E) of the attachment anchor 245 provides an improved stability in maintaining a cylindrical shape over the embodiment shown in FIG. 10A–10C due to the closed diamond shaped structure or closed configuration formed by the nodes 365 and struts 370 of the present embodiment in comparison to the series alignment of nodes and struts shown in the embodiment of FIGS. 10A–10C. All reference numerals correspond to those elements previously or otherwise described.

Attachment Anchor with Barbs

Figure 11A:
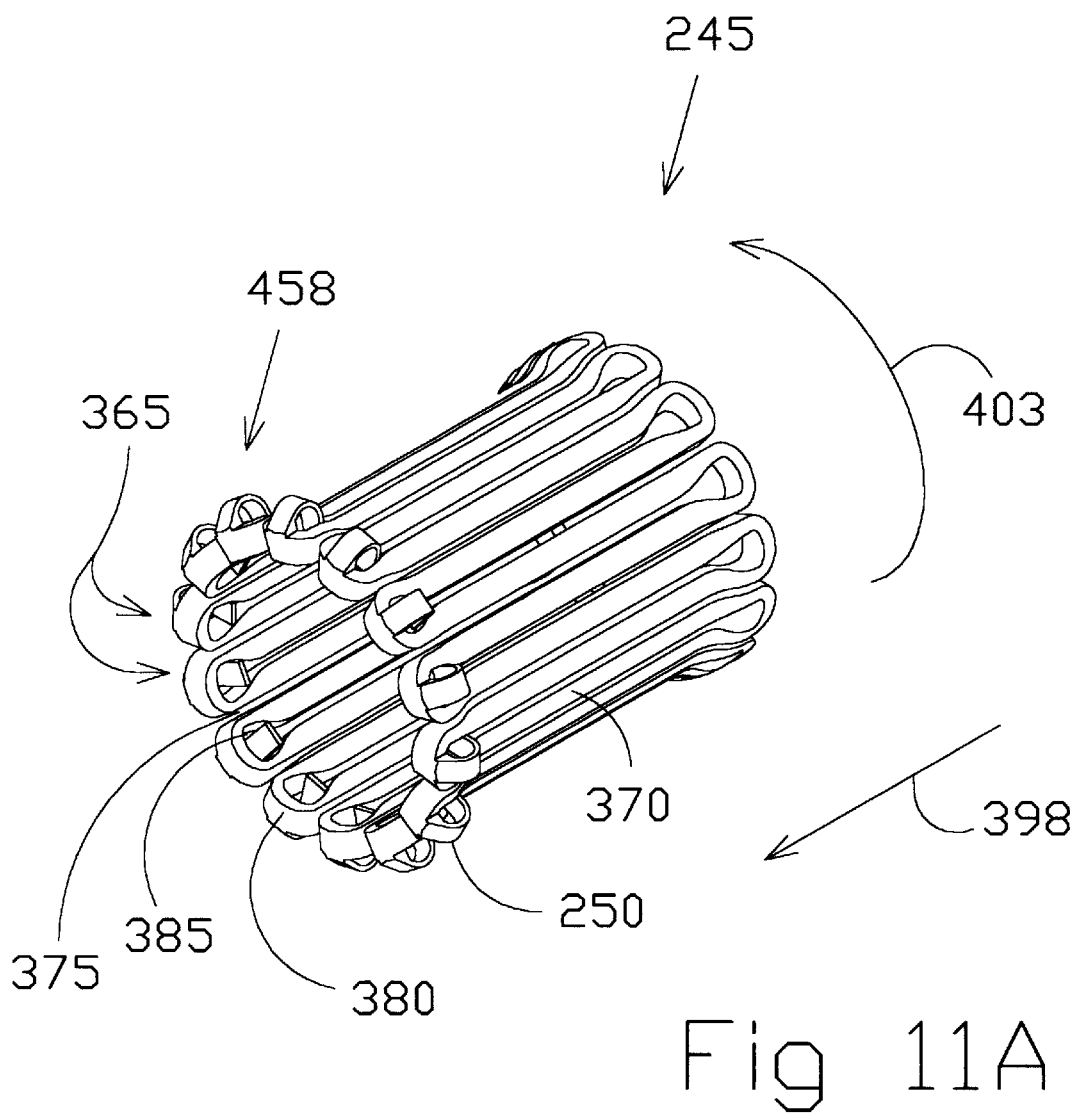
FIG. 11A is an isometric view of an attachment anchor with barbs in a nondeployed state.
Figure 11D:
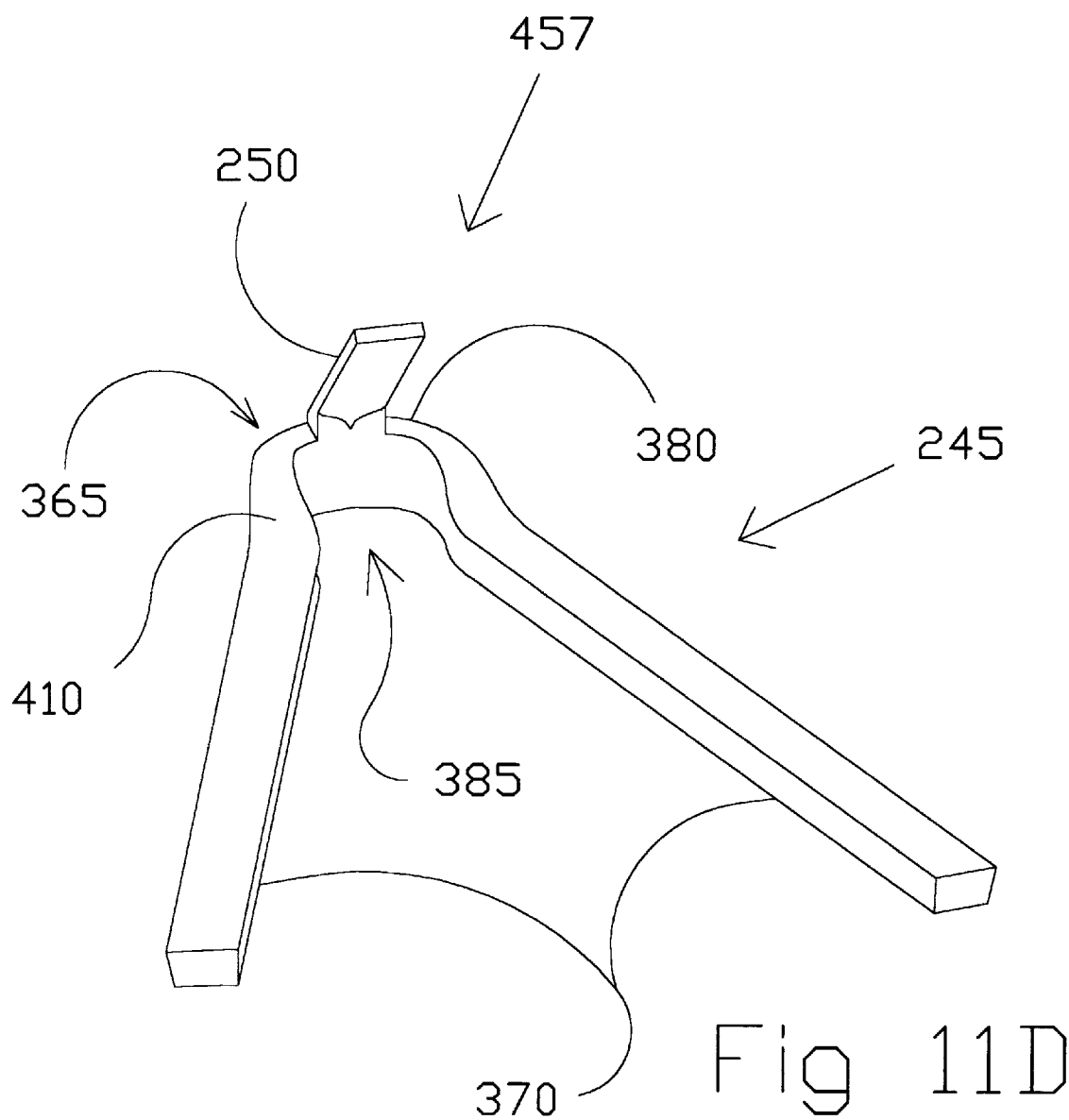
FIG. 11D is an enlarged view of a portion of an attachment anchor with barbs in a deployed state.

FIGS. 11A–11D shows another embodiment for the attachment anchor 245 of the present invention with barbs 250 joined to nodes 365 along an attachment anchor outside end 458. The node 365 of this embodiment as shown in FIGS. 11B and 11D include the hinge 380, the transition regions 410, and the barb 250. The barbs 250 can be contiguously joined to any portion of a node 365 including a hub 457 or a hinge 380 & 455. FIG. 11A shows the attachment anchor 245 of this embodiment in a nondeployed state or an insertion state. An isometric view of a portion of the attachment anchor 245 shown in FIG. 11A in a nondeployed state is shown in FIG. 11B. The barb 250 has been folded over into the intranodal opening 385 and is being held in a protected conformation by the struts 370 and the transition regions 410. FIG. 11C shows the attachment anchor 245 in a deployed or implanted state with barbs 250 extending outward to the side. An isometric view of a portion of the attachment anchor 245 shown in FIG. 11C is shown in FIG. 11D. As the struts 370 expanded during the deployment of the attachment anchor 245, they released the barb 250 allowing the barb 250 to extend outwards in its fully extended state. The barbs 250 of the present attachment anchor 245 are folded and protected when the attachment anchor 245 is in a nondeployed state. As the attachment anchor is expanded, the barbs 250 are completely released by the struts 370 such that they extend outward to their fullest extent. This is in contrast to the barbs of other prior art attachment means that are deployed an increasing amount as the attachment means is extended to a greater amount. The barbs 250 of the present invention are designed to deploy fully and extend outward once the attachment anchor 245 has been extended enough such that the struts 370 allow the barbs 250 to be released from its folded position as shown in FIG. 11B. When the attachment anchor 245 is expanded by either allowing it to self-expand or through expansion with a dilitation balloon, each of the barbs 250 is released by the struts 370 and transition regions 410 and the intranodal opening 385 and allowed to extend outwards. The barbs 250 provide anchoring of the attachment anchor 245 and the intravascular tubular member 85 of the present invention or other intravascular stent-graft to the aortic vessel wall or other arterial wall. Such anchoring can help to prevent migration of the intravascular tubular member and help to prevent further aneurysmal dilitation of the aorta. In a nondeployed state the barbs 250 are folded up such that they cannot catch or snag on the intravascular tubular member 85 or other intravascular stent-graft device or tissue components. The barbs 250 can be machined using mechanical, laser, electrochemical, or other machining techniques as described for machining the attachment anchor into the same metal tube that forms the attachment anchor 245. The barbs 250 can be machined such that they are continuous and contiguous with each node 365 without the need for an attachment of the barbs 250 to the nodes 365. The barbs 250 can be contiguous with the hinges 380 or with the hubs 454 if such hubs are present on the node. Each barb 250 is considered to be a component of the node 365. The strength of the barbs 250 is therefore increased and their resistance to stress cracking or fracture will be reduced. Attachment wires or barbs used in other prior art attachment devices have been attached by welding, brazing, or other techniques and have suffered problems with metal failure and fracture of the attachment wires. The present attachment anchor 245 does not have such welds, brazes, or other forms of attachment of the barbs 250 to the attachment anchor 245.

FIG. 12A shows the attachment anchor 245 attached near the inlet end 145 and near the outlet end 148 of an intravascular tubular member 85. The intravascular tubular member can be any surgical vascular graft, intravascular tubular member, other intravascular stent-graft, or other vascular tubular member that is in need of an attachment anchor 245 to hold either the inlet end 145 or the outlet end 148 of the vascular tubular member into contact with a native artery or vein. The intravascular tubular member 85 can be formed from ePTFE, knitted or woven polyester, polyurethane, silicone or any other material use in surgical vascular grafts, intravascular grafts, intravascular stent-grafts, or vascular conduits. The intravascular tubular member 85 can be a straight or bifurcated vascular graft, intravascular graft, or intravascular stent-graft. The attachment anchor 245 holds the intravascular tubular member outward against the native vessel wall, prevents leakage of blood between the vascular tubular member and the native lumen, and prevents distal migration of the vascular tubular member. The attachment anchor 245 can be attached to the intravascular tubular member with securing fibers 255. Such securing fibers 255 can include sutures, polyester fiber, polytetrafluoroethylene fiber, metal wire, staples, biocompatible and biostable fiber, or other securing means. The securing fibers 255 can extend through and attach to any or all of the intranodal openings 385 found in the nodes 365 of the attachment anchor 245. The attachment anchor 245 positioned at the inlet end 145 can have barbs 250 attached or the attachment anchor 245 can be one without barbs 250 as shown on the outlet end 148. If the attachment anchor 245 has barbs 250, the wall of the intravascular tubular member 85 or other prior art intravascular stent-graft can be attached to the attachment anchor 245 such that the barbs 250 can extend outward without snagging the intravascular tubular member, or other device component such as the delivery sheath 225 (see FIGS. 2C, 2D, 4C, and 4D). If the attachment anchor 245 does not have barbs 250 such as the attachment anchor 245 positioned, for example, at the outlet end 148, the attachment anchor 245 can be attached to the wall of the intravascular tubular member such that it does not protrude beyond the outlet end 148. The securing fibers 255 can extend through the intranodal openings 385 of the attachment anchor 245 without pinching or cutting the securing fibers 255.

FIG. 12B shows the attachment anchor 245 attached near the inlet end 145 and near the outlet end 148 of the straight intravascular folded tubular member 95. The straight intravascular folded tubular member 95 can be the intravascular tubular member 85 shown in FIGS. 2A–2D that can be in need of an attachment anchor 245 to hold either the inlet end 145 or the outlet end 148 of the straight folded intravascular tubular member 85 into contact with a native artery such as the abdominal aorta or with a vein. The attachment anchor 245 is held to the straight intravascular folded tubular member 95 with securing fibers 255 as described in FIG. 12A. The attachment anchor 245 positioned at the inlet end 145 can have barbs 250 attached or the attachment anchor 245 can be one without barbs 250. If the attachment anchor 245 has barbs 250, the straight proximal tubular section wall 170 can be attached to the attachment anchor 245 such that the attachment anchor 245 extends beyond the inlet end 145 of the straight intravascular folded tubular member 95 and the barbs 250 can extend outward without snagging the straight intravascular folded tubular member 95. If the attachment anchor 245 does not have barbs 250 such as the attachment anchor 245 positioned at the outlet end 148, the attachment anchor 245 can be attached to the distal tubular section wall 190 of the straight intravascular folded tubular member 95 such that it does not protrude beyond the outlet end 148. The securing fibers 255 can extend through the intranodal opening 385 of the attachment anchor 245 without pinching or cutting the securing fiber 255.

FIG. 12C shows the attachment anchor 245 attached near the inlet end 145 and near each outlet end 148 of the bifurcated intravascular folded tubular member 260. The bifurcated intravascular folded tubular member 260 can be the bifurcated intravascular folded tubular member 260 shown in FIG. 5 that is in need of an attachment anchor 245 to hold either the inlet end 145 or the outlet end 148 of the bifurcated intravascular folded tubular member 260 into contact with a native artery such as the abdominal aorta. The attachment anchor 245 is held to the bifurcated intravascular folded tubular member 260 with securing fibers 255 as described in FIG. 12A. It is preferred that the attachment anchor 245 positioned at the inlet end 145 may have barbs 250 attached although the attachment anchor 245 can be one without barbs 250. If the attachment anchor 245 has barbs 250, the wall of the bifurcated intravascular folded tubular member 260 can be attached to the attachment anchor 245 such that the attachment anchor 245 extends beyond the inlet end 145 of the bifurcated intravascular folded tubular member 260 and the barbs 250 can extend outward without snagging the bifurcated intravascular folded tubular member 260. If the attachment anchor 245 does not have barbs 250 such as shown for each attachment anchor 245 that is positioned at each outlet end 148, the attachment anchor 245 can be attached to the distal tubular section wall 190 of the bifurcated intravascular folded tubular member 260 such that it does not protrude beyond the outlet end 148. The securing fibers 255 can extend through the intranodal opening 385 of the attachment anchor 245 without pinching or cutting the securing fibers 255.

The straight intravascular folded tubular member 95 and bifurcated intravascular folded tubular member 260 with the attachment anchor 245 shown in FIGS. 12B and 12C have specific advantages that provide these embodiments with distinct advantages when used together. The straight intravascular folded tubular member 95 and bifurcated intravascular folded tubular member 260 can be in need of an attachment means 87 that is attached to the intravascular folded tubular member and provides for better attachment than that provided by other prior art attachment means. The straight intravascular folded tubular member 95 and bifurcated intravascular folded tubular member 260 with the attachment anchor 245 of the present invention provides the inlet end 145 and outlet end 148 with a more firm anchoring to the native vessel than with other prior art attachment means. The short nondeployed attachment anchor length 400 allows the attachment anchor 245 to be placed precisely where it is needed. For example, in the treatment of abdominal aortic aneurysm 5 it can be important to place the attachment anchor 245 as close as possible to the left renal artery 45 and right renal artery 50 where the abdominal aortic wall 70 is not distended (see FIGS. 1A and 1B). Other prior art attachment means with a longer length often can extend into the thrombotic lining of the aorta where it is not possible to provide a firm attachment to the vessel wall. The short deployed attachment anchor length 395 (see FIG. 9C) allows the attachment anchor 245 of the present invention to have a greater number of nodes 365 positioned around the circumference to allow for a better attachment to the native vessel. The increased number of nodes 365 offers the opportunity of the present attachment anchor 245 to have a greater number of barbs 250 attached. In a nondeployed state, the barbs 250 are protected such that snagging of the barb 250 on the intravascular folded tubular member or delivery sheath 225 (see FIGS. 2C, 2D, 4C, and 4D) is not possible. Upon deployment the increased number of barbs 250 provides an improved attachment to the vessel wall that can further reduce the chances for further aneurysm dilation and can reduce the chances for distal migration of the intravascular folded tubular member. Once the inlet end 145 of the straight intravascular folded tubular member 95 (see FIG. 12B) or bifurcated intravascular folded tubular member 260 is attached to the native vessel proximal to the vessel injury using the attachment anchor 245 it is more likely to remain attached without migration as the outlet end 148 of each distal tubular section 130 is placed into appropriate location at a site distal to the vessel injury. Placement of the outlet end 148 causes each folded tubular section 125 to unfold and can place a force on the attachment anchor 245 at the inlet end 145 to move distally. Therefore the attachment anchor 245 of the present invention provides the necessary advantages to specifically improve the function of the straight intravascular folded tubular member 95 or bifurcated intravascular folded tubular member 260. Furthermore, since the straight intravascular folded tubular member 95 or bifurcated intravascular folded tubular member 260 is a one-piece construction and not a modular system such as many prior art devices, blood leakage cannot occur except at an inlet end 145 or outlet end 148. Placing the attachment anchor 245 at the inlet end 145 and at each outlet end 148 will provide a better seal of the intravascular folded tubular member with the native lumen of the blood vessel. This is due to the increased number of struts 370 (see FIG. 9A) and nodes 365 that provide a more uniform force along the circumference of the intravascular folded tubular member. The resulting straight intravascular folded tubular member 95 and bifurcated intravascular folded tubular member 260 will provide a leak free one-piece intravascular folded tubular member that can isolate an aneurysm better than a multi-tubular modular system. Other prior art one-piece systems that cannot provide a positive length determination in situ as with the present intravascular folded tubular member. These prior art one-piece systems require an estimation of their length in comparison to the actual vessel lesion length prior to implant. This often results in placing the inlet end 245 or outlet end 148 in a vessel location that is either thrombus 60 laden, blocks a side branch vessel such as an internal iliac artery 80 in the case of abdominal aortic aneurysm repair (see FIG. 1A and 1B), or is of inappropriate vessel diameter to match the diameter of the prior art device. The present straight intravascular folded tubular member 95 (see FIG. 12B) or bifurcated intravascular folded tubular member 260 (see FIG. 12C) can have its inlet end 145 and each outlet end 148 placed precisely after the intravascular folded tubular member has been delivered within the blood vessel. The inlet end 145 and outlet end 148 of the present intravascular folded tubular member can therefore be placed in a vessel location that is better able to form a leak free seal if it is combined with the improved attachment anchor 245 of the present invention.

Wall Structure

Figure 13A:
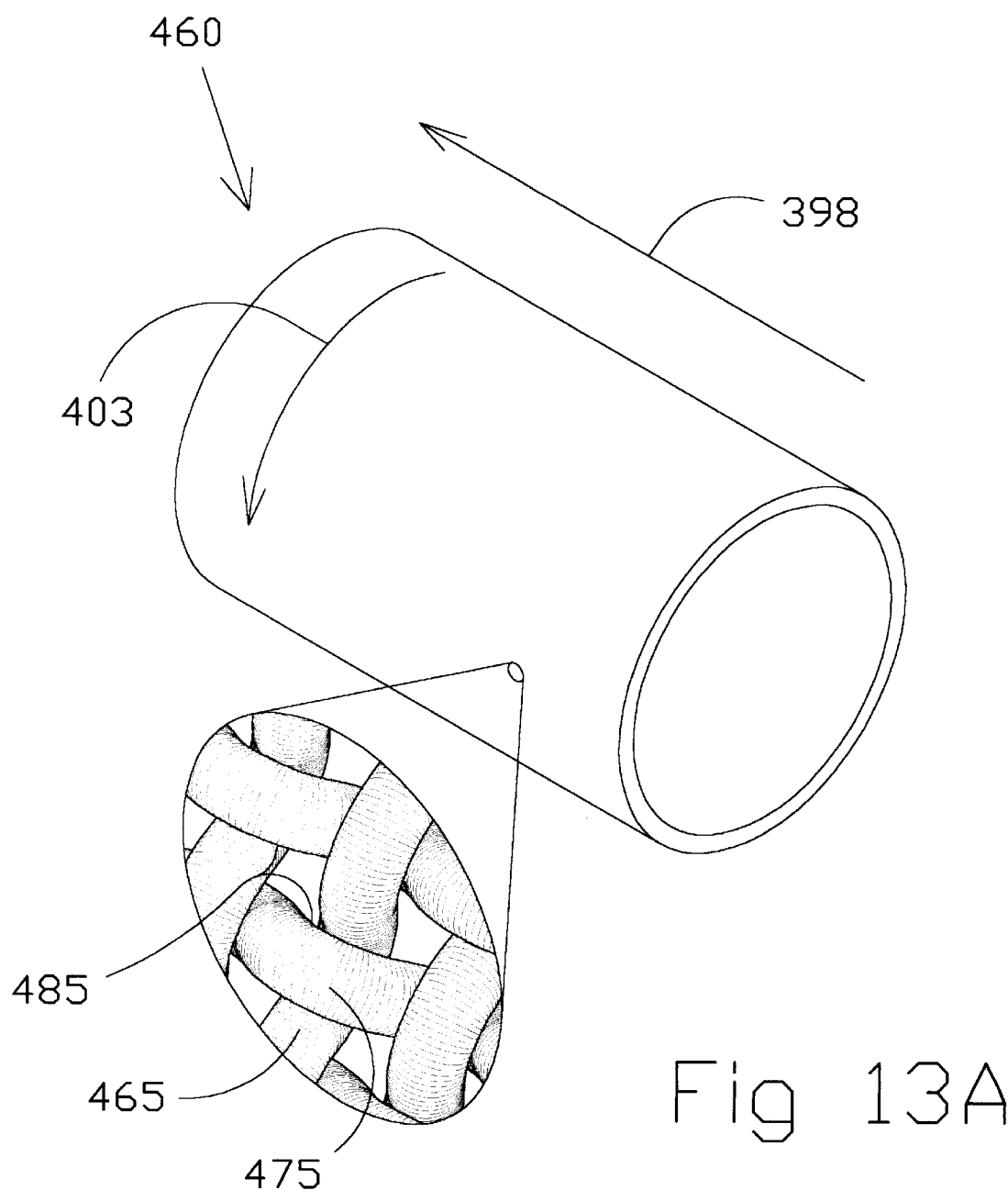
FIG. 13A is a perspective view of a woven vascular tubular member.
Figure 13B:
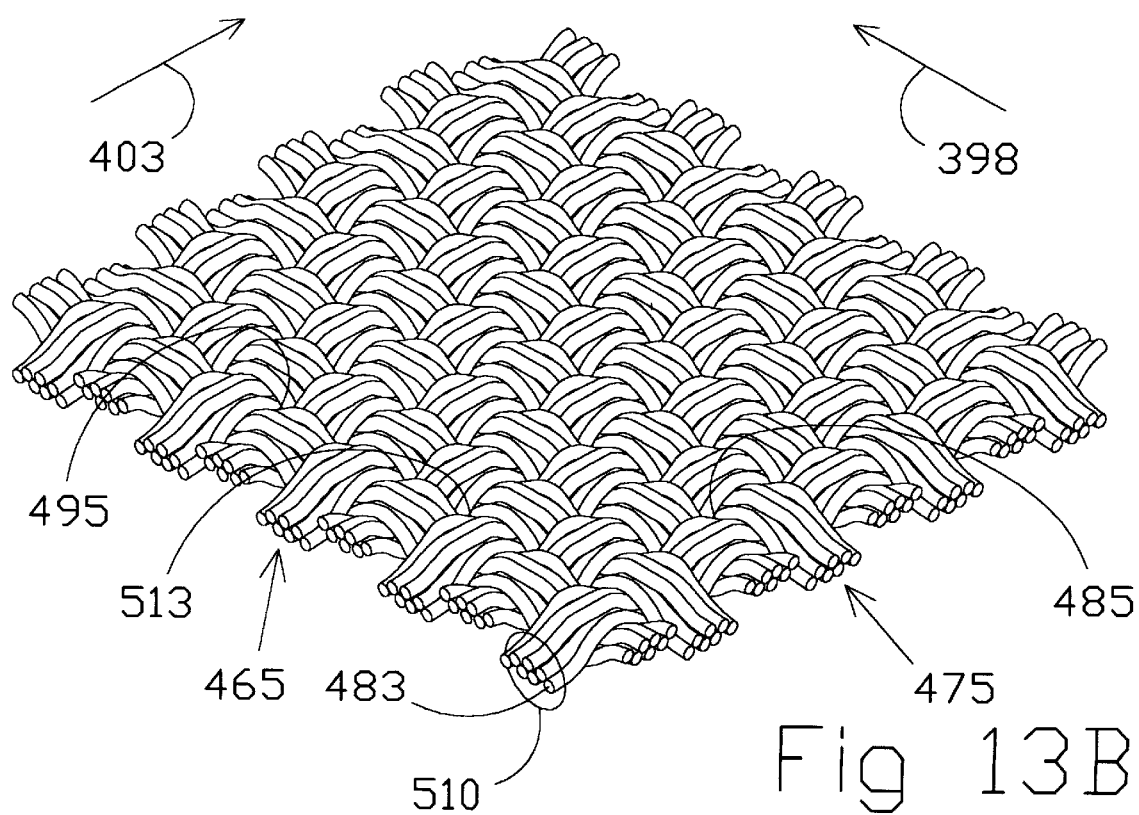
FIG. 13B is a perspective view of a woven multifilament strand wall structure for a vascular tubular member.

The wall structure for a surgical vascular graft, an intravascular tubular member, an intravascular folded tubular member, or other vascular tubular member, can be formed by weaving fibers or strands of polymeric material, metallic material, or other material to form a woven vascular tubular member 460 as shown in FIGS. 13A–13M. The description of these figures and reference to individual components and their reference numerals will proceed together. The woven vascular tubular member 460 can have a tight tubular weave that will not leak blood serum or blood cellular elements after implant. Generally one or more circumferential fibers or circumferential strands 465 are woven with a gradual helical wind in a generally circumferential direction 470 and a plurality of axial fibers or axial strands 475 are woven in a generally axial direction 398 and interface or cross over the circumferential strands 465 as shown in FIG. 13A. The axial strands 475 or circumferential strands 465 can be formed of a single filament or can be formed of many filaments 483 as shown in FIG. 13B. Following the formation of the woven vascular tubular member 460 the axial strands 475 tend to reorient slightly to become perpendicular to the generally circumferential strands 465 and will have a small helical wind to them. In the weave of the strands the points where the generally circumferential strands 465 cross over the generally axial strands 475 will be referred to as crossover points 485 (see FIG. 13A). The woven vascular tubular member 460 can be used as a surgical vascular graft for surgical implant or can be used as an intravascular tubular member 85 that can be delivered and implanted percutaneously or delivered through a delivery sheath 225 (see FIG. 4D) placed in a blood vessel that was accessed through a small cutdown procedure to access the blood vessel.

Figure 13C:
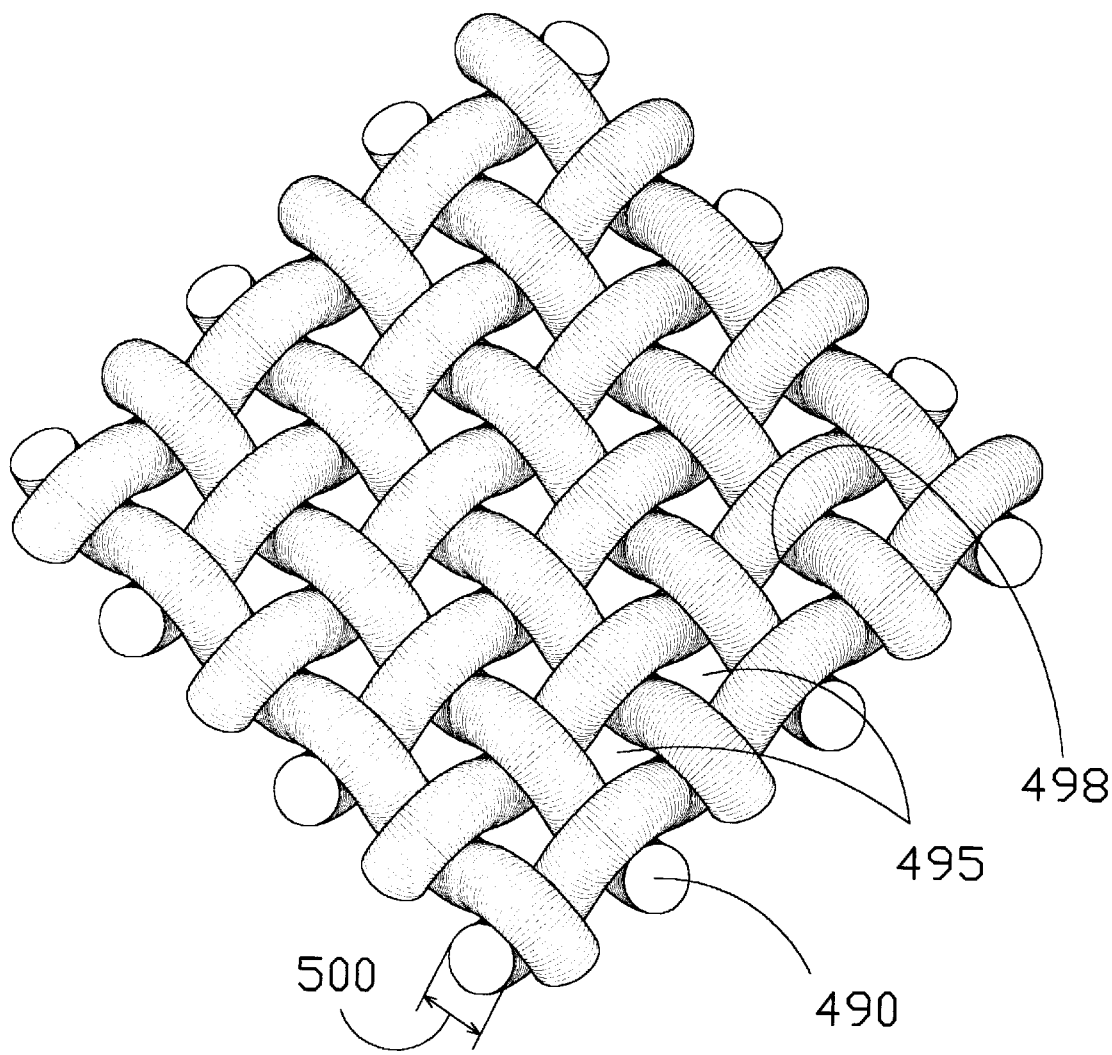
FIG. 13C is a perspective view of a woven monofilament strand wall structure.

Polymeric strands used to weave a woven vascular tubular member 460 can be formed of a single monofilament strand 490 and are referred to as polymeric monofilament strands 490 or monofilament fibers as shown in the woven monofilament wall structure of FIG. 13C. A woven vascular tubular member 460 formed from polymeric monofilament strands 490 will have small gaps or leakage sites 495 for blood leakage at or near the monofilament strand crossover points 498. The size of the leakage sites 495 is dependent upon the monofilament strand diameter 500 as well as how tightly they are packed. The size of the gaps or leakage sites 495 can be approximately as large as the monofilament strand diameter 500. To prevent blood cellular elements from passing through the leakage sites 495, the gaps cannot be significantly larger than the cellular elements found in the blood. With small leakage sites 495, red blood cells and pletetes can become trapped and create thrombosis that will prevent leakage from that gap or leakage site. Red blood cells are typically 8 micrometers in the larger diameter of the red blood cell. Monofilament strands 490 with a monofilament strand diameter 500 of only 8 micrometers would be too small, too weak, and impractical to weave or braid into a vascular graft, intravascular tubular member 460, or woven vascular tubular member 460. Fibers or strands formed from many smaller filaments 483 can form a multifilament strand 510 that will provide the necessary sealing at multifilament crossover points 513 of a multifilament strands 510 in generally the axial direction 398 with multifilament strands 510 in generally the circumferential direction 470; these multifilament strands form a woven multifilament strand wall structure shown in FIG. 13B.

A multifilament strand formed from approximately 3 to 100 filaments 483 will deform in the crossover points 485 and will seal the gaps or leakage sites 495 at or near crossover points 485 in a weave of the multifilament strands 510 as shown in FIG. 13B. A filament diameter 515 can range from approximately 1 to 200 micrometers and the multifilament strand diameter 520 or fiber diameter can range from approximately 0.001 to 0.040 inches (see FIG. 13D). The multifilament strand 510 or fiber will have significant flexibility due to the small filament diameter 515 and the multifilament strand will have strength due to the presence of many filaments 483. At the crossover points 485 the multifilament strands 510 will spread the filaments 483 out to form a more flattened cross section for the strand and this spreading out of the filaments 483 will reduce the size of the gap or leakage site 495 such that leakage of blood will not occur as shown in FIG. 13B.

Figure 13E:
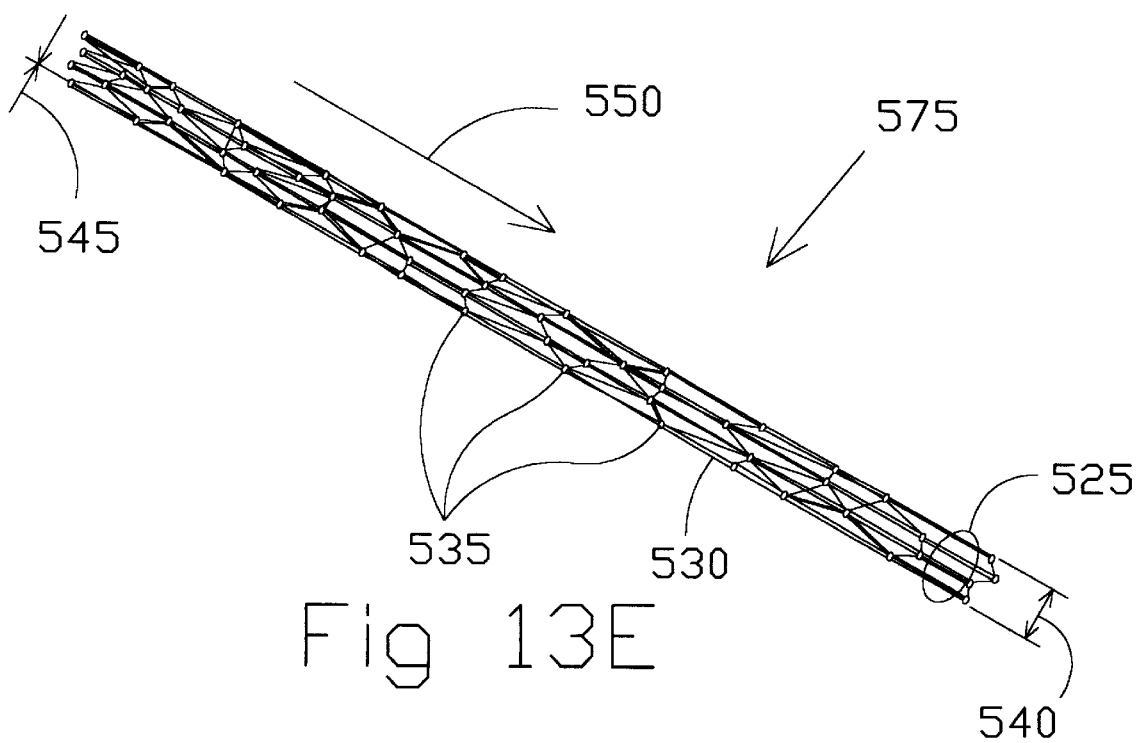
FIG. 13E is a perspective view of an expanded polytetrafluoroethylene filament.

Polymeric strands can be formed from filaments 483 of expanded polytetrafluoroethylene (ePTFE), polyester, polyethylene terephthalate, polyurethane, silicone, or copolymers or block copolymers involving these polymers or filaments 483 formed from other polymeric materials that are suitable for implant within the body from the standpoint of biocompatibility, biostability, strength, flexibility, and other properties. An expanded polytetrafluoroethylene filament 525 (ePTFE filament 525) as shown in FIG. 13E is formed from paste extrusion and can be stretched under high temperature, and sintered at very high sintering temperature to increase the axial strength thereby forming an ePTFE filament 525 that is well suited to forming an ePTFE multifilament strand 510 that can be woven into the wall structure of the present invention. The wall structure for a vascular tubular member 83 includes the general material of construction, such as polymeric or metallic, and physical description of the wall such as woven or braided. Each ePTFE filament 525 can include one or more expanded polytetrafluoroethylene microfilaments 530 (ePTFE microfilaments 530) within a cross section; such microfilaments tend to contain significant polymeric molecule orientation along its length which contributes to its excellent axial strength. An ePTFE filament 525 can contain nodal regions 535 of polytetrafluoroethylene which can provide sites of junction between ePTFE microfilaments 530 such that ePTFE microfilaments 530 are connected together with polytetrafluoroethylene to form a single ePTFE filament 525 that cannot be easily divided into individual ePTFE microfilaments 530 throughout the length of the ePTFE filament 525. The expanded polytetrafluoroethylene multifilament strand 510 (ePTFE multifilament strand 510) for use in weaving surgical vascular grafts, intravascular tubular members 85, or other vascular tubular members 83 can have a multifilament strand diameter 520 (see FIG. 13D) that ranges from approximately 0.001 to 0.040 inches, an expanded polytetrafluoroethylene filament diameter 540 (ePTFE filament diameter 540) that ranges from approximately 1–200 micrometers, and an expanded polytetrafluoroethylene microfilament diameter 545 (ePTFE microfilament diameter 545) that ranges from approximately 0.01 to 200 micrometers. The ePTFE multifilament strand 510 used in larger diameter surgical vascular grafts, intravascular tubular members, or vascular tubular members ranging in diameter from approximately 8 to 30 millimeters such as those used in abdominal aortic aneurysm repair has a preferred multifilament strand diameter 520 that ranges from approximately 0.003 to 0.040 inches, a preferred ePTFE filament diameter 540 that ranges from approximately 2.5 to 200 micrometers, and a preferred expanded polytetrafluoroethylene microfilament diameter 545 (ePTFE microfilament diameter 545) that ranges from approximately 0.01 to 200 micrometers. In weaving a surgical vascular graft, intravascular tubular member, or vascular tubular member for coronary or other small diameter vascular applications with a smaller vascular tubular member diameter ranging from approximately a 3 to 6 millimeter diameter, for example, an ePTFE multifilament strand 510 can have a preferred multifilament strand diameter 520 that ranges from 0.001 to 0.020 inches, a preferred ePTFE filament diameter 540 that ranges from approximately 1 to 200 micrometers, and a preferred ePTFE microfilament diameter 545 that ranges from approximately 0.01 to 200 micrometers. An ePTFE multifilament strand 510 of the preferred embodiments contains at least three ePTFE filaments 525 or at least three ePTFE microfilaments 530 in order to provide adequate sealing at multifilament strand crossover points 513 and each filament is comprised of one or more microfilaments.

A surgical vascular graft or vascular implant 82, intravascular tubular member 85, or vascular tubular member 83 formed from weaving multifilament strands 510 of polyester or other polymeric material could have a wall structure for the vascular tubular member 83 of the present invention formed from multifilament strands 510 and filaments 483 with diameters having a similar range to that discussed above for the polytetrafluoroethylene multifilament strands 510 and ePTFE filaments 525.

Figure 13F:
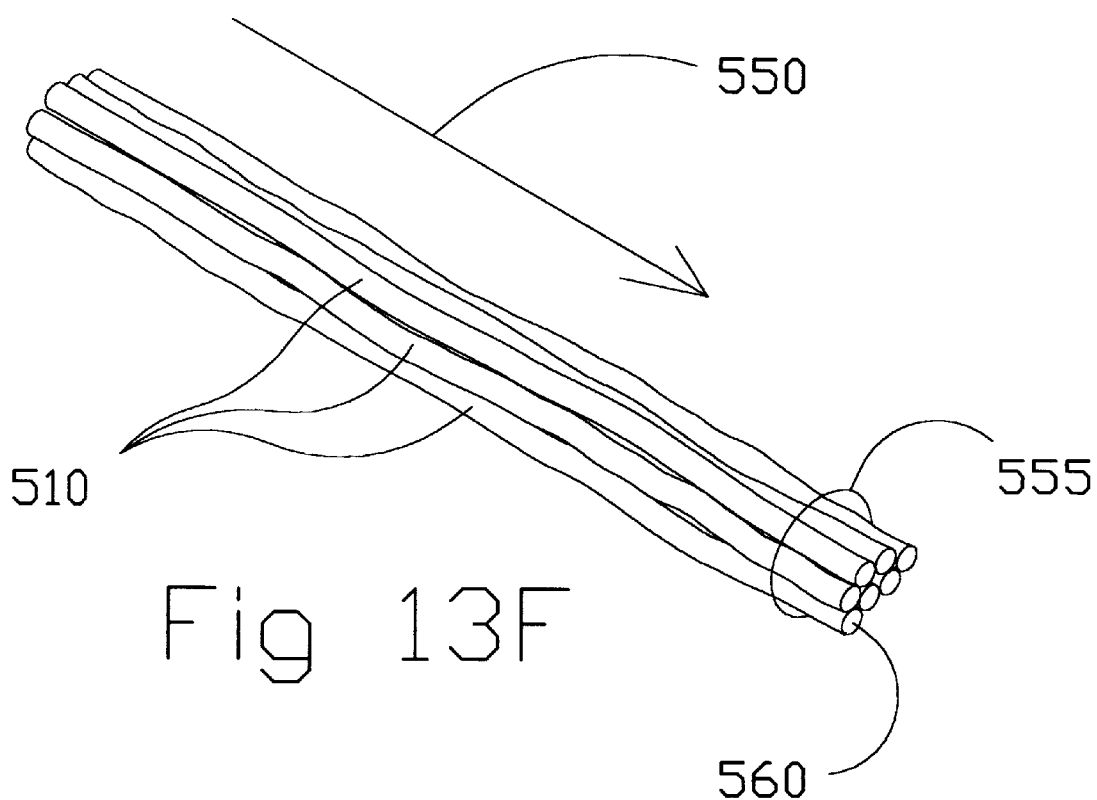
FIG. 13F is a perspective view of a straight multifilament strand formed of straight filaments.
Figure 13G:
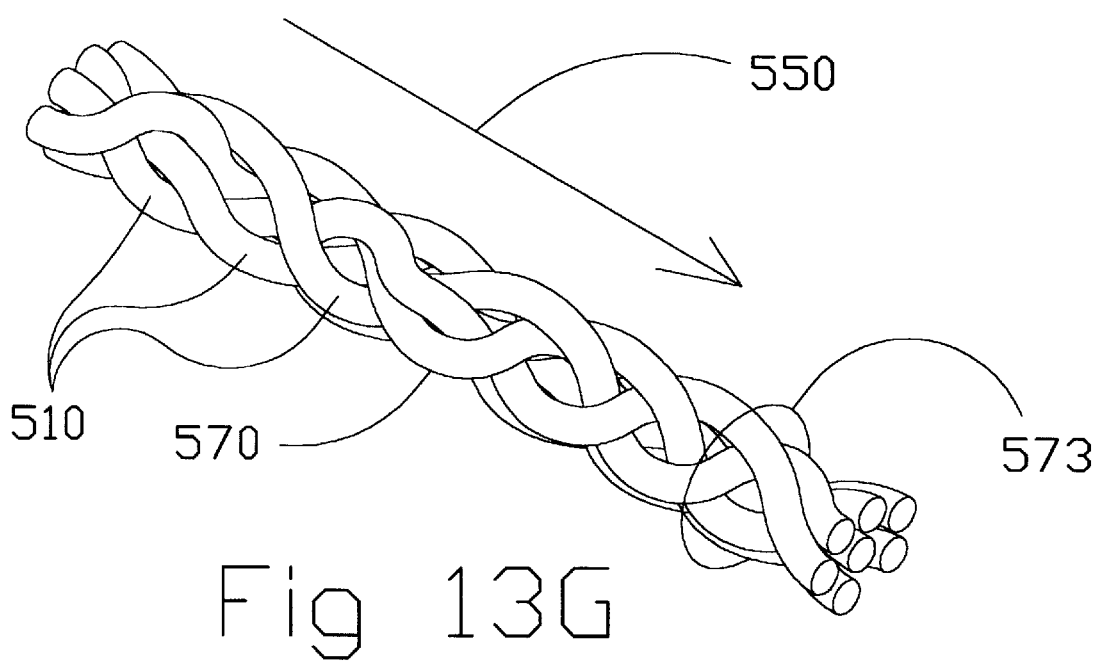
FIG. 13G is a perspective view of a curved multifilament strand formed of curved filaments.
Figure 13H:
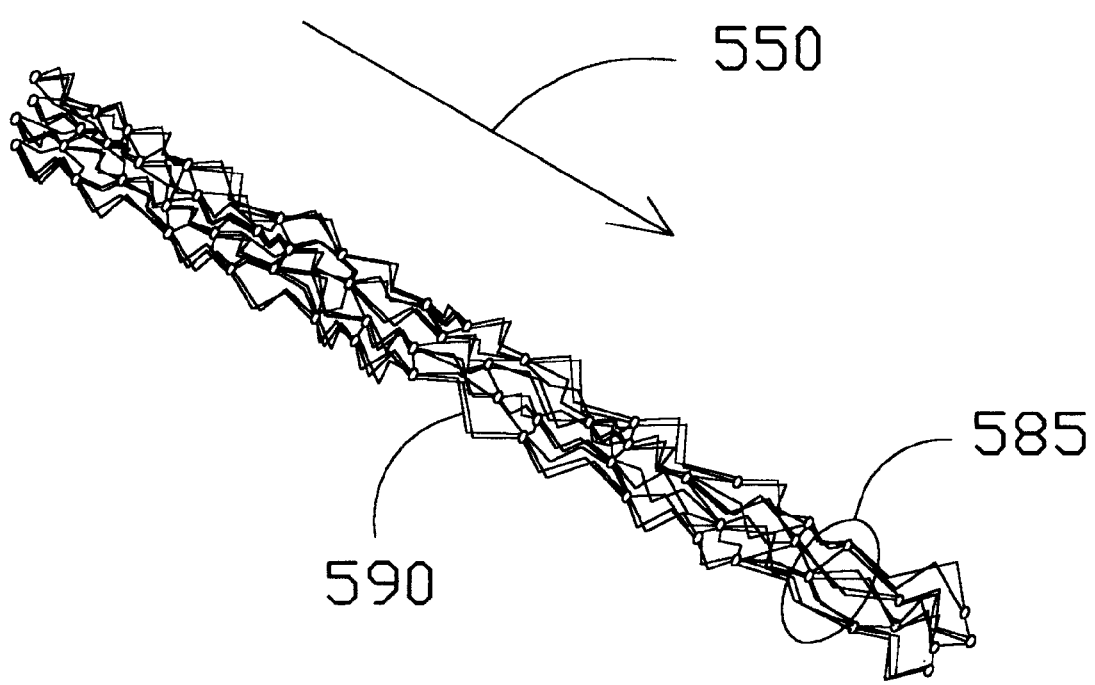
FIG. 13H is a perspective view of a curved expanded polytetrafluoroethylene filament formed of microfilaments.

Polymeric multifilament strands 510 used in forming the woven wall structure of some embodiments of the present invention can extend along their linear axis 550 with a generally linear or straight shape forming straight multifilament strands 555 (see FIG. 13F). The strands can be formed of straight filaments 560 that also have a linear or straight shape along their linear axis 550. Polymeric multifilament strands 510 formed from such straight filaments 560 that are straight will not in general have significant stretch characteristics in the direction of their linear axis 550. Alternately, polymeric multifilament strands 510 can be formed from curved filaments 570 that have a zig zag shape, a sinusoidal shape, helical shape, or some other form of curved shape extending in the direction of their linear axis 550 forming a curved multifilament strand 573 as shown in FIG. 13G. A curved multifilament strand 573 formed from such curved filaments 570 will exhibit extension or stretch characteristics in the linear axis 550 direction of the fiber (see FIG. 13G). The amount of zig zag or curved shape that can be formed into the curved filaments 570 is such that it can provide the curved multifilament fiber or curved multifilament strand 573 with a stretch amount ranging from approximately one to fifty percent of its length along its linear axis 550. Such curved filaments 570 can be formed by thermal, chemical, or mechanical treatment of the filaments 483 of the strand to form a set shape found in the curved filaments 570 with at least some temporary memory of the set shape under normal conditions of use for the vascular or intravascular graft. A straight expanded polytetrafluoroethylene filament 575 (see FIG. 13E) containing straight expanded polytetrafluoroethylene microfilaments 580 can be exposed to high temperature while fixing or holding a specific length along its axis 550 to generate a curved shape for the microfilaments as shown in FIG. 13H. This specific length is shorter than its elongated length when exposed to axial stress. This high temperature is lower than the very high temperature used during the sintering step mentioned earlier. This process results in a curved expanded polytetrafluoroethylene filament 585 with curved expanded polytetrafluoroethylene microfilaments 590. The curved shape for the curved ePTFE microfilaments 590 and curved ePTFE filament 585 will not easily return to a straight shape unless exposed to high temperature while held under stress. Expanded polytetrafluoroethylene multifilament strands 510 formed from curved ePTFE filaments 585 that have curved ePTFE microfilaments 590 will provide significant axial stretch. Thermal treatment can also be applied to polyester multifilament strands 510 or to other polymeric multifilament strands 510 to form a curved filaments 570 and curved multifilament strands 573 using techniques known in the textile industry.

Figure 13I:
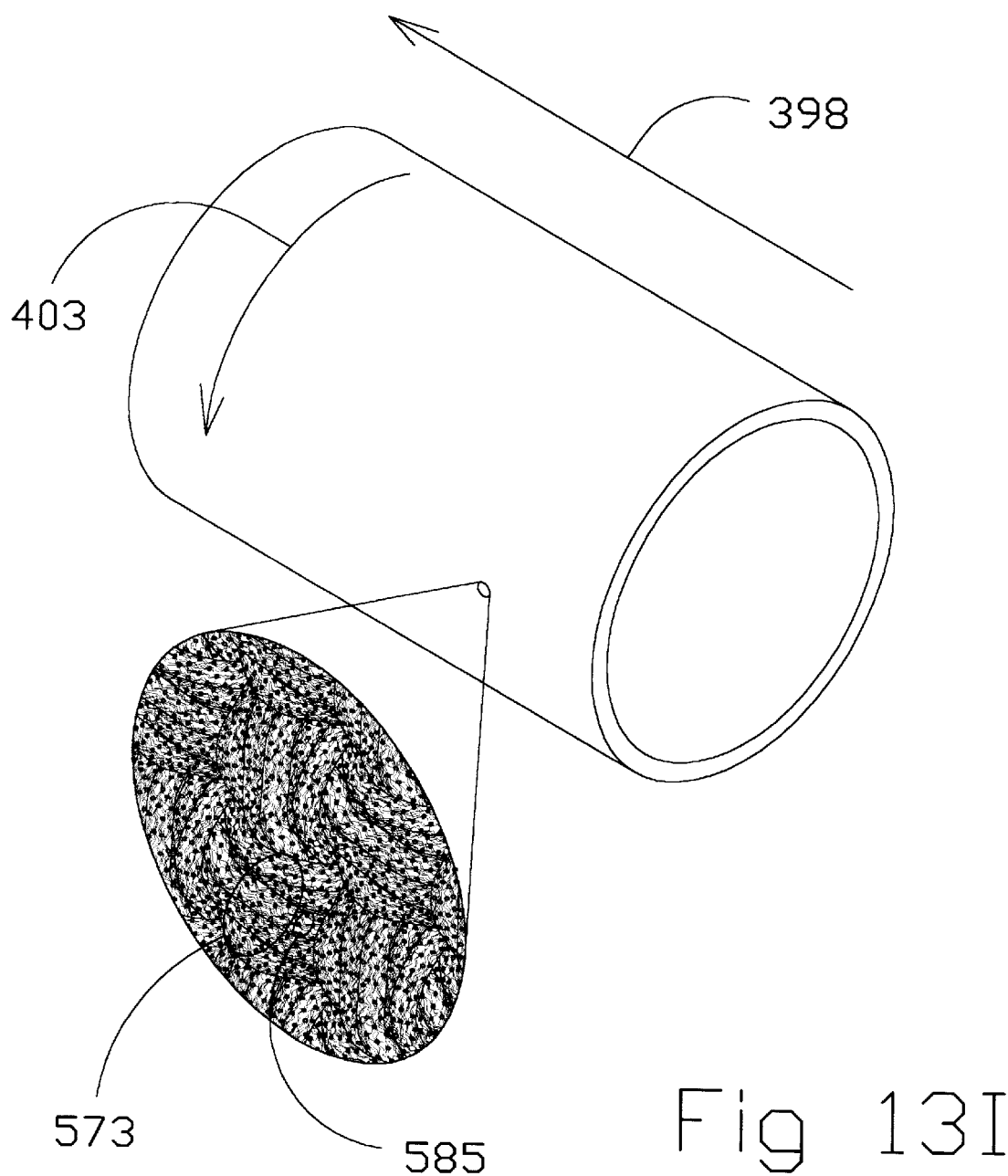
FIG. 13I is a perspective view of a vascular tubular member formed of expanded polytetrafluoroethylene strands.

A surgical vascular graft, an intravascular tubular member 85, or other vascular tubular member can be formed by weaving ePTFE multifilament strands 510 or other polymeric multifilament strands 510 into a tubular form. The multifilament strands 510 can either have straight ePTFE filaments 575 or curved ePTFE filaments 585 and weaving a vascular tubular member 83 out of curved multifilament strands 573 will give stretch characteristics in the direction or their linear axis 550 as they are woven in the axial direction 398, circumferential direction 470, or both directions (see FIGS. 13B and 13G). An embodiment of a vascular tubular member formed from ePTFE multifilament strands 510 of curved ePTFE filaments 585 is shown in FIG. 13I. Curved multifilament strands 573 formed from curved ePTFE filaments 585 could be woven in the circumferential direction 470 (see FIG. 13A) with straight multifilament strands 555 in the axial direction. Such a structure approximates the radial compliance found in native blood vessels and can provide improved healing at the junction sites of the vascular tubular member with the native vessel. Expanded polytetrafluoroethylene curved multifilament strands 573 can be woven in the axial direction 398 with straight multifilament strands 555 in the circumferential direction 470. Such a wall structure can provide improved flexibility with excellent kink resistance. Curved multifilament strands 573 formed from curved ePTFE filaments 585 can be woven in each direction to provide a woven vascular tubular member 460 with stretch characteristics in both directions (see FIG. 13I). Such a wall structure can have both radial and axial compliance and be resistant to kinking. Such a woven vascular tubular member 460 could be used for standard surgical arterial reconstruction, as a component of a stent-graft, or a the wall structure for and intravascular tubular member for treatment of vascular injury such as abdominal aortic aneurysm repair. A similar vascular tubular member can be woven from straight or curved polymeric multifilament strands 510 of polyester or other polymer to form a vascular tubular member similar to FIG. 13I.

Figure 13J:
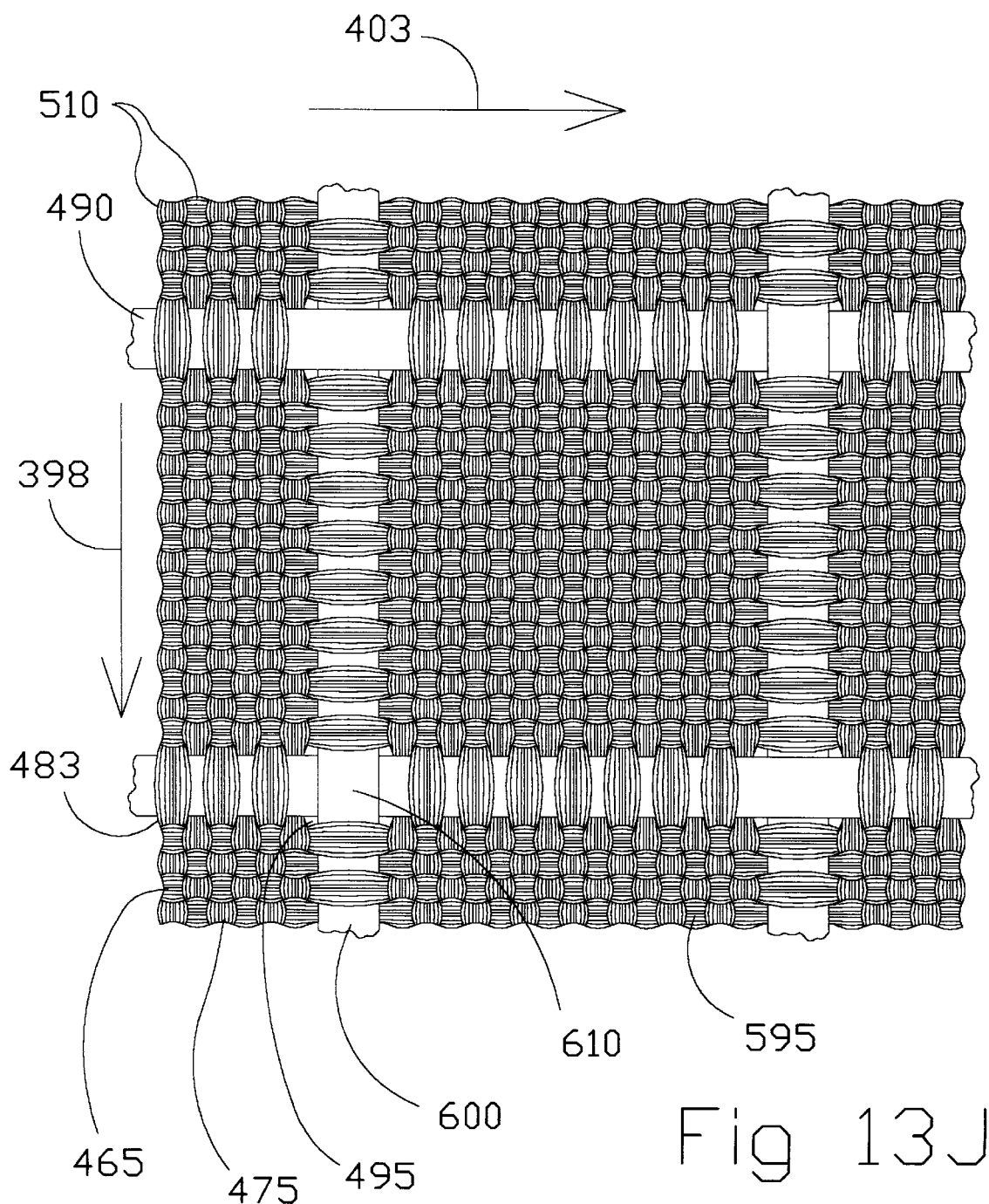
FIG. 13J is a perspective view of a wall structure formed of metallic strands woven along with polymeric multifilament strands.
Figure 13K:
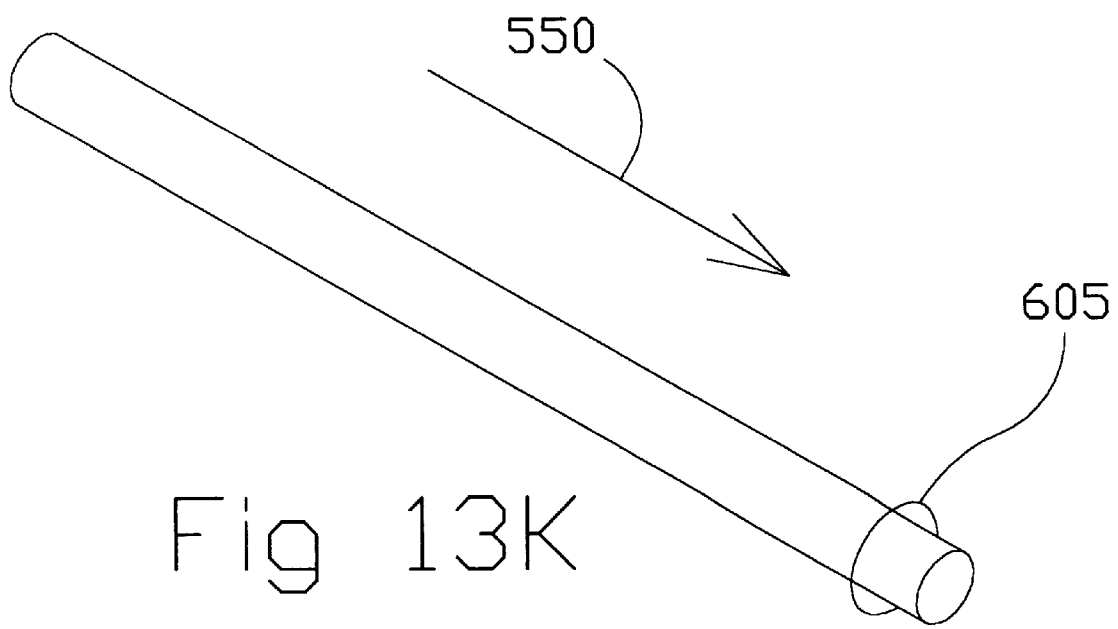
FIG. 13K is a perspective view of a straight monofilament strand.

Circumferential strands 465 and axial strands 475 formed of metal material can be woven along with the multifilament polymeric strands 595 formed of filaments 483 of polymeric material in the generally circumferential direction 470, the generally axial direction 398, or both directions as shown in FIG. 13J to form the woven vascular tubular member 460 shown in FIG. 13A. Metallic strands 600 woven along with the polymeric strands 595 can be a metallic monofilament strand 490 of a circular cross section or metallic multifilament strands 510 formed from a plurality of smaller diameter metal filaments 483. The metallic strands 600 can be formed out of stainless steel, Nitinol, tantalum, titanium, an alloy of these metals, other metal used in the formation of implanted stents, or other metal capable of being implanted and having adequate strength to support the stresses found in a surgical vascular graft, intravascular graft, or vascular tubular member. The metallic strands 600 can have a generally linear or straight shape in the direction of their linear axis 550 forming metallic straight monofilament strands 605 or metallic straight multifilament strands 555 (see FIGS. 13K and 13F). In a preferred embodiment the metallic strands 600 are metallic monofilament strands 490 and are woven along with the multifilament polymeric strands 595 to form a wall structure for the woven vascular tubular member 460 as shown in FIG. 13J. At the metal to metal crossover points 610, leakage sites 495 can be created that could allow blood leakage out of the woven vascular tubular member 460 formed of the wall structure of this embodiment.

Figure 13L:
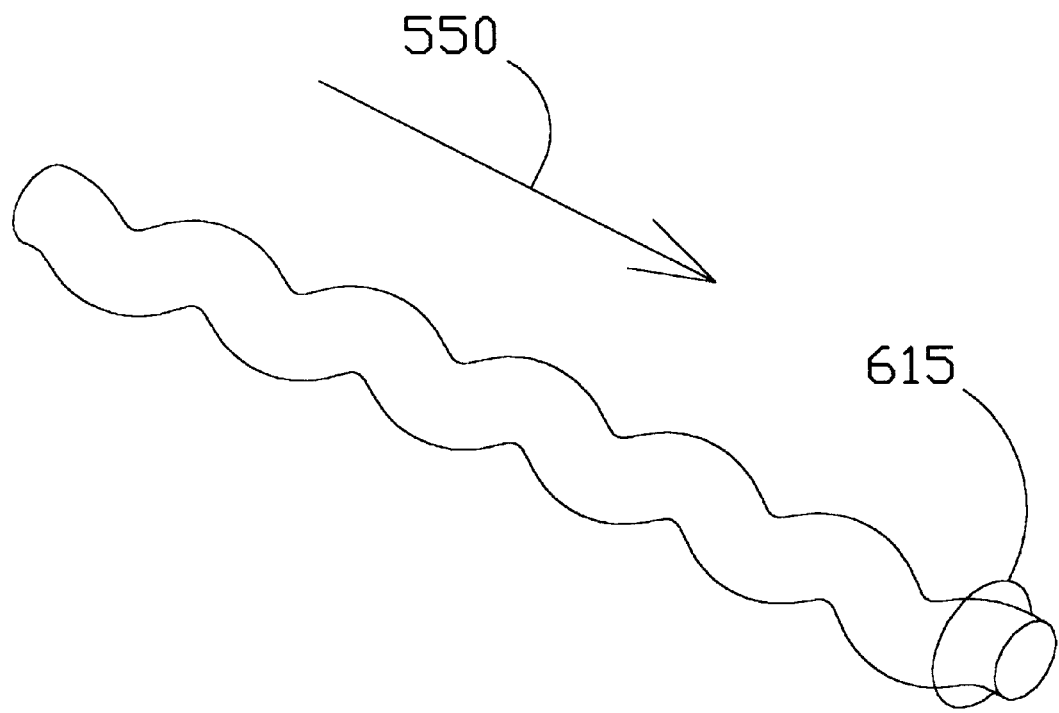
FIG. 13L is a perspective view of a curved monofilament strand.

Alternately, the metallic strands 600 can be bent or formed by mechanical, chemical, or thermal methods into a zig zag, sinusoidal, helical, or other curved shape forming a metallic curved monofilament strand 615 or a metallic curved multifilament strand 570 as shown in FIGS. 13L and 13G. The metallic curved monofilament strand 615 has a direction of its linear axis 550 determined by the overall direction of the curved monofilament strand 615 along its length. The metallic curved monofilament strand 615 is able to extend in a generally linear axis 550 direction by an amount that ranges from one to fifty percent of its generally axial length. The metallic monofilament strand diameter 500 or multifilament strand diameter 520 can range from 0.001 to 0.020 inches. The metallic monofilament strand 490 can provide an outward expansion force to the wall structure of the woven vascular tubular member 460 and provide resistance to axial compressive forces generated by the native tissue surrounding the woven vascular tubular member 460.

The wall structure as shown in FIG. 13J for a surgical vascular graft, intravascular graft, an intravascular folded tubular member, or a vascular tubular member 83 used in the treatment of abdominal aortic aneurysm or the treatment of other large diameter vessels with a diameter of 8 to 30 millimeters, the metallic monofilament strand diameter 500 (see FIG. 13C) is preferably approximately 0.003 to 0.020 inches. For a vascular graft or intravascular graft for treatment or coronary vessels or vessels less than 6 millimeters, the preferred metallic monofilament strand diameter 500 or metallic multifilament strand diameter 520 is approximately 0.001 to 0.016 inches. The presence of metallic strands 600 in the circumferential direction 470 (see FIG. 13J) provides the surgical vascular graft, intravascular tubular member 85, or vascular tubular member 83 made from this wall structure with the property of exerting an outward force against the native vessel, holding the native vessel outward in an open and patent conformation, and resisting against vessel contraction due to tissue scarring and healing. Due to the circumferential direction 470 of some of the metallic strands 600, the amount of outward extensional force generated by a metallic strand 600 of smaller diameter is greater than that provided by a larger diameter but more zig zag or bent metallic strands such as those disclosed in prior art stent-graft devices. The metallic strands 600 in the axial direction 398 provide the surgical vascular graft, or intravascular graft formed from this wall structure with resistance to compressive length changes. The intravascular tubular member 85 or vascular tubular member 83 as shown in FIGS. 2A, 2B, 4A, 4B, and in other embodiments can have a woven wall structure as described in the embodiments of FIGS. 13A–13M and can undergo a change in diameter from a smaller or nondeployed diameter 305 in its nondeployed state as it is being inserted into the vascular system to a larger or deployed diameter 237 in its deployed state after it is implanted in the appropriate location. The woven vascular tubular member 460 (see FIG. 13A) of the present invention can be formed entirely out of woven metallic strands 600.

In a preferred embodiment, metallic strands 600 formed of straight 605 and curved 615 monofilaments of metallic material are woven along with the multifilament polymeric strands 595 in either the axial direction 398, the circumferential direction 470, or both directions as shown in FIG. 13J. When metallic strands 600 are woven along with the multifilament polymeric strands in the circumferential direction 470 as shown in FIG. 13J, the number of metallic strands per length of woven vascular tubular member 460 can range from one metallic strand 600 approximately every 0.060 inches to one metallic strand 600 every 1.5 inches. It is preferred to place a metallic strand 600 in the circumferential direction 470 approximately every 0.10 to 0.90 inches along the length of the woven vascular tubular member 460. For the metallic strands 600 in the axial direction 398, the spacing range between metallic strands 600 in the circumferential direction 470 is the same as the spacing range along the axial direction 398 of the woven vascular tubular member 460 with a wall structure as shown in FIG. 13J. This spacing for metallic strands applies to the wall structures which are shown in FIGS. 14, 16A–16C, 17A–17C, 18A, and 18B.

The metallic strands 600 can be formed of a metal with a high yield strength that will remain elastic during the deployment of the intravascular tubular member from the nondeployed state to the deployed state. The high yield strength metallic strands 600 will provide the intravascular graft with a self-expandable property. Such an intravascular tubular member can be contained completely within a delivery sheath 225 (see FIGS. 2C, 2D, 4C, and 4D) during the delivery of the intravascular tubular member 85 to the site of the vessel lesion that is to be treated by the intravascular tubular member. Upon release of the self-expandable intravascular tubular member 85 from the delivery sheath 225, it expands outward to its vascular tubular member deployed diameter 237 and the woven wall structure of the present invention is placed into contact with the native vessel or thrombus.

Alternately, the metallic strands 600 shown in FIG. 13J can be formed from a metal with a yield strength that will allow plastic deformation to occur during the deployment of the woven intravascular tubular member 460. This embodiment of the woven intravascular tubular member 460 formed of this wall structure can be expanded internally by a mechanical expanding means such as a balloon of a balloon dilitation catheter to force the intravascular tubular member 85 to expand from its smaller vascular tubular member nondeployed diameter 238 to a larger vascular tubular member deployed diameter 237. The metallic strands of this embodiment undergo a plastic deformation during the deployment from the vascular tubular member nondeployed diameter 238 to the vascular tubular member deployed diameter 237 as shown in FIGS. 2B, 2C, 4B, and 4D.

Figure 13M:
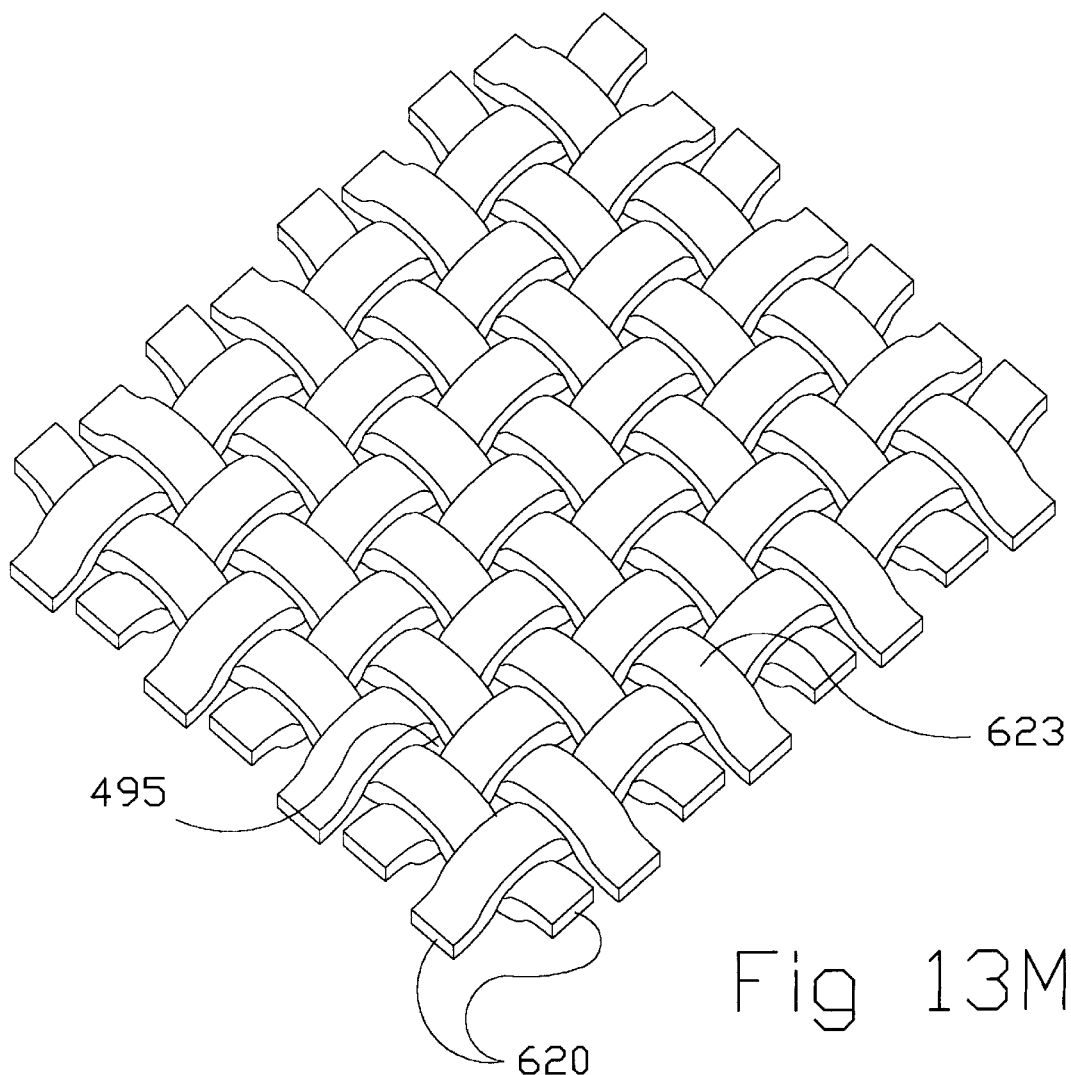
FIG. 13M is a perspective view of a woven wall structure of flattened metallic strands.

The metallic strands 600 used in the wall structure of the present invention as shown in FIG. 13J can be flattened metallic strands 620 with approximately a rectangular cross sectional shape (see FIG. 13M). The advantages of this form of metallic strand is that it provides a closer packing with another flattened metallic strands 620 at a flattened crossover point 623 in a weave that contains flattened metallic strands 620 with a smaller gap and smaller leakage site 495. The flattened metallic strands 620 can be woven along with multifilament polymeric strands 595 as shown in FIG. 13J such that minimal blood leakage will occur at crossover points. Flattened metallic strands 620 can be more difficult to weave than round strands due to required orientation of the flattened strands during weaving.

Woven Wall Structure

The woven wall structures shown in the embodiments shown in the following figures, FIGS. 14, 15, 16A–C, 17A–C, 18A and 18B apply to a vascular tubular member 83 that can be implanted as a surgical vascular graft, as an intravascular tubular member 85 without a folded tubular section 125, as an intravascular folded tubular member including a folded tubular section 125, or as any other vascular tubular member. The intravascular tubular member can be a straight intravascular folded tubular member 95, a bifurcated intravascular folded tubular member 260, or a straight intravascular tubular member, without a folded tubular section 125 or a bifurcated intravascular tubular member without a folded tubular section 125. The woven tubular structures of the present invention are intended to be formed without a seam and are therefore seamless. It is further understood that a woven material of the wall structure described in this invention could be formed of a flat woven wall structure that is then formed into a straight or bifurcated tube with a wall structure as described. These figures are intended to represent various combinations of multifilament strands 510 and monofilament strands 500 of metallic material or polymeric material with a straight or curved conformation used to form the wall structure of the present vascular tubular member 83. The actual woven structures showing woven strands of various types is shown in FIGS. 13A–13M. It is further noted that the circumferentially oriented strands actually are woven with a helical wind as discussed earlier. This helical wind can be gradual so that it appears as a generally circumferentially wound strand as shown in these figures. It is understood that the circumferential strands 465 or circumferentially oriented strands can have a significant helical wind to them. This significant helical wind is accomplished by winding more than one strand or several strands in the circumferential direction 470 at the same time. An even greater helical wind can be accomplished in the circumferential direction by generating a double helical wind with each helix involving several strands. A double helix can be formed, for example by introducing circumferential strands into the tubular weave from two positions located 180 degrees apart. Axial strands tend to orient themselves such that they are perpendicular to the circumferentially oriented strands giving the axial strands a helical wind or turn to them.

The present invention for a vascular tubular member 83 includes the wall structure for the vascular tubular member. The woven wall structures shown in FIGS. 14, 16A–16C, 17A–17C, 18A, 18B, 20A–20D, 21, 22A, 22B, and 23 are included in the preferred embodiments of this invention. The strands that are of a polymeric material used to form these wall structures are woven with only multifilament strands 510 of polymer material. Polymer material can be any of the polymers indicated including ePTFE, polyester, or other suitable polymer material. The multifilament strands 510 can be woven in either a generally axial direction 398 or a generally circumferential direction 470. These multifilament strands of polymeric material can be formed of filaments 483 that are either curved filaments or straight filaments; and hence the multifilament strands 510 of polymeric material will be referred to as curved axial polymeric strands 625, curved circumferential polymeric strands 630, straight axial polymeric strands 635, and straight circumferential polymeric strands 640. The present invention for a vascular tubular member 83 includes a wall structure that can be formed from woven metallic strands 600. The metallic strands 600 can be metallic monofilament strands 490 or metallic multifilament strands 510. In the preferred embodiments of the above indicated figures, FIGS. 14, 16A–16C, 17A–17C, 18A, 18B, 19, 20A–20D, 21, 22A, 22B, and 23, the metallic strands are metallic monofilament strands 490 woven along with the multifilament strands 510 of polymeric material in either the axial direction 398, circumferential direction 470, or both directions forming monofilament strands 490 of metallic material. The monofilament strands 490 of metallic material can be formed of straight monofilament strands 605 or curved monofilament strands 615 and hence the monofilament strands 490 of metallic material will be referred to as curved axial metallic strands 645, curved circumferential metallic strands 650, straight axial metallic strands 655, and straight circumferential metallic strands 660.

The wall structures described in FIGS. 14, 16A–16C, 17A–17C, 18A, 18B, and 19 can all be applied as a vascular tubular member 83 that is suitable for vascular surgery, as an intravascular tubular member 85 that is suitable for intravascular implant either with percutaneous access or with a small surgical cutdown in an adjoining vessel either proximal or distal to the site of vascular injury. As an intravascular tubular member 85, it can be used without an attachment means as shown in these drawings, or it can be used with any attachment means found in the prior art, or with the attachment anchor 245 disclosed earlier in this disclosure as a part of this invention. The wall structures can be formed into a straight intravascular folded tubular member 95, or a bifurcated intravascular folded tubular member 260 as shown in FIGS. 2A, 2B, 4A, and 4B. Each vascular tubular member presented has an inlet end 145, an outlet end 148, an inner surface 135, an outer surface 140, a vascular tubular member wall 662, and a wall thickness 663.

Figure 14:
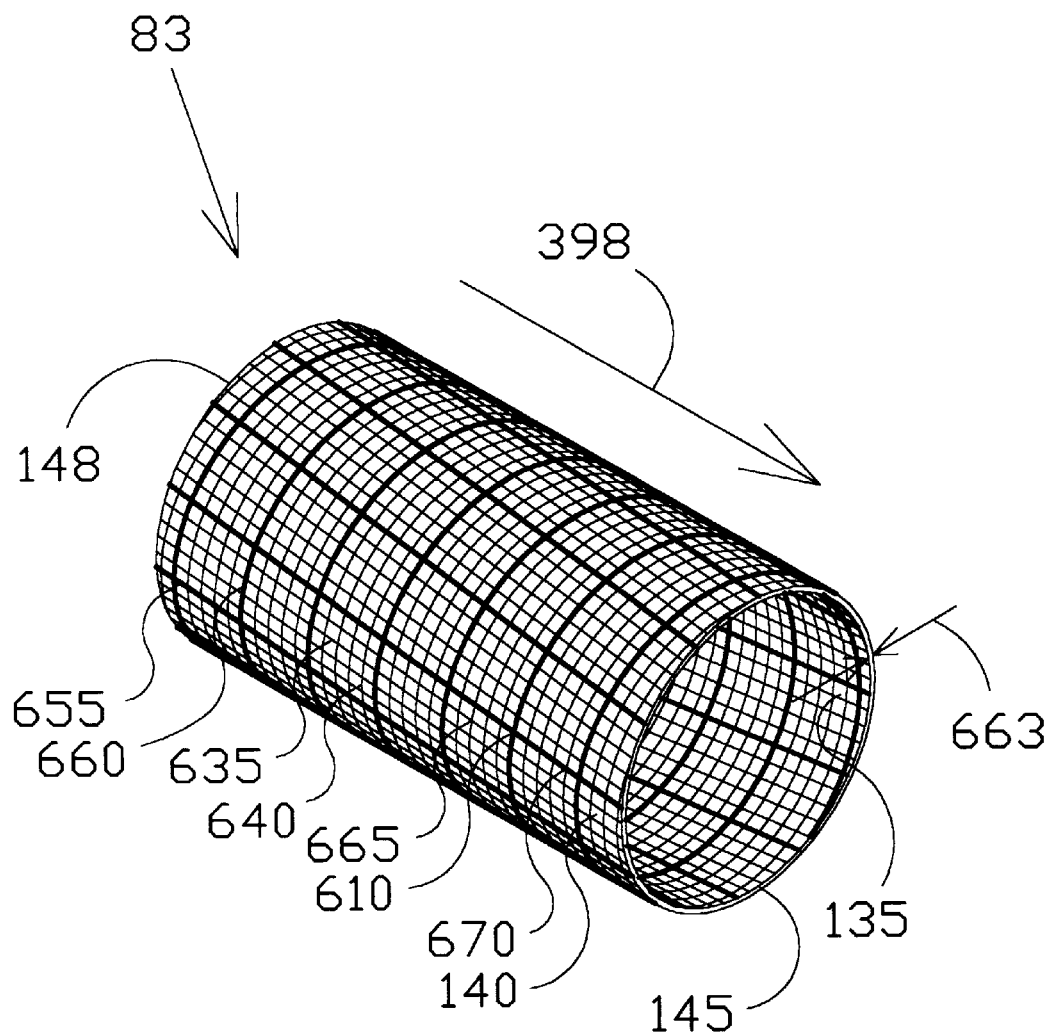
FIG. 14 is a representation of a vascular tubular member with a woven wall structure having straight axial metallic, straight axial polymeric, straight circumferential metallic, and straight circumferential polymeric strands.

FIG. 14 shows an embodiment for the wall structure for the surgical vascular graft, the intravascular tubular member 85, or the vascular tubular member 83 of this invention. All reference numerals correspond to those elements previously or otherwise described. This structure has straight axial metallic strand 655 and straight circumferential metallic strands 660 woven along with straight axial polymeric strands 635 and straight circumferential polymeric strands 640. The straight axial polymeric strands 635 or straight circumferential polymeric strands 640 tend to seal polymer to polymer crossover points 665 between these strands and can effectively seal polymer to metal crossover points 670 such as between a straight axial polymeric strand 635 with a straight circumferential metallic strand 660. The straight circumferential metallic strands 660 provide outward force of this tubular member against the aortic wall in it deployed state. The straight circumferential metallic strands 660 help to resist kinking by helping to maintain a round cross section. The straight axial metallic strands 655 provide the tubular member with strength in the axial direction 398 to overcome compressive forces that may act to reduce its axial length. The straight axial metallic strands 655 enhance the ability of the folded tubular section 125 of a straight 95 or bifurcated 260 intravascular folded tubular member to unfold easily without wrinkling of the folded tubular section center wall 160. The presence of the straight axial metallic strands 655 generates axial stiffness in the tubular member causing it to be less flexible in negotiating tortuous turns found in the iliac, femoral, and other arteries of the body.

Figure 15:
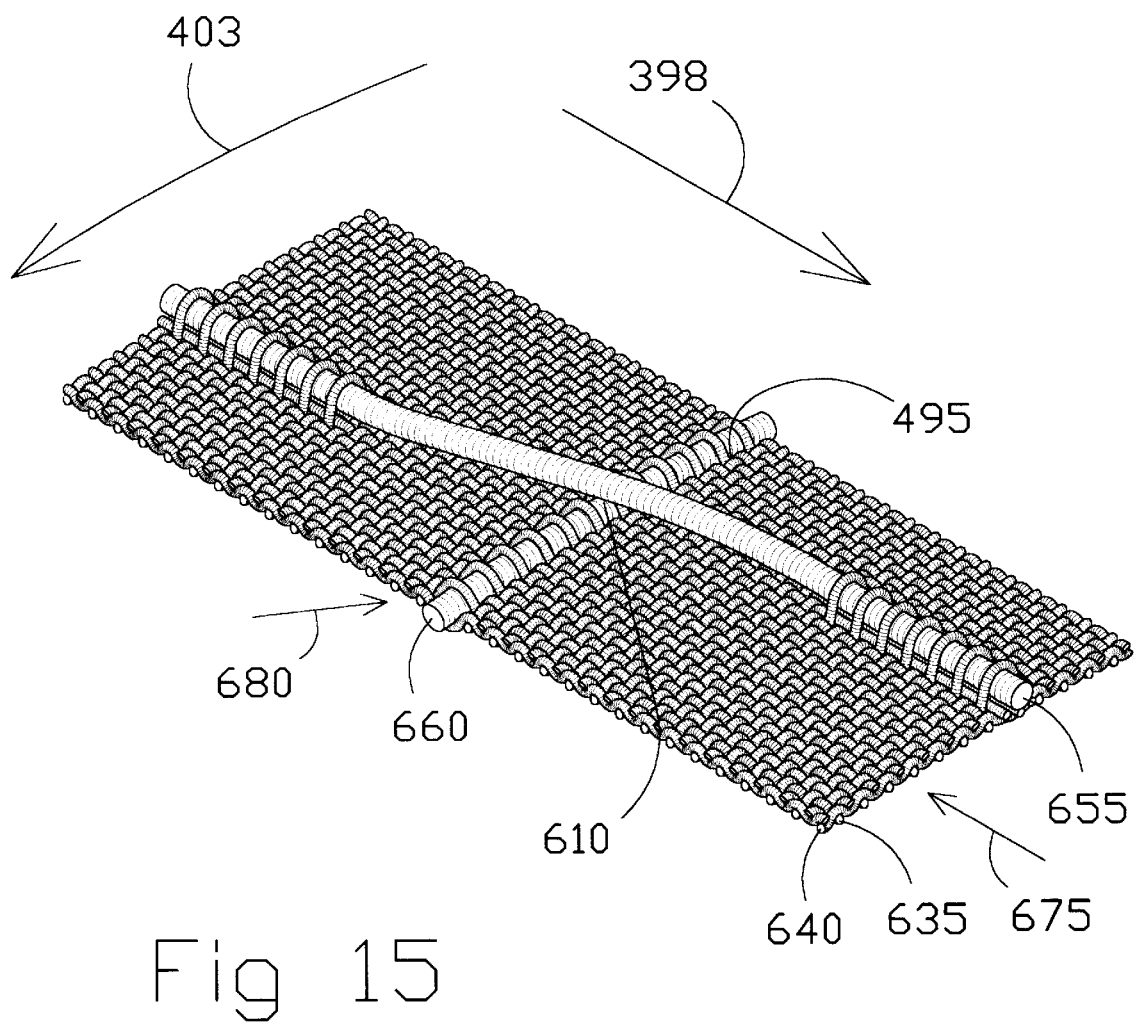
FIG. 15 is a perspective view of double weaving at a metal to metal crossover point.

FIGS. 14 and 13J show a metal to metal crossover point 610 of a straight circumferential metallic strand 660 with a straight axial metallic strand 655. FIGS. 14 and 13J will be used as an example to describe the process of forming a double weave. It is understood that the double weave can be equally well applied to any wall structure that involves a metallic strand 600 crossing over another metallic strand 600. To prevent leakage from occurring at gaps or leakage sites 495 of such metal to metal crossover points 610 a tubular double weave is created as shown in FIG. 15. For example, in the axial direction 398 both the straight axial polymeric strands 635 and the straight axial metallic strands 655 are woven together in the weave plane 675 to the left of the metal to metal crossover point 610. Near the metal to metal crossover point 610 the straight axial metallic strands 655 are brought out of the weave plane 675 and above the straight circumferential metallic strand 660 and back into the weave plane 675 to the right of the metal to metal crossover point 610. Underneath the straight axial metallic strands 655 at the crossover point the straight axial polymeric strands 635 are woven with the straight circumferential polymeric strands 640 and the straight circumferential metallic strand 660 such that a continuous woven layer 680 is located beneath the straight axial metallic strand 655 that was brought out of the weave plane 675. The result is a leak free wall structure with metallic strands being woven in two directions, axial direction 398 and circumferential direction 470.

Figure 16A:
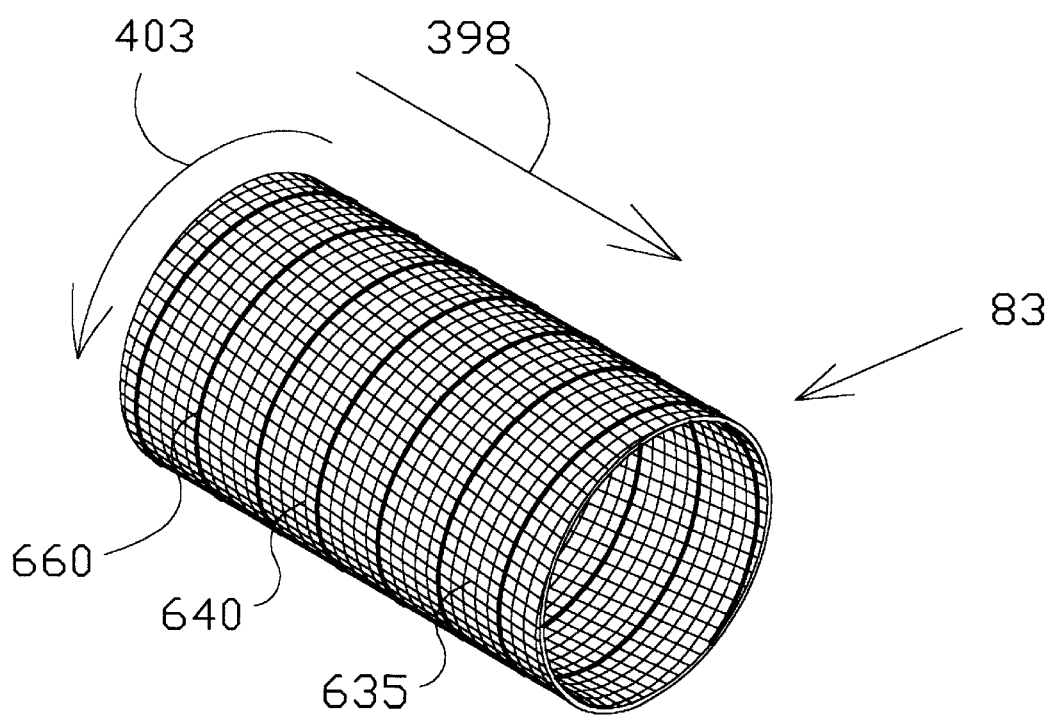
FIG. 16A is a representation of a vascular tubular member with a woven wall structure having straight axial polymeric, straight circumferential polymeric, and straight circumferential metallic strands.

FIG. 16A shows another embodiment for the wall structure of the present invention. In this embodiment straight circumferential polymeric strands 640 and straight circumferential metallic strands 660 are woven circumferentially and only straight axial polymeric strands 635 are woven axially. This embodiment does not have the axial compressive force capability described in the embodiment of FIG. 14 but it has excellent kink resistance due to the straight circumferential metallic strands 660 and has excellent flexibility through tortuous turns since only the flexible polymeric strands are positioned axially.

Figure 16B:
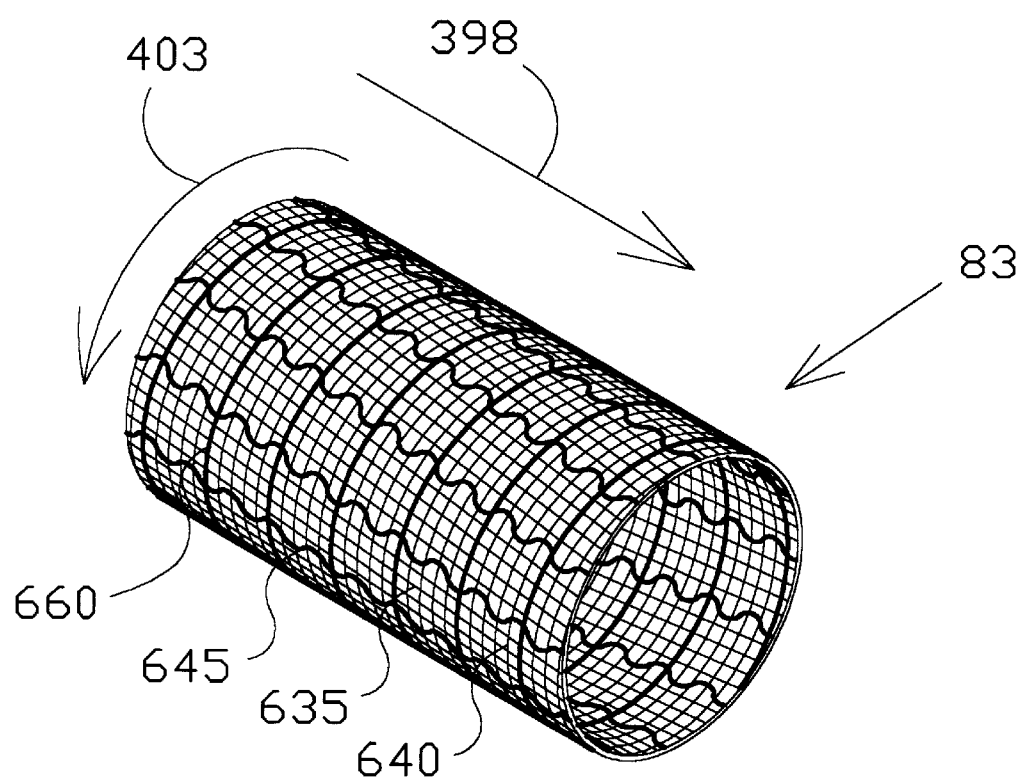
FIG. 16B is a representation of a vascular tubular member with a woven wall structure having straight axial polymeric, curved axial metallic, straight circumferential polymeric, and straight circumferential metallic strands.

FIG. 16B shows still another vascular tubular member wall structure with a curved axial metallic strand 645 woven along with a straight axial polymeric strand 635 in the axial direction 398 instead of the straight axial metallic strand 655 as shown in FIG. 14. The curved axial metallic strand 645 also provides the vascular graft, the intravascular graft, or the tubular member with good axial support against compressive forces generated by the thrombus 60 and other physiological forces that can be placed upon the tubular member. The curved axial metallic strand 645 can compress elastically and thereby will provide this tubular member wall structure with good axial flexibility to extend around tortuous turns in a blood vessel. The curved axial metallic strand 645 provides a benefit to the folded tubular section 125 of a straight intravascular folded tubular member 95 or bifurcated intravascular folded tubular member 260 by resisting wrinkling during the unfolding process. The curved axial metallic strand 645 can prevent the center wall of the folded tubular section 125 from forming wrinkles (see FIG. 7E) and can help the intravascular folded tubular section 125 to unfold evenly during the deployment of the folded tubular member.

Figure 16C:
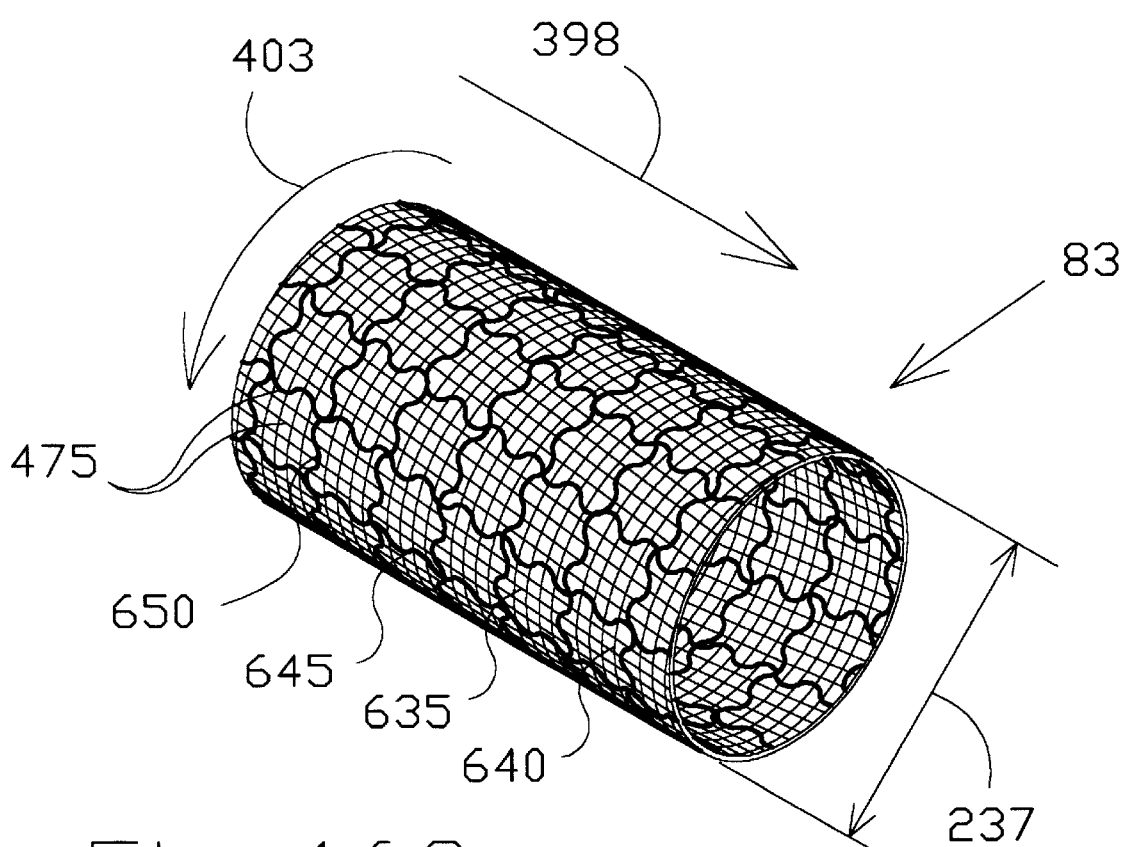
FIG. 16C is a representation of a vascular tubular member with a woven wall structure having straight axial polymeric, curved axial metallic, straight circumferential polymeric, and curved circumferential metallic strands.

FIG. 16C shows yet another wall structure for the surgical vascular graft, intravascular tubular member 85, or vascular tubular member 83 having a similar structure to that of FIG. 16B only with a curved circumferential metallic strand 650 in the circumferential direction instead of the straight circumferential metallic strand 660. The axial strands 475 have remained the same as in FIG. 16B. The curved circumferential metallic strand 650 found in this structure allows the folded tubular section 125 of a straight intravascular folded tubular member 95 or bifurcated intravascular folded tubular member 260 to unfold with greater ease due to their ability to elongate diametrically as one curved circumferential metallic strand 650 located in an folded tubular section inner wall 165 or folded tubular section outer wall 155 passes adjacent to another curved circumferential metallic strand 650 located in the folded tubular section center wall 160. The curves or bends in the curved circumferential metallic strands 650 also allows the intravascular folded tubular member to expand out uniformly to its deployed diameter 237 and provide uniform contact with the wall or the native vessel or aortic wall in the case of abdominal aortic aneurysm. The deployed diameter 237 of the vascular tubular member 83 used as an intravascular tubular member 85 (see FIG. 1B) of the present invention can be smaller than the equilibrium diameter that the intravascular tubular member could attain if not constrained by the native vessel in the deployed state.

Figure 17A:
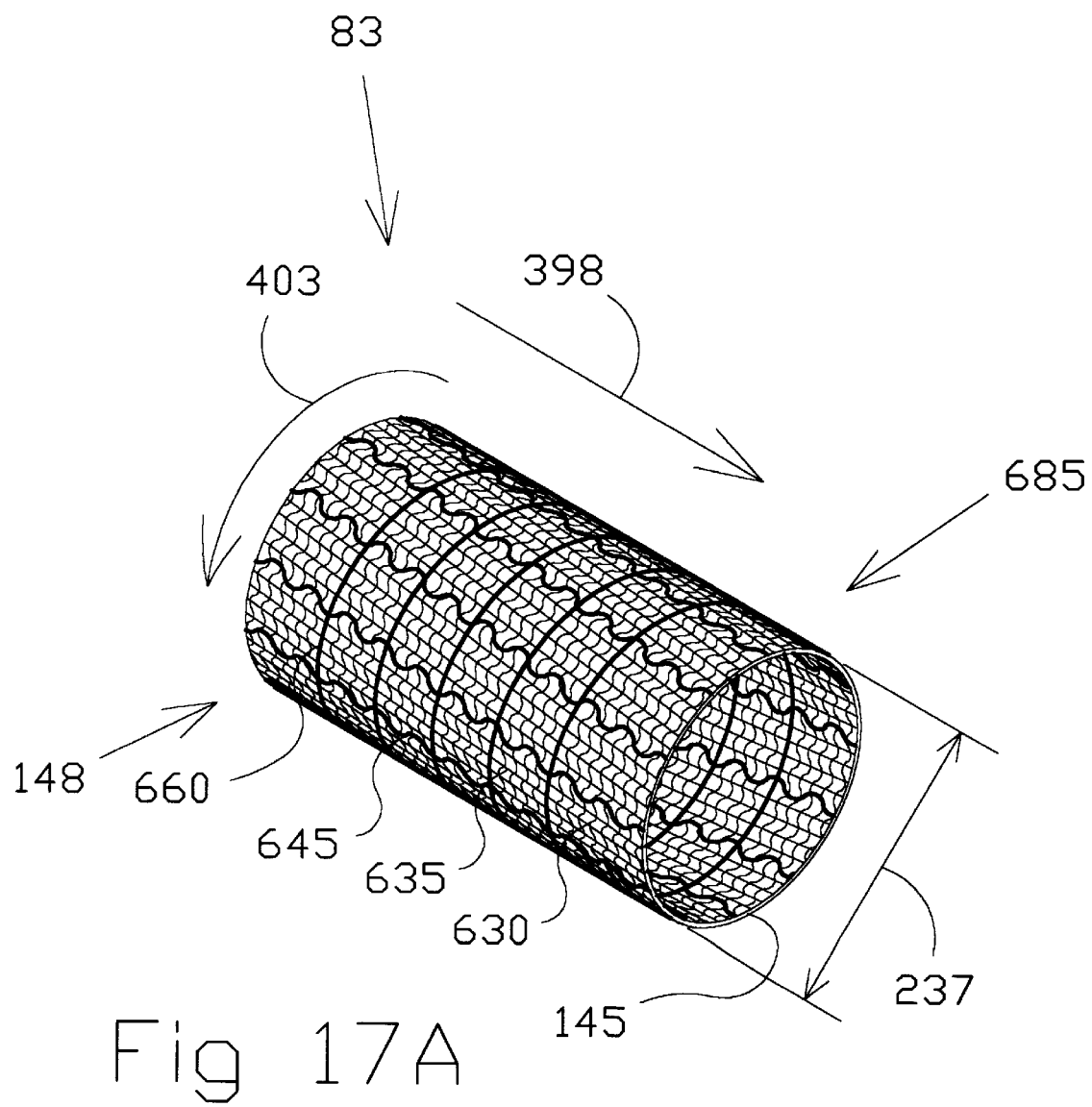
FIG. 17A is a representation of a vascular tubular member with a woven wall structure having straight axial polymeric, curved axial metallic, curved circumferential polymeric, and straight circumferential metallic strands.

FIG. 17A shows one more vascular tubular member 83 wall structure with a curved circumferential polymeric strand 630 woven along with a straight circumferential metallic strand 660 in the circumferential direction and a straight axial polymeric strand 635 is woven along with a curved axial metallic strand 645 in the axial direction 398. The curved circumferential polymeric strand 630 provides an amount of circumferential stretch in the diametric direction. The straight circumferential metallic strands 660 and curved axial metallic strands 645 restrict excessive circumferential stretch of the curved circumferential polymeric strands 630. This wall structure can also be modified slightly to provide an additional characteristic. Near the inlet portion 685 of the tubular means the straight circumferential metallic strand 660 can be eliminated thereby allowing the vascular tubular member to expand to a larger circumference. This circumferential expansion allows the vascular tubular member of the present invention to accommodate a reasonable tolerance in the estimated diameter of the artery such as an estimation of the diameter of the aortic neck. The inlet end 145 of the vascular tubular member 83 can accommodate a tolerance in the estimation of the aortic neck diameter and provide a leak free seal of the vascular tubular member with the vessel wall without overlap of excess material at the inlet end 145 or outlet end 148 due to an oversized diameter of the vascular tubular member 83. Similar circumferential accommodation also applies to accommodating the estimated diameter of an artery or blood vessel such as the iliac or femoral artery with the outlet end 148 of the vascular tubular member 83.

Accommodation of the estimated aortic diameter or other blood vessel diameter with a vascular tubular member 83 of a fixed non-flexible wall material in the circumferential direction 470 with a maximum diameter can also be accomplished by ensuring that the vascular tubular member chosen can expand to a larger maximum deployed diameter 237 than the arterial diameter in which the device is to be placed. For the abdominal aortic aneurysm application this is accomplished by choosing a vascular tubular member 83 with an equilibrium diameter or maximum dimension of the deployed diameter 237 that is larger than the aortic diameter plus any tolerance in diameter estimation associated with measuring technique errors. Any excess intravascular tubular member wall material due to a slight oversized tubular member diameter will result in an overlap of excess wall material. Provided that this overlap material is held tightly against the aortic wall by the proximal attachment means 87, leakage at the proximal site will not occur.

Figure 17B:
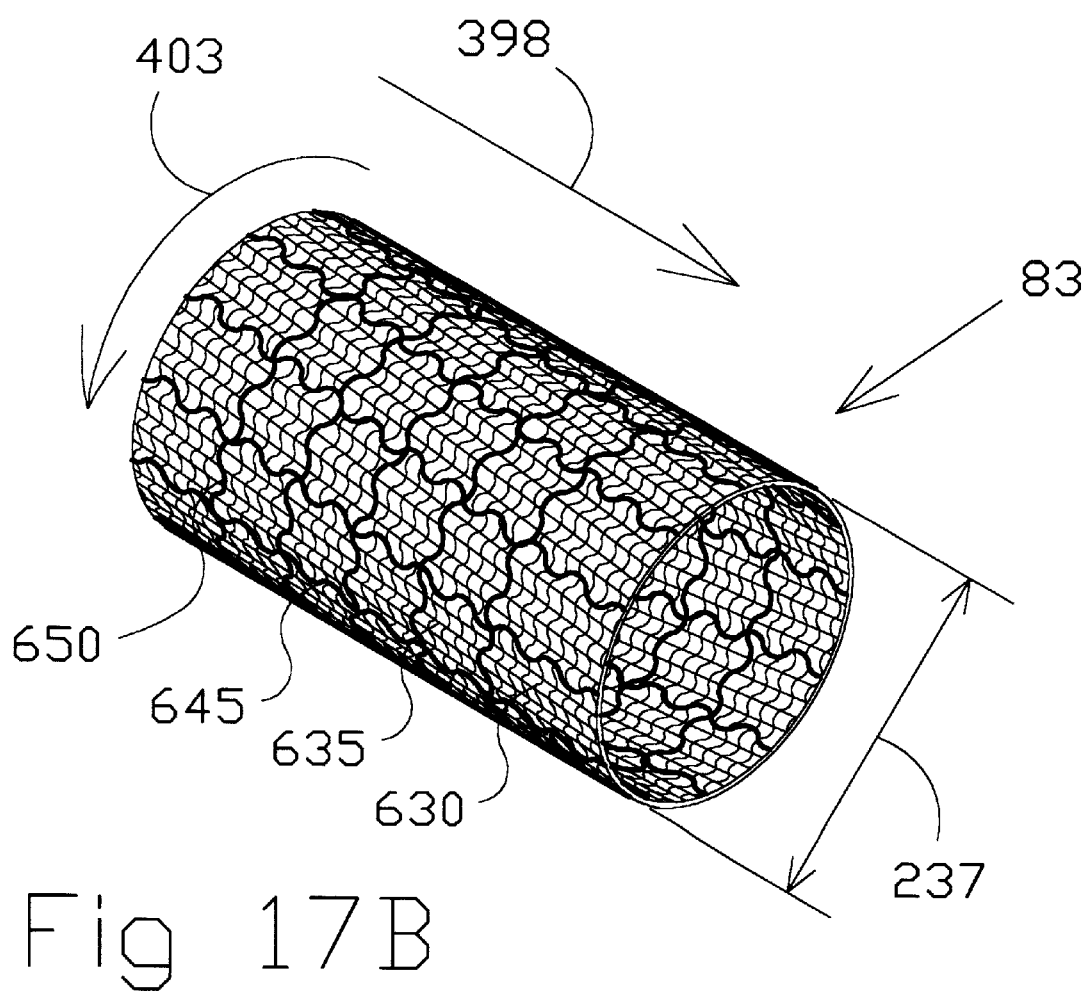
FIG. 17B is a representation of a vascular tubular member with a woven wall structure having straight axial polymeric, curved axial metallic, curved circumferential polymeric, and curved circumferential metallic strands.

FIG. 17B shows yet one more vascular tubular member wall structure which is the same as that of FIG. 17A except that a curved circumferential metallic strand 650 has replaced the straight circumferential metallic strand 660. This structure offers the ability to stretch in the circumferential direction 470 to a limited extent controlled by the amount of curvature provided to the curved circumferential metallic strands 650 and curved circumferential polymeric strands 630. This vascular tubular member 83 wall structure provides good anti-kink characteristics, good axial support against compression, good flexibility, and will accommodate a reasonable tolerance in the diameter of the proximal aortic neck, and a tolerance on the iliac artery diameter.

Figure 17C:
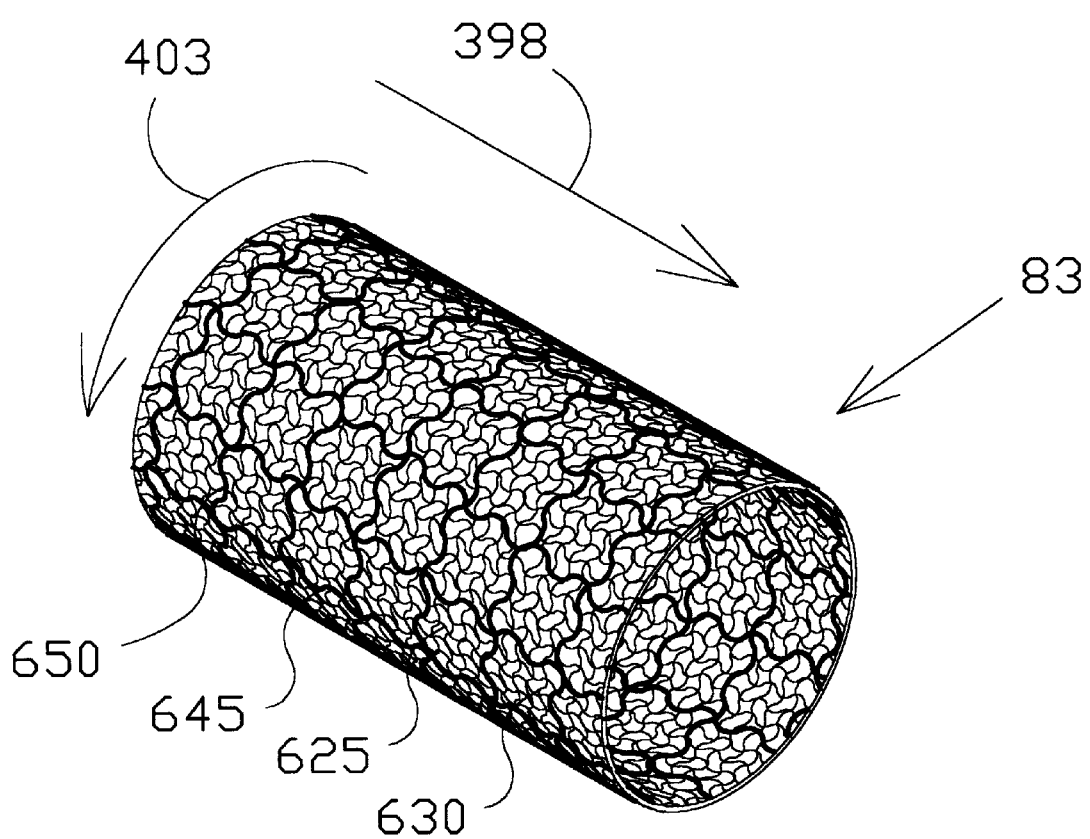
FIG. 17C is a representation of a vascular tubular member with a woven wall structure having curved axial polymeric, curved axial metallic, curved circumferential polymeric, and curved circumferential metallic strands.

FIG. 17C shows still one more vascular tubular member wall structure with a curved circumferential polymeric strand 630, a curved circumferential metallic strand 650, a curved axial polymeric strand 625 interwoven, and a curved axial metallic strand 645. This structure offers the ability to stretch in the circumferential direction 470 and axial direction 398 to a limited extent controlled by the amount of curvature provided to the strands. This structure can extend throughout the entire tubular means. This vascular tubular member wall structure provides good anti-kink characteristics, good axial support against compression, good flexibility, and will accommodate a reasonable tolerance in the aortic neck diameter, and a tolerance on the iliac artery diameter.

Figure 18A:
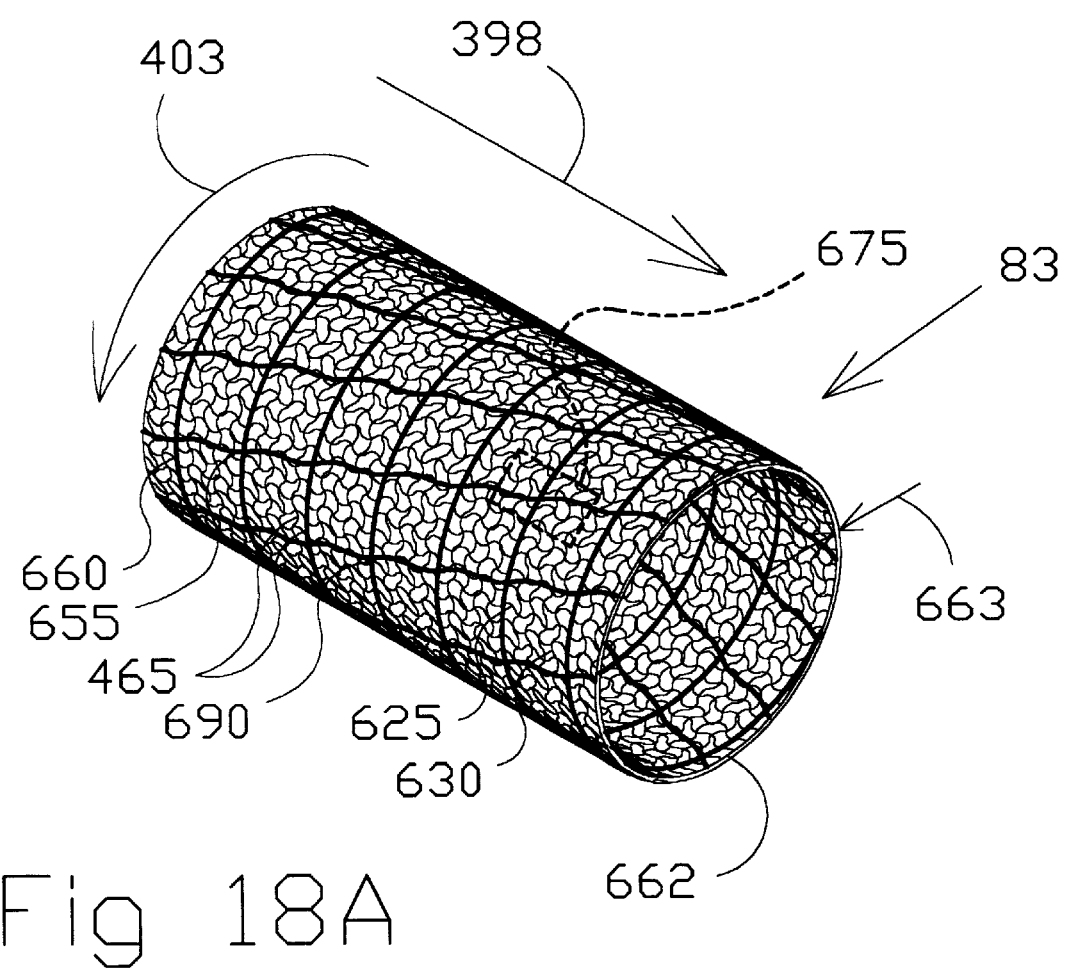
FIG. 18A is a representation of a vascular tubular member with a woven wall structure having curved circumferential polymeric, straight circumferential metallic, curved axial polymeric, and straight axial metallic strands having a circumferential step-over.
Figure 18B:
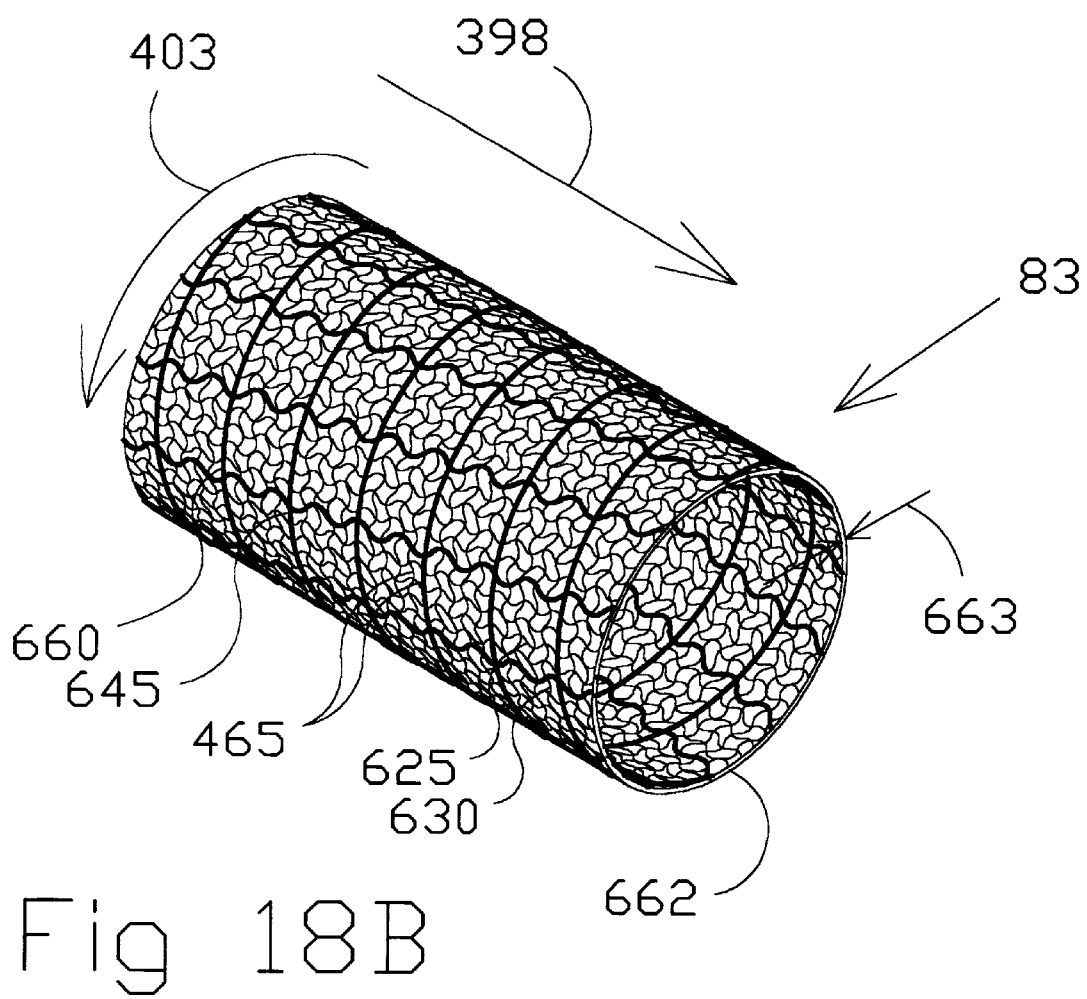
FIG. 18B is a representation of a vascular tubular member with a woven wall structure having having curved circumferential polymeric, curved axial polymeric, straight circumferential metallic, and curved axial metallic strands with augmented helical turn.

FIGS. 18A and 18B show further embodiments of the wall structure that can be applied to the vascular tubular member 83 of the present invention. The vascular tubular member wall structures presented in FIGS. 14, 16A–16C, 17A–17C that contain curved axial metallic strands 645 or straight axial metallic strands 655 which can be directed with an augmented amount of helical turn. This augmented helical turn is accomplished by taking the straight axial metallic strands 655 out of the weave plane 675, creating a step-over 690 by stepping the straight axial metallic strands 655 over to a new site that is displaced circumferentially, and inserting the strands 655 back into the plane of the weave 675 as shown in FIG. 18A. This stepping over process allows the axial metallic strand 655 to assume a helical pathway along the axial direction 398 of the vascular tubular member 83. This augmented amount of helical turn is in addition to the gradual helical turn naturally found in the axially oriented metallic strands 600 due to their natural desire to orient perpendicular to the generally circumferential strands 465 such as the straight circumferential metallic strands 660 and curved circumferential polymeric strands 630 which also have a slight helical turn since they are wound in a continuous helix as shown in FIG. 18A. The augmented helical turn of the metallic strand in the generally axial direction 398 provides the stent-graft with an ability to bend without kinking even when straight metallic strands are used in the axial direction 398. In FIG. 18B two straight circumferential metallic strands 660 are wound in a double helix with a greater angle with respect to the circumference. This induces the curved axial metallic strands 645 to orient at an angle with respect to the axial direction 480.

In the embodiments of the wall structure of the present invention shown in FIGS. 18A and 18B curved circumferential polymeric strands 630 and curved axial polymeric strands 625 are wound in the circumferential 470 and axial direction 398 to provide the vascular tubular member 83 with a supple feel and good bending characteristics without kinking. For simplicity of manufacturing, a straight circumferential metallic strand 660 is wound in the circumferential direction 470. Either a curved axial metallic strand 645 (see FIG. 18B) or a straight axial metallic strand 655 (see FIG. 18A) with the step over characteristic described above is used in the axial direction 398 to provide the necessary compressive strength as well as provide good flexibility to the vascular tubular member 83.

An entire straight vascular tubular member or bifurcated vascular tubular member can be formed from a single contiguous woven material comprised of the polymeric multifilament strands 510 or the combined polymeric multifilament strands 510 and metallic monofilament strands 490 described in FIGS. 14, 16A–16C, 17A–17C, 18A, and 18B. The bifurcated intravascular folded tubular member 260 can be woven without seam in its proximal tubular section, folded tubular section 125, or distal tubular section 130. This is accomplished by weaving the main trunk 270 with approximately twice the number of polymeric multifilament strands 510 and metallic monofilament strands 490 in the axial 398 and circumferential 470 directions as will be used in each proximal leg tube 275, folded tubular section 125, or distal tubular section 130 (see FIG. 13J and 14). The weaving of two proximal leg tubes 275 from the main trunk 270 can proceed continuously without seam as approximately half of the strands in the axial direction 398 and circumferential direction 470 are directed from the main trunk 270 to each proximal leg tube. The weave plane 675 for each proximal leg tube 275 (see FIG. 4A) is continued to form the weave plane 675 for the wall structure for the folded tubular section 125 and the distal tubular section 130. The wall thickness 663 of the woven vascular tubular member 460 (see FIG. 13A) can be formed to minimal wall thickness 663 while maintaining strength of the vascular tubular member wall 662.

Braided Wall Structure

Figure 19:
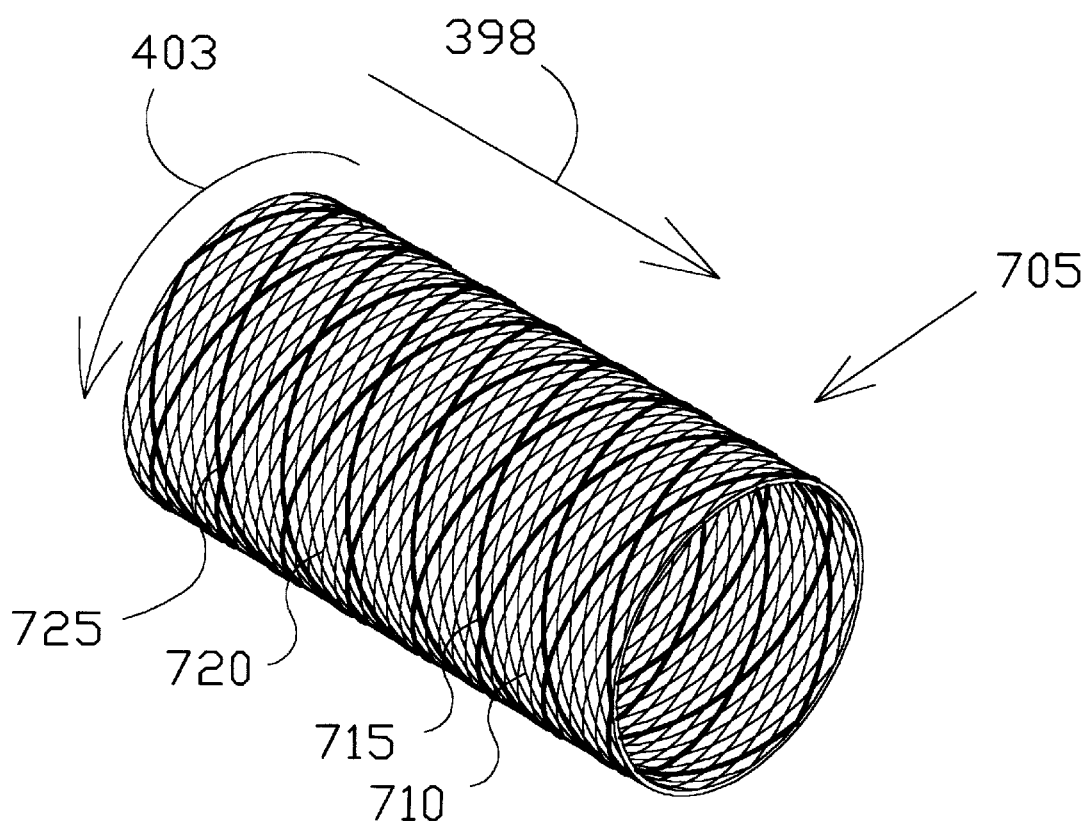
FIG. 19 is a representation of a vascular tubular member with a braided wall structure having left and right spirals of multifilament polymeric and monofilament metallic strands.

FIG. 19 shows a wall structure of the braided vascular tubular member 705 of the present invention formed from a braiding process with similar nomenclature being used as used for the woven vascular tubular member 460. The braided vascular tubular member 705 has straight polymeric and straight metallic strands braided in a right hand spiral forming a straight right spiral polymeric strand 710 and a straight right spiral metallic strand 715, and in a left hand spiral forming a straight left spiral polymeric strand 720 and a straight left spiral metallic strand 725. The braiding process provides some ability for this wall structure to accommodate reasonable tolerances in the estimation of the proximal aortic neck diameter in order to provide a good diametric fit between the braided vascular tubular member 705 and the proximal aortic neck. The strands 710, 715, 720, and 725 can be made with localized bends or curves in them as described earlier, and these strands can be braided as described for the embodiments of FIGS. 14, 16A–16C, 17A–17C, 18A, and 18B, and these stands can be braided as described in FIG. 19. The presence of the straight or curved metallic monofilament strands 605 and 615 (see FIGS. 13L and 13K) provides good axial and circumferential strength and stability against compression in the radial or axial direction 398. The metallic curved monofilament strands 615 or curved polymeric multifilament strands 573 can provide the vascular tubular member with a greater flexibility due to the ability of these strands to compress or extend as the braided vascular tubular member 705 is exposed to a tortuous pathway. The spacing between the right spiral metallic strands 715 or the left spiral metallic strands 725 braided in either the right or left spiral to form a braided vascular tubular member 705 is similar to the spacing ranges stated for the woven vascular tubular member 460.

Applications of Wall Structure

The wall structure described in FIGS. 13A–13M, 14, 15, 16A–16C, 17A–17C, 18A, 18B, and 19 can be applied to a surgical vascular graft, an intravascular tubular member 85, or other vascular tubular member 83. As a surgical vascular graft with a woven or braided wall structure, the metallic straight 605 and curved 615 monofilament strands offer improved kink resistance and can provide crush resistance to the vascular graft when placing the graft across a knee joint or other vascular space that is exposed to compressive forces. For the woven vascular tubular member 460 the curved circumferential polymeric strands 630 and curved circumferential metallic strands 650 offer enhanced diametric flexibility or diametric compliance which can lead to improved healing at anastamoses of the vascular tubular member with the native vessel. The curved axial metallic strands 645 or straight axial metallic strands 655 of the woven tubular member offer resistance to axial compressive forces which can also lead to kinking and allow the vascular graft to be pulled through tunnels during implantation without concern for damage to the vascular graft due to excessive axial stretching. As an intravascular tubular member the woven and braided wall structures offer the benefit of a built-in stent. For the woven vascular tubular member 460 the straight circumferential metallic strands 660 and curved circumferential metallic strands 650 offer a thin wall structure with excellent expansion elastic forces acting outward against the native vessel wall or native lumen. Since the straight 660 and curved 650 circumferential metallic strands can be positioned regularly within the wall structure throughout the weave, there can be more of them and their diameter can be smaller than stent wires for most prior art stents. For the woven vascular tubular members 460 the straight 660 and curved 650 circumferential metallic strands are nearly circumferential; they exert a greater outward force for a thinner strand diameter than a zig zag shaped stent or as stent with large bends that require their struts 370 to extend in a non-circumferential direction. The straight 655 and curved 645 axial metallic strands of the woven vascular tubular members 460 also provide a built-in structure onto which any attachment means can be attached firmly to either the inlet 145 or outlet end 148. The woven wall structures with curved circumferential metallic strands 650 and curved circumferential polymeric strands 630 are able to stretch circumferentially and accommodate errors in estimated diameter of the native blood vessel. The woven wall structures with curved circumferential polymeric strands 630 along with straight or curved circumferential metallic strands 650 can also accommodate errors in the estimation of native vessel diameter by removing the straight 660 or curved 650 circumferential metallic strands near the inlet end 145 or the outlet end 148 of the intravascular tubular member. The curved circumferential polymeric strands 630 of the woven wall structure will allow the intravascular tubular member 85 to stretch and accommodate errors in the diameter estimation such that any attachment means 87 placed at the inlet end 145 or outlet end 148 can form a leak tight seal with the artery either proximal or distal to the vessel injury. The woven 460 or braided 705 vascular tubular member formed from polymeric multifilament strands 510 can also be used as an intravascular tubular member 85 and offers the strongest and safest wall structure for the thinnest wall thickness 663. The safety associated with weaving or braiding multifilament strands 510 of ePTFE relates to its ability to avoid a catastrophic tear in the wall structure. Standard tubular ePTFE vascular grafts can form an axial or circumferential tear that can lead to significant complications or possibly patient death. The woven vascular tubular member 460 formed from multifilament strands 510 of ePTFE would not allow a local defect found in the wall structure to extend in an axial direction 398 or circumferential direction 470. The multifilament strands allows the woven vascular tubular member 460 formed from the strands containing ePTFE filaments 525 to seal against blood leakage at crossover points 485 of the ePTFE strands.

The wall structure described in FIGS. 13A–13E, 14, 15, 16A–16C, 17A–17C, 18A, and 18B are well suited to the straight intravascular folded tubular member 95 and bifurcated intravascular folded tubular member 260 with associated advantages. The woven wall structure, woven from polymeric multifilament strands 510 in one embodiment and in other embodiments with metallic straight 605 or curved 615 monofilament strands also woven along with the polymeric multifilament strands 510, offers the greatest strength with one of the thinnest wall thicknesses 663. Since the folded tubular section 125 of the straight intravascular folded tubular member 95 or bifurcated intravascular folded tubular member 260 has three folded tubular section walls 330, it is important that each wall be of a minimum wall thickness 663. Also of importance is ensuring that the straight or bifurcated proximal tubular section wall 170, folded tubular section walls 330, and distal tubular section wall 190 cannot be easily torn which can lead to a life threatening sequelae for the patient. These safety and performance characteristics can be obtained by weaving multifilament strands 510 of ePTFE or multifilament strands 510 of polyester as described in FIGS. 13A–13M. The folded tubular section 125 requires that the folded tubular section inner wall 165, folded tubular section outer wall 155, and folded tubular section center wall 160 can slide with respect to each other as the straight intravascular folded tubular member 95 or bifurcated intravascular folded tubular member 260 is deployed from a partially deployed state of smaller length to a fully deployed state of greater length. The woven wall structures with straight circumferential metallic strands 660 or curved circumferential metallic strands 650 provide a substantially smooth wall structure without significant protrusions that can provide ease of unfolding in the folded tubular section 125. The weaving of metallic straight 605 or curved 615 monofilament strands in the circumferential direction 470 into the wall structure provides an optimum way of providing a built-in metallic stent to provide outward expansion forces while minimizing the thickness of the three folded tubular section walls 330. Since the metallic straight 605 or curved 615 monofilament strands are acting in a nearly circumferential direction 470, their strength to provide the outward expansion forces is greatest for the least metallic strand 600 diameter.

Figure 20:
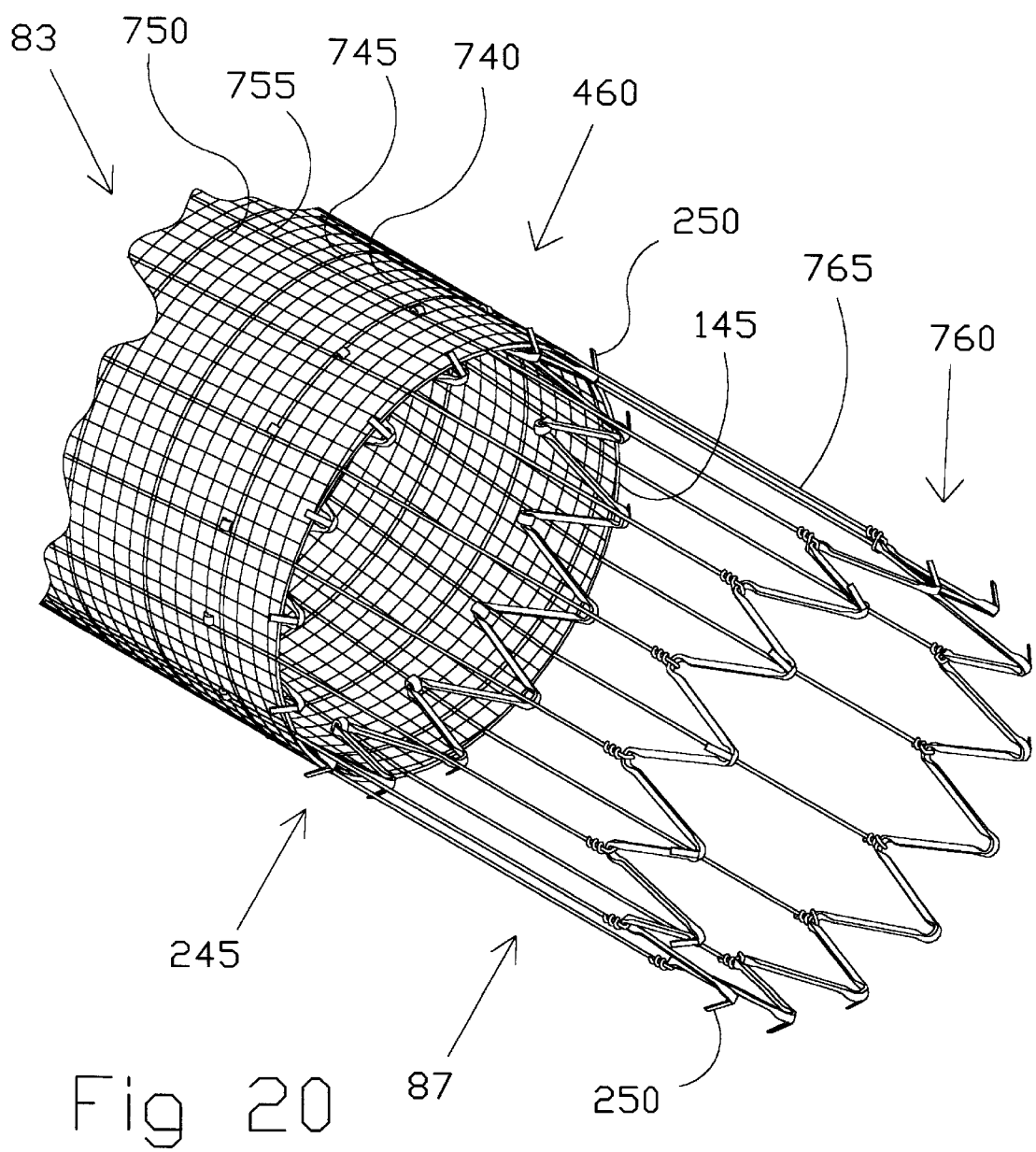
FIG. 20 is a partially sectioned view of an intravascular tubular member formed of a woven wall structure with multifilament polymeric strands and axially directed metallic strands interwoven and a displaced attachment anchor.

FIG. 20 shows the inlet end 145 and outlet end 148 of an intravascular tubular member 85 with a wall structure similar to an embodiment shown in FIGS. 14, 16A–16C, 17A–17C, 18A, or 18B. The woven wall structure can be formed of any combination of weave involving either straight multifilament strands, straight monofilament strands, curved multifilament strands, or curved monofilament strands used to weave generally circumferential polymeric strands 740, generally circumferential metallic strands 745, generally axial polymeric strands 750, and generally axial metallic strands 755 as described in the previous embodiments or otherwise intended. Thus for example, a generally circumferential polymeric strand 740 is understood to mean a straight 640 or curved 630 circumferential polymeric strand, a generally circumferential metallic strand 745 means a straight 660 or curved 650 circumferential metallic strand, a generally axial polymeric strand 750 means a straight 635 or a curved 625 axial polymeric strand, and a generally axial metallic strand 755 means a straight 655 or a curved 645 axial metallic strand. This definition shall also be applicable to FIGS. 21–23. Attached to the inlet end 145 is an attachment means 87. The attachment means can be the attachment anchor 245 described in FIGS. 9A, 9B, 10A–10C, and 11A–11D. A displaced attachment anchor 760 is located at a position displaced away from the inlet end 145 in a proximal direction and not in contact with the woven wall structure. The displaced attachment anchor 760 is the attachment anchor 245 that is located away from the inlet end 145. The distance that the displaced attachment anchor is located from the inlet end 145 can range from approximately 5 millimeters to 40 millimeters. For an abdominal aortic aneurysm application the displaced attachment anchor 760 can be displaced approximately 10 to 25 millimeters away from the inlet end 145. The displaced anchor is attached to the intravascular tubular member with axially oriented attachment strands 765. The attachment strands 765 can be attached to the displaced attachment anchor 760 through selected intranodal openings 385 (see FIG. 9A) of the displaced attachment anchor 760. The attachment strands 765 can be extensions of the generally axial metallic strands 755 or generally axial polymeric strands 750. Preferably the attachment strands 765 are generally axial metallic strands 755 which are continuous with the generally axial metallic strands 755 found in the weave of the intravascular tubular member 85. Thus, the woven wall structure of the intravascular tubular member 85 with generally axial metallic strands 755 has the structure inherent in the woven intravascular tubular member to simply extend some or all of the generally axial metallic strands 755 proximally beyond the inlet end 145 and use them to attach to the displaced attachment anchor 760. The displaced attachment anchor 760 provides a proximal anchoring site that is positioned farther away proximally from the vessel injury than the inlet end 145. Vessel side branches such as the left renal artery 45 and right renal artery 50 in the case of abdominal aortic aneurysm that can extend from the aorta adjacent and proximal to the inlet end 145 of the intravascular tubular member 85 are able to receive blood flow from the native vessel between the inlet end 145 or the intravascular tubular member and the displaced attachment anchor 760. In the case of treating abdominal aortic aneurysm the right and left renal arteries 45 & 50 can be located between the displaced attachment anchor 760 and the inlet end 145 of the vascular tubular member. Only a minimal number of attachment strands 765 are needed to attach the displaced attachment anchor 760 to the inlet end 145 of the tubular member, ranging from two to approximately sixteen. Preferably the number of attachment strands 765 ranges from approximately three to six. The likelihood of an attachment strand crossing over a vessel side branch is reduced with a smaller number of attachment strands 765. A single attachment strand 765 extending from a generally axial metallic strand 755 that crosses over an inlet to a vessel branch will not significantly affect the flow rate of blood to that side branch vessel. The displaced attachment anchor 760 can have barbs 250 to help provide a more firm attachment to the vessel wall such as the vessel wall of the aorta. Either the displaced anchor 760 or the attachment anchor 245 attached at or near the inlet end 145 of the tubular member can have barbs 250 or can be provided without barbs 250.

The attachment anchor 245 positioned at the inlet end 145 or outlet end 148 of the intravascular tubular member can also be efficiently attached to any generally axial metallic strands 755 or generally axial polymeric strands 750 of the wall structure described in FIGS. 14, 16A–16C, 17A–17C, 18A, 18B, or 20. Preferably the attachment anchor 245 is attached to a plurality of generally axial metallic strands 755 that can form a firm attachment to the attachment anchor 245. The general axial metallic strands 755 can efficiently attach to the attachment anchor 245 using the intranodal openings 385 as sites for attachment. A generally circumferential metallic strand 745 near the inlet end 145 or outlet end 148 of the vascular tubular member can be removed to provide the intravascular tubular member 85 formed with curved circumferential polymeric strands 630 with stretchability with an ability to accommodate error in the estimated diameter of the native vessel as was discussed in FIG. 17A. This wall structure allows the inlet end 145 or outlet end 148 to stretch and enlarge in diameter by up to approximately fifty percent and provide a better diametrical fit to the native vessel without leakage. The attachment anchor 245 attached to the stretchable inlet end 145 or outlet end 148 of the intravascular tubular member can make a tighter seal with the native vessel wall without requiring overlap of the wall structure near the inlet end 145 or outlet end 148 between the attachment anchor 245 and the native vessel wall or native lumen. The braided wall structure of the vascular tubular member shown in FIG. 19 can also be used with the displaced attachment anchor 760. A plurality of right spiral metallic strands 715 or left spiral metallic strands 725 can be extended proximally beyond the inlet end 145 and attached to the displaced attachment anchor 760 in a manner similar to that described for the woven vascular tubular member 460.

Figure 21:
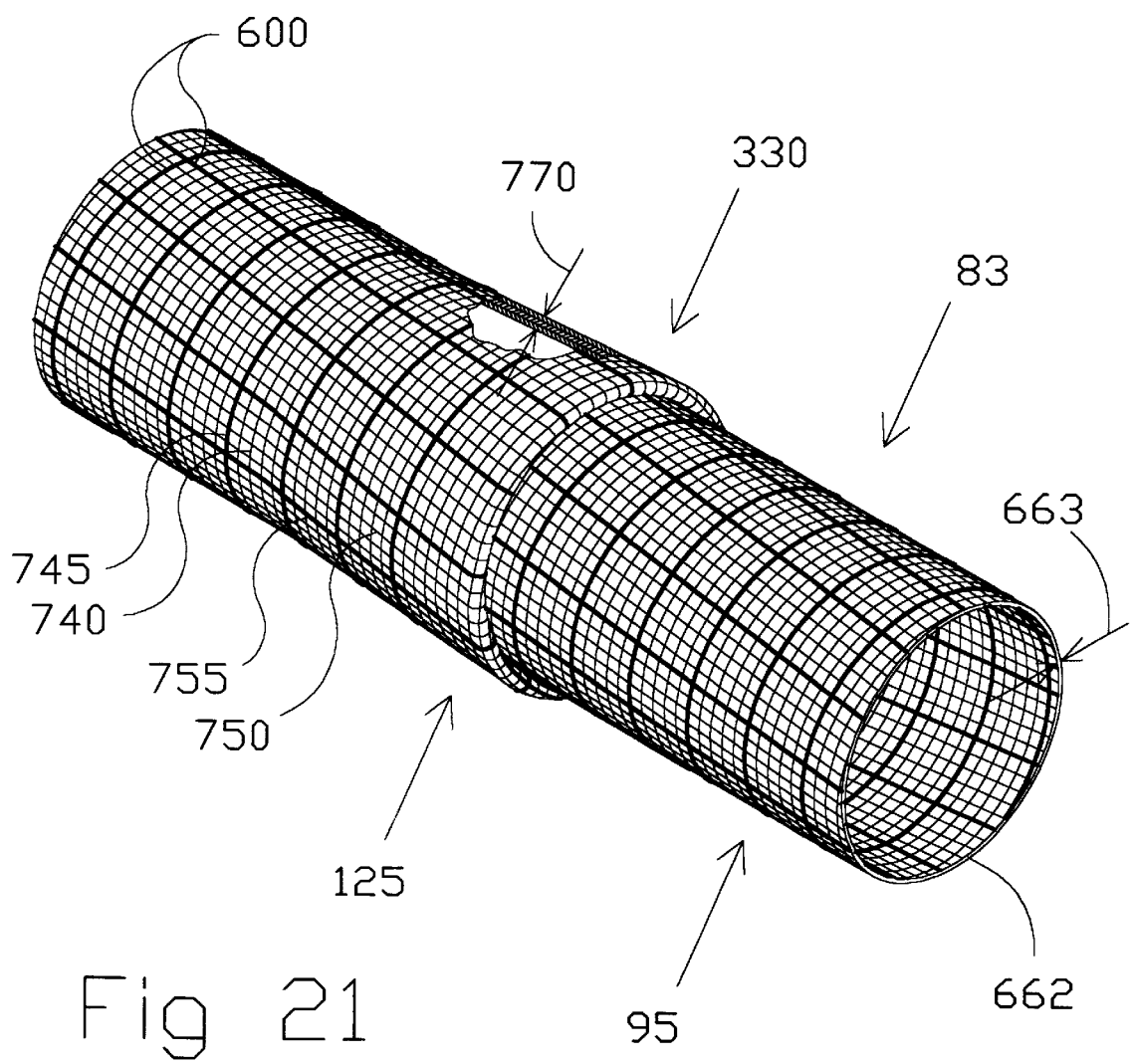
FIG. 21 is an intravascular folded tubular member formed with a woven wall structure of multifilament polymeric strands interwoven along with monofilament metallic strands.
Figure 22:
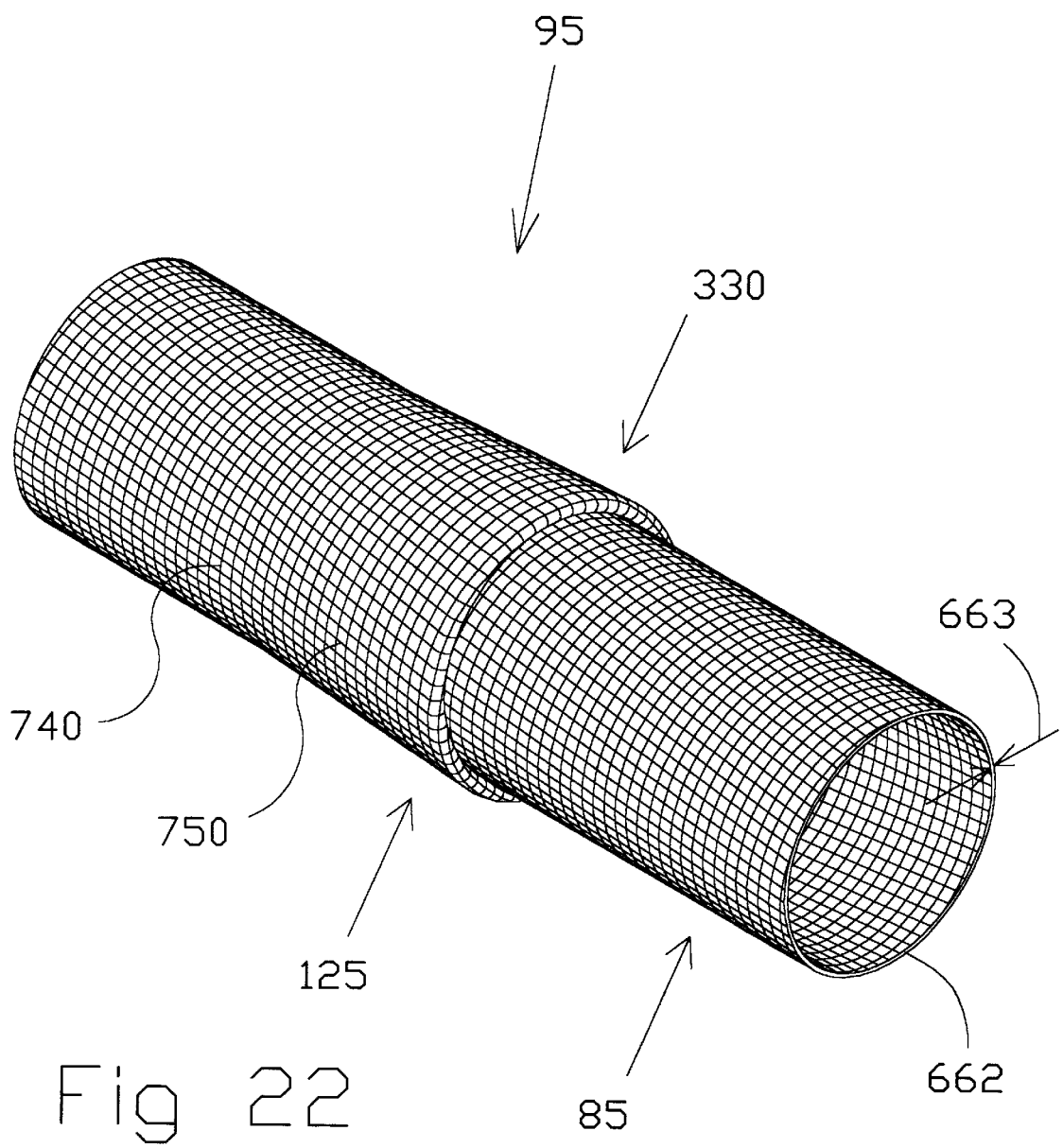
FIG. 22 is an intravascular folded tubular member formed with a woven wall structure formed entirely of multifilament polymeric strands.

FIG. 21 shows a vascular tubular member 83 with a folded tubular section 125 and with a woven wall structure as described in FIGS. 14, 16A–16C, 17A–17C, 18A, and 18B. The woven wall structure can be formed from generally circumferential metallic strands 745, generally circumferential polymeric strands 740, generally axial metallic strands 755 and generally axial polymeric strands 750 that have been defined in the description of FIG. 20. The woven structure containing metallic monofilalment strands 490 and polymeric multifilament strands 510 is well suited to forming the folded tubular section 125 of the straight intravascular folded tubular member 95 or the bifurcated intravascular folded tubular member 260. The folded tubular section 125 can be formed with a minimal triple wall thickness 770 for the folded tubular section walls 330 due to the wall structure of the present invention. Having the generally axial metallic strands 755 and generally circumferential metallic strands 745 woven into the wall provides the present invention with the advantage that a greater number of smaller thickness metallic strands 600 can be used to provide the outward force generated by the generally circumferential metallic strands 745. Also the generally circumferential metallic strands 745 and generally axial metallic strands 755 do not require an additional binding means to bind them to the vascular tubular member 83 as required by other prior art devices. Providing the general circumferential metallic strands 745 as part of the weave also allows the folded tubular section 125 to unfold smoothly and evenly without catching or snagging such as on a protruding metal wire or stents attached to the outside of the walls of other prior art stent-graft devices. The woven wall structure of the present invention will allow the folded tubular section 125 to unfold with a steady uniform force as the intravascular folded tubular member extends in length from a partially deployed state to a deployed state. It is understood that the woven structure described in this invention can be applied to straight intravascular folded tubular member 95 or bifurcated intravascular folded tubular member 260. In addition, the woven structure can be applied to the straight intravascular folded tubular member 95 or the bifurcated intravascular folded tubular member 260 that do not contain a folded tubular section 125 and are intended for intravascular use. Also, the woven wall structure can be applied to straight or bifurcated vascular tubular members 83 that can be used for standard surgical implant for treatment of vascular injuries. The straight 95 or bifurcated 260 intravascular folded tubular member is also well suited to be formed entirely from only generally circumferential polymeric strands 740 and generally axial polymeric strands 750 as shown in FIG. 22. The thin wall thickness 663 provides the folded tubular section walls 330 with a thin overall wall thickness for the three walls. The smooth wall structure formed from the woven polymeric multifilament strands 510 will allow for smooth and uniform unfolding of the folded tubular section 125 without binding as it unfolds during deployment to a fully deployed state. All reference numerals correspond to those elements previously or otherwise described. The woven vascular tubular member 460 shown in FIGS. 14, 16A–C, 17A–C, 18A, and 18B are well suited to forming a straight 95 or bifurcated 260 intravascular folded tubular member. In placing the outlet end 148 in its appropriate position it is important that the woven vascular tubular member 460 does not reduce in diameter as the outlet end 148 is being placed and the folded tubular section 125 is unfolding. The woven vascular tubular member 460 does not reduce in diameter if it is pulled from each end in tension. The woven vascular tubular member 460 does not reduce in diameter when used as a straight 95 or bifurcated 260 intravascular folded tubular member that is being extended in length and forms a fully deployed state. The presence of straight 660 or curved 650 circumferential metallic strands further helps to maintain the deployed diameter 237 at a constant value without necking down or reducing in diameter in extending to a fully deployed state. The woven wall structure is also well suited to the straight 95 or bifurcated 260 intravascular folded tubular member because the axial strands 475 provide a significant resistance to axial length change in the material itself. Thus during deployment from a partially deployed state to a fully deployed state the extension to a deployed tubular member length will occur primarily due to the unfolding of the folded tubular section 125.

FIG. 23 shows a bifurcated intravascular folded tubular member 260 formed with a woven wall structure. The woven wall structure can be formed from generally circumferential metallic strands 745, generally circumferential polymeric strands 740, generally axial metallic strands 755 and generally axial polymeric strands 750 that have been defined in the description of FIG. 20. The folded tubular sections 125 are formed from the woven wall structure. The inlet end 145 has an attachment anchor 245 attached, the attachment anchor 245 having barbs 250. Each outlet end 148 has an attachment anchor 245 attached, each attachment anchor 245 at the outlet end 148 being without barbs 250. As shown in FIG. 23, this bifurcated intravascular folded tubular member 260 is intended as an intravascular tubular member 85 that is delivered to the site of a vascular injury through a proximal or distal vessel adjacent to and connecting to the injured vessel. One common application for this intravascular tubular member is for the treatment of abdominal aortic aneurysm. For this application, the tubular member is generally delivered through a smaller diameter delivery sheath 225 (see FIG. 4C) that is capable of being introduced into one of the common femoral arteries 30. Typically, a small surgical cutdown may be required to access the femoral artery and provide access for a delivery sheath 225 through which the bifurcated intravascular folded tubular member 260 is delivered. The common femoral artery 30 which provides the main access for the intravascular tubular member 85 including the access for the inlet end 145 of the intravascular tubular member 85 will be referred to as the ipsilateral artery or the ipsilateral side. The intravascular tubular member 85 is delivered to the injury site in a nondeployed state, with a smaller bifurcated nondeployed inlet end diameter 230 and nondeployed outlet end diameter 235, and a shorter bifurcated nondeployed tubular member length 280 (see FIG. 4B). The bifurcated intravascular folded tubular member 260 is preferred to have an attachment anchor 245 at the inlet end 145 of the intravascular tubular member to ensure a tight and leak free fit with the aorta in a deployed state although the attachment anchor 245 is not required of the present invention. It is understood that the bifurcated intravascular folded tubular member 260 can have generally circumferential metallic strands 745 woven within the wall structure of the tubular member. Therefore, it is not a requirement that the bifurcated intravascular folded tubular member 260 of the present invention have an attachment anchor 245 at the inlet end 145 or at the outlet end 148. It is preferred to have an attachment anchor 245 at the inlet end 145 to better and more firmly attach the intravascular folded tubular member to the blood vessel wall proximal to the vessel injury without blood leakage at that site or migration of the intravascular folded tubular member. The bifurcated intravascular folded tubular member 260 can be a self-expandable tubular member that is contained within the smaller diameter tubular delivery sheath 225 (see FIG. 4C and 4D) for delivery and assist in deployment. Upon removal of the intravascular tubular member from the delivery sheath 225, the bifurcated intravascular folded tubular member 260 and each attachment anchor 245 is capable of expanding outward and can exert an outward force against the aortic or other arterial wall. The bifurcated intravascular folded tubular member 260 can also be a balloon-expandable tubular member that can be delivered to the site of vessel injury mounted on a balloon catheter. Either the folded tubular member 125, each attachment anchor 245, or both the folded tubular member 125 and the attachment anchors 245 can require expansion from a dilitation balloon to force them outward and into close approximation with the aorta, the wall of the native lumen, or to a radially deployed inlet end diameter 105 and deployed attachment anchor diameter 320. Whether the intravascular tubular member and attachment anchor 245 are self-expandable or balloon-expandable, the attachment anchor 245 located at the inlet end 145 of the tubular member is carefully placed such that it is positioned adjacent and just distal to the renal arteries or within the proximal aortic neck 90 prior to deployment (see FIG. 1B). For treatment of abdominal aortic aneurysm the short axial length of the attachment anchor 245, along with the understanding that the attachment anchor 245 is formed of a metal such as tantalum or contains metal that can be easily visualized under fluoroscopy, allows the attachment anchor 245 to be positioned accurately and close to the renal arteries. Barbs 250 can be located on the attachment anchor 245 to ensure that the attachment anchor 245 is well seated into the aorta and cannot migrate distally although they are not required for all embodiments of this invention. It is further understood that a displaced attachment anchor 760 can also be located proximal to the renal arteries and attached to the bifurcated intravascular folded tubular member 260 using attachment strands 765 as described earlier.

After the inlet end 145 of the bifurcated intravascular folded tubular member 260 has been deployed and attached to the aorta for the case of abdominal aortic aneurysm repair with the attachment anchor 245, each outlet end 148 of the tubular member is moved into its appropriate location within the iliac 20 & 25 or femoral 30 artery. As the outlet ends 148 of the bifurcated tubular member are moved to their appropriate location, the folded tubular sections 125 of each leg can be unfolded to allow the distal tubular section 130 and bifurcated proximal tubular section 265 to extend in length. An attachment anchor 245 can be located at each outlet end 148 although it is not required for the present invention to have any such attachment anchor 245. The attachment anchor 245 located at each outlet end 148 of the bifurcated intravascular folded tubular member 260 can be of a self-expandable or balloon-expandable nature as described earlier for the attachment anchor 245 that can be located at the inlet end 145. The attachment anchor 245 at each outlet end 148 is then expanded or allowed to expand placing the distal tubular section 130 into close contact with the wall of the native vessel or the native lumen wall. The bifurcated intravascular folded tubular member 260 has then been fully deployed to its radially deployed inlet end diameter 105 and radially deployed outlet end diameter 110 and to its bifurcated deployed tubular member length 290 (see FIG. 4B). Each outlet end 148 can be placed precisely in its desired position in the iliac or femoral artery while observing or real time fluoroscopy the placement of each outlet end 148.

The firm anchoring provided by the attachment anchor 245 of this invention will ensure that the inlet end 145 of the bifurcated intravascular folded tubular member 260 will not migrate during the unfolding of the folded tubular section 125 and after the bifurcated intravascular folded tubular member 260 is implanted. The attachment anchor 245 combined with the one-piece construction provides a leak free seal to completely isolate the aneurysmal space from the blood flow passage 100 within the bifurcated intravascular folded tubular member 260. The wall structure allows a displaced attachment anchor 760 (see FIG. 20) to be attached to the bifurcated intravascular folded tubular member 260. The generally axial metallic strands 755 can extend proximally beyond the inlet end 145 and form a direct attachment to the displaced attachment anchor 760 (see FIG. 20) by attaching to the intranodal openings 385. It is understood that a straight intravascular folded tubular member 95 could have similarly been shown with the woven wall structure and attachment anchor 245 described in this embodiment. The present invention is intended to include both straight 95 and bifurcated 260 intravascular folded tubular member including all of the features described in this disclosure.

Delivery Procedure

It is further an additional embodiment of this invention to provide a bifurcated intravascular folded tubular member 260 that can be delivered and fully deployed either percutaneously or through a small surgical cutdown in one common femoral artery 30 and placed within the aorta for treatment of abdominal aortic aneurysm without the need for access to the contralateral artery such as the contralateral common femoral artery 30. This can be accomplished by first delivering the bifurcated intravascular folded tubular member 260 to the abdominal aorta at the site of the abdominal aortic aneurysm 5 between the renal arteries and the aorto-iliac bifurcation 57 (see FIG. 1A and 1B). After the inlet end 145 of the bifurcated intravascular folded tubular member 260 has been placed proximal to the aortic injury, the entire bifurcated intravascular folded tubular member as shown in FIG. 4B, 5, or 23 can be located entirely within the abdominal aorta and proximal to aorto-iliac bifurcation 57 (see FIG. 1B). One outlet end 148 of the bifurcated intravascular folded tubular member 260 on the ipsilateral side can be deployed to its appropriate position in the iliac or femoral artery. The outlet end 148 of the bifurcated intravascular folded tubular member 260 on the contralateral side can then be placed into appropriate position with a contralateral side outlet end placement means. This contralateral side outlet end placement means is introduced through the ipsilateral femoral artery and can move the outlet end 148 of the bifurcated intravascular folded tubular member 260 such that the folded tubular section 125 can unfold allowing the proximal or distal section to extend and provide an extension of the tubular member on the contralateral side so as to place the outlet end 148 in an appropriate position. The attachment anchor 245 located on the contralateral side is expanded or allowed to expand to hold the outlet end 148 of the bifurcated intravascular folded tubular member 260 securely in contact with the arterial wall or the inside of the vessel lumen.

The present invention includes a one piece bifurcated intravascular folded tubular member 260 which is different than the modular systems described in the prior art for treating abdominal aortic aneurysm. The one piece construction of the present invention cannot form leak pathways such as those that occur between the union of various segments found in modular systems. The present intravascular tubular member provides a device for treating vascular injury such as abdominal aortic aneurysm where the axial length of the native lumen extending through the aortic aneurysm is very difficult to measure using angiographic means. Estimating the length angiographically will very often lead to an incorrect estimation of the length of intravascular graft that is needed. The result can be the implantation or another prior art stent-graft device that is too short and does not extend beyond the injured artery to the region that is not injured or healthy. If the prior art stent-graft is too long, it can extend beyond an appropriate point in the iliac or femoral artery and can block a side branch such as the internal iliac artery 80. With the intravascular tubular member 85 of the present invention, the length of the intravascular tubular member 85 or vascular tubular member 83 is determined in situ or while it is being placed. Therefore, the intravascular tubular member 85 of the present invention can be extended precisely to the appropriate length without concern for the inaccuracies associated with trying to estimate the length of the tortuous path for the intravascular tubular member.

Various modifications can be made to the present invention without departing from the apparent scope hereof.

REFERENCE NUMERALS IN THE DRAWINGS

5 Abdominal Aortic Aneurysm
10 Abdominal Aorta
15 Left Renal Vein
20 Common Iliac Artery
25 External Iliac Artery
30 Common Femoral Artery
35 Left Kidney
40 Inferior Vena Cava
45 Left Renal Artery
50 Right Renal Artery
53 Native Lumen
55 Suprarenal Aorta
57 Aorto-Iliac Bifurcation
60 Thrombus
70 Abdominal Aortic Wall
75 Lumbar Arteries
80 Internal Iliac Artery
82 Vascular Implant
83 Vascular Tubular Member
85 Intravascular Tubular Member
87 Attachment Means
90 Proximal Aortic Neck
95 Straight Intravascular Folded Tubular Member
100 Blood Flow Passage
105 Radially Deployed Inlet End Diameter
110 Radially Deployed Outlet End Diameter
115 Straight Nondeployed Tubular Member Length
120 Straight Proximal Tubular Section
125 Folded Tubular Section
130 Distal Tubular Section
135 Inner Surface
140 Outer Surface
143 Intravascular Tubular Member Wall
145 Inlet End
148 Outlet End
150 Straight Nondeployed Proximal Tubular Section Length
155 Folded Tubular Section Outer Wall
160 Folded Tubular Section Center Wall
165 Folded Tubular Section Inner Wall
170 Straight Proximal Tubular Section Wall
175 Proximal Circumferential Fold Line
180 Distal Circumferential Fold Line
185 Nondeployed Folded Tubular Section Length
187 Folded Tubular Section Upstream End
188 Folded Tubular Section Downstream End 190 Distal Tubular Section Wall
200 Nondeployed Distal Tubular Section Length
205 Straight Deployed Tubular Member Length
210 Deployed Folded Tubular Section Length
215 Straight Deployed Proximal Tubular Section Length
220 Deployed Distal Tubular Section Length
225 Delivery Sheath
230 Nondeployed Inlet End Diameter
235 Nondeployed Outlet End Diameter
237 Deployed Diameter
240 Straight Unfolded Tubular Member Length
245 Attachment Anchor
250 Barbs
255 Securing Fibers
260 Bifurcated Intravascular Folded Tubular Member
265 Bifurcated Proximal Tubular Section
270 Main Trunk
275 Proximal Leg Tubes
280 Bifurcated Nondeployed Tubular Member Length
285 Bifurcated Nondeployed Proximal Tubular Section Length
290 Bifurcated Deployed Tubular Member Length
295 Bifurcated Deployed Proximal Tubular Section Length
298 Guidewire
300 Balloon Dilitation Catheter
305 Nondeployed Diameter
315 Bifurcated Unfolded Tubular Member Length
320 Deployed Attachment Anchor Diameter
325 Bonding Agent
330 Folded Tubular Section Walls
335 Circle
340 Square
345 Point-up Triangle
350 Point-down Triangle
355 Rectangle
360 Holding Pins
365 Nodes
370 Struts
375 Interstrut Openings
380 Hinge
385 Intranodal Opening
386 Hinge Width Radius of Curvature
387 Nondeployed Attachment Anchor Diameter
390 Strut Length
395 Deployed Attachment Anchor Length
398 Axial Direction
400 Nondeployed Attachment Anchor Length
403 Circumferential Direction
404 Uniformly Curved Attachment Anchor Surface
405 Deployment Angle
410 Transition Regions
415 Hinge Length
420 Hinge Width
425 Hinge Radial Dimension
430 Strut Width
435 Strut Radial Dimension
440 Transition Width
445 Transition Radial Dimension
447 Strut Cross Sectional Area
448 Hinge Cross Sectional Area
449 Nondeployed Attachment Anchor Perimeter
451 Deployed Attachment Anchor Perimeter
452 Transition Region Length
453 Oval Attachment Anchor Surface
455 Hinges
457 Hub
458 Attachment Anchor Outside End
460 Woven Vascular Tubular Member
465 Circumferential Strands
475 Axial Strands
483 Filaments
485 Crossover Points
490 Monofilament Strands
495 Leakage Sites
498 Monofilament Strand Crossover Point
500 Monofilament Strand Diameter
510 Multifilament Strands
513 Multifilament Crossover Points
515 Filament Diameter
520 Multifilament Strand Diameter
525 Expanded Polytetrafluoroethylene Filament
530 Expanded Polytetrafluoroethylene Microfilaments
535 Nodal Regions
540 Expanded Polytetrafluoroethylene Filament Diameter
545 Expanded Polytetrafluoroethylene Microfilament Diameter
550 Linear Axis
555 Straight Multifilament Strand
560 Straight Filaments
570 Curved Filaments
573 Curved Multifilament Strand
575 Straight Expanded Polytetrafluoroethylene filament
580 Straight Expanded Polytetrafluoroethylene Microfilaments
585 Curved Expanded Polytetrafluoroethylene Filament
590 Curved Expanded Polytetrafluoroethylene Microfilaments
595 Multifilament Polymeric Strands
600 Metallic Strands
605 Straight Monofilament Strands
610 Metal to Metal Crossover Points
615 Curved Monofilament Strand
620 Flattened Metallic Strands
623 Flattened Crossover Point
625 Curved Axial Polymeric Strands
630 Curved Circumferential Polymeric Strands
635 Straight Axial Polymeric Strands
640 Straight Circumferential Polymeric Strands
645 Curved Axial Metallic strands
650 Curved Circumferential Metallic Strands
655 Straight Axial Metallic Strands
660 Straight Circumferential Metallic Strands
662 Vascular Tubular Member Wall
663 Wall Thickness
665 Polymer to Polymer Crossover Point
670 Polymer to Metal Crossover Point
675 Weave Plane
680 Continuous Woven Layer
685 Inlet Portion
690 Step-Over
705 Braided Vascular Tubular Member
710 Straight Right Spiral Polymeric Strand
715 Straight Right Spiral Metallic Strand
720 Straight Left Spiral Polymeric Strand
725 Straight Left Spiral Metallic Strand
740 Generally Circumferential Polymeric Strands
745 Generally Circumferential Metallic Strands
750 Generally Axial Polymeric Strands
755 Generally Axial Metallic Strands
760 Displaced Attachment Anchor
765 Attachment Strands
770 Triple Wall Thickness

What is claimed is:

1. An intravascular tubular member for use in treatment of an injured artery that conveys blood flow from a proximal arterial region proximal to the injured artery to one or more distal arterial vessels and is introduced in an nondeployed state with a smaller nondeployed diameter through an artery that supplies blood to or receives blood from the injured artery and expands upon deployment to a larger deployed diameter and is implanted in a fully deployed state, said intravascular tubular member comprising;

A. a proximal tubular section with an open free inlet end to provide passage for blood flow into said intravascular tubular member from the proximal arterial region;

B. one or more distal tubular sections, each of said one or more distal tubular sections having an open free outlet end to provide passage of blood flow out of said intravascular tubular member to one or more distal arterial vessels;

C. an intravascular tubular member wall extending between said inlet end of said proximal tubular section and said outlet end of each of said one or more distal tubular sections;

D. one or more folded tubular sections, each of said one or more folded tubular sections having an upstream end and a downstream end, said upstream end of each of said one or more folded tubular sections being joined to said proximal tubular section and said downstream end of each of said one or more folded tubular sections being joined to one of said one or more distal tubular sections, each of said one or more folded tubular sections having said intravascular tubular member wall folded back and forth upon itself forming an inner wall, a center wall, and an outer wall;

whereby said intravascular tubular member extends in an axial length from said inlet end to said outlet end during the deployment from the nondeployed state to the fully deployed state as said center wall decreases in length.

2. The intravascular tubular member of claim 1 for use in the treatment of an injured artery further comprising an inlet attachment means positioned at said inlet end to hold said intravascular tubular member into contact with the proximal arterial region, said attachment means having a smaller nondeployed diameter and a larger deployed diameter.

3. The intravascular tubular member of claim 2 further comprising an outlet attachment means positioned at said outlet end of at least one of said one or more distal tubular sections to hold said intravascular tubular member into contact with the one or more distal arterial vessels.

4. The intravascular tubular member of claim 3 wherein said outlet attachment means is comprised of hinges and struts, said hinges and struts being connected to each other to form a circular band shape, said hinge having a hinge width that is smaller than a strut width.

5. The intravascular tubular member of claim 4 wherein at least one of said outlet attachment means comprises a barb which extends outwardly during the deployment of said outlet attachment means.

6. The intavascular tubular member of claim 2 wherein said inlet attachment means is comprised of hinges and struts, said hinges and struts being connected to each other to form a circular band shape, said hinge having a hinge width that is smaller than a strut width.

7. The intravascular tubular member of claim 6 wherein said inlet attachment means comprises at least one elastically deformed barb which is held in a nondeployed position by at least one of said struts of said attachment means and is released by at least one of said struts to allow said barb to extend outward elastically during the deployment of said attachment means.

8. The intravascular tubular member of claim 6 wherein said struts are attached to said hinges via transition regions, said attachment means being further comprised of at least one elastically deformed barb which is held in a nondeployed position by one or more of said transition regions and are released by one or more of said transition regions to allow said barb to extend outwardly elastically during the deployment of said attachment means.

9. The attachment means of claim 6 wherein said hinge undergoes a plastic deformation as said attachment means undergoes the expansion deformation from a smaller diameter in a nondeployed state to a larger diameter in a deployed state.

10. The attachment means of claim 6 wherein said hinge undergoes an elastic deformation as said attachment means undergoes the expansion deformation from a smaller diameter in a nondeployed state to a larger diameter in a deployed state.

11. The intravascular tubular member of claim 2 wherein said inlet attachment means comprises one or more barbs that extend outwardly during deployment of said inlet attachment means.

12. The intravascular tubular member of claim 2 wherein said attachment means undergoes a plastic deformation in going from a smaller nondeployed diameter to a larger deployed diameter.

13. The intravascular tubular member of claim 2 wherein said attachment means undergoes an elastic deformation in going from a smaller nondeployed diameter to a larger deployed diameter.

14. The intravascular tubular member of claim 1 wherein;

A. said one or more distal tubular sections comprises one distal tubular section, said distal tubular section having an outlet end to provide passage of blood flow out of said intravascular tubular member to a distal arterial vessel;

B. said one or more folded tubular sections comprises one folded tubular section, said folded tubular section having an upstream end and a downstream end, said upstream end being joined to said proximal tubular section and said downstream end being joined to said distal tubular section, said folded tubular section having said intravascular tubular member wall folded back and forth upon itself forming an inner wall, a center wall, and an outer wall.

15. The intravascular tubular member of claim 1 for use in the treatment of abdominal aortic aneurysm wherein;

A. said one or more distal tubular sections comprise two distal tubular sections, each of said two distal tubular sections having an outlet end to provide passage of blood flow out of said intravascular tubular member to two distal arterial vessels;

B. said one or more folded tubular sections comprise two folded tubular sections, each of said two folded tubular sections having an upstream end and a downstream end, said upstream end of each of said two folded tubular sections being joined to said proximal tubular section and said downstream end of each of said two folded tubular sections being joined to one of said two distal tubular sections, each of said two folded tubular sections having said intravascular tubular member wall folded back and forth upon itself forming an inner wall, a center wall, and an outer wall.

16. The intravascular tubular member of claim 15 further comprising an inlet attachment means positioned at said inlet end to hold said intravascular tubular member into contact with the proximal arterial region.

17. The intravascular tubular member of claim 15 further comprising an outlet attachment means positioned at said outlet end of each of said two distal tubular sections to hold said intravascular tubular member into contact with the two distal arterial vessels.

18. The intravascular tubular member of claim 1 further comprising a bonding agent placed within at least one of said one or more folded tubular sections.

19. The intravascular tubular member of claim 1 wherein a holding means is placed in said one or more folded tubular sections in a deployed state to prevent unfolding of said folded tubular section.

20. The intravascular tubular member of claim 19 wherein said holding means comprises one or more holding pins which penetrate through two or more walls of said folded tubular section.

21. The intravascular tubular member of claim 1 wherein said intravascular tubular member wall is comprised of polymeric multifilament strands woven in a generally circumferential direction and woven in the axial direction, said multifilament strands providing for sealing against blood leakage at crossover points and preventing blood leakage and tear propagation due to strand breakage.

22. The intravascular tubular member of claim 21 wherein said intravascular tubular member wall is further comprised of metallic monofilament strands woven along with said polymeric multifilament strands in a generally circumferential direction, said metallic strands woven in a generally circumferential direction providing outward expansion force for a thin wall thickness and provide for kink resistance.

23. The intravascular tubular member of claim 22 further comprising metallic monofilament strands woven along with said polymeric multifilament strands in a generally axial direction, said metallic strands woven in a generally axial direction providing axial compressive strength for a thin wall thickness.

24. The intravascular tubular member of claim 23 for intravascular use within a blood vessel wherein at least a fractional number of said metallic monofilament strands extend proximally beyond an inlet end of the intravascular tubular member and are attached to an attachment means that attaches said metallic monofilament strands to the proximal arterial region remote from and proximal to said inlet end of said intravascular tubular member.

25. The intravascular tubular member of claim 21 wherein said polymeric multifilament strands are formed from a polymer taken from the group which includes expanded polytetrafluoroethylene, polyester, polyurethane, silicone, and copolymers of these polymers.

26. The intravascular tubular member of claim 25 comprised of woven expanded polytetrafluoroethylene multifilament strands in a generally axial and generally circumferential direction, said expanded polytetrafluoroethylene multifilament strands providing for resistance to leakage at crossover points, and said woven structure providing for safety due to a resistance to tear propagation.

27. The vascular tubular member of claim 21 wherein said expanded polytetrafluoroethylene multifilament strands woven in the axial direction are comprised of expanded polytetrafluoroethylene filaments, said expanded polytetrafluoroethylene filaments being comprised of polytetrafluoroethylene microfilaments having a curved structure to provide a stretch characteristic to said expanded polytetrafluoroethylene multifilament strands, to provide the vascular tubular member with kink resistance, and to provide compliance to the vascular tubular member.

28. The vascular tubular member of claim 21 wherein said expanded polytetrafluoroethylene multifilament strands woven in the circumferential direction are comprised of expanded polytetrafluoroethylene filaments, said expanded polytetrafluoroethylene filaments being comprised of polytetrafluoroethylene microfilaments having a curved structure to provide a stretch characteristic to said expanded polytetrafluoroethylene multifilament strands, to provide intravascular tubular member with kink resistance, and to provide compliance to the vascular tubular member.

29. The intravascular tubular member of claim 1 wherein said intravascular tubular member wall is comprised of polymeric multifilament strands braided in a right hand and left hand spiral, said multifilament strands providing for sealing against blood leakage at crossover points and preventing blood leakage and tear propagation due to strand breakage.

30. The intravascular tubular member of claim 29 wherein said intravascular tubular member wall is further comprised of metallic monofilament strands braided in a right hand and left hand spiral along with said polymeric multifilament strands, said metallic monofilament strands providing outward expansion force for a thin wall thickness and provide for kink resistance.

31. The intravascular tubular member of claim 29 wherein said polymeric multifilament strands are formed from a polymer taken from the group which includes expanded polytetrafluoroethylene, polyester, polyurethane, silicone, and copolymers of these polymers.

32. An intravascular tubular member for use in treatment of an injured artery that conveys blood flow from a proximal arterial region proximal to the injured artery to one or more distal arterial vessels and is introduced in an nondeployed state with a smaller nondeployed diameter through an artery that supplies blood to or receives blood from the injured artery and expands upon deployment to a larger deployed diameter and is implanted in a deployed state, said intravascular tubular member comprising;

A. a proximal tubular section with an inlet end to provide passage for blood flow into said intravascular tubular member from the proximal arterial region;

B. one or more distal tubular sections, each of said one or more distal tubular sections having an outlet end to provide passage of blood flow out of said intravascular tubular member to one or more distal arterial vessels;

C. said intravascular tubular member having an outer surface extending between said inlet end of said proximal tubular section and said outlet end of each of said one or more distal tubular sections;

D. one or more folded tubular sections, each of said one or more folded tubular sections having an upstream end and a downstream end, said upstream end of each of said one or more folded tubular sections being joined to said proximal tubular section and said downstream end of each of said one or more folded tubular sections being joined to each of said one or more distal tubular sections, each of said one or more folded tubular sections having a first portion of said outer surface in apposition with a second portion of said outer surface over an entire length of said folded tubular section, and both of said portions being nearly parallel to an axis of said folded tubular section;

whereby said intravascular tubular member can extend in an axial length from said inlet end to said outlet end during the deployment from the nondeployed state to the deployed state.

33. The intravascular tubular member of claim 32 wherein a bonding agent is placed between said first portion of said outer surface and said second portion of said outer surface.

34. An intravascular tubular member for implantable use within a human body for treatment of abdominal aortic aneurysm that conveys blood flow from a proximal aortic region proximal to an injured artery to one or more distal arterial vessels and is introduced in an nondeployed state with a smaller nondeployed insertion diameter using a minimally invasive vascular access through an artery that supplies blood to or receives blood from the aorta and expands upon deployment to a larger deployed diameter and is implanted within the human body in an implanted state, said intravascular tubular member comprising;

A. a proximal tubular section having an open free inlet end to provide passage for blood flow into said proximal tubular section from the proximal aorta, said proximal tubular section being joined to at least one folded tubular section, said at least one folded tubular section providing for a change in axial length for said intravascular tubular member, each of said at least one folded tubular section being joined to a distal tubular section, said distal tubular section having an outlet end to provide for passage of blood flow out of said distal tubular section into the one or more distal arterial vessels;

B. said at least one folded tubular section having said intravascular tubular member wall longitudinally overlapped in an axial direction whereby said at least one folded tubular section can unfold during deployment from the nondeployed state to the implanted state to provide a decrease in length of said at least one folded tubular section.

35. An intravascular tubular member for use in treatment of an injured artery that conveys blood flow from a proximal arterial region proximal to the injured artery to one or more distal arterial vessels and is introduced in an nondeployed state with a smaller nondeployed diameter through an artery that supplies blood to or receives blood from the injured artery and expands upon deployment to a larger deployed diameter and is implanted in a deployed state, said intravascular tubular member comprising;

A. a proximal tubular section with an open free inlet end to provide passage for blood flow into said intravascular tubular member from the proximal arterial region;

B. one or more distal tubular sections, each of said one or more distal tubular sections having an open free outlet end to provide passage of blood flow out of said intravascular tubular member to one or more distal arterial vessels;

C. an intravascular tubular member wall extending between said inlet end of said proximal tubular section and said outlet end of each of said one or more distal tubular sections;

D. one or more folded tubular sections, each of said one or more folded tubular sections having an upstream end and a downstream end, said upstream end of each of said one or more folded tubular sections being joined to said proximal tubular section and said downstream end of each of said one or more folded tubular sections being joined to one of said one or more distal tubular sections, each of said one or more folded tubular sections having said intravascular tubular member wall folded in a proximal and distal direction upon itself forming an inner wall, a center wall, and an outer wall, and said walls all being generally parallel to each other;

whereby said intravascular tubular member can extend in an axial length from said inlet end to said outlet end during the deployment from the nondeployed state to the fully deployed state.

36. A method of treatment of an injured artery that conveys blood flow from a proximal arterial region proximal to the injured artery to one or more distal arterial vessels and is introduced in an nondeployed state with a smaller nondeployed diameter through an artery that supplies blood to or receives blood from the injured artery and expands upon deployment to a larger deployed diameter and is implanted in a deployed state, the method comprising;

A. providing an intravascular tubular member in a non-radially deployed state and a non-axially deployed state into the vasculature, said intravascular tubular member having a proximal tubular section with an inlet end to provide passage for blood flow into said intravascular tubular member from the proximal arterial region and one or more distal tubular sections, each of said one or more distal tubular sections having an outlet end to provide passage of blood flow out of said intravascular tubular member to one or more distal arterial vessels, said intravascular tubular member having an intravascular tubular member wall extending between said inlet end of said proximal tubular section and said outlet end of each of said one or more distal tubular sections;

B. unfolding in an axial direction a portion of one or more folded tubular sections, each of said one or more folded tubular sections having an upstream end and a downstream end, said upstream end of each of said one or more folded tubular sections being joined to said proximal tubular section and said downstream end of each of said one or more folded tubular sections being joined to one of said one or more distal tubular sections, each of said one or more folded tubular sections having said intravascular tubular member wall folded proximally and distally upon itself forming an inner wall, a center wall, and an outer wall that are all generally parallel to each other;

whereby the unfolding of said one or more folded tubular sections provides said intravascular tubular member with a longer axial length.

37. The method of claim 36 wherein said intravascular tubular member is a one-piece structure that is continuous from the inlet end of said proximal tubular section to the outlet end of said one or more distal tubular sections.

38. The method of claim 36 wherein said intravascular tubular member is attached at a proximal end to the proximal arterial region using an inlet attachment means to hold the intravascular tubular member against the proximal arterial region prior to unfolding said one or more folded tubular sections.

39. The method of claim 38 wherein said one or more distal tubular sections are attached to the one or more distal arterial vessels following unfolding of said one or more folded tubular sections with an outlet attachment means to hold the intravascular tubular member against the one or more distal arterial vessels.

40. The method of claim 36 further comprising inserting a holding means after unfolding a portion of one or more folded tubular sections to hold together at least two walls of said one or more folded tubular sections and prevent further unfolding.

41. The method of claim 36 for treatment of abdominal aortic aneurysm wherein;

A. said one or more distal tubular sections comprise two distal tubular sections, each of said two distal tubular sections having an outlet end to provide passage of blood flow out of said intravascular tubular member to two distal arterial vessels;

B. said one or more folded tubular sections comprise two folded tubular sections, each of said two folded tubular sections having an upstream end and a downstream end, said upstream end of each of said two folded tubular sections being joined to said proximal tubular section and said downstream end of each of said two folded tubular sections being joined to one of said two distal tubular sections.

42. The method of claim 41 wherein said unfolding of said two folded tubular sections is attained via access through a single distal arterial vessel.

43. The method of claim 41 wherein one of said two folded tubular sections is unfolded via access from one of the distal arterial vessels and the other of said two folded tubular sections is unfolded via access through another of the distal arterial vessels.

44. A method of treatment of an abdominal aorta aneurysm that conveys blood flow from a proximal aortic region proximal to the abdominal aortic aneurysm to one or more distal arterial vessels and is introduced in an nondeployed state with a smaller nondeployed diameter using a minimally invasive vascular access through an artery that supplies blood to or receives blood from the aorta and expands upon deployment to a larger deployed diameter and is implanted in a deployed state, the method comprising;

A. providing an intravascular tubular member in a non-radially deployed state and a non-axially deployed state into the aortic vasculature, said intravascular tubular member having a proximal tubular section with an inlet end to provide passage for blood flow into said intravascular tubular member from the proximal aortic region and one or more distal tubular sections, each of said one or more distal tubular sections having an outlet end to provide passage of blood flow out of said intravascular tubular member to one or more distal arterial vessels, said intravascular tubular member having an intravascular tubular member wall extending between said inlet end of said proximal tubular section and said outlet end of each of said one or more distal tubular sections;

B. expanding the inlet end of said intravascular tubular member into contact with the proximal aortic region using an attachment means to hold the intravascular tubular member outwards against the proximal aortic region;

C. unfolding in an axial direction one or more folded tubular sections, each of said one or more folded tubular sections having an upstream end and a downstream end, said upstream end of each of said one or more folded tubular sections being joined to said proximal tubular section and said downstream end of each of said one or more folded tubular sections being joined to one of said one or more distal tubular sections, each of said one or more folded tubular sections having said intravascular tubular member wall folded back and forth upon itself forming an inner wall, a center wall, and an outer wall that are all generally parallel to an each other;

D. expanding the outlet end of said one or more distal tubular sections into contact with the one or more distal arterial vessels using an attachment means to hold the intravascular tubular member outwards;

whereby the unfolding of said one or more folded tubular sections provides said intravascular tubular member with a longer axial length.

* * * * *